US011028064B2

(12) United States Patent
Gamage et al.

(10) Patent No.: US 11,028,064 B2
(45) Date of Patent: Jun. 8, 2021

(54) TRICYCLIC HETEROCYCLIC DERIVATIVES AND USES THEREOF

(71) Applicant: AUCKLAND UNISERVICES LIMITED, Auckland (NZ)

(72) Inventors: Swarnalatha Akuratiya Gamage, Auckland (NZ); Peter Robin Shepherd, Auckland (NZ); Jack Urquhart Flanagan, Auckland (NZ); Gordon William Rewcastle, Auckland (NZ); Andrew James Marshall, Auckland (NZ); Christina Maree Buchanan, Auckland (NZ); Guo-Liang Lu, Auckland (NZ); Muriel Bonnet, Auckland (NZ); Stephen Michael Frazer Jamieson, Auckland (NZ); William Alexander Denny, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 0 days.

(21) Appl. No.: 16/347,420

(22) PCT Filed: Nov. 3, 2017

(86) PCT No.: PCT/IB2017/056848
§ 371 (c)(1),
(2) Date: May 3, 2019

(87) PCT Pub. No.: WO2018/083635
PCT Pub. Date: May 11, 2018

(65) Prior Publication Data
US 2019/0276423 A1 Sep. 12, 2019

(30) Foreign Application Priority Data
Nov. 4, 2016 (NZ) ........................ 725767

(51) Int. Cl.
| C07D 311/86 | (2006.01) |
| C07D 219/08 | (2006.01) |
| C07D 335/16 | (2006.01) |
| C07D 405/06 | (2006.01) |
| C07D 405/12 | (2006.01) |
| C07D 405/14 | (2006.01) |
| C07D 409/02 | (2006.01) |
| C07D 221/04 | (2006.01) |
| C07D 409/12 | (2006.01) |
| C07D 335/18 | (2006.01) |
| A61K 45/06 | (2006.01) |

(52) U.S. Cl.
CPC .......... *C07D 311/86* (2013.01); *C07D 219/08* (2013.01); *C07D 221/04* (2013.01); *C07D 335/16* (2013.01); *C07D 335/18* (2013.01); *C07D 405/06* (2013.01); *C07D 405/12* (2013.01); *C07D 405/14* (2013.01); *C07D 409/02* (2013.01); *C07D 409/12* (2013.01); *A61K 45/06* (2013.01)

(58) Field of Classification Search
None
See application file for complete search history.

(56) References Cited

U.S. PATENT DOCUMENTS

| 3,755,319 A | 8/1973 | Bays |
| 8,350,041 B2 | 1/2013 | Carson et al. |
| 8,350,065 B2 | 1/2013 | Li et al. |
| 8,410,161 B2 | 4/2013 | Huang |
| 8,841,455 B2 | 9/2014 | Boys et al. |
| 9,174,981 B2 | 11/2015 | Boys et al. |
| 9,657,043 B2 | 5/2017 | Hamada et al. |
| 2006/0030585 A1 | 2/2006 | Dax et al. |
| 2015/0087620 A1 | 3/2015 | Hamada et al. |

FOREIGN PATENT DOCUMENTS

| CN | 101195609 A | 6/2008 |
| CN | 101279967 B | 11/2010 |
| EP | 0 278 176 B1 | 3/1994 |
| GB | 2498976 A | 8/2013 |
| WO | 03/088897 A2 | 10/2003 |
| WO | 2004/041210 A2 | 5/2004 |
| WO | 2006/044707 A1 | 4/2006 |
| WO | 2007/121484 A2 | 10/2007 |
| WO | 2008/016661 A2 | 2/2008 |

(Continued)

OTHER PUBLICATIONS

Goldberg et al, Journal of the Chemical Society, pp. 4234-4241, Jun. 5 (Year: 1958).*
Sandra Montalvo-Quiros et al., "Antiprotozoal Activity and DNA Binding of Dicationic Acridones," Journal of Medicinal Chemistry, Feb. 2, 2015, pp. 1940-1949, vol. 58.
International Search Report of PCT/I62017/056848 dated Jun. 13, 2018.
Murray et al., "SU11248 inhibits tumor growth and CSF-1R-dependent osteolysis in an experimental breast cancer bone metastasis model", Clinical & Experimental Metastasis, 2003, vol. 20, pp. 757-766.
Vandyke et al., "The Tyrosine Kinase Inhibitor Dasatinib Dysregulates Bone Remodeling Through Inhibition of Osteoclasts In Vivo", Journal of Bone and Mineral Research, vol. 25, No. 8, Aug. 2010, pp. 1759-1770.

(Continued)

*Primary Examiner* — Zinna Northington Davis
(74) *Attorney, Agent, or Firm* — Sughrue Mion, PLLC

(57) ABSTRACT

Disclosed are tricyclic heterocyclic compounds having kinase inhibitory activity, pharmaceutical compositions and kits comprising the compounds, and use of the compounds in the treatment of or in medicaments for the treatment of various diseases and conditions. In particular, disclosed are tricyclic heterocyclic compounds of the formula (I) having CSF-1R (c-FMS kinase) inhibitory activity and their use in the treatment of various diseases and conditions, such as those mediated by CSF-1R, including proliferative or neoplastic diseases and conditions, including cancers, and bone, inflammatory, and autoimmune diseases and conditions.

18 Claims, 1 Drawing Sheet

(56) References Cited

FOREIGN PATENT DOCUMENTS

| WO | 2008/048117 A2 | 4/2008 |
|---|---|---|
| WO | 2009/043672 A3 | 4/2009 |
| WO | 2009073620 A2 | 6/2009 |
| WO | 2009/156459 A1 | 12/2009 |
| WO | 2010/045551 A8 | 4/2010 |
| WO | 2011/056652 A1 | 5/2011 |
| WO | 2011/079076 A1 | 6/2011 |
| WO | 2012/082689 A1 | 6/2012 |
| WO | 2012/142237 A1 | 10/2012 |
| WO | 2013/087647 A1 | 6/2013 |
| WO | 2013/132044 A1 | 9/2013 |

OTHER PUBLICATIONS

El-Gamal et al., "FMS Kinase Inhibitors: Current Status and Future Prospects", Medicinal Research Reviews, 2013, vol. 33, No. 3, pp. 599-636.
Pollard, "Tumour-educated macrophages promote tumour progression and metastasis", Nature Reviews, Cancer, Jan. 2004, vol. 4, pp. 71-78.
Lewis et al., "Distinct Role of Macrophages in Different Tumor Microenvironments", Cancer Res., Jan. 15, 2006, pp. 605-612 (9 pages total).
Condeelis et al., "Macrophages: Obligate Partners for Tumor Cell Migration, Invasion, and Metastasis", Leading Edge Minireview, Cell 124, Jan. 27, 2006, pp. 263-266.
Patel et al., "Colony-Stimulating Factor-1 Receptor Inhibitors for the Treatment of Cancer and Inflammatory Disease", Current Topics in Medicinal Chemistry, 2009, vol. 9, No. 7, pp. 599-610.
Lin et al., "Colony-stimulating Factor 1 Promotes Progression of Mammary Tumors to Malignancy", J. Exp. Med., Mar. 19, 2001, vol. 193, No. 6, pp. 727-739.
Priceman et al., "Targeting distinct tumor-infiltrating myeloid cells by inhibiting CSF-1 receptor: combating tumor evasion of antiangiogenic therapy", Vascular Biology, Blood, Feb. 18, 2010, vol. 115, No. 7, pp. 1461-1471.
Firestein, "Evolving concepts of rheumatoid arthritis", Nature, vol. 423, May 15, 2003, pp. 356-361.
Hume et al., "Therapeutic applications of macrophage colony-stimulating factor-1 (CSF-1) and antagonists of CSF-1 receptor (CSF-1R) signaling", Blood, Feb. 23, 2012, vol. 119, No. 8, pp. 1810-1820.
Huang et al., "Pyrido[2,3-d]pyrimidin-5-ones: A Novel Class of Anti-inflammatory Macrophage Colony-Stimulating Factor-1 Receptor Inhibitors", J. Med. Chem., 2009, vol. 52, No. 4, pp. 1081-1099.
Dai et al., "Targeted disruption of the mouse colony-stimulating factor 1 receptor gene results in osteopetrosis, mononuclear phagocyte deficiency, increased primitive progenitor cell frequencies, and reproductive defects", Blood, Jan. 1, 2002, vol. 99, No. 1, pp. 111-120.
Illig et al., "Discovery of novel FMS kinase inhibitors as anti-inflammatory agents", Bioorg. Med. Chem. Lett., vol. 18, 2008, pp. 1642-1648.
Ohno et al., "The orally-active and selective c-Fms tyrosine kinase inhibitor Ki20227 inhibits disease progression in a collagen-induced arthritis mouse model", Eur. J. Immunol., vol. 38, 2008, pp. 283-291.
Paniagua et al., "c-Fms-mediated differentiation and priming of monocyte lineage cells play a central role in autoimmune arthritis", Arthritis Research and Therapy, vol. 12:R32, 2010, pp. 1-15.
Hamilton, "Rheumatoid arthritis: opposing actions of haemopoietic growth factors and slow-acting anti-rheumatic drugs", The Lancet, vol. 342, Aug. 28, 1993, pp. 536-539 (4 pages total).
Campbell et al., "The colony-stimulating factors and collagen-induced arthritis: exacerbation of disease by M-CSF and G-CSF and requirement for endogenous M-CSF", Journal of Leukocyte Biology, vol. 68, Jul. 2000, pp. 144-150.
Van Wesenbeeck et al., "The osteopetrotic mutation toothless (tl) is a loss-of-function frameshift mutation in the rat Csf1 gene: Evidence of a crucial role for CSF-1 in osteoclastogenesis and endochondral ossification", PNAS, Oct. 29, 2002, vol. 99 No. 22, pp. 14303-14308.
Uemura et al., "The selective M-CSF receptor tyrosine kinase inhibitor Ki20227 suppresses experimental autoimmune encephalomyelitis", Journal of Neuroimmunology, vol. 195, 2008, pp. 73-80.
Marshall et al., "Blockade of Colony Stimulating Factor-1 (CSF-1) Leads to Inhibition of DSS-Induced Colitis", Inflamm. Bowel Dis., vol. 13, No. 2, Feb. 2007, pp. 219-224.
Isbel et al., "Local macrophage proliferation correlates with increased renal M-CSF expression in human glomerulonephritis", Nephrology Dialysis Transplantation, vol. 16, 2001, pp. 1638-1647.
Jose et al., "Blockade of Macrophage Colony-Stimulating Factor Reduces Macrophage Proliferation and Accumulation in Renal Allograft Rejection", American Journal of Transplantation, vol. 3, 2003, pp. 294-300.
Rosenfeld et al., "Macrophage Colony-stimulating Factor mRNA and Protein in Atherosclerotic Lesions of Rabbits and Humans", American Journal of Pathology, vol. 140, No. 2, Feb. 1992, pp. 291-300.
González-Bobes et al., "Amino Alcohols as Ligands for Nickel-Catalyzed Suzuki Reactions of Unactivated Alkyl Halides, Including Secondary Alkyl Chlorides, with Arylboronic Acids", J. Amer. Chem. Soc., 2006, vol. 128, No. 16, pp. 5360-5361.
Waibel et al., "Phenethyl pyridines with non-polar internal substituents as selective ligands for estrogen receptor beta", European Journal of Medicinal Chemistry, vol. 44, 2009, pp. 3560-3570.
Nanasawa et al., "Thermochromism of metallophthalein in acrylamide copolymers with pendant pyridine substituents", Reactive Polymers, vol. 24, 1995, pp. 139-143.
Maiti et al., "Cu-Catalyzed Arylation of Phenols: Synthesis of Sterically Hindered and Heteroaryl Diaryl Ethers", J. Org. Chem., 2010, vol. 75, No. 5, pp. 1791-1794.
Liu et al., "Regioselective Copper-Catalyzed C—N and C—S Bond Formation Using Amines, Thiols and Halobenzoic Acids", Synthesis, 2007, No. 22, pp. 3519-3527.
Hasegawa et al., "Discovery of Novel Benzimidazoles as Potent Inhibitors of TIE-2 and VEGFR-2 Tyrosine Kinase Receptors", J. Med. Chem., 2007, vol. 50, No. 18, pp. 4453-4470.
Meyers et al., "Structure-based drug design enables conversion of a DFG-in binding CSF-1R kinase inhibitor to a DFG-out binding mode", Bioorganic & Medicinal Chemistry Letters, 2010, vol. 20, pp. 1543-1547.
Garris et al., "Therapeutically reeducating macrophages to treat GBM", Nature Medicine, vol. 19, No. 10, Oct. 2013, pp. 1207-1208.
Zhu et al., "CSF1/CSF1R Blockade Reprograms Tumor-Infiltrating Macrophages and Improves Response to T-cell Checkpoint Immunotherapy in Pancreatic Cancer Models", Cancer Research, 2014, vol. 74, No. 18, pp. 5057-5069 (14 pages total).
Inaba et al., "Induction of Sustained Expression of Proto-oncogene c-fms by Platelet-derived Growth Factor, Epidermal Growth Factor, and Basic Fibroblast Growth Factor, and Its Suppression by Interferon-y and Macrophage Colony-stimulating Factor in Human Aortic Medial Smooth Muscle Cells", c-fms in Vascular Smooth Muscle Cell, J. Clin. Invest., Mar. 1995, vol. 95, pp. 1133-1139.
Klebl et al., "Expression of macrophage-colony stimulating factor in normal and inflammatory bowel disease intestine", Journal of Pathology, 2001, vol. 195, pp. 609-615.
Liang et al., Anthraquinone Derivatives as Potent Inhibitors of c-Met Kinase and the Extracellular Signaling Pathway, ACS Med. Chem. Lett., 2013, vol. 4, pp. 408-413.
MacrophagesInCancerFig1, 1 page, retrieved from http://atlasgeneticsoncology.org/Deep/Images/MacrophagesInCancerFig1.png on Apr. 5, 2013.
Plexxikon's PLX3397 Preclinical Data Demonstrate Potential of Novel, "First-in-Class" Cancer Drug, Phase 1 Clinical Trial Under Way in Patients with Metastatic Cancers, Apr. 20, 2010, pp. 1-2 [[http://www.plexxikon.com/view.cfm/73/press-releases]].

(56) References Cited

OTHER PUBLICATIONS

Plexxikon Announces Data Presentations of Oncology Pipeline at ASCO 2011, Saturday Review, Drug Trials, Jun. 16, 2020, 2 pages total.
Bruce C Baguley, "Antivascular therapy of cancer: DMXAA", Lancet Oncol., Reviews, Mar. 2003, vol. 4, pp. 141-148.
Graham J. Atwell et al., "An improved synthesis of 5,6-dimethylxanthenone-4-acetic acid (DMXAA)", European Journal of Medicinal Chemistry, 2002, vol. 37, pp. 825-828.
Silvia Gobbi et al., "Synthesis and Antitumor Activity of New Derivatives of Xanthen-9-one-4-acetic Acid", J. Med. Chem., 2002, vol. 45, No. 22, pp. 4931-4939.
Silvia Gobbi et al., "New derivatives of xanthenone-4-acetic acid: Synthesis, pharmacological profile and effect on TNF-α and NO production by human immune cells", Bioorganic & Medicinal Chemistry, 2006, vol. 14, pp. 4101-4109.
Brian D. Palmer et al., "Synthesis and Biological Activity of Azido Analogues of 5,6-Dimethylxanthenone-4-acetic Acid for Use in Photoaffinity Labeling", Journal of Medicinal Chemistry, Aug. 9, 2007, vol. 50, No. 16, pp. 3757-3764.
Shangjin Yang et al., "A new short synthesis of 5,6-dimethylxanthenone-4-acetic acid (ASA404, DMXAA)", Tetrahedron Letters, 2009, vol. 50, pp. 3945-3947.
Swarna A. Gamage et al., "Structure-activity relationships for substituted 9-oxo-9,10-dihydroacridine-4-acetic acids: analogues of the colon tumour active agent xanthenone-4-acetic acid", Anti-Cancer Drug Design, 1992, vol. 7, pp. 403-414.
Dazhong Ding et al., "Discovery of Novel Benzoxaborole-Based Potent Antitrypanosomal Agents", ACS Medicinal Chemistry Letters, 2010, vol. 1, pp. 165-169.
Chun-Liang Chen et al., "Synthesis and evaluation of new 3-substituted-4-chloro-thioxanthone derivatives as potent anti-breast cancer agents", Arabian Journal of Chemistry, 2015, pp. 1-14.
Silvia Gobbi et al., "Targeting Steroidogenic Cytochromes P450 (CYPs) with 6-Substituted 1-Imidazolylmethylxanthones", CHEMMEDCHEM, 2016, vol. 11, pp. 1770-1777.
Yumeng Mao et al., "Targeting Suppressive Myeloid Cells Potentiates Checkpoint Inhibitors to Control Spontaneous Neuroblastoma", Clin Cancer Res, Aug. 1, 2016, vol. 22, No. 15, pp. 3849-3859.
M.E. Sousa et al., "Synthesis of Xanthones: An Overview", Current Medicinal Chemistry, 2005, vol. 12, No. 21, pp. 2447-2479.
A.M. Paiva et al., "A Century of Thioxanthones: Through Synthesis and Biological Applications", Current Medicinal Chemistry, 2013, vol. 20, No. 19, pp. 2438-2457.
Carlos Miguel Gonçalves Azevedo et al., "Routes to Xanthones: An Update on the Synthetic Approaches", Current Organic Chemistry, 2012, vol. 16, No. 23, pp. 2818-2867.
Gang Liu et al., "Discovery of AC710, a Globally Selective Inhibitor of Platelet-Derived Growth Factor Receptor-Family Kinases", ACS Medicinal Chemistry Letters, 2012, vol. 3, pp. 997-1002.
J. Bendell et al., "A Phase 1 Study of ARRY-382, an Oral Inhibitor of Colony-stimulating Factor-1 Receptor (CSF1R), in Patients with Advanced or Metastatic Cancers", Array Biopharma, 2013, 1 page.
XAA derivatives targeting VEGFR-mediated angiogenesis Biopharma update, Oct. 2012, 12 pages.
Ioannis N. Houpis et al., "Carboxylate Directed Cross-Coupling Reactions in the Synthesis of Trisubstituted Benzoic Acids", Organic Letters, 2008, vol. 10, No. 24, pp. 5601-5604.
Xiaobo Wan et al., "A New Target for an Old Drug: Identifying Mitoxantrone as a Nanomolar Inhibitor of PIM1 Kinase via Kinome-Wide Selectivity Modeling", Journal of Medicinal Chemistry, 2013, vol. 56, pp. 2619-2629.
Gordon W. Rewcastle et al., "Potential Antitumor Agents. 58. Synthesis and Structure-Activity Relationships of Substituted Xanthenone-4-acetic Acids Active against the Colon 38 Tumor in Vivo", J. Med. Chem., 1989, vol. 32, No. 4, pp. 793-799.
Graham J. Atwell et al., "Potential Antitumor Agents. 60. Relationships between Structure and in Vivo Colon 38 Activity for 5-Substituted 9-Oxoxanthene-4-acetic Acids", J. Med. Chem., 1990, vol. 33, No. 5, pp. 1375-1379.
Gordon W. Rewcastle et al., "Potential Antitumor Agents. 61. Structure Activity Relationships for in Vivo Colon 38 Activity among Disubstituted 9-Oxo-9H-xanthene-4-acetic Acids", J. Med. Chem., 1991, vol. 34, No. 1, pp. 217-222.
Gordon W. Rewcastle et al., "Potential Antitumor Agents. 63. Structure-Activity Relationships for Side-Chain Analogues of the Colon 38 Active Agent 9-Oxo-9H-xanthene-4-acetic Acid", J. Med. Chem., 1991, vol. 34, No. 9, pp. 2864-2870.
Christina M. Buchanan et al., "DMXAA (Vadimezan, ASA404) is a multi-kinase inhibitor targeting VEGFR2 in particular", Clinical Science, 2012, vol. 122, pp. 449-457 (17 pages total).
D. Xu et al., "Recent Progress of Small Molecular VEGFR Inhibitors as Anticancer Agents", Mini-Reviews in Medicinal Chemistry, 2011, vol. 11, No. 1, pp. 18-31.
Francesca Musumeci et al., "Vascular Endothelial Growth Factor (VEGF) Receptors: Drugs and New Inhibitors", Journal of Medicinal Chemistry, 2012, vol. 55, pp. 10797-10822.
Michele McTigue et al., "Molecular conformations, interactions, and properties associated with drug efficiency and clinical performance among VEGFR TK Inhibitors", PNAS, Nov. 6, 2012, vol. 109, No. 45, pp. 18281-18289.
Cunlong Zhang et al., "Selective VEGFR Inhibitors for Anticancer Therapeutics in Clinical Use and Clinical Trials", Current Pharmaceutical Design, 2012, vol. 18, No. 20, pp. 2921-2935.
John P. Wolfe et al., "An Ammonia Equivalent for the Palladium-Catalyzed Amination of Aryl Halides and Triflates", Tetrahedron Letters, 1997, vol. 38, No. 36, pp. 6367-6370.
Su et al., "Synthesis of the Acridone Alkaloids Glyfoline and Congeners. Structure-Activity Relationship Studies of Cytotoxic Acridones", J Med Chem, 1992, vol. 35, No. 14, pp. 2703-2710.

* cited by examiner

"TRICYCLIC HETEROCYCLIC DERIVATIVES AND USES THEREOF

FIELD OF THE INVENTION

The present invention generally relates to tricyclic heterocyclic compounds having kinase inhibitory activity, pharmaceutical compositions and kits comprising the compounds, and use of the compounds in the treatment of or in medicaments for the treatment of various diseases and conditions. In particular, the present invention relates to compounds having CSF-1R (c-FMS kinase) inhibitory activity and their use in the treatment of various diseases and conditions, such as those mediated by CSF-1R, including various proliferative or neoplastic diseases and conditions, including cancers, and bone, inflammatory, and autoimmune diseases and conditions.

BACKGROUND OF THE INVENTION

Colony stimulating factor 1 receptor (CSF-1R, also known as c-FMS kinase) is a tyrosine-protein kinase and the exclusive receptor for CSF-1 and IL-34. CSF-1R is a member of the class III Receptor Tyrosine Kinases along with c-Kit, Flt3 and PDGFRα. CSF-1 signalling through its receptor (CSF-1R) promotes the differentiation of myeloid progenitors into heterogeneous populations of monocytes, macrophages, dendritic cells, and bone-resorbing osteoclasts.

In normal conditions CSF-1 promotes monocyte development and macrophage proliferation in a tightly controlled negative feedback loop. An increase in CSF-1 indicates disease; drives the increase in proliferation of resident macrophages and an increase in recruitment of monocytes.

Cellular sources of CSF-1 are primarily mesenchymal in origin but macrophages and tumours also secrete CSF-1, and expression levels of CSF-1 and CSF-1R correlate with tumour cell invasiveness and adverse clinical prognosis in breast, ovarian and prostate cancers (Murray, L. J., T. J. Abrams, et al. (2003). "SU11248 inhibits tumor growth and CSF-1R-dependent osteolysis in an experimental breast cancer bone metastasis model." *Clin Exp Metastasis* 20(8): 757-766; Vandyke, K., A. L. Dewar, et al. (2010). "The tyrosine kinase inhibitor dasatinib dysregulates bone remodeling through inhibition of osteoclasts in vivo." *J Bone Miner Res* 25(8): 1759-1770; El-Gamal, M. I., H. S. Anbar, et al. (2013). "FMS Kinase Inhibitors: Current Status and Future Prospects." *Med Res Rev* 33(3): 599-636). CSF-1 and CSF-1R are integral for monocyte/macrophage proliferation and development, including the development of tumour-associated macrophages (TAMs). TAMs promote tumour progression and metastasis (Pollard, J. W. (2004). "Tumour-educated macrophages promote tumour progression and metastasis." *Nat Rev Cancer* 4(1): 71-78; Lewis, C. E. and J. W. Pollard (2006). "Distinct role of macrophages in different tumor microenvironments." *Cancer Res* 66(2): 605-612) via release of growth factors and proteases involved in growth and motility/invasion of tumour cells, and angiogenesis (El-Gamal, Anbar et al. 2013).

Tumour-associated macrophages, which express and rely on signalling through CSF-1R promote tumour invasion and metastasis (J. Condeelis and J. W. Pollard, Cell, 2006, 124: 263; S. Patel and M. R. Player, Current Topics in Medicinal Chemistry, 2009, 9, 599). Conversely, inhibition of CSF-1R limits metastasis and tumour progression in a murine model of breast cancer (E. Y. Lin et al, Journal of Experimental Medicine (2001) 193: 727). CSF-1R inhibitors combined with VEGFR-2 inhibitors suppress tumour growth (S. J. Priceman, et al. Blood, 2010, 115: 1461). Autoimmune diseases such as arthritis represent significant human diseases of high morbidity and prevalence (Firestein, G. S., Nature, 2003, 423, 356). Furthermore, CSF-1R blockade has been shown to reduce tumour-infiltrating myeloid cells (Hume, D. A. and K. P. MacDonald (2012). "Therapeutic applications of macrophage colony-stimulating factor-1 (CSF-1) and antagonists of CSF-1 receptor (CSF-1R) signaling." *Blood* 119(8): 1810-1820). CSF-1 also has direct effects on tumour growth and the release of tumour-derived inflammatory mediators (Huang, H., D. A. Hutta, et al. (2009). "Pyrido[2,3-d]pyrimidin-5-ones: a novel class of antiinflammatory macrophage colony-stimulating factor-1 receptor inhibitors." *J Med Chem* 52(4): 1081-1099). In this way inhibiting CSF-1R targets both the tumour stroma and the tumour itself to prevent tumour growth and metastasis. Clinical studies to date have shown that CSF-1R inhibitors are well tolerated and have shown responses even in phase 1 trials across multiple tumour types.

In normal tissue CSF-1 regulates osteoclastogenesis (El-Gamal, Anbar et al. 2013), and mice with a point mutation in CSF-1 (op/op mice) show severe osteoclast deficiency and have skeletal deformities associated with their chronic inability to remodel bone (Dai, X. M., G. R. Ryan, et al. (2002). "Targeted disruption of the mouse colony-stimulating factor 1 receptor gene results in osteopetrosis, mononuclear phagocyte deficiency, increased primitive progenitor cell frequencies, and reproductive defects." *Blood* 99(1): 111-120). CSF-1 is also overexpressed in metastatic bone disease and rheumatoid arthritis, and in these instances CSF-1R inhibition can contribute to bone protection (Dai, Ryan et al. 2002). Sunitinib, a non-specific CSF-1R inhibitor has been shown to inhibit CSF-1R-dependent osteolysis in a model of bone metastatic breast cancer (Murray, Abrams et al. 2003), and GW2580, ameliorated bone degradation in vitro and in vivo. Three further structurally unrelated CSF-1R inhibitors, including Ki20227 (Illig, C. R., J. Chen, et al. (2008). "Discovery of novel FMS kinase inhibitors as anti-inflammatory agents." *Bioorg Med Chem Lett* 18(5): 1642-1648; Ohno, H., Y. Uemura, et al. (2008). "The orally-active and selective c-Fms tyrosine kinase inhibitor Ki20227 inhibits disease progression in a collagen-induced arthritis mouse model." *Eur J Immunol* 38(1): 283-291; Huang, Hutta et al. 2009) have also been shown to protect bone in murine models of collagen-induced arthritis (CIA), proving the class effect for these drugs on bone protection.

CSF-1 and/or CSF-1R are overexpressed in a number of inflammatory disorders, with most research focus ebing on rheumatoid arthritis (RA). CSF-1R is associated with the proliferation and differentiation of monocytes into synoviocytes, macrophages and osteoclasts, which mediate joint damage and promote rheumatoid arthritis (Paniagua, R. T. et al, Arthritis Research & Therapy, 2010, 12, R32). CSF-1 is a component in a positive feedback loop involved in chronic inflammation (Hamilton, J. A. (1993). "Rheumatoid arthritis: opposing actions of haemopoietic growth factors and slow-acting anti-rheumatic drugs." *Lancet* 342(8870): 536-539) whereby macrophages secrete TNF and IL-1, which induce stromal expression of CSF-1, further increasing macrophage numbers and TNF/IL-1 levels etc (Campbell, I. K., M. J. Rich, et al. (2000). "The colony-stimulating factors and collagen-induced arthritis: exacerbation of disease by M-CSF and G-CSF and requirement for endogenous M-CSF." *J Leukoc Biol* 68(1): 144-150; Van Wesenbeeck, L., P. R. Odgren, et al. (2002). "The osteopetrotic mutation toothless (tl) is a loss-of-function frameshift mutation in the rat Csf1 gene: Evidence of a crucial role for CSF-1 in osteoclastogenesis and endochondral ossification." *Proc Natl Acad Sci USA* 99(22): 14303-14308). CSF-1R blockade with Ki20227 decreases macrophage numbers in inflammatory tissues, reducing inflammatory arthritis and encephalomyelitis (Ohno, Uemura et al. 2008; Uemura, Y., H. Ohno, et al. (2008). "The selective M-CSF receptor tyrosine kinase inhibitor Ki20227 suppresses experimental autoimmune encephalomyelitis." *J Neuroimmunol* 195(1-2): 73-80).

In addition to RA, overexpression of CSF-1 and/or CSF-1R has been detected in Crohn's disease (Marshall, D., J. Cameron, et al. (2007). "Blockade of colony stimulating factor-1 (CSF-I) leads to inhibition of DSS-induced colitis." *Inflamm Bowel Dis* 13(2): 219-224); inflammatory bowel disease (Klebl, F. H., J. E. Olsen, et al. (2001). "Expression of macrophage-colony stimulating factor in normal and inflammatory bowel disease intestine." *J Pathol* 195(5): 609-615); sarcoidosis (Kreipe, H., H. J. Radzun, et al. (1990). "Proliferation, macrophage colony-stimulating factor, and macrophage colony-stimulating factor-receptor expression of alveolar macrophages in active sarcoidosis." *Lab Invest* 62(6): 697-703); glomerulonephritis (Isbel, N. M., D. J. Nikolic-Paterson, et al. (2001). "Local macrophage proliferation correlates with increased renal M-CSF expression in human glomerulonephritis." *Nephrol Dial Transplant* 16(8): 1638-1647); allograft rejection (Jose, M. D., Y. Le Meur, et al. (2003). "Blockade of macrophage colony-stimulating factor reduces macrophage proliferation and accumulation in renal allograft rejection." *Am J Transplant* 3(3): 294-300); arteriosclerosis (Rosenfeld, M. E., S. Yla-Herttuala, et al. (1992). "Macrophage colony-stimulating factor mRNA and protein in atherosclerotic lesions of rabbits and humans." *Am J Pathol* 140(2): 291-300) and atherosclerosis (Inaba, T., T. Gotoda, et al. (1995). "Induction of sustained expression of proto-oncogene c-fms by platelet-derived growth factor, epidermal growth factor, and basic fibroblast growth factor, and its suppression by interferon-gamma and macrophage colony-stimulating factor in human aortic medial smooth muscle cells." *J Clin Invest* 95(3): 1133-1139).

There is an ongoing need for compounds having inhibitory activity against kinases, such as CSF-1R, preferably selective kinase inhibitory activity, for use in the treatment of diseases and conditions mediated by such kinases. It is object of the present invention to go some way to meeting this need and/or to at least provide the public with a useful choice.

Other objects of the invention may become apparent from the following description which is given by way of example only.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect, the present invention broadly consists in a compound of formula (I):

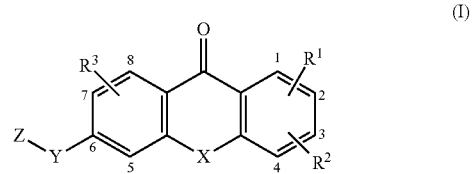

wherein:
X is $NR^4$, O, S, SO, $SO_2$, Se or Te and $R^2$ is G at any one of positions 2 to 4; or
X is $NG^1$ and $R^2$ is H, D, $NR^6R^7$, $OR^6$, $SR^8$, halogen, $CF_3$, $OCF_3$, CN, $NR^6COR^8$, $NR^6SO_2R^8$, or $C_{1-4}$alkyl optionally substituted with one or more independently selected $R^a$;
Y is $CHR^6$, CO, $CHR^6NR^5$, $CHR^6O$, $CHR^6S$, $CHR^6SO_2$, $CONR^5$, $NR^5$, $NR^5CO$, $NR^5SO_2$, O, $OCHR^6$, S, SO, $SO_2$, $SCHR^6$, $SO_2CHR^6$, or $SO_2NR^5$;
Z is W or $-W^1-Y-W^2$;
$R^1$ and $R^3$ are each independently H, D, $NR^6R^7$, $OR^6$, $SR^8$, halogen, $CF_3$, $OCF_3$, CN, $NR^6COR^8$, $NR^6SO_2R^8$, or $C_{1-4}$alkyl optionally substituted with one or more independently selected $R^a$;
$R^4$ is H or $C_{1-6}$alkyl optionally substituted with one or more independently selected $R^b$;
$R^5$ is H or $C_{1-4}$alkyl optionally substituted with one or more independently selected $R^c$;
$R^6$ and $R^7$ at each instance are each independently H or unsubstituted $C_{1-4}$alkyl;
$R^8$ at each instance is independently unsubstituted $C_{1-4}$alkyl;
G is $-J^1-L^1-NR^{9a}R^{10a}$, $-J^1-L^2-NR^{9b}R^{10b}$, $-J^1-L^3-CR^{11}R^{12}R^{13}$, $-L^{10}-NR^{9a}R^{10a}$, $-L^{20}-NR^{9b}R^{10b}$, or $-L^{30}-CR^{11}R^{12}R^{13}$;
$G^1$ is $-L^1-NR^{9a}R^{10a}$, $-L^2-NR^{9b}R^{10b}$, or $-L^3-CR^{11}R^{12}R^{13}$;
$J^1$ is O, $NR^6$, S, $-(C_{1-3}$alkylene)O$-*$, $-(C_{1-3}$alkylene)$NR^6-*$, or $-(C_{1-3}$alkylene)S$-*$, wherein each alkylene is unsubstituted and wherein * denotes the bond to $L^1$, $L^2$, or $L^3$;
$L^1$ and $L^2$ are each independently $C_{2-6}$alkylene, $-C_{2-3}$alkylene-$J^2$-$C_{2-3}$alkylene-*, $-(C_{1-3}$alkyl ene)$_a$-A-$(C_{1-3}$ alkyl ene)$_b$-*, $-C_{2-3}$ alkylene-$J^2$-$(C_{1-3}$alkylene)$_a$-A-$(C_{1-3}$alkylene)$_b$-*, or $-(C_{1-3}$ alkylene)$_a$-A-$(C_{1-3}$ alkylene)$_b$-$J^2$-$C_{2-3}$ alkylene-*, wherein each alkylene is unsubstituted and wherein * denotes the bond to $NR^{9a}R^{10a}$ or $NR^{9b}R^{10b}$;
$L^3$ is a bond, $C_{1-6}$alkylene, $-C_{2-6}$alkylene-$J^2$-*, $-C_{2-3}$alkylene-$J^2$-$C_{1-3}$alkylene-*, $-(C_{1-3}$alkyl ene)$_a$-A-$(C_{1-3}$ alkyl ene)$_b$-*, $-C_{2-3}$ alkylene-$J^2$-$(C_{1-3}$alkylene)$_a$-A-$(C_{1-3}$alkylene)$_b$-*, or $-(C_{1-3}$ alkyl ene)$_a$-A-$(C_{1-3}$ alkylene)$_b$-$J^2$-$(C_{1-3}$alkylene)$_c$-*, wherein each alkylene is unsubstituted and wherein * denotes the bond to $CR^{11}R^{12}R^{13}$;
$L^{10}$ and $L^{20}$ are each independently $C_{1-6}$alkylene, $-C_{1-3}$alkylene-$J^2$-$C_{2-3}$alkylene-*, $-(C_{1-3}$alkylene)$_a$-A-$(C_{1-3}$alkylene)$_b$-*, $-C_{1-3}$alkylene-$J^2$-$(C_{1-3}$alkylene)$_a$-A-$(C_{1-3}$alkylene)$_b$-*, or $-(C_{1-3}$ alkylene)$_a$-A-$(C_{1-3}$alkylene)$_b$-$J^2$-$C_{2-3}$ alkylene-*, wherein each alkylene is unsubstituted and wherein * denotes the bond to $NR^{9a}R^{10a}$ or $NR^{9b}R^{10b}$;
$L^{30}$ is $C_{1-6}$alkylene, $-C_{1-6}$alkylene-$J^2$-*, $-C_{1-3}$alkylene-$J^2$-$C_{1-3}$alkylene-*, $-(C_{1-3}$alkylene)$_a$-A-$(C_{1-3}$ alkylene)$_b$-*, $-C_{1-3}$alkylene-$J^2$-$(C_{1-3}$alkylene)$_a$-A-$(C_{1-3}$alkylene)$_b$-*, or $-(C_{1-3}$alkylene)$_a$-A-$(C_{1-3}$alkylene)$_b$-J$^2$-(C$_{1-3}$ alkylene)$_c$-*, wherein each alkylene is unsubstituted and wherein * denotes the bond to CR$^{11}$R$^{12}$R$^{13}$;

A is 3 to 7-membered cycloalkylene optionally substituted with one or more independently selected R$^d$;

J$^2$ is O, NR$^6$, or S;

a, b, and c are each independently 0 or 1;

R$^{9a}$ and R$^{10a}$ are each independently H, unsubstituted C$_{1-6}$alkyl, or unsubstituted 3 to 10-membered cycloalkyl;

R$^{9b}$ and R$^{10b}$ together with the nitrogen atom to which they are attached form a 4 to 10-membered heterocyclyl or 5 to 10-membered heteroaryl, optionally substituted with one or more independently selected R$^g$;

R$^{11}$ and R$^{12}$ together with the carbon atom to which they are attached form a 4 to 10-membered heterocyclyl comprising at least one ring nitrogen atom, optionally substituted with one or more independently selected R$^g$; and R$^{13}$ is H, C$_{1-4}$alkyl optionally substituted with one or more independently selected R$^h$, or the second bond of a double bond between R$^{11}$ or R$^{12}$ and the carbon atom to which they are attached; or R$^{11}$ and R$^{12}$ together with the carbon atom to which they are attached form a 5 to 10-membered heteroaryl comprising at least one ring nitrogen atom, optionally substituted with one or more independently selected R$^g$; and R$^{13}$ is the second bond of a double bond between R$^{11}$ or R$^{12}$ and the carbon atom to which they are attached;

W is 6 to 10-membered aryl or 5 to 10-membered heteroaryl, optionally substituted with one or more independently selected R$^i$;

W$^1$ is phenylene or 5 or 6-membered hetereoarylene, optionally substituted with one or more independently selected R$^x$;

Y$^1$ is C$_{1-6}$alkylene, -J$^4$-*, —(C$_{1-3}$alkylene)-J$^4$-*, —(C$_{1-3}$alkylene)-J$^5$-(C$_{1-3}$alkylene)-*, -J$^5$-(C$_{1-3}$alkylene)-*, or -J$^6$-C$_{1-3}$alkylene-J$^7$-*, wherein each alkylene is unsubstituted and wherein * denotes the bond to W$^2$;

J$^4$ is O, NR$^{14}$, S, NR$^{15}$CO, CONR$^{14}$, NR$^{15}$CONR$^{14}$, OCONR$^{14}$, or NR$^{15}$COO;

J$^5$ is O, NR$^{15}$, S, NR$^{15}$CO, CONR$^{15}$, NR$^{15}$CONR$^{15}$, OCONR$^{15}$, or NR$^{15}$COO;

J$^6$ is O, NR$^{15}$, or S;

J$^7$ is O, NR$^{14}$, S, NR$^{15}$CO, or CONR$^{14}$;

R$^{14}$ and R$^{15}$ at each instance are each independently H or C$_{1-3}$alkyl optionally substituted with one or more independently selected R$^j$;

W$^2$ is:

(a) 3 to 10-membered cycloalkyl or 4 to 10-membered heterocyclyl, optionally substituted with one or more independently selected R$^m$, or (b) 6 to 10-membered aryl or 5 to 10-membered heteroaryl, optionally substituted with one or more independently selected R$^n$;

or R$^{14}$ and W$^2$ together with the nitrogen atom to which they are attached form:

(a) a 4 to 10-membered heterocyclyl, optionally substituted with one or more independently selected R$^m$, or (b) a 5 to 10-membered heteroaryl, optionally substituted with one or more independently selected R$^n$;

R$^a$, R$^b$, R$^c$, and R$^h$ at each instance are each independently selected from F, OCF$_3$, and O(unsubstituted C$_{1-4}$alkyl), for example OCH$_3$;

R$^d$ and R$^g$ at each instance are each independently selected from D, NR$^6$R$^7$, OR$^6$, SR$^8$, halogen, CF$_3$, OCF$_3$, CN, SO$_2$R$^8$, NR$^6$COR$^8$, NR$^6$SO$_2$R$^8$, and C$_{1-4}$alkyl optionally substituted with one or more substituents independently selected from F, OCF$_3$, and O(unsubstituted C$_{1-4}$alkyl), for example OCH$_3$;

R$^i$, R$^x$, and R$^n$ at each instance are each independently selected from D, NR$^6$R$^7$, OR$^6$, SR$^8$, halogen, CF$_3$, OCF$_3$, CN, SO$_2$R$^8$, and C$_{1-4}$alkyl optionally substituted with one or more substituents independently selected from F, OCF$_3$, and O(unsubstituted C$_{1-4}$ alkyl), for example OCH$_3$;

R$^j$ at each instance is independently selected from F and D;

R$^m$ at each instance is independently selected from D, NR$^6$R$^7$, OR$^6$, SR$^8$, F, CF$_3$, OCF$_3$, CN, SO$_2$R$^8$, and C$_{1-4}$alkyl optionally substituted with one or more substituents independently selected from F, OCF$_3$, and O(unsubstituted C$_{1-4}$alkyl), for example OCH$_3$;

or a pharmaceutically acceptable salt, solvate, or stereoisomer thereof.

In another aspect, the present invention broadly consists in a pharmaceutical composition comprising a compound of the formula (I) or a pharmaceutically acceptable salt, solvate, or stereoisomer thereof; and a pharmaceutically acceptable carrier.

In another aspect, the present invention broadly consists in a kit comprising a compound of the formula (I) or a pharmaceutically acceptable salt, solvate, or stereoisomer thereof; and optionally instructions for use.

In another aspect, the present invention broadly consists in a kit comprising a compound of the formula (I) or a pharmaceutically acceptable salt, solvate, or stereoisomer thereof; one or more additional therapeutic agents, for example one or more anticancer agents; and optionally instructions for use.

In another aspect, the present invention broadly consists in a method of inhibiting CSF-1R in a subject in need thereof, comprising administering to the subject a therapeutically effective amount of a compound of the formula (I) or a pharmaceutically acceptable salt, solvate, or stereoisomer thereof.

In another aspect, the present invention broadly consists in a method of treating a disease or condition mediated by CSF-1R in a subject in need thereof, comprising administering to the subject a therapeutically effective amount of a compound of the formula (I) or a pharmaceutically acceptable salt, solvate, or stereoisomer thereof.

In another aspect, the present invention broadly consists in a compound of the formula (I) or a pharmaceutically acceptable salt, solvate, or stereoisomer thereof for use in inhibiting CSF-1R.

In another aspect, the present invention broadly consists in a compound of the formula (I) or a pharmaceutically acceptable salt, solvate, or stereoisomer thereof for use in treating disease or condition mediated by CSF-1R.

In another aspect, the present invention broadly consists in use of a compound of formula (I) or a pharmaceutically acceptable salt, solvate, or stereoisomer thereof in the manufacture of a medicament for inhibiting CSF-1R.

In another aspect, the present invention broadly consists in use of a compound of formula (I) or a pharmaceutically acceptable salt, solvate, or stereoisomer thereof in the manufacture of a medicament for treating a disease or condition mediated by CSF-1R.

In another aspect, the present invention broadly consists in use of:

(i) a compound of the formula (I) or a pharmaceutically acceptable salt, solvate, or stereoisomer thereof; and (ii) one or more additional therapeutic agents, for example one or more anticancer agents,
in the manufacture of a medicament for inhibiting CSF-1R,
wherein the compound of formula (I) or pharmaceutically acceptable salt, solvate, or stereoisomer thereof and the one or more additional therapeutic agents are for administration simultaneously, sequentially, or separately.

In another aspect, the present invention broadly consists in use of:
(i) a compound of the formula (I) or a pharmaceutically acceptable salt, solvate, or stereoisomer thereof; and
(ii) one or more additional therapeutic agents, for example one or more anticancer agents,
in the manufacture of a medicament for treating a disease or condition mediated by CSF-1R,
wherein the compound of formula (I) or pharmaceutically acceptable salt, solvate, or stereoisomer thereof and the one or more additional therapeutic agents are for administration simultaneously, sequentially, or separately.

In another aspect, the present invention broadly consists in a method of inhibiting CSF-1R comprising contacting a cell and a compound of the formula (I) or a pharmaceutically acceptable salt, solvate, or stereoisomer thereof in an amount effective to inhibit CSF-1R.

In another aspect, the present invention broadly consists in a method of treating a disease or condition selected from the group consisting of proliferative or neoplastic disease and conditions including cancers; bone diseases or conditions; inflammatory diseases or conditions; and autoimmune diseases and conditions, in a subject in need thereof, comprising administering to the subject a therapeutically effective amount of a compound of the formula (I) or a pharmaceutically acceptable salt, solvate, or stereoisomer thereof.

In another aspect, the present invention broadly consists in a compound of the formula (I) or a pharmaceutically acceptable salt, solvate, or stereoisomer thereof for use in treating a disease or condition selected from the group consisting of proliferative or neoplastic disease and conditions including cancers; bone diseases or conditions; inflammatory diseases or conditions; and autoimmune diseases and conditions.

In another aspect, the present invention broadly consists in use of a compound of formula (I) or a pharmaceutically acceptable salt, solvate, or stereoisomer thereof in the manufacture of a medicament for treating a disease or condition selected from the group consisting of proliferative or neoplastic disease and conditions including cancers; bone diseases or conditions; inflammatory diseases or conditions; and autoimmune diseases and conditions.

In another aspect, the present invention broadly consists in use of:
(i) a compound of the formula (I) or a pharmaceutically acceptable salt, solvate, or stereoisomer thereof; and
(ii) one or more additional therapeutic agents, for example one or more anticancer agents,
in the manufacture of a medicament for treating a disease or condition selected from the group consisting of proliferative or neoplastic disease and conditions including cancers; bone diseases or conditions; inflammatory diseases or conditions; and autoimmune diseases and conditions,
wherein the compound of formula (I) or pharmaceutically acceptable salt, solvate, or stereoisomer thereof and the one or more additional therapeutic agents are for administration simultaneously, sequentially, or separately.

The following embodiments and preferences may relate alone or in any combination of any two or more to any of the above aspects.

In various embodiments, the compound of formula (I) is a compound of formula (I-1), (I-2), or (I-3):

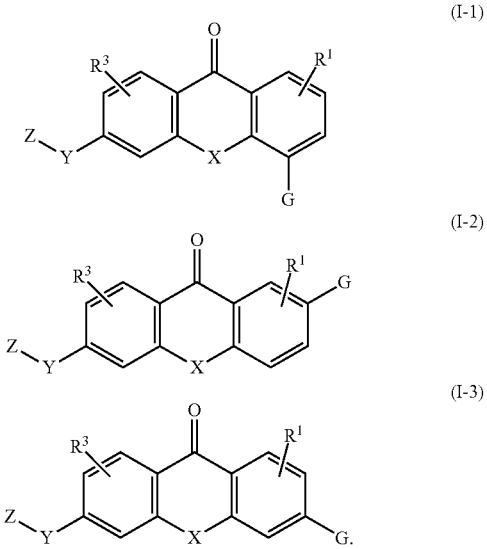

In various embodiments, the compound of formula (I) is a compound of formula (I-1) or (I-2):

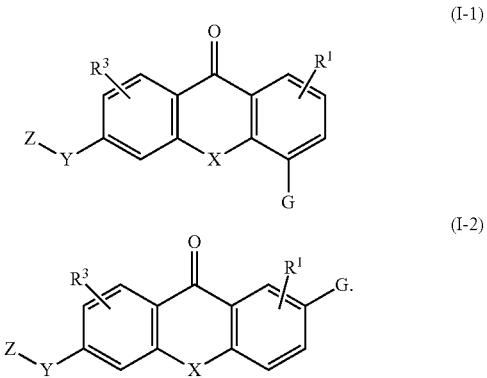

In various embodiments, the compound of formula (I) is a compound of formula (I-1):

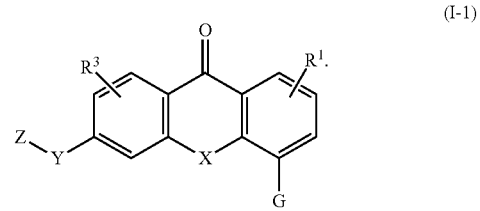

In various embodiments, the compound of formula (I) is a compound of the formula (I-1a) or (I-2a):

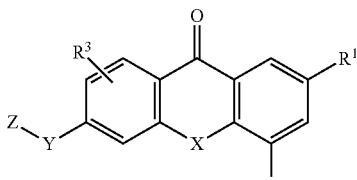

(I-1a)

In various embodiments, the compound of formula (I) is a compound of the formula (I-1a):

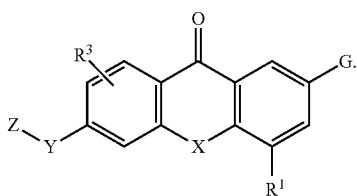

(I-2a)

In various embodiments, the compound of formula (I) is a compound of the formula (I-1a):

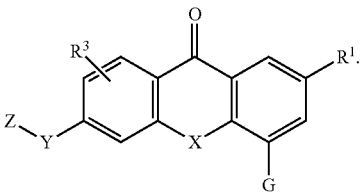

(I-1a)

In various embodiments, the compound wherein X is $NR^4$, O, S, SO, or $SO_2$.

In certain embodiments, the compound wherein X is $NR^4$, O, or S.

In exemplary embodiments, the compound wherein X is O or S.

In various embodiments, the compound of formula (I) is a compound of the formula (I-4):

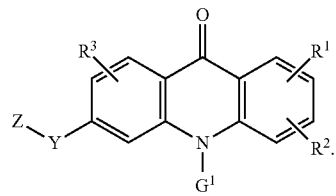

(I-4)

In various embodiments, the compound of formula (I) is a compound of the formula (I-4a):

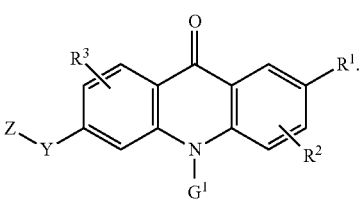

(I-4a)

In various embodiments:
$L^1$ is $C_{2-6}$alkylene, —$C_{2-3}$alkylene-$J^2$-$C_{2-3}$alkylene-*, —($C_{1-3}$alkylene)$_a$-A-($C_{1-3}$alkylene)$_b$-*, —$C_{2-3}$alkylene-$J^2$-($C_{1-3}$alkylene)$_a$-A-($C_{1-3}$alkylene)$_b$-*, or —($C_{1-3}$alkylene)$_a$-A-($C_{1-3}$alkylene)$_b$-$J^2$-$C_{2-3}$alkylene-*;

$L^2$ is $C_{2-6}$alkylene or —$C_{2-3}$alkylene-$J^2$-$C_{2-3}$ alkylene-*;

$L^3$ is a bond, $C_{1-6}$alkylene, —$C_{2-6}$alkylene-$J^2$-*, or $C_{2-3}$alkylene-$J^2$-$C_{1-3}$alkylene-*;

$L^{10}$ is $C_{1-6}$alkylene, —$C_{1-3}$alkylene-$J^2$-$C_{2-3}$ alkylene-*, —($C_{1-3}$alkylene)$_a$-A-($C_{1-3}$alkylene)$_b$-*, —$C_{1-3}$alkylene-$J^2$-($C_{1-3}$alkylene)$_a$-A-($C_{1-3}$alkylene)$_b$ or ($C_{1-3}$alkylene)$_a$-A-($C_{1-3}$alkylene)$_b$-$J^2$-$C_{2-3}$alkylene-*;

$L^{20}$ is $C_{1-6}$alkylene or —$C_{1-3}$alkylene-$J^2$-$C_{2-3}$alkylene-*;

$L^{30}$ is $C_{1-6}$alkylene, —$C_{1-6}$alkylene-$J^2$-*, or —$C_{1-3}$alkylene-$J^2$-$C_{1-3}$alkylene-*.

In certain embodiments:
$L^1$ is $C_{2-6}$alkylene or —$C_{2-3}$alkylene-$J^2$-$C_{2-3}$alkylene-*;
$L^2$ is $C_{2-6}$alkylene or —$C_{2-3}$alkylene-$J^2$-$C_{2-3}$ alkylene-*;
$L^3$ is a bond, $C_{1-6}$alkylene, —$C_{2-6}$alkylene-$J^2$-*, or $C_{2-3}$alkylene-$J^2$-$C_{1-3}$alkylene-*;
$L^{10}$ is $C_{1-6}$alkylene or —$C_{1-3}$alkylene-$J^2$-$C_{2-3}$alkylene-*;
$L^{20}$ is $C_{1-6}$alkylene or —$C_{1-3}$alkylene-$J^2$-$C_{2-3}$alkylene-*;
$L^{30}$ is $C_{1-6}$alkylene, —$C_{1-6}$alkylene-$J^2$-*, or —$C_{1-3}$alkylene-$J^2$-$C_{1-3}$alkylene-*.

In certain embodiments:
$L^1$ is $(CH_2)_{2-6}$ or $(CH_2)_{2-3}$-$J^2$-$(CH_2)_{2-3}$;
$L^2$ is $(CH_2)_{2-6}$ or $(CH_2)_{2-3}$-$J^2$-$(CH_2)_{2-3}$;
$L^3$ is a bond, $(CH_2)_{1-6}$, $(CH_2)_{2-6}$-$J^2$, or $(CH_2)_{2-3}$-$J^2$-$(CH_2)_{1-3}$;
$L^{10}$ is $(CH_2)_{1-6}$ or $(CH_2)_{1-3}$-$J^2$-$(CH_2)_{2-3}$;
$L^{20}$ is $(CH_2)_{1-6}$ or $(CH_2)_{1-3}$-$J^2$-$(CH_2)_{2-3}$;
$L^{30}$ is $(CH_2)_{1-6}$, $(CH_2)_{1-6}$-$J^2$, or $(CH_2)_{1-3}$-$J^2$-$(CH_2)_{1-3}$.

In exemplary embodiments:
G is -$J^1$-$L^1$-$NR^{9a}R^{10a}$, -$J^1$-$L^2$-$NR^{9b}R^{10b}$, or -$J^1$-$L^3$-$CR^{11}R^{12}R^{13}$; and
$L^1$ is $(CH_2)_{2-4}$;
$L^2$ is $(CH_2)_{2-4}$; and
$L^3$ is a bond or $(CH_2)_{1-4}$.

In exemplary embodiments:
G is -$J^1$-$L^1$-$NR^{9a}R^{10a}$, -$J^1$-$L^2$-$NR^{9b}R^{10b}$, or -$J^1$-$L^3$-$CR^{11}R^{12}R^{13}$; and
$L^1$ is $(CH_2)_{2-4}$;
$L^2$ is $(CH_2)_{2-4}$; and
$L^3$ is $(CH_2)_{1-4}$.

In exemplary embodiments:
$L^1$ is $(CH_2)_{2-4}$;
$L^2$ is $(CH_2)_{2-4}$; and
$L^3$ is $(CH_2)_{1-4}$.

In certain embodiments, G is -$J^1$-$L^1$-$NR^{9a}R^{10a}$, -$J^1$-$L^2$-$NR^{9b}R^{10b}$, or -$J^1$-$L^3$-$CR^{11}R^{12}R^{13}$.

In various embodiments, $J^1$ is O, $NR^6$, S, —$(CH_2)_{1-3}$O—*, —$(CH_2)_{1-3}NR^6$—*, or —$(CH_2)_{1-3}$S—*.

In certain embodiments, $J^1$ is O, $NR^6$, S, —$CH_2$O—*, —$CH_2NR^6$—*, or —$CH_2$S—*.

In exemplary embodiments, $J^1$ is O.

In exemplary embodiments, G is —O—$(CH_2)_{2-4}$—$NR^{9a}R^{10a}$, —O—$(CH_2)_{2-4}$—$NR^{9b}R^{10b}$, —O—$(CH_2)_{1-4}$—$CR^{11}R^{12}R^{13}$, or —O—$CR^{11}R^{12}R^{13}$.

In exemplary embodiments, G is —O—$(CH_2)_{2-4}$—$NR^{9a}R^{10a}$, —O—$(CH_2)_{2-4}$—$NR^{9b}R^{10b}$, or —O—$(CH_2)_{1-4}$—$CR^{11}R^{12}R^{13}$.

In exemplary embodiments, G is —O—$CR^{11}R^{12}R^{13}$.

In certain embodiments, $R^{9a}$ and $R^{10a}$ are each independently H or unsubstituted $C_{1-6}$alkyl, for example $CH_3$.

In exemplary embodiments, $R^{9a}$ and $R^{10a}$ are each independently H or $CH_3$.

In various embodiments, $R^{9b}$ and $R^{10b}$ together with the nitrogen atom to which they are attached form an optionally substituted 4 to 10-membered heterocyclyl.

In various embodiments, $R^{9b}$ and $R^{10b}$ together with the nitrogen atom to which they are attached form an optionally substituted 4 to 7-membered heterocyclyl, for example an optionally substituted 5 or 6-membered heterocyclyl, or optionally substituted 5 or 6-membered heteroaryl.

In certain embodiments, $R^{9b}$ and $R^{10b}$ together with the nitrogen atom to which they are attached form an optionally substituted 5 or 6-membered heterocyclyl or optionally substituted 5 or 6-membered heteroaryl.

In certain embodiments, the compound wherein $R^{9b}$ and $R^{10b}$ together with the nitrogen atom to which they are attached form an optionally substituted 5 or 6-membered heterocyclyl.

In exemplary embodiments, $NR^{9b}R^{10b}$ is:

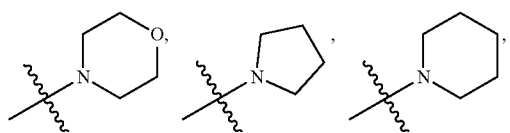

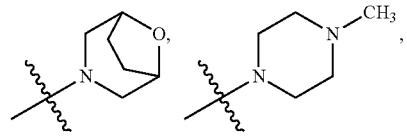

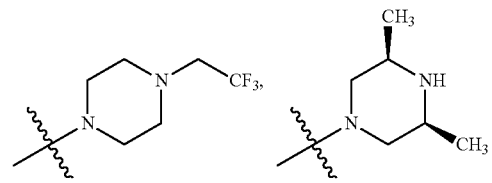

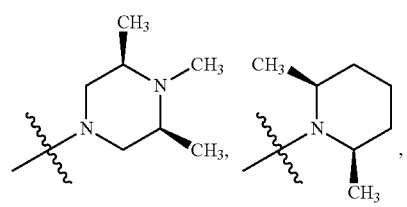

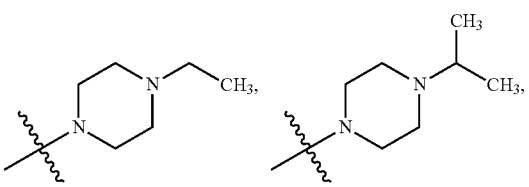

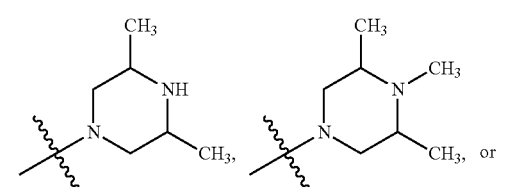

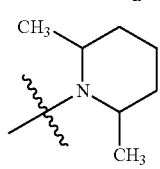

In exemplary embodiments, $NR^{9b}R^{10b}$ is:

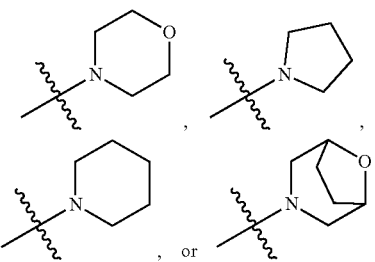

In exemplary embodiments, $NR^{9b}R^{10b}$ is:

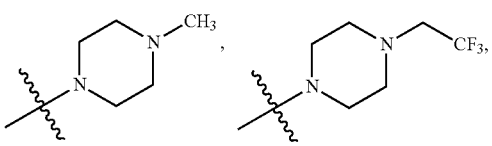

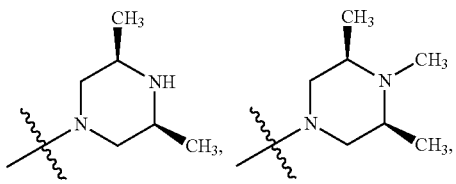

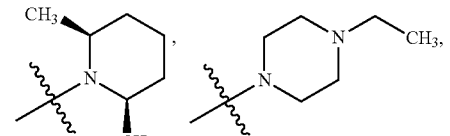

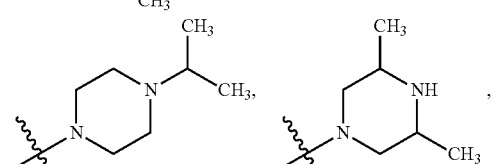

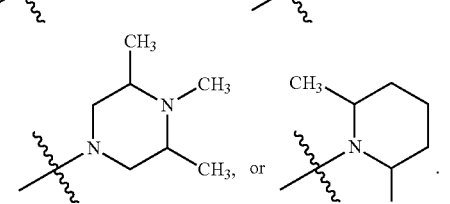

In exemplary embodiments, $NR^{9b}R^{10b}$ is:

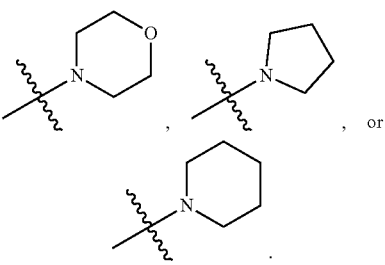

In various embodiments, $R^{11}$ and $R^{12}$ together with the carbon atom to which they are attached form an optionally substituted 4 to 10-membered heterocyclyl.

In various embodiments, $R^{11}$ and $R^{12}$ together with the carbon atom to which they are attached form an optionally substituted 4 to 7-membered heterocyclyl, for example an optionally substituted 5 or 6-membered heterocyclyl, or an optionally substituted 5 or 6-membered heteroaryl.

In certain embodiments, $R^{11}$ and $R^{12}$ together with the carbon atom to which they are attached form an optionally substituted 5 or 6-membered heterocyclyl or an optionally substituted 5 or 6-membered heteroaryl.

In certain embodiments, $R^{11}$ and $R^{12}$ together with the carbon atom to which they are attached form an optionally substituted 5 or 6-membered heterocyclyl.

In exemplary embodiments, $CR^{11}R^{12}R^{13}$ is

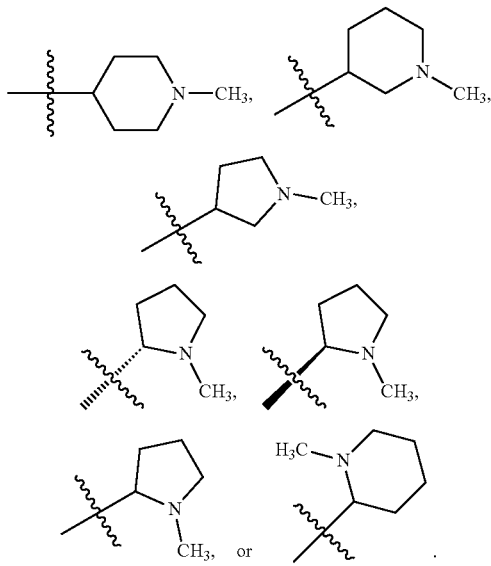

In exemplary embodiments, $CR^{11}R^{12}R^{13}$ is

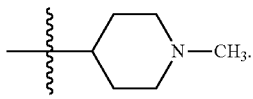

In exemplary embodiments, $CR^{11}R^{12}R^{13}$ is

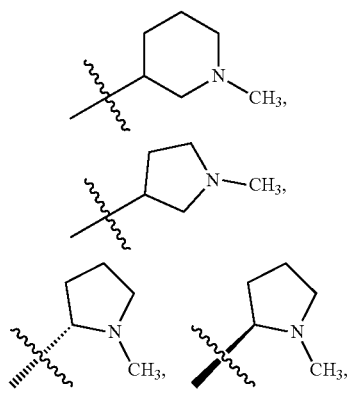

In various embodiments, Y is $CH_2$, CO, $CH_2NR^5$, $CH_2O$, $CH_2S$, $CH_2SO_2$, $CONR^5$, $NR^5$, $NR^5CO$, $NR^5SO_2$, O, $OCH_2$, S, SO, $SO_2$, $SCH_2$, $SO_2CH_2$, or $SO_2NR^5$.

In various embodiments, Y is O, $NR^5$, $CHR^6$, CO, S, SO, or $SO_2$.

In certain embodiments, Y is O, $NR^5$, $CH_2$, CO, S, SO, or $SO_2$.

In certain embodiments, Y is O, $CHR^6$, CO, or S.

In exemplary embodiments, Y is O, $CH_2$, CO, or S.

In exemplary embodiments, Y is O.

In various embodiments, Z is —$W^1$—$Y^1$—$W^2$.

In various embodiments, W is an optionally substituted phenyl or an optionally substituted 5 or 6-membered heteroaryl.

In certain embodiments, W is an optionally substituted phenyl or an optionally substituted 6-membered heteroaryl, for example an optionally substituted 6-membered heteroaryl comprising from one to three ring nitrogen atoms, one or two ring nitrogen atoms, or one ring nitrogen atom.

In certain embodiments, W is an optionally substituted phenyl or optionally substituted pyridyl.

In exemplary embodiments, W is:

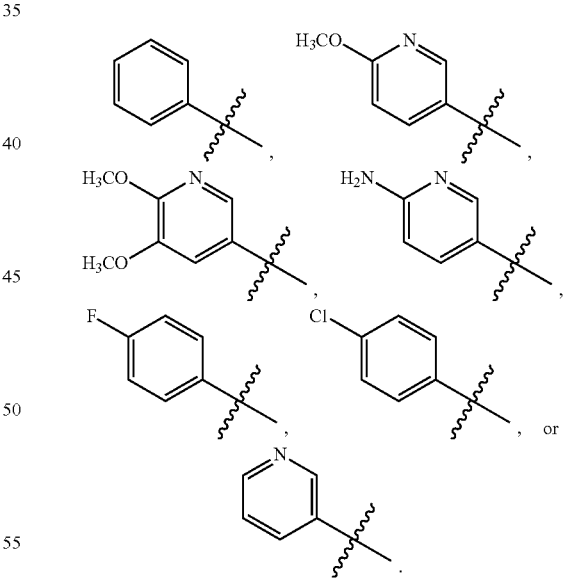

In exemplary embodiments, W is:

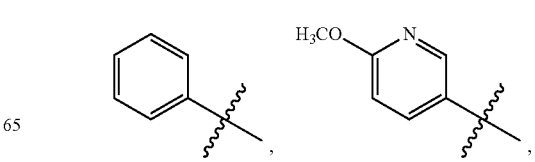

-continued

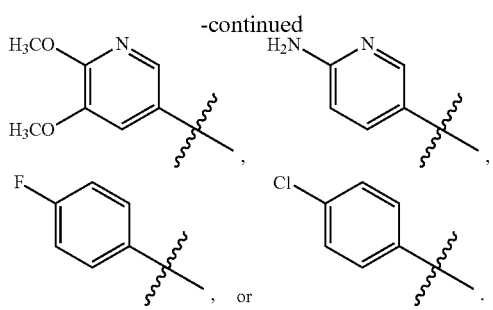

, or .

In exemplary embodiments, W is:

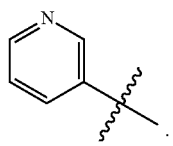 [SMILES: *c1cccnc1]

.

In various embodiments, $W^1$ is an optionally substituted 5-membered heteroarylene attached to Y and $Y^1$ in a 1,3-relationship or an optionally substituted phenylene or optionally substituted 6-membered heteroarylene attached to Y and $Y^1$ in a 1,3- or 1,4-relationship.

In various embodiments, $W^1$ is an optionally substituted phenylene or optionally substituted 6-membered heteroarylene, for example an optionally substituted 6-membered heteroaryl comprising from one to three ring nitrogen atoms, one or two ring nitrogen atoms, or one ring nitrogen atom.

In certain embodiments, $W^1$ is an optionally substituted phenylene or optionally substituted pyridylene.

In exemplary embodiments, $W^1$ is:

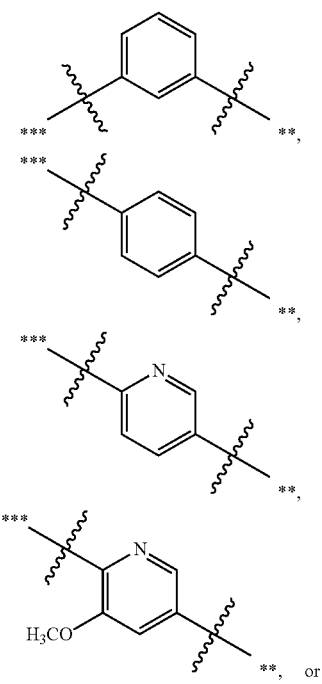

-continued

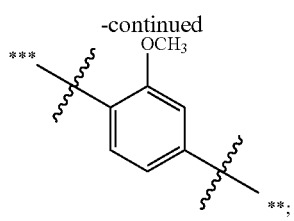

;

wherein:
*** denotes the bond to Y; and
** denotes the bond to $Y^1$.

In various embodiments, $Y^1$ is $(CH_2)_{1-6}$, $-J^4-*$, $-(CH_2)_{1-3}-J^4-*$, $-(CH_2)_{1-3}-J^5-(CH_2)_{1-3}-*$, $-J^5-(CH_2)_{1-3}-*$, or $-J^6-(CH_2)_{1-3}-J^7-*$.

In various embodiments:
$J^4$ is O, $NR^{14}$, $NR^{15}CO$, $CONR^{14}$, or $NR^{15}CONR^{14}$;
$J^5$ is O, $NR^{15}$, $NR^{15}CO$, $CONR^{15}$, or $NR^{15}CONR^{15}$;
$J^6$ is O or $NR^{15}$;
$J^7$ is O, $NR^{14}$, $NR^{15}CO$, or $CONR^{14}$.

In certain embodiments, $Y^1$ is $-(CH_2)_{1-4}-*$, $-CONR^{14}-*$, $-NR^{15}CONR^{14}-*$, $-O(CH_2)_{1-3}-*$, $-NR^{15}(CH_2)_{1-3}-*$, $-(CH_2)_{1-3}CONR^{14}-*$, $-(CH_2)_{1-3}NR^{15}CO-*$, $-NR^{15}(CH_2)_{1-3}CONR^{14}-*$, or $-(CH_2)_{1-3}NR^{15}CONR^{14}-*$.

In exemplary embodiments, $Y^1$ is $-CH_2CH_2-*$, $-CONR^{14}-*$, $-NR^{15}CONR^{14}-*$, $-OCH_2-*$, $-NR^{15}CH_2-*$, $-CH_2CH_2CONR^{14}-*$, $-CH_2CH_2NR^{15}CO-*$, $-NR^{15}CH_2CONR^{14}-*$, or $-CH_2CH_2NR^{15}CONR^{14}-*$.

In various embodiments:
$W^2$ is an optionally substituted 4 to 7-membered cycloalkyl, for example an optionally substituted 5 or 6-membered cycloalkyl, optionally substituted 4 to 7-membered heterocyclyl, for example an optionally substituted 5 or 6-membered heterocyclyl, optionally substituted 5 or 6-membered heteroaryl, or optionally substituted phenyl;
or $R^{14}$ and $W^2$ together with the nitrogen atom to which they are attached form an optionally substituted 5 or 6-membered heterocyclyl or optionally substituted 5 or 6-membered heteroaryl.

In certain embodiments:
$W^2$ is an optionally substituted 5 or 6-membered cycloalkyl, optionally substituted 5 or 6-membered heterocyclyl, optionally substituted 5 or 6-membered heteroaryl, or optionally substituted phenyl;
or $R^{14}$ and $W^2$ together with the nitrogen atom to which they are attached form an optionally substituted 5 or 6-membered heterocyclyl or optionally substituted 5 or 6-membered heteroaryl.

In certain embodiments:
$W^2$ is an optionally substituted 5 or 6-membered cycloalkyl, optionally substituted 5 or 6-membered heterocyclyl, optionally substituted 5 or 6-membered heteroaryl, or optionally substituted phenyl;
or $R^{14}$ and $W^2$ together with the nitrogen atom to which they are attached form an optionally substituted 5 or 6-membered heterocyclyl.

In exemplary embodiments:

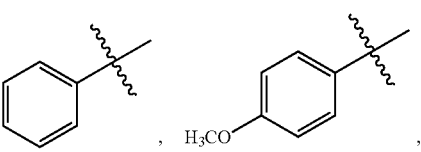

,

-continued

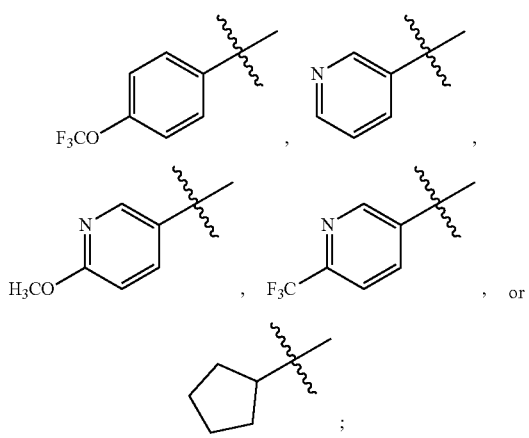

or
R$^{14}$ and W$^2$ or R$^{15}$ and W$^2$ together with the nitrogen atom to which they are attached form

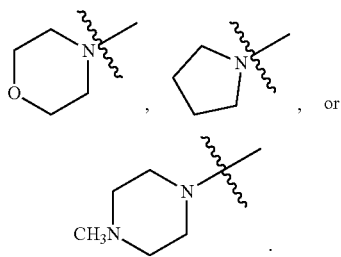

In exemplary embodiments:
W$^2$ is

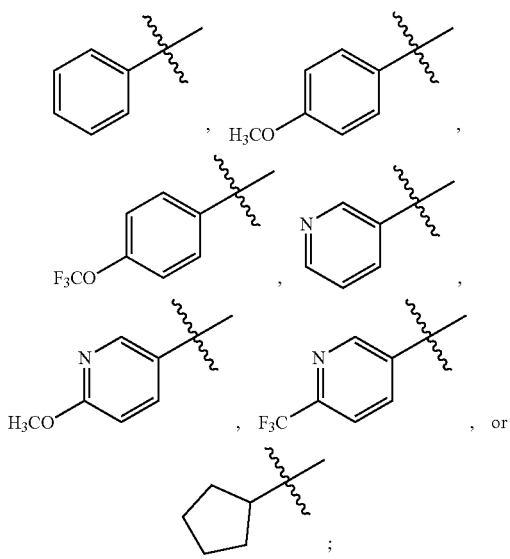

or
R$^{14}$ and W$^2$ or R$^{15}$ and W$^2$ together with the nitrogen atom to which they are attached form

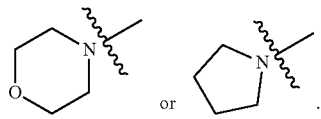

or

In exemplary embodiments:
R$^{14}$ and W$^2$ or R$^{15}$ and W$^2$ together with the nitrogen atom to which they are attached form

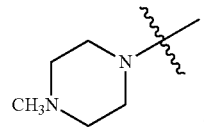

In various embodiments:
(a) Y$^1$ is C$_{1-6}$alkylene, -J$^4$-*, —(C$_{1-3}$alkylene)-J$^5$-(C$_{1-3}$alkylene)-*, or -J$^5$-(C$_{1-3}$alkylene)-*; and W$^2$ is an optionally substituted 6 to 10-membered aryl or an optionally substituted 5 to 10-membered heteroaryl; or
(b) Y$^1$ is —(C$_{1-3}$alkylene)-J$^4$-* or -J$^6$-C$_{1-3}$alkylene-J$^7$-*; and W$^2$ is an optionally substituted 3 to 10-membered cycloalkyl, optionally substituted 4 to 10-membered heterocyclyl, optionally substituted 6 to 10-membered aryl, optionally substituted 5 to 10-membered heteroaryl; or R$^{14}$ and W$^2$ together with the nitrogen atom to which they are attached form an optionally substituted 4 to 10-membered heterocyclyl or an optionally substituted 5 to 10-membered heteroaryl.

In certain embodiments:
(a) Y$^1$ is C$_{1-6}$alkylene, -J$^4$-*, —(C$_{1-3}$alkylene)-J$^5$-(C$_{1-3}$alkylene)-*, or -J$^5$-(C$_{1-3}$alkylene)-*; and W$^2$ is an optionally substituted 5 or 6-membered heterocyclyl or optionally substituted 5 or 6-membered heteroaryl; or
(b) Y$^1$ is —(C$_{1-3}$alkylene)-J$^4$-* or -J$^6$-C$_{1-3}$alkylene-J$^7$-*; and W$^2$ is an optionally substituted 4 to 7-membered cycloalkyl, for example an optionally substituted 5 or 6-membered cycloalkyl, optionally substituted 4 to 7-membered heterocyclyl, for example an optionally substituted 5 or 6-membered heterocyclyl, optionally substituted phenyl, or optionally substituted 5 or 6-membered heteroaryl; or R$^{14}$ and W$^2$ together with the nitrogen atom to which they are attached form an optionally substituted 4 to 7-membered heterocyclyl, for example an optionally substituted 5 or 6-membered heterocyclyl, or an optionally substituted 5 or 6-membered heteroaryl.

In certain embodiments:
(a) Y$^1$ is —(CH$_2$)$_{1-4}$—*, —CONR$^{14}$—*, —NR$^{15}$CONR$^{14}$—*, —O(CH$_2$)$_{1-3}$—*, —NR$^{15}$(CH$_2$)$_{1-3}$—*, —(CH$_2$)$_{1-3}$NR$^{15}$CO—*, or —(CH$_2$)$_{1-3}$NR$^{15}$CONR$^{14}$—*; and W$^2$ is an optionally substituted 5 or 6-membered heteroaryl or optionally substituted phenyl; or
(b) Y$^1$ is —(CH$_2$)$_{1-3}$CONR$^{14}$—*, or —NR$^{15}$(CH$_2$)$_{1-3}$CONR$^{14}$—*; and W$^2$ is an optionally substituted 4 to 7-membered cycloalkyl, for example an optionally substituted 5 or 6-membered cycloalkyl, optionally substituted 4 to 7-membered heterocyclyl, for example an optionally substituted 5 or 6-membered heterocyclyl, optionally substituted phenyl, or optionally substituted 5 or 6-membered heteroaryl; or R$^{14}$ and W$^2$ together with the nitrogen atom to which they are attached form an optionally substituted 4 to 7-membered heterocyclyl, for example an optionally substituted 5 or 6-membered heterocyclyl, or an optionally substituted 5 or 6-membered heteroaryl.

In various embodiments, X is NG$^1$ and R$^1$, R$^2$ and R$^3$ are each independently H, D, NR$^6$R$^7$, OR$^6$, halogen, CF$_3$, OCF$_3$, CN, NR$^6$COR$^8$, NR$^6$SO$_2$R$^8$, or C$_{1-4}$alkyl optionally substituted with one or more independently selected R$^a$.

In various embodiments, R$^1$ and R$^3$ are each independently H, D, NR$^6$R$^7$, OR$^6$, halogen, NR$^6$COR$^8$, NR$^6$SO$_2$R$^8$, or C$_{1-4}$alkyl optionally substituted with one or more independently selected R$^a$.

In various embodiments:
  X is NG$^1$ and R$^1$, R$^2$, and R$^3$ are each independently H, D, NR$^6$R$^7$, OR$^6$, halogen, NR$^6$COR$^8$, NR$^6$SO$_2$R$^8$, or unsubstituted C$_{1-4}$alkyl; or
  R$^2$ is G and R$^1$ and R$^3$ are each independently H, D, NR$^6$R$^7$, OR$^6$, halogen, NR$^6$COR$^8$, NR$^6$SO$_2$R$^8$, or unsubstituted C$_{1-4}$alkyl.

In various embodiments, X is NG$^1$ and R$^2$ is H.

In various embodiments, R$^3$ is H.

In various embodiments, R$^1$ is H, D, OR$^6$, halogen, or unsubstituted C$_{1-4}$alkyl.

In various embodiments, R$^1$ is H, OCH$_3$, Cl, Br, or CH$_3$.

In various embodiments, R$^4$ is H or unsubstituted C$_{1-6}$alkyl.

In various embodiments, R$^5$ is H or unsubstituted C$_{1-4}$alkyl.

In various embodiments, R$^{14}$ is H or unsubstituted C$_{1-3}$alkyl, or R$^{14}$ and W$^2$ together with the nitrogen atom to which they are attached form an optionally substituted heterocyclyl or optionally substituted heteroaryl; and/or R$^{15}$ at each instance is H or unsubstituted C$_{1-3}$alkyl.

In various embodiments, R$^d$ and R$^g$ at each instance is independently selected from D, NR$^6$R$^7$, OR$^6$, halogen, CF$_3$, OCF$_3$, CN, SO$_2$R$^8$, SR$^8$, NR$^6$COR$^8$, NR$^6$SO$_2$R$^8$, and unsubstituted C$_{1-4}$alkyl, for example methyl or ethyl.

In various embodiments, R$^i$, R$^x$, and R$^n$ at each instance are each independently selected from D, NR$^6$R$^7$, OR$^6$, SR$^8$, halogen, CF$_3$, OCF$_3$, CN, SO$_2$R$^8$, and unsubstituted C$_{1-4}$alkyl.

In various embodiments, R$^i$ at each instance is independently selected from D, NR$^6$R$^7$, OR$^6$, halogen, and OCF$_3$.

In various embodiments, R$^x$ at each instance is independently OR$^6$.

In various embodiments, R$^n$ at each instance is independently selected from OR$^6$, CF$_3$, and OCF$_3$.

In various embodiments, R$^m$ at each instance is independently selected from D, NR$^6$R$^7$, OR$^6$, SR$^8$, F, CF$_3$, OCF$_3$, CN, SO$_2$R$^8$, and unsubstituted C$_{1-4}$alkyl.

In various embodiments, the compound of formula (I) is a compound of formula (IA-1), (IA-2), or (IA-3):

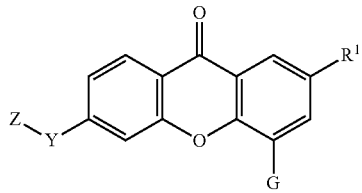
(IA-1)

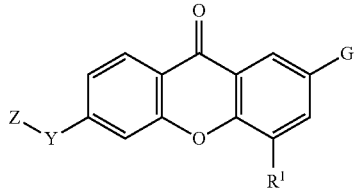
(IA-2)

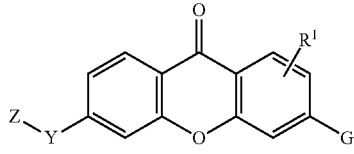
(IA-3)

wherein:
  G is —O—(CH$_2$)$_{2-4}$—NR$^{9a}$R$^{10a}$, —O—(CH$_2$)$_{2-4}$—NR$^{9b}$R$^{10b}$, —O—(CH$_2$)$_{1-4}$—CR$^{11}$R$^{12}$R$^{13}$, or —O—CR$^{11}$R$^{12}$R$^{13}$.

In various embodiments, the compound of formula (I) is a compound of formula (IA-1), (IA-2), or (IA-3):

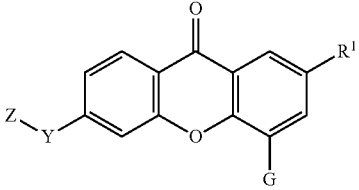
(IA-1)

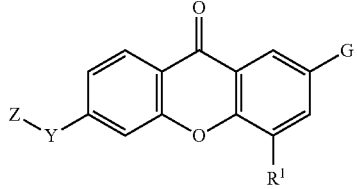
(IA-2)

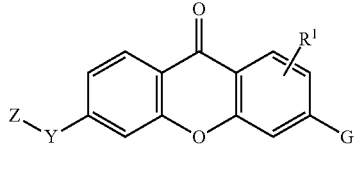
(IA-3)

wherein:
  G is —O—(CH$_2$)$_{2-4}$—NR$^{9a}$R$^{10a}$, —O—(CH$_2$)$_{2-4}$—NR$^{9b}$R$^{10b}$, or —O—(CH$_2$)$_{1-4}$—CR$^{11}$R$^{12}$R$^{13}$.

In various embodiments, the compound of formula (I) is a compound of formula (IA-1), (IA-2), or (IA-3):

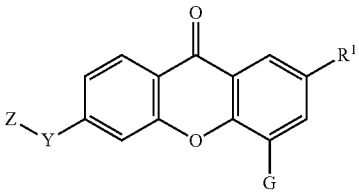
(IA-1)

-continued

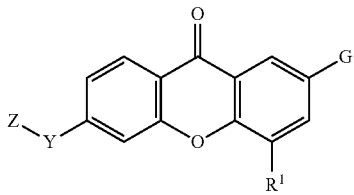
(IA-2)

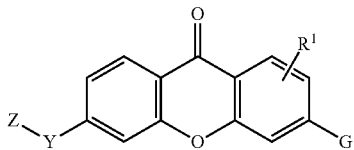
(IA-3)

wherein:
G is —O—CR$^{11}$R$^{12}$R$^{13}$.

In various embodiments, the compound of formula (I) is a compound of formula (IA-1) or (IA-2), wherein G is —O—(CH$_2$)$_{2-4}$—NR$^{9a}$R$^{10a}$, —O—(CH$_2$)$_{2-4}$—NR$^{9b}$R$^{10b}$, —O—(CH$_2$)$_{1-4}$—CR$^{11}$R$^{12}$R$^{13}$, or —O—CR$^{11}$R$^{12}$R$^{13}$.

In various embodiments, the compound of formula (I) is a compound of formula (IA-1) or (IA-2), wherein G is —O—(CH$_2$)$_{2-4}$—NR$^{9a}$R$^{10a}$, —O—(CH$_2$)$_{2-4}$—NR$^{9b}$R$^{10b}$, or —O—(CH$_2$)$_{1-4}$—CR$^{11}$R$^{12}$R$^{13}$.

In various embodiments, the compound of formula (I) is a compound of formula (IA-1) or (IA-2), wherein G is —O—CR$^{11}$R$^{12}$R$^{13}$.

In certain embodiments, the compound of formula (I) is a compound of formula (IA-1), wherein G is —O—(CH$_2$)$_{2-4}$—NR$^{9a}$R$^{10a}$, —O—(CH$_2$)$_{2-4}$—NR$^{9b}$R$^{10b}$, —O—(CH$_2$)$_{1-4}$—CR$^{11}$R$^{12}$R$^{13}$, or —O—CR$^{11}$R$^{12}$R$^{13}$.

In certain embodiments, the compound of formula (I) is a compound of formula (IA-1), wherein G is —O—(CH$_2$)$_{2-4}$—NR$^{9a}$R$^{10a}$, —O—(CH$_2$)$_{2-4}$—NR$^{9b}$R$^{10b}$, or —O—(CH$_2$)$_{1-4}$—CR$^{11}$R$^{12}$R$^{13}$.

In certain embodiments, the compound of formula (I) is a compound of formula (IA-1), wherein G is —O—CR$^{11}$R$^{12}$R$^{13}$.

In various embodiments, the compound of formula (I) is a compound of formula (IC-1):

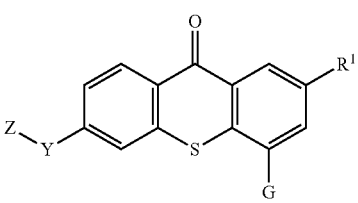
(IC-1)

wherein:
G is —O—(CH$_2$)$_{2-4}$—NR$^{9a}$R$^{10a}$, —O—(CH$_2$)$_{2-4}$—NR$^{9b}$R$^{10b}$, or —O—(CH$_2$)$_{1-4}$—CR$^{11}$R$^{12}$R$^{13}$.

In various embodiments, the compound of formula (I) is a compound of the formula (ID):

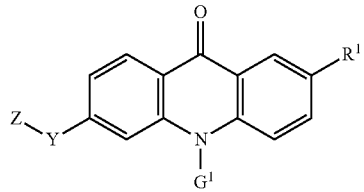
(ID)

wherein:
G$^1$ is —(CH$_2$)$_{2-4}$—NR$^{9a}$R$^{10a}$, —(CH$_2$)$_{2-4}$—NR$^{9b}$R$^{10b}$, or —(CH$_2$)$_{1-4}$—CR$^{11}$R$^{12}$R$^{13}$.

In various embodiments, the compound of formula (I) is:
5-[2-(Dimethylamino)ethoxy]-3-phenoxy-9H-xanthen-9-one;
3-({5-[2-(Dimethylamino)ethoxy]-9-oxo-9H-xanthen-3-yl}oxy)-N-phenylbenzamide;
5-[2-(Dimethylamino)ethoxy]-3-({6-[2-(4-methoxyphenyl)ethyl]-3-pyridinyl}oxy)-9H-xanthen-9-one;
4-[2-(Dimethylamino)ethoxy]-2-methyl-6-phenoxy-9H-xanthen-9-one;
3-((5-(2-(Dimethylamino)ethoxy)-7-methyl-9-oxo-9H-xanthen-3-yl)oxy)-N-phenylbenzamide;
1-(3-((5-(2-(Dimethylamino)ethoxy)-7-methyl-9-oxo-9H-xanthen-3-yl)oxy)phenyl)-3-phenylurea;
4-(2-(Dimethylamino)ethoxy)-6-(3-methoxy-4-((4-methylbenzyl)oxy)phenoxy)-2-methyl-9H-xanthen-9-one;
4-(2-(Dimethylamino)ethoxy)-6-((6-methoxypyridin-3-yl)oxy)-2-methyl-9H-xanthen-9-one;
6-((5,6-Dimethoxypyridin-3-yl)oxy)-4-(2-(dimethylamino)ethoxy)-2-methyl-9H-xanthen-9-one;
4-(2-(Dimethylamino)ethoxy)-6-((6-((4-methoxybenzyl)oxy)pyridin-3-yl)oxy)-2-methyl-9H-xanthen-9-one;
4-(2-(Dimethylamino)ethoxy)-6-((6-((6-methoxypyridin-3-yl)methoxy)pyridin-3-yl)oxy)-2-methyl-9H-xanthen-9-one;
4-(2-(Dimethylamino)ethoxy)-6-((5-methoxy-6-((4-methoxybenzyl)oxy)pyridin-3-yl)oxy)-2-methyl-9H-xanthen-9-one;
4-(2-(Dimethylamino)ethoxy)-2-methyl-6-((6-((6-(trifluoromethyl)pyridin-3-yl)methoxy)-pyridin-3-yl)oxy)-9H-xanthen-9-one;
4-(2-(Dimethylamino)ethoxy)-6-((6-((4-methoxybenzyl)amino)pyridin-3-yl)oxy)-2-methyl-9H-xanthen-9-one;
4-(2-(Dimethylamino)ethoxy)-2-methyl-6-((6-((4-(trifluoromethoxy)benzyl)amino)-pyridin-3-yl)oxy)-9H-xanthen-9-one;
4-(2-(Dimethylamino)ethoxy)-6-((6-(((6-methoxypyridin-3-yl)methyl)amino)pyridin-3-yl)oxy)-2-methyl-9H-xanthen-9-one;
6-((6-Aminopyridin-3-yl)oxy)-4-(2-(dimethylamino)ethoxy)-2-methyl-9H-xanthen-9-one;
4-(2-(Dimethylamino)ethoxy)-6-((6-(4-methoxyphenethyl)pyridin-3-yl)oxy)-2-methyl-9H-xanthen-9-one;
4-(2-(Dimethylamino)ethoxy)-6-((6-methoxypyridin-3-yl)methyl)-2-methyl-9H-xanthen-9-one;
(2-(Dimethylamino)ethoxy)-6-(6-((4-methoxybenzyl)oxy)nicotinoyl)-2-methyl-9H-xanthen-9-one;
3-(5-((5-(2-(Dimethylamino)ethoxy)-7-methyl-9-oxo-9H-xanthen-3-yl)oxy)pyridin-2-yl)-N-(pyridin-3-yl)propanamide;
N-Cyclopentyl-3-(5-((5-(2-(dimethyl amino)ethoxy)-7-methyl-9-oxo-9H-xanthen-3-yl)-oxy)pyridin-2-yl)propanamide;

4-(2-(Dimethylamino)ethoxy)-2-methyl-6-((6-(3-oxo-3-(pyrrolidin-1-yl)propyl)pyridin-3-yl)oxy)-9H-xanthen-9-one;

4-(2-(Dimethylamino)ethoxy)-2-methyl-6-((6-(3-morpholino-3-oxopropyl)pyridin-3-yl)oxy)-9H-xanthen-9-one;

N-Cyclopentyl-2-((5-((5-(2-(dimethylamino)ethoxy)-7-methyl-9-oxo-9H-xanthen-3-yl)-oxy)pyridin-2-yl)amino)acetamide;

N-(2-(5-((5-(2-(Dimethylamino)ethoxy)-7-methyl-9-oxo-9H-xanthen-3-yl)oxy)pyridin-2-yl)ethyl)cyclopentanecarboxamide;

N-(2-(5-((5-(2-(Dimethylamino)ethoxy)-7-methyl-9-oxo-9H-xanthen-3-yl)oxy)pyridin-2-yl)ethyl)pyrrolidine-1-carboxamide;

3-(5-((5-(2-Aminoethoxy)-7-methyl-9-oxo-9H-xanthen-3-yl)oxy)pyridin-2-yl)-N-cyclopentylpropanamide;

N-Cyclopentyl-3-(5-((7-methyl-S-(2-(methylamino)ethoxy)-9-oxo-9H-xanthen-3-yl)oxy)-pyridin-2-yl)propanamide;

4-[3-(Dimethylamino)propoxy]-2-methyl-6-phenoxy-9H-xanthen-9-one;

3-((5-(3-(Dimethylamino)propoxy)-7-methyl-9-oxo-9H-xanthen-3-yl)oxy)-N-phenyl-benzamide;

1-(3-((5-(3-(Dimethylamino)propoxy)-7-methyl-9-oxo-9H-xanthen-3-yl)oxy)phenyl)-3-phenylurea;

2-Methyl-4-(3-morpholinopropoxy)-6-phenoxy-9H-xanthen-9-one;

4-(4-(Dimethylamino)butoxy)-2-methyl-6-phenoxy-9H-xanthen-9-one;

2-Methyl-4-((1-methylpiperidin-4-yl)methoxy)-6-phenoxy-9H-xanthen-9-one;

2-Methyl-4-(2-(1-methylpiperidin-4-yl)ethoxy)-6-phenoxy-9H-xanthen-9-one;

N-Cyclopentyl-3-(5-((7-methyl-9-oxo-5-(2-(pyrrolidin-1-yl)ethoxy)-9H-xanthen-3-yl)-oxy)pyridin-2-yl)propanamide;

N-Cyclopentyl-3-(5-((7-methyl-9-oxo-5-(2-(piperidin-1-yl)ethoxy)-9H-xanthen-3-yl)oxy)pyridin-2-yl)propanamide;

2-Chloro-4-[2-(dimethylamino)ethoxy]-6-phenoxy-9H-xanthen-9-one;

3-({7-Chloro-5-[2-(dimethylamino)ethoxy]-9-oxo-9H-xanthen-3-yl}oxy)-N-phenyl-benzamide;

2-Chloro-4-[2-(dimethyl amino)ethoxy]-6-({6-[2-(4-methoxyphenyl)ethyl]-3-pyridinyl}-oxy)-9H-xanthen-9-one;

3-(5-((7-Bromo-5-(2-(dimethylamino)ethoxy)-9-oxo-9H-xanthen-3-yl)oxy)pyridin-2-yl)-N-cyclopentylpropanamide;

N-Cyclopentyl-3-(5-((5-(2-(dimethyl amino)ethoxy)-7-methyl-9-oxo-9H-xanthen-3-yl)thio)pyridin-2-yl)propanamide;

N-Cyclopentyl-3-(5-((7-(2-(dimethylamino)ethoxy)-9-oxo-9H-xanthen-3-yl)oxy)pyridin-2-yl)propanamide;

N-Cyclopentyl-3-(5-((7-(2-(dimethyl amino)ethoxy)-5-methyl-9-oxo-9H-xanthen-3-yl)oxy)pyridin-2-yl)propanamide;

N-Cyclopentyl-3-(5-((7-(2-(dimethylamino)ethoxy)-5-methoxy-9-oxo-9H-xanthen-3-yl)oxy)pyridin-2-yl)propanamide;

N-Cyclopentyl-3-(5-((6-(2-(dimethylamino)ethoxy)-9-oxo-9H-xanthen-3-yl)oxy)phenyl)propanamide;

4-(2-(Dimethylamino)ethoxy)-2-methyl-6-phenoxy-9H-thioxanthen-9-one;

3-((5-(2-(Dimethylamino)ethoxy)-7-methyl-9-oxo-9H-thioxanthen-3-yl)oxy)-N-phenylbenzamide;

4-(2-(Dimethylamino)ethoxy)-6-((6-(4-methoxyphenethyl)pyridin-3-yl)oxy)-2-methyl-9H-thioxanthen-9-one;

N-Cyclopentyl-3-(5-((5-(2-(dimethylamino)ethoxy)-7-methyl-9-oxo-9H-thioxanthen-3-yl)oxy)pyridin-2-yl)propanamide;

10-(3-(Dimethylamino)propyl)-2-methyl-6-(phenylthio)acridin-9(10H)-one;

4-(2-(Dimethylamino)ethoxy)-2-methyl-6-(pyridin-3-yloxy)-9H-xanthen-9-one;

4-(2-(Dimethylamino)ethoxy)-2-methyl-6-((6-(3-(4-methylpiperazin-1-yl)-3-oxopropyl)pyridin-3-yl)oxy)-9H-xanthen-9-one;

N-Cyclopentyl-3-(5-((5-(2-(diethylamino)ethoxy)-7-methyl-9-oxo-9H-xanthen-3-yl)oxy)pyridin-2-yl)propanamide;

N-Cyclopentyl-3-[5-({7-methyl-5-[2-(4-morpholinyl)ethoxy]-9-oxo-9H-xanthen-3-yl}oxy)-2-pyridinyl]propanamide;

N-Cyclopentyl-3-[5-({5-[2-(diisopropylamino)ethoxy]-7-methyl-9-oxo-9H-xanthen-3-yl}oxy)-2-pyridinyl]propanamide;

N-Cyclopentyl-3-(5-((7-methyl-5-(2-(4-methylpiperazin-1-yl)ethoxy)-9-oxo-9H-xanthen-3-yl)oxy)pyridin-2-yl)propanamide;

N-Cyclopentyl-3-(5-((7-methyl-9-oxo-5-(2-(4-(2,2,2-trifluoroethyl)piperazin-1-yl)ethoxy-9H-xanthen-3-yl)oxy)pyridin-2-yl)propanamide;

N-Cyclopentyl-3-(5-((7-methyl-5-((1-methylpiperidin-3-yl)oxy)-9-oxo-9H-xanthen-3-yl)oxy)pyridin-2-yl)propanamide;

N-Cyclopentyl-3-(5-((5-(2-((3S,5R)-3,5-dimethylpiperazin-1-yl)ethoxy)-7-methyl-9-oxo-9H-xanthen-3-yl)oxy)pyridin-2-yl)propanamide;

N-Cyclopentyl-3-(5-((7-methyl-9-oxo-5-(2-((3S,5R)-3,4,5-trimethylpiperazin-1-yl)ethoxy)-9H-xanthen-3-yl)oxy)pyridin-2-yl)propanamide;

N-Cyclopentyl-3-(5-((5-(3-(dimethylamino)propoxy)-7-methyl-9-oxo-9H-xanthen-3-yl)oxy)pyridin-2-yl)propanamide;

N-Cyclopentyl-3-(5-((5-(3-((2R,6S)-2,6-dimethylpiperidin-1-yl)propoxy)-7-methyl-9-oxo-9H-xanthen-3-yl)oxy)pyridin-2-yl)propanamide;

N-Cyclopentyl-3-(5-((5-(3-(4-ethylpiperazin-1-yl)propoxy)-7-methyl-9-oxo-9H-xanthen-3-yl)oxy)pyridin-2-yl)propanamide;

N-Cyclopentyl-3-(5-((5-(3-(4-isopropylpiperazin-1-yl)propoxy)-7-methyl-9-oxo-9H-xanthen-3-yl)oxy)pyridin-2-yl)propanamide;

N-Cyclopentyl-3-(5-((5-(3-((3 S,5R)-3,5-dimethylpiperazin-1-yl)propoxy)-7-methyl-9-oxo-9H-xanthen-3-yl)oxy)pyridin-2-yl)propanamide;

N-Cyclopentyl-3-(5-((7-methyl-9-oxo-5-(3-((3S,5R)-3,4,5-trimethylpiperazin-1-yl)propoxy)-9H-xanthen-3-yl)oxy)pyridin-2-yl)propanamide;

N-Cyclopentyl-3-[5-({7-methyl-5-[3-(4-morpholinyl)propoxy]-9-oxo-9H-xanthen-3-yl}oxy)-2-pyridinyl]propanamide;

N-Cyclopentyl-3-(5-((7-methyl-5-((1-methylpyrrolidin-3-yl)oxy)-9-oxo-9H-xanthen-3-yl)oxy)pyridin-2-yl)propanamide;

N-Cyclopentyl-3-[5-({7-methyl-5-[(1-methyl-4-piperidinyl)oxy]-9-oxo-9H-xanthen-3-yl}oxy)-2-pyridinyl]propanamide;

(R)—N-Cyclopentyl-3-(5-((7-methyl-5-((1-methylpyrrolidin-2-yl)methoxy)-9-oxo-9H-xanthen-3-yl)oxy)pyridin-2-yl)propanamide;

(S)—N-Cyclopentyl-3-(5-((7-methyl-5-((1-methylpyrroli-din-2-yl)methoxy)-9-oxo-9H-xanthen-3-yl)oxy)pyridin-2-yl)propanamide;

N-Cyclopentyl-3-(5-((7-methyl-5-((1-methylpiperidin-2-yl)methoxy)-9-oxo-9H-xanthen-3-yl)oxy)pyridin-2-yl)propanamide;

N-Cyclopentyl-3-(5-((7-methyl-5-(2-(1-methylpyrrolidin-2-yl)ethoxy)-9-oxo-9H-xanthen-3-yl)oxy)pyridin-2-yl)propanamide;

N-Cyclopentyl-3-(5-((7-methyl-5-((1-methylpiperidin-3-yl)methoxy)-9-oxo-9H-xanthen-3-yl)oxy)pyridin-2-yl)propanamide; or a pharmaceutically acceptable salt, solvate, or stereoisomer thereof.

In various embodiments, the compound of formula (I) is:

5-[2-(Dimethylamino)ethoxy]-3-phenoxy-9H-xanthen-9-one;

3-({5-[2-(Dimethylamino)ethoxy]-9-oxo-9H-xanthen-3-yl}oxy)-N-phenylbenzamide;

5-[2-(Dimethylamino)ethoxy]-3-({6-[2-(4-methoxyphenyl)ethyl]-3-pyridinyl}oxy)-9H-xanthen-9-one;

4-[2-(Dimethylamino)ethoxy]-2-methyl-6-phenoxy-9H-xanthen-9-one;

3-((5-(2-(Dimethylamino)ethoxy)-7-methyl-9-oxo-9H-xanthen-3-yl)oxy)-N-phenylbenz-amide;

1-(3-((5-(2-(Dimethylamino)ethoxy)-7-methyl-9-oxo-9H-xanthen-3-yl)oxy)phenyl)-3-phenylurea;

4-(2-(Dimethylamino)ethoxy)-6-(3-methoxy-4-((4-methylbenzyl)oxy)phenoxy)-2-methyl-9H-xanthen-9-one;

4-(2-(Dimethylamino)ethoxy)-6-((6-methoxypyridin-3-yl)oxy)-2-methyl-9H-xanthen-9-one;

6-((5,6-Dimethoxypyridin-3-yl)oxy)-4-(2-(dimethylamino)ethoxy)-2-methyl-9H-xanthen-9-one;

4-(2-(Dimethylamino)ethoxy)-6-((6-((4-methoxybenzyl)oxy)pyridin-3-yl)oxy)-2-methyl-9H-xanthen-9-one;

4-(2-(Dimethylamino)ethoxy)-6-((6-((6-methoxypyridin-3-yl)methoxy)pyridin-3-yl)oxy)-2-methyl-9H-xanthen-9-one;

4-(2-(Dimethylamino)ethoxy)-6-((5-methoxy-6-((4-methoxybenzyl)oxy)pyridin-3-yl)oxy)-2-methyl-9H-xanthen-9-one;

4-(2-(Dimethylamino)ethoxy)-2-methyl-6-((6-((6-(trifluoromethyl)pyridin-3-yl)methoxy)-pyridin-3-yl)oxy)-9H-xanthen-9-one;

4-(2-(Dimethylamino)ethoxy)-6-((6-((4-methoxybenzyl)amino)pyridin-3-yl)oxy)-2-methyl-9H-xanthen-9-one;

4-(2-(Dimethylamino)ethoxy)-2-methyl-6-((6-((4-(trifluoromethoxy)benzyl)amino)-pyridin-3-yl)oxy)-9H-xanthen-9-one;

4-(2-(Dimethylamino)ethoxy)-6-((6-(((6-methoxypyridin-3-yl)methyl)amino)pyridin-3-yl)oxy)-2-methyl-9H-xanthen-9-one;

6-((6-Aminopyridin-3-yl)oxy)-4-(2-(dimethylamino)ethoxy)-2-methyl-9H-xanthen-9-one;

4-(2-(Dimethylamino)ethoxy)-6-((6-(4-methoxyphenethyl)pyridin-3-yl)oxy)-2-methyl-9H-xanthen-9-one;

4-(2-(Dimethylamino)ethoxy)-6-((6-methoxypyridin-3-yl)methyl)-2-methyl-9H-xanthen-9-one;

(2-(Dimethylamino)ethoxy)-6-(6-((4-methoxybenzyl)oxy)nicotinoyl)-2-methyl-9H-xanthen-9-one;

3-(5-((5-(2-(Dimethylamino)ethoxy)-7-methyl-9-oxo-9H-xanthen-3-yl)oxy)pyridin-2-yl)-N-(pyridin-3-yl)propanamide;

N-Cyclopentyl-3-(5-((5-(2-(dimethylamino)ethoxy)-7-methyl-9-oxo-9H-xanthen-3-yl)-oxy)pyridin-2-yl)propanamide;

4-(2-(Dimethylamino)ethoxy)-2-methyl-6-((6-(3-oxo-3-(pyrrolidin-1-yl)propyl)pyridin-3-yl)oxy)-9H-xanthen-9-one;

4-(2-(Dimethylamino)ethoxy)-2-methyl-6-((6-(3-morpholino-3-oxopropyl)pyridin-3-yl)oxy)-9H-xanthen-9-one;

N-Cyclopentyl-2-((5-((5-(2-(dimethylamino)ethoxy)-7-methyl-9-oxo-9H-xanthen-3-yl)-oxy)pyridin-2-yl)amino)acetamide;

N-(2-(5-((5-(2-(Dimethylamino)ethoxy)-7-methyl-9-oxo-9H-xanthen-3-yl)oxy)pyridin-2-yl)ethyl)cyclopentanecarboxamide;

N-(2-(5-((5-(2-(Dimethylamino)ethoxy)-7-methyl-9-oxo-9H-xanthen-3-yl)oxy)pyridin-2-yl)ethyl)pyrrolidine-1-carboxamide;

3-(5-((5-(2-Aminoethoxy)-7-methyl-9-oxo-9H-xanthen-3-yl)oxy)pyridin-2-yl)-N-cyclo-pentylpropanamide;

N-Cyclopentyl-3-(5-((7-methyl-5-(2-(methylamino)ethoxy)-9-oxo-9H-xanthen-3-yl)oxy)-pyridin-2-yl)propanamide;

4-[3-(Dimethylamino)propoxy]-2-methyl-6-phenoxy-9H-xanthen-9-one;

3-((5-(3-(Dimethylamino)propoxy)-7-methyl-9-oxo-9H-xanthen-3-yl)oxy)-N-phenyl-benzamide;

1-(3-((5-(3-(Dimethylamino)propoxy)-7-methyl-9-oxo-9H-xanthen-3-yl)oxy)phenyl)-3-phenylurea;

2-Methyl-4-(3-morpholinopropoxy)-6-phenoxy-9H-xanthen-9-one;

4-(4-(Dimethylamino)butoxy)-2-methyl-6-phenoxy-9H-xanthen-9-one;

2-Methyl-4-((1-methylpiperidin-4-yl)methoxy)-6-phenoxy-9H-xanthen-9-one;

2-Methyl-4-(2-(1-methylpiperidin-4-yl)ethoxy)-6-phenoxy-9H-xanthen-9-one;

N-Cyclopentyl-3-(5-((7-methyl-9-oxo-5-(2-(pyrrolidin-1-yl)ethoxy)-9H-xanthen-3-yl)-oxy)pyridin-2-yl)propanamide;

N-Cyclopentyl-3-(5-((7-methyl-9-oxo-5-(2-(piperidin-1-yl)ethoxy)-9H-xanthen-3-yl)oxy)pyridin-2-yl)propanamide;

2-Chloro-4-[2-(dimethylamino)ethoxy]-6-phenoxy-9H-xanthen-9-one;

3-({7-Chloro-5-[2-(dimethylamino)ethoxy]-9-oxo-9H-xanthen-3-yl}oxy)-N-phenyl-benzamide;

2-Chloro-4-[2-(dimethylamino)ethoxy]-6-({6-[2-(4-methoxyphenyl)ethyl]-3-pyridinyl}-oxy)-9H-xanthen-9-one;

3-(5-((7-Bromo-5-(2-(dimethylamino)ethoxy)-9-oxo-9H-xanthen-3-yl)oxy)pyridin-2-yl)-N-cyclopentylpropanamide;

N-Cyclopentyl-3-(5-((5-(2-(dimethylamino)ethoxy)-7-methyl-9-oxo-9H-xanthen-3-yl)thio)pyridin-2-yl)propanamide;

N-Cyclopentyl-3-(5-((7-(2-(dimethylamino)ethoxy)-9-oxo-9H-xanthen-3-yl)oxy)pyridin-2-yl)propanamide;

N-Cyclopentyl-3-(5-((7-(2-(dimethylamino)ethoxy)-5-methyl-9-oxo-9H-xanthen-3-yl)oxy)pyridin-2-yl)propanamide;

N-Cyclopentyl-3-(5-((7-(2-(dimethylamino)ethoxy)-5-methoxy-9-oxo-9H-xanthen-3-yl)oxy)pyridin-2-yl)propanamide;

N-Cyclopentyl-3-(5-((6-(2-(dimethylamino)ethoxy)-9-oxo-9H-xanthen-3-yl)oxy)phenyl)propanamide;

4-(2-(Dimethylamino)ethoxy)-2-methyl-6-phenoxy-9H-thioxanthen-9-one;

3-((5-(2-(Dimethylamino)ethoxy)-7-methyl-9-oxo-9H-thioxanthen-3-yl)oxy)-N-phenylbenzamide;

4-(2-(Dimethylamino)ethoxy)-6-((6-(4-methoxyphenethyl) pyridin-3-yl)oxy)-2-methyl-9H-thioxanthen-9-one;

N-Cyclopentyl-3-(5-((5-(2-(dimethylamino)ethoxy)-7-methyl-9-oxo-9H-thioxanthen-3-yl)oxy)pyridin-2-yl)propanamide; or 10-(3-(Dimethylamino)propyl)-2-methyl-6-(phenylthio) acridin-9(10H)-one; or a pharmaceutically acceptable salt, solvate, or stereoisomer thereof.

In various embodiments, the compound of formula (I) is:

4-(2-(Dimethylamino)ethoxy)-2-methyl-6-(pyridin-3-yloxy)-9H-xanthen-9-one;

4-(2-(Dimethylamino)ethoxy)-2-methyl-6-((6-(3-(4-methylpiperazin-1-yl)-3-oxopropyl)pyridin-3-yl)oxy)-9H-xanthen-9-one;

N-Cyclopentyl-3-(5-((5-(2-(diethylamino)ethoxy)-7-methyl-9-oxo-9H-xanthen-3-yl)oxy)pyridin-2-yl)propanamide;

N-Cyclopentyl-3-[5-({7-methyl-5-[2-(4-morpholinyl) ethoxy]-9-oxo-9H-xanthen-3-yl}oxy)-2-pyridinyl]propanamide;

N-Cyclopentyl-3-[5-({5-[2-(diisopropylamino)ethoxy]-7-methyl-9-oxo-9H-xanthen-3-yl}oxy)-2-pyridinyl]propanamide;

N-Cyclopentyl-3-(5-((7-methyl-5-(2-(4-methylpiperazin-1-yl)ethoxy)-9-oxo-9H-xanthen-3-yl)oxy)pyridin-2-yl)propanamide;

N-Cyclopentyl-3-(5-((7-methyl-9-oxo-5-(2-(4-(2,2,2-trifluoroethyl)piperazin-1-yl)ethoxy)-9H-xanthen-3-yl)oxy) pyridin-2-yl)propanamide;

N-Cyclopentyl-3-(5-((7-methyl-5-((1-methylpiperidin-3-yl) oxy)-9-oxo-9H-xanthen-3-yl)oxy)pyridin-2-yl)propanamide;

N-Cyclopentyl-3-(5-((5-(2-((3S,5R)-3,5-dimethylpiperazin-1-yl)ethoxy)-7-methyl-9-oxo-9H-xanthen-3-yl)oxy)pyridin-2-yl)propanamide;

N-Cyclopentyl-3-(5-((7-methyl-9-oxo-5-(2-((3S,5R)-3,4,5-trimethylpiperazin-1-yl)ethoxy)-9H-xanthen-3-yl)oxy) pyridin-2-yl)propanamide;

N-Cyclopentyl-3-(5-((5-(3-(dimethylamino)propoxy)-7-methyl-9-oxo-9H-xanthen-3-yl)oxy)pyridin-2-yl)propanamide;

N-Cyclopentyl-3-(5-((5-(3-((2R,6S)-2,6-dimethylpiperidin-1-yl)propoxy)-7-methyl-9-oxo-9H-xanthen-3-yl)oxy) pyridin-2-yl)propanamide;

N-Cyclopentyl-3-(5-((5-(3-(4-ethylpiperazin-1-yl) propoxy)-7-methyl-9-oxo-9H-xanthen-3-yl)oxy)pyridin-2-yl)propanamide;

N-Cyclopentyl-3-(5-((5-(3-(4-isopropylpiperazin-1-yl) propoxy)-7-methyl-9-oxo-9H-xanthen-3-yl)oxy)pyridin-2-yl)propanamide;

N-Cyclopentyl-3-(5-((5-(3-((3 S,5R)-3,5-dimethylpiperazin-1-yl)propoxy)-7-methyl-9-oxo-9H-xanthen-3-yl) oxy)pyridin-2-yl)propanamide;

N-Cyclopentyl-3-(5-((7-methyl-9-oxo-5-(3-((3S,5R)-3,4,5-trimethylpiperazin-1-yl)propoxy)-9H-xanthen-3-yl)oxy) pyridin-2-yl)propanamide;

N-Cyclopentyl-3-[5-({7-methyl-5-[3-(4-morpholinyl) propyl]-9-oxo-9H-xanthen-3-yl})oxy)-2-pyridinyl]propanamide;

N-Cyclopentyl-3-(5-((7-methyl-5-((1-methylpyrrolidin-3-yl)oxy)-9-oxo-9H-xanthen-3-yl)oxy)pyridin-2-yl)propanamide;

N-Cyclopentyl-3-[5-({7-methyl-5-[(1-methyl-4-piperidinyl)oxy]-9-oxo-9H-xanthen-3-yl}oxy)-2-pyridinyl]propanamide;

(R)—N-Cyclopentyl-3-(5-((7-methyl-5-((1-methylpyrrolidin-2-yl)methoxy)-9-oxo-9H-xanthen-3-yl)oxy)pyridin-2-yl)propanamide;

(S)—N-Cyclopentyl-3-(5-((7-methyl-5-((1-methylpyrrolidin-2-yl)methoxy)-9-oxo-9H-xanthen-3-yl)oxy)pyridin-2-yl)propanamide;

N-Cyclopentyl-3-(5-((7-methyl-5-((1-methylpiperidin-2-yl) methoxy)-9-oxo-9H-xanthen-3-yl)oxy)pyridin-2-yl)propanamide;

N-Cyclopentyl-3-(5-((7-methyl-5-(2-(1-methylpyrrolidin-2-yl)ethoxy)-9-oxo-9H-xanthen-3-yl)oxy)pyridin-2-yl)propanamide;

N-Cyclopentyl-3-(5-((7-methyl-5-((1-methylpiperidin-3-yl) methoxy)-9-oxo-9H-xanthen-3-yl)oxy)pyridin-2-yl)propanamide; or a pharmaceutically acceptable salt, solvate, or stereoisomer thereof.

In various embodiments, the compound of formula (I) is:

5-[2-(Dimethylamino)ethoxy]-3-phenoxy-9H-xanthen-9-one;

3-({5-[2-(Dimethylamino)ethoxy]-9-oxo-9H-xanthen-3-yl}oxy)-N-phenylbenzamide;

5-[2-(Dimethylamino)ethoxy]-3-({6-[2-(4-methoxyphenyl) ethyl]-3-pyridinyl}oxy)-9H-xanthen-9-one;

4-[2-(Dimethylamino)ethoxy]-2-methyl-6-phenoxy-9H-xanthen-9-one;

3-((5-(2-(Dimethylamino)ethoxy)-7-methyl-9-oxo-9H-xanthen-3-yl)oxy)-N-phenylbenzamide;

1-(3-((5-(2-(Dimethylamino)ethoxy)-7-methyl-9-oxo-9H-xanthen-3-yl)oxy)phenyl)-3-phenylurea;

4-(2-(Dimethylamino)ethoxy)-6-(3-methoxy-4-((4-methylbenzyl)oxy)phenoxy)-2-methyl-9H-xanthen-9-one;

4-(2-(Dimethylamino)ethoxy)-6-((6-methoxypyridin-3-yl) oxy)-2-methyl-9H-xanthen-9-one;

6-((5,6-Dimethoxypyridin-3-yl)oxy)-4-(2-(dimethylamino) ethoxy)-2-methyl-9H-xanthen-9-one;

4-(2-(Dimethylamino)ethoxy)-6-((6-((4-methoxybenzyl) oxy)pyridin-3-yl)oxy)-2-methyl-9H-xanthen-9-one;

4-(2-(Dimethylamino)ethoxy)-6-((6-((6-methoxypyridin-3-yl)methoxy)pyridin-3-yl)oxy)-2-methyl-9H-xanthen-9-one;

4-(2-(Dimethylamino)ethoxy)-6-((5-methoxy-6-((4-methoxybenzyl)oxy)pyridin-3-yl)oxy)-2-methyl-9H-xanthen-9-one;

4-(2-(Dimethylamino)ethoxy)-2-methyl-6-((6-((6-(trifluoromethyl)pyridin-3-yl)methoxy)-pyridin-3-yl)oxy)-9H-xanthen-9-one;

4-(2-(Dimethylamino)ethoxy)-6-((6-((4-methoxybenzyl) amino)pyridin-3-yl)oxy)-2-methyl-9H-xanthen-9-one;

4-(2-(Dimethylamino)ethoxy)-2-methyl-6-((6-((4-(trifluoromethoxy)benzyl)amino)-pyridin-3-yl)oxy)-9H-xanthen-9-one;

4-(2-(Dimethylamino)ethoxy)-6-((6-(((6-methoxypyridin-3-yl)methyl)amino)pyridin-3-yl)oxy)-2-methyl-9H-xanthen-9-one;

6-((6-Aminopyridin-3-yl)oxy)-4-(2-(dimethylamino) ethoxy)-2-methyl-9H-xanthen-9-one;

4-(2-(Dimethylamino)ethoxy)-6-((6-(4-methoxyphenethyl) pyridin-3-yl)oxy)-2-methyl-9H-xanthen-9-one;

4-(2-(Dimethylamino)ethoxy)-6-((6-methoxypyridin-3-yl) methyl)-2-methyl-9H-xanthen-9-one;

(2-(Dimethylamino)ethoxy)-6-(6-((4-methoxybenzyl)oxy) nicotinoyl)-2-methyl-9H-xanthen-9-one;

3-(5-((5-(2-(Dimethylamino)ethoxy)-7-methyl-9-oxo-9H-xanthen-3-yl)oxy)pyridin-2-yl)-N-(pyridin-3-yl)propanamide;

N-Cyclopentyl-3-(5-((5-(2-(dimethyl amino)ethoxy)-7-methyl-9-oxo-9H-xanthen-3-yl)-oxy)pyridin-2-yl)propanamide;
4-(2-(Dimethylamino)ethoxy)-2-methyl-6-((6-(3-oxo-3-(pyrrolidin-1-yl)propyl)pyridin-3-yl)oxy)-9H-xanthen-9-one;
4-(2-(Dimethylamino)ethoxy)-2-methyl-6-((6-(3-morpholino-3-oxopropyl)pyridin-3-yl)oxy)-9H-xanthen-9-one;
N-Cyclopentyl-2-((5-((5-(2-(dimethylamino)ethoxy)-7-methyl-9-oxo-9H-xanthen-3-yl)-oxy)pyridin-2-yl)amino) acetamide;
N-(2-(5-((5-(2-(Dimethylamino)ethoxy)-7-methyl-9-oxo-9H-xanthen-3-yl)oxy)pyridin-2-yl)ethyl)cyclopentanecarboxamide;
N-(2-(5-((5-(2-(Dimethylamino)ethoxy)-7-methyl-9-oxo-9H-xanthen-3-yl)oxy)pyridin-2-yl)ethyl)pyrrolidine-1-carboxamide;
3-(5-((5-(2-Aminoethoxy)-7-methyl-9-oxo-9H-xanthen-3-yl)oxy)pyridin-2-yl)-N-cyclo-pentylpropanamide;
N-Cyclopentyl-3-(5-((7-methyl-S-(2-(methylamino) ethoxy)-9-oxo-9H-xanthen-3-yl)oxy)-pyridin-2-yl)propanamide;
4-[3-(Dimethylamino)propoxy]-2-methyl-6-phenoxy-9H-xanthen-9-one;
3-((5-(3-(Dimethylamino)propoxy)-7-methyl-9-oxo-9H-xanthen-3-yl)oxy)-N-phenyl-benzamide;
1-(3-((5-(3-(Dimethylamino)propoxy)-7-methyl-9-oxo-9H-xanthen-3-yl)oxy)phenyl)-3-phenylurea;
2-Methyl-4-(3-morpholinopropoxy)-6-phenoxy-9H-xanthen-9-one;
4-(4-(Dimethylamino)butoxy)-2-methyl-6-phenoxy-9H-xanthen-9-one;
2-Methyl-4-((1-methylpiperidin-4-yl)methoxy)-6-phenoxy-9H-xanthen-9-one;
2-Methyl-4-(2-(1-methylpiperidin-4-yl)ethoxy)-6-phenoxy-9H-xanthen-9-one;
N-Cyclopentyl-3-(5-((7-methyl-9-oxo-5-(2-(pyrrolidin-1-yl)ethoxy)-9H-xanthen-3-yl)-oxy)pyridin-2-yl)propanamide;
N-Cyclopentyl-3-(5-((7-methyl-9-oxo-5-(2-(piperidin-1-yl)ethoxy)-9H-xanthen-3-yl)oxy)pyridin-2-yl)propanamide;
2-Chloro-4-[2-(dimethylamino)ethoxy]-6-phenoxy-9H-xanthen-9-one;
3-({7-Chloro-5-[2-(dimethylamino)ethoxy]-9-oxo-9H-xanthen-3-yl}oxy)-N-phenyl-benzamide;
2-Chloro-4-[2-(dimethylamino)ethoxy]-6-({6-[2-(4-methoxyphenyl)ethyl]-3-pyridinyl}-oxy)-9H-xanthen-9-one;
3-(5-((7-Bromo-5-(2-(dimethylamino)ethoxy)-9-oxo-9H-xanthen-3-yl)oxy)pyridin-2-yl)-N-cyclopentylpropanamide;
N-Cyclopentyl-3-(5-((5-(2-(dimethylamino)ethoxy)-7-methyl-9-oxo-9H-xanthen-3-yl)thio)pyridin-2-yl)propanamide;
N-Cyclopentyl-3-(5-((7-(2-(dimethylamino)ethoxy)-9-oxo-9H-xanthen-3-yl)oxy)pyridin-2-yl)propanamide;
N-Cyclopentyl-3-(5-((7-(2-(dimethylamino)ethoxy)-5-methyl-9-oxo-9H-xanthen-3-yl)oxy)pyridin-2-yl)propanamide;
N-Cyclopentyl-3-(5-((7-(2-(dimethylamino)ethoxy)-5-methoxy-9-oxo-9H-xanthen-3-yl)oxy)pyridin-2-yl)propanamide; or
N-Cyclopentyl-3-(5-((6-(2-(dimethylamino)ethoxy)-9-oxo-9H-xanthen-3-yl)oxy)phenyl)propanamide; or
a pharmaceutically acceptable salt, solvate, or stereoisomer thereof.

In various embodiments, the compound of formula (I) is:
4-(2-(Dimethylamino)ethoxy)-2-methyl-6-phenoxy-9H-thioxanthen-9-one;
3-((5-(2-(Dimethylamino)ethoxy)-7-methyl-9-oxo-9H-thioxanthen-3-yl)oxy)-N-phenylbenzamide;
4-(2-(Dimethylamino)ethoxy)-6-((6-(4-methoxyphenethyl) pyridin-3-yl)oxy)-2-methyl-9H-thioxanthen-9-one; or
N-Cyclopentyl-3-(5-((5-(2-(dimethylamino)ethoxy)-7-methyl-9-oxo-9H-thioxanthen-3-yl)oxy)pyridin-2-yl)propanamide; or
a pharmaceutically acceptable salt, solvate, or stereoisomer thereof.

In various embodiments, the compound of formula (I) is:
10-(3-(Dimethylamino)propyl)-2-methyl-6-(phenylthio) acridin-9(10H)-one; or
a pharmaceutically acceptable salt, solvate, or stereoisomer thereof.

In various embodiments, the compound of formula (I) is:
N-cyclopentyl-3-(5-((5-(2-(dimethylamino)ethoxy)-7-methyl-9-oxo-9H-xanthen-3-yl)-oxy)pyridin-2-yl)propanamide; or
a pharmaceutically acceptable salt, solvate, or stereoisomer thereof.

In various embodiments, the pharmaceutical composition comprises one or more additional therapeutic agents, for example one or more anticancer agents.

In various embodiments, the kit comprises one or more additional therapeutic agents, for example one or more anticancer agents.

In various embodiments, the method comprises administering a therapeutically effective amount of the compound of formula (I) or pharmaceutically acceptable salt, solvate, or stereoisomer thereof and one or more additional therapeutic agents simultaneously, sequentially, or separately.

In various embodiments, the compound for use wherein the compound of formula (I) or pharmaceutically acceptable salt, solvate, or stereoisomer thereof is for administration simultaneously, sequentially, or separately with one or more additional therapeutic agents, for example one or more anticancer agents.

In various embodiments, the medicament further comprises one or more additional therapeutic agents, for example one or more anticancer agents.

In various embodiments, the medicament is for administration simultaneously, sequentially, or separately with one or more additional therapeutic agents, for example one or more anticancer agents.

In some embodiments, inhibiting CSF-1R comprises treating a disease or condition mediated by CSF-1R.

In some embodiments, inhibiting CSF-1R comprises treating a disease or condition selected from the group consisting of proliferative or neoplastic disease and conditions including cancers; bone diseases or conditions; inflammatory diseases or conditions; and autoimmune diseases and conditions.

In various embodiments, the CSF-1R mediated disease or condition is selected from the group consisting of proliferative or neoplastic disease and conditions including cancers; bone diseases or conditions; and inflammatory diseases or conditions; and autoimmune diseases and conditions.

In various embodiments, the disease or condition is selected from the group consisting of proliferative or neoplastic disease and conditions including cancers.

In certain embodiments, the disease or condition is a cancer.

In various embodiments, the compound of formula (I) or pharmaceutically acceptable salt, solvate, or stereoisomer thereof or the medicament is administered or is for administration in combination with one or more anticancer agents, and/or in combination with radiation therapy.

In various embodiments, the anticancer agent is an immunomodulatory agent.

In various embodiments, the immunomodulatory agent is checkpoint inhibitor, such as an antibody checkpoint inhibitor, for example an PD-1, PDL-1, or CTLA-4 antibody, or an indoleamine dioxygenase IDO inhibitor.

In various embodiments, the pharmaceutical composition, compound of formula (I) or pharmaceutically acceptable salt, solvate, or stereoisomer thereof or medicament is administered or is for administration orally.

In various embodiments, the compound has an $IC_{50}$ value for the inhibition of CSF-1R of about 50 µM or less, for example 45, 40, 35, 30, 25, 20, 15, 10, 9, 8, 7, 6, 5, 4, or 3 µM or less.

In various embodiments, the compound has an $IC_{50}$ value for the inhibition of CSF-1R at least about 5 fold less, preferably 10, 15, 20, 25, 30, 40, 50, 75, or 100 fold less, than the $IC_{50}$ value for the inhibition of VEGFR2.

In various embodiments, the compound of formula (I) provides a reduction in the levels of CD11b positive cells and/or CD24 positive cells, for example when tested in mice with melanoma xenografts as described in the Examples, at least 40%, 50%, 60%, 70%, 80%, 90%, 95%, or 99% of the reduction provided by PLX3397.

In various embodiments, the compound of formula (I) provides a reduction in the levels of leukocytes, for example when tested in mice with melanoma xenografts as described in the Examples, at least 40%, 50%, 60%, 70%, 80%, 90%, 95%, or 99% of the reduction provided by PLX3397.

In various embodiments, the leukocytes are monocytes, macrophages, natural killer cells, and/or neutrophils.

In various embodiments, the leukocytes are macrophages.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

Although the present invention is broadly as defined above, those persons skilled in the art will appreciate that the invention is not limited thereto and that the invention also includes embodiments of which the following description gives examples.

BRIEF DESCRIPTION OF THE FIGURES

The present invention will be described with reference to the accompanying figures, in which.

DETAILED DESCRIPTION OF THE INVENTION

Definitions

Figure 1:
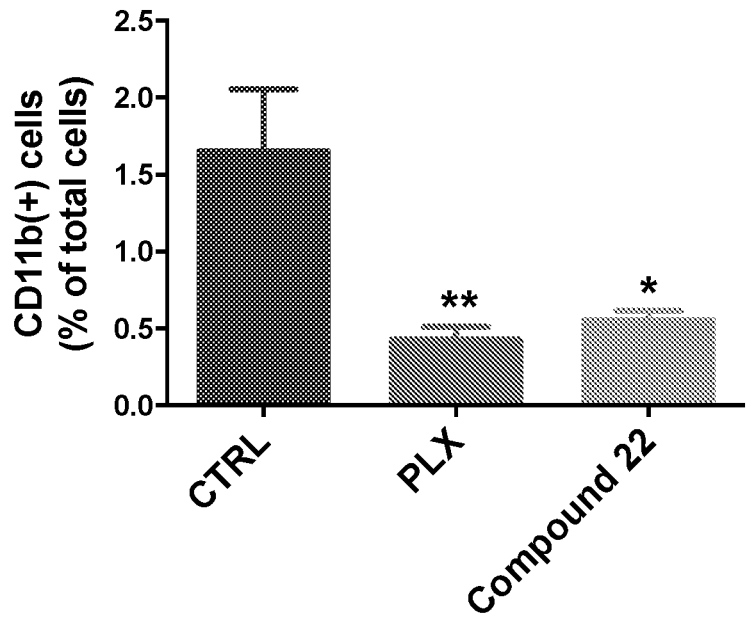
FIG. 1 is a graph showing the levels of CD11b positive cells (CD11b(+)) following treatment of mice bearing melanoma xenografts with the dimethanesulfonate salt of compound 22 of the invention ("Compound 22"), PLX3397 (Pexidartinib, "PLX"), and a control ("CTRL").

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

As used herein the term "and/or" means "and" or "or", or both.

As used herein "(s)" following a noun means the plural and/or singular forms of the noun.

The term "treatment", and related terms such as "treating" and "treat", as used herein, in the context of treating a disease or condition, relates generally to treatment, of a human or a non-human subject, in which some desired therapeutic effect is achieved. The therapeutic effect may, for example, be inhibition, reduction, amelioration, halt, or prevention of the disease or condition.

A "subject" refers to a human or a non-human animal, preferably a vertebrate that is a mammal. Non-human mammals include, but are not limited to, farm animals, such as, cattle, sheep, swine, deer, and goats; sport and companion animals, such as, dogs, cats, and horses; and research animals, such as, mice, rats, rabbits, and guinea pigs. Preferably, the subject is a human.

A "therapeutically effective amount" (or "effective amount") is an amount sufficient to effect beneficial or desired results, including clinical results. A therapeutically effective amount can be administered in one or more administrations by various routes of administration. The therapeutically effective amount of the compound to be administered to a subject depends on, for example, the purpose for which the compound is administered, mode of administration, nature and dosage of any co-administered compounds, and characteristics of the subject, such as general health, other diseases, age, sex, genotype, body weight and tolerance to drugs. A person skilled in the art will be able to determine appropriate dosages having regard to these any other relevant factors.

The general chemical terms used in the formulae herein have their usual meanings.

The term "halo" or "halogen" used alone or in combination with other terms, unless indicated otherwise, refers to F, Cl, Br, and I.

The term "alkyl" as used herein alone or in combination with other terms, unless indicated otherwise, refers to a radical of a straight-chain or branched saturated hydrocarbon group. In some embodiments, alkyl groups have from 1 to 6, from 1 to 4, from 2 to 6, from 2 to 4, from 1 to 3, or 2 or 3 carbon atoms. Such groups may be referred to herein as $C_{1-6}$alkyl, $C_{1-4}$alkyl, $C_{2-6}$alkyl, $C_{2-4}$alkyl, $C_{1-3}$alkyl, or $C_{2-3}$alkyl groups. Examples of alkyl groups include but are not limited to methyl, ethyl, n-propyl, isopropyl, n-butyl, tert-butyl, sec-butyl, iso-butyl, n-pentyl, 3-pentanyl, amyl, neopentyl, 3-methyl-2-butanyl, tertiary amyl, n-hexyl, and the like.

The term "alkylene" as used herein alone or in combination with other terms, unless indicated otherwise, refers to a diradical of an alkyl group. In some embodiments, alkylene groups have from 1 to 6, from 1 to 4, from 2 to 6, from 2 to 4, from 1 to 3, or 2 or 3 carbon atoms. Such groups may be referred to herein as $C_{1-6}$alkylene, $C_{1-4}$alkylene, $C_{2-6}$alkylene, $C_{2-4}$alkylene, $C_{1-3}$alkylene, or $C_{2-3}$alkylene groups. The radicals of an alkylene group may be on the same carbon atom or different carbon atoms of the group.

The term "aryl" as used herein alone or in combination with other terms, unless indicated otherwise, refers to a radical of a cyclic aromatic hydrocarbon group. Aryl groups include monocyclic and bicyclic ring systems. Aryl groups also include aromatic-cycloalkyl and aromatic-cycloalkenyl fused ring systems. Examples of aryl groups include, but are not limited to, phenyl, naphthyl, azulenyl, pentalenyl, indenyl, indanyl, dihydronaphthyl, tetrahydronaphthyl, and the like. In some embodiments, aryl groups have from 6 to 10 ring carbon atoms. Such groups may be referred to herein as 6 to 10-membered aryl groups. In some embodiments, aryl groups are phenyl groups.

The term "arylene" as used herein alone or in combination with other terms, unless indicated otherwise, refers to a diradical of an aryl group. In some embodiments, arylene groups have from 6 to 10 ring carbon atoms. Such groups may be referred to herein as 6 to 10-membered arylene groups. In some embodiments, arylene groups are phenylene groups, for example 1,3-phenylene or 1,4-phenylene.

The term "cycloalkyl" as used herein alone or in combination with other terms, unless indicated otherwise, refers to a radical of a cyclic saturated hydrocarbon group. Cycloalkyl groups include monocyclic, bicyclic, and tricyclic ring systems. In some embodiments, cycloalkyl groups are monocyclic or bicyclic. In certain embodiments, cycloalkyl groups are monocyclic. Examples of monocyclic cycloalkyl groups include, but are not limited to, cyclopropyl, cyclobutyl, cyclopentyl, cyclohexyl, cycloheptyl, and cyclooctyl. Bi- and tricyclic ring systems include bridged, spiro, and fused cycloalkyl ring systems. Examples of bi- and tricyclic ring cycloalkyl systems include, but are not limited to, bicyclo[2.1.1]hexanyl, bicyclo[2.2.1]heptanyl, adamantyl, and decalinyl. In some embodiments, cycloalkyl groups have from 3 to 10, from 4 to 10, from 3 to 7, from 4 to 7, from 3 to 6, from 4 to 6, from 3 to 5, 5 or 6, or 4 or 5 ring carbon atoms. Such groups may be referred to herein as 3 to 10-, 4 to 10-, 3 to 7-, 4 to 7-, 3 to 6-, 4 to 6-, 3 to 5-, 5 or 6-, or 4 or 5-membered cycloalkyl groups. In certain embodiments, cycloalkyl groups have from 3 to 10 ring carbon atoms, from 3 to 7 ring carbon atoms or from 4 to 7 ring carbon atoms. In certain specifically contemplated embodiments, cycloalkyl groups have 5 or 6 ring carbon atoms.

The term "cycloalkylene" as used herein alone or in combination with other terms, unless indicated otherwise, refers to a diradical of a cycloalkyl group. In some embodiments, cycloalkylene groups have from 3 to 10, from 4 to 10, from 3 to 7, from 4 to 7, from 3 to 6, from 4 to 6, from 3 to 5, 5 or 6, or 4 or 5 ring carbon atoms. Such groups may be referred to herein as 3 to 10-, 4 to 10-, 3 to 7-, 4 to 7-, 3 to 6-, 4 to 6-, 3 to 5-, 5 or 6-, or 4 or 5-membered cycloalkylene groups. In certain embodiments, cycloalkylene groups have from 3 to 10 ring carbon atoms, from 3 to 7 ring carbon atoms or from 4 to 7 ring carbon atoms. In certain specifically contemplated embodiments, cycloalkylene groups have 5 or 6 ring carbon atoms.

The term "cycloalkenyl" as used herein alone or in combination with other terms, unless indicated otherwise, refers to a radical of a non-aromatic cyclic hydrocarbon group having at least one double bond between two ring carbon atoms. Cycloalkenyl groups include monocyclic, bicyclic, and tricyclic ring systems. In some embodiments, cycloalkenyl groups are monocyclic or bicyclic. In certain embodiments, cycloalkenyl groups are monocyclic. In some embodiments, cycloalkenyl groups have from 3 to 10, from 4 to 10, from 3 to 7, from 4 to 7, from 3 to 6, from 4 to 6, from 3 to 5, 5 or 6, or 4 or 5 ring carbon atoms. Such groups may be referred to herein as 3 to 10-, 4 to 10-, 3 to 7-, 4 to 7-, 3 to 6-, 4 to 6-, 3 to 5-, 5 or 6-, or 4 or 5-membered cycloalkenyl groups. In certain embodiments, cycloalkenyl groups have from 3 to 7 ring carbon atoms or from 4 to 7 ring carbon atoms. In certain specifically contemplated embodiments, cycloalkenyl groups have 5 or 6 ring carbon atoms. Examples of cycloalkenyl groups include, but are not limited to, cyclohexenyl, cyclopentenyl, cyclohexadienyl, and the like.

The term "heterocyclyl" as used herein alone or in combination with other terms, unless indicated otherwise, refers to a radical of a non-aromatic ring system containing 4 or more ring atoms of which one or more is a heteroatom selected from nitrogen, oxygen, and sulfur. In some embodiments, the heterocyclyl group contains from one to three ring heteroatoms selected from nitrogen, oxygen, and sulfur. In some embodiments, at least one of the ring heteroatoms is nitrogen. Nitrogen and sulfur heteroatoms in the ring(s) may be in present in oxidised form. For example, a tertiary ring nitrogen atom may be present as an N-oxide and a sulfur ring heteroatom may be present as a sulfinyl or sulfonyl. Heterocyclyl groups include monocyclic, bicyclic, and tricyclic ring systems. In some embodiments, heterocyclyl groups are monocyclic or bicyclic. In certain embodiment, heterocyclyl groups are monocyclic. In some embodiments, heterocyclyl groups have from 4 to 10, from 4 to 8, from 4 to 7, from 4 to 6, or 5 or 6 ring atoms. Such groups may be referred to herein as 4 to 10-, 4 to 8-, 4 to 7-, 4 to 6-, or 5 or 6-membered heterocyclyl groups. In certain embodiments, heterocyclyl groups have from 4 to 10 ring atoms or from 4 to 7 ring atoms. In certain specifically contemplated embodiments, heterocyclyl groups have 5 or 6 ring atoms. Heterocyclyl groups include partially unsaturated and saturated ring systems, for example, imidazolinyl and imidazolidinyl. Heterocyclyl groups include fused, spiro and bridged ring systems containing a heteroatom, for example, 2-oxa-6-azaspiro[3.3]heptyl, 2,6-diazaspiro[3.3]heptyl, quinuclidyl, and the like. Examples of heterocyclyl groups include, but are not limited to, azetidinyl, azepanyl, diazepanyl, 1,3-dioxanyl, 1,3-dioxolanyl, isoxazolidinyl, morpholinyl, piperazinyl, piperidinyl, pyranyl, pyrazolidinyl, pyrrolinyl, pyrrolidinyl, tetrahydrofuranyl, tetrahydrothienyl, thiadiazolidinyl, trithianyl, and the like.

The term "heterocyclylene" as used herein alone or in combination with other terms, unless indicated otherwise, refers to a diradical of a heterocyclyl group. In some embodiments, heterocyclylene groups have from 4 to 10, from 4 to 8, from 4 to 7, from 4 to 6, or 5 or 6 ring atoms. Such groups may be referred to herein as 4 to 10-, 4 to 8-, 4 to 7-, 4 to 6-, or 5 or 6-membered heterocyclylene groups. In certain embodiments, heterocyclyl groups have from 4 to 10 ring atoms or from 4 to 7 ring atoms. In certain specifically contemplated embodiments, heterocyclyl groups have 5 or 6 ring atoms.

The term "heteroaryl" as used herein alone or in combination with other terms, unless indicated otherwise, refers to a radical of an aromatic ring system containing 5 or more ring atoms of which one or more is a heteroatom selected from nitrogen, oxygen, and sulfur. In some embodiments, heteroaryl groups comprise from one to three ring heteroatoms selected from nitrogen, oxygen, and sulfur. In some embodiments, at least one of the ring heteroatoms is nitrogen. Nitrogen and sulfur heteroatoms in the ring(s) may be in present in oxidised form. For example, a tertiary ring nitrogen atom may be present as an N-oxide and a sulfur ring heteroatom may be present as a sulfinyl or sulfonyl. Heteroaryl groups include monocyclic and bicyclic ring systems. In certain embodiments, heteroaryl groups are monocyclic. Heteroaryl groups include fused ring systems in which all of the rings are aromatic, for example, indolyl, and fused ring systems in which only one of the rings is aromatic, for example, 2,3-dihydroindolyl. Examples of heteroaryl groups include, but are not limited to, pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, pyrazolopyridinyl, triazolopyridinyl, benzotriazolyl, benzoxazolyl, benzothiazolyl, imidazopyridinyl, isoxazolopyridinylxanthinyl, guaninyl, quinolinyl, isoquinolinyl, tetrahydroquinolinyl, quinoxalinyl, and quinazolinyl. In some embodiments, heteroaryl groups have from 5 to 10, from 5 to 8, or 5 or 6 ring atoms. Such groups may be referred to herein as 5 to 10-, 5 to 8-, or 5 or 6-membered heteroaryl groups. In certain embodiments, heteroaryl groups have from 5 to 10 or 5 or 6 ring atoms. In certain embodiments, heteroaryl groups have 5 or 6 ring atoms.

The term "heteroarylene" as used herein alone or in combination with other terms, unless indicated otherwise, refers to a diradical of a heteroaryl group. In some embodiments, heteroarylene groups have from 5 to 10 ring atoms, from 5 to 8, or from 5 or 6 ring atoms. Such groups may be referred to herein as 5 to 10-, 5 to 8-, or 5 or 6-membered heteroarylene groups. In certain embodiments, heteroarylene groups have from 5 to 10 or 5 or 6 ring atoms. In certain embodiments, heteroarylene groups have 5 or 6 ring atoms.

As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound. Suitable substituents include the optional substituents indicated herein.

The term "stable" as used herein refers to compounds which possess stability sufficient to allow manufacture and which maintain their integrity for a period of time sufficient to be useful for the purposes described herein.

Asymmetric or chiral centers may exist in the compounds of the invention. Asymmetric or chiral centers may be designated as (R) or (S), depending on the configuration of substituents in three dimensional space at the chiral atom. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are included herein.

Individual enantiomers can be prepared synthetically from commercially available enantiopure starting materials or by preparing enantiomeric mixtures and resolving the mixture into individual enantiomers. Resolution methods include conversion of the enantiomeric mixture into a mixture of diastereomers and separation of the diastereomers by, for example, recrystallization or chromatography, and any other appropriate methods known in the art. Starting materials of defined stereochemistry may be commercially available or made and, if necessary, resolved by techniques well known in the art.

The compounds of the invention may also exist as conformational or geometric stereoisomers, including cis, trans, syn, anti, entgegen (E), and zusammen (Z) isomers. All such stereoisomers and any mixtures thereof are within the scope of the invention. Also within the scope of the invention are any tautomeric isomers or mixtures thereof of the compounds of the invention. As would be appreciated by those skilled in the art, a wide variety of functional groups and other structures may exhibit tautomerism. Examples include, but are not limited to, keto/enol, imine/enamine, and thioketone/enethiol tautomerism.

The compounds of the invention may also exist as isotopologues and isotopomers, wherein one or more atoms in the compounds are replaced with different isotopes. Suitable isotopes include, for example, 1H, $^2$H (D), $^3$H (T), $^{12}$C, $^{13}$C, $^{14}$C, $^{16}$O, and $^{18}$O. Procedures for incorporating such isotopes into the compounds will be apparent to those skilled in the art. Isotopologues and isotopomers of the compounds are also within the scope of the invention.

Also within the scope of the invention are pharmaceutically acceptable salts of the compounds of the invention. Such salts include, acid addition salts, base addition salts, and quaternary salts of basic nitrogen-containing groups.

Acid addition salts can be prepared by reacting compounds, in free base form, with inorganic or organic acids. Examples of inorganic acids include, but are not limited to, hydrochloric, hydrobromic, nitric, sulfuric, and phosphoric acid. Examples of organic acids include, but are not limited to, acetic, trifluoroacetic, propionic, succinic, glycolic, lactic, malic, tartaric, citric, ascorbic, maleic, fumaric, pyruvic, aspartic, glutamic, stearic, salicylic, methanesulfonic, benzenesulfonic, isethionic, sulfanilic, adipic, butyric, and pivalic. Base addition salts can be prepared by reacting compounds, in free acid form, with inorganic or organic bases. Examples of inorganic base addition salts include alkali metal salts, alkaline earth metal salts, and other physiologically acceptable metal salts, for example, aluminium, calcium, lithium, magnesium, potassium, sodium, or zinc salts. Examples of organic base addition salts include amine salts, for example, salts of trimethylamine, diethylamine, ethanolamine, diethanolamine, and ethylenediamine. Quaternary salts of basic nitrogen-containing groups in the compounds may be may be prepared by, for example, reacting the compounds with alkyl halides such as methyl, ethyl, propyl, and butyl chlorides, bromides, and iodides, dialkyl sulfates such as dimethyl, diethyl, dibutyl, and diamyl sulfates, and the like.

N-Oxides of the compounds of the invention are also within the scope of the present invention.

The compounds of the invention may form or exist as solvates with various solvents. If the solvent is water, the solvate may be referred to as a hydrate, for example, a mono-hydrate, a di-hydrate, or a tri-hydrate. All solvated forms and unsolvated forms of the compounds are within the scope of the invention.

Compounds of the Invention and Therapeutic Methods

The present invention relates to tricyclic heterocyclic compounds of formula (I) as defined herein, and pharmaceutically acceptable salts, solvates, and stereoisomers thereof:

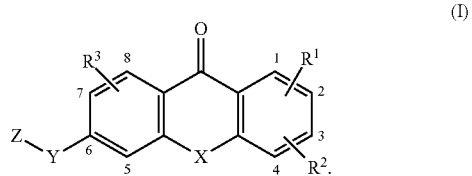

(I)

It will be appreciated by those skilled in the art that numbering system indicated in formula (I) is used herein for convenience and that this numbering system may differ from the numbering in systematic names of compounds of formula (I) depending on the relative priority of the various substituents attached to the tricyclic core.

The inventors have surprisingly found that the compounds of formula (I) have useful inhibitory activity against CSF-1R (c-FMS).

The inventors have also surprisingly found that in certain embodiments compounds of formula (I) have selective inhibitory activity against CSF-1R compared to other kinases, for example VEGFR-2. VEGFR-2 is a tyrosine kinase receptor closely related to CSF-1R but is not known to target macrophage inhibition. Without wishing to be bound by any theory, the inventors believe that this selectivity for CSF-1R (for example, over VEGFR-2) may translate to lower off-target clinical toxicity.

The term "selective" as used herein with reference to the inhibition of a target refers to the ability of a compound to preferentially inhibit the activity of the target as compared to off-target activity. "Selective" inhibition is not intended mean complete absence of off-target inhibitory activity.

The inhibitory activity of compounds of formula (I) against kinases such as CSF-1R and VEGFR-2 may be determined using assays well known in the art, such as those described in the Examples below. Compounds of formula (I) may have an $IC_{50}$ value for the inhibition of CSF-1R of about 50 µM or less, for example 45, 40, 35, 30, 25, 20, 15, 10, 9, 8, 7, 6, 5, 4, or 3 µM or less, as measured by the method outlined the Examples below. Compounds of formula (I) may also have an $IC_{50}$ value for the inhibition of CSF-1R at least about 5 fold less, preferably 10, 15, 20, 25, 30, 40, 50, 75, or 100 fold less, than the $IC_{50}$ value for the inhibition of VEGFR2.

The present invention also relates to methods of, compounds for use in, and uses of the compounds of formula (I) in the manufacture of medicaments for inhibiting CSF-1R and treating diseases and conditions mediated by CSF-1R. Examples of diseases and conditions mediated by CSF-1R include, but are not limited to, proliferative or neoplastic diseases and conditions such as cancers and bone, inflammatory, and autoimmune diseases or conditions. Thus, the present invention also relates to methods of, compounds for use in, and uses of the compounds of formula (I) in the manufacture of medicaments for treating a disease or condition is selected from the group consisting of proliferative or neoplastic disease and conditions including cancers; bone diseases or conditions; inflammatory diseases or conditions; and autoimmune diseases and conditions. Such diseases and conditions include, but are not limited to, those described in WO 2007/121484 and the scientific literature referred to therein, all of which are incorporated herein by reference.

The term "proliferative" as used herein with reference to a disease or condition refers to a disease or condition characterised by abnormal cellular growth and proliferation, including neoplastic diseases and conditions. The term "neoplastic" as used herein with reference to a disease or condition refers to a disease or condition characterised by neoplastic cell growth, including benign tumours and malignant tumours such as carcinomas, sarcomas, leukemias, neurofibromatosis, and the like.

In some embodiments, the disease or condition is selected from the group consisting of breast cancer, colon cancer, hairy cell leukemia, Hodgkin's lymphoma, lung cancer, ovarian cancer, prostate cancer, stomach cancer, uterine cancer, melanoma, glioblastoma, multiple myeloma, bone cancer, including metastatic bone cancer, lymphoma, acute myeloid leukaemia, chronic myelocytic leukemia, bladder cancer, cervical cancer, endometrial cancer, gastric cancer, idiopathic myelofibrosis, Kaposi's sarcoma, liver cancer, kidney cancer, myelodysplasia, metastases of such cancers, tenosynovial giant cell tumours, neoplasia, cancer cell growth, tumour growth, tumour metastasis, tumour angiogenesis, arthritis, including rheumatoid arthritis, collagen-induced arthritis, and inflammatory arthritis, systemic lupus erythematosus, inflammatory bowel disease, Crohn's disease, asthma, pigmented villonodular synovitis, psoriasis, ulcerative colitis, ostealgia, multiple sclerosis, allograft rejection, arteriosclerosis, atherosclerosis, sarcoidosis, glomerulonephritis, including chronic glomerular nephritis, encephalomyelitis, osteoporosis, bone resorption, bone loss due to cancer chemotherapy, chronic inflammation, endometriosis, glucocorticoid-induced osteoporosis, histiocytosis X, inflammation, osteolytic bone lesions, osteolytic bone disease, Paget's disease of bone, periodontitis, periprosthetic osteolysis, prostatitis, psiratic arthritis, and schistosomiasis.

In certain embodiments, the disease or condition is selected from the group consisting of breast cancer, colon cancer, hairy cell leukemia, Hodgkin's lymphoma, lung cancer, ovarian cancer, prostate cancer, stomach cancer, uterine cancer, melanoma, glioblastoma, multiple myeloma, bone cancer, including metastatic bone cancer, lymphoma, acute myeloid leukaemia, chronic myelocytic leukemia, bladder cancer, cervical cancer, endometrial cancer, gastric cancer, idiopathic myelofibrosis, Kaposi's sarcoma, liver cancer, kidney cancer, myelodysplasia, metastases of such cancers, tenosynovial giant cell tumours, neoplasia, cancer cell growth, tumour growth, tumour metastasis, and tumour angiogenesis.

In certain embodiments, the disease or condition is selected from the group consisting of arthritis (including rheumatoid arthritis), systemic lupus erythematosus (SLE), inflammatory bowel disease (IBD), Crohn's disease, asthma, and pigmented villonodular synovitis bone resorption, bone loss due to cancer chemotherapy, chronic inflammation, endometriosis, glucocorticoid-induced osteoporosis, histiocytosis X, inflammation, neoplasia, osteolytic bone lesions, osteolytic bone disease, Paget's disease of bone, periodontitis, periprosthetic osteolysis, prostatitis, psiratic arthritis, schistosomiasis, and osteoclastogenesis.

In various embodiments, the disease or condition is cancer. In some embodiments, disease or condition is lung cancer, non small cell lung (NSCL) cancer, bronchioloalviolar cell lung cancer, bone cancer, metastatic bone cancer, pancreatic cancer, skin cancer, cancer of the head or neck, melanoma, cutaneous or intraocular melanoma, uterine cancer, ovarian cancer, rectal cancer, cancer of the anal region, stomach cancer, gastric cancer, colon cancer, breast cancer, carcinoma of the fallopian tubes, carcinoma of the endometrium, carcinoma of the cervix, carcinoma of the vagina, carcinoma of the vulva, Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cancer, renal cell carcinoma, carcinoma of the renal pelvis, mesothelioma, hepatocellular cancer, biliary cancer, neoplasms of the central nervous system (CNS), spinal axis tumors, brain stem glioma, glioblastoma, glioblastoma multiforme, astrocytomas, schwanomas, ependymonas, medulloblastomas, meningiomas, squamous cell carcinomas, pituitary adenoma, lymphoma, lymphocytic leukemia, multiple myeloma, acute myeloid leukaemia, myelocytic leukemia, including chronic myelocytic leukemia, idiopathic myelofibrosis, myelodysplasia, Kaposi's sarcoma, cervical cancer, ovarian cancer, endometrial cancer, prostate cancer, hepatocellular cancer, refractory and metastatic versions of any of the above cancers, or a combination of one or more of the above cancers. In some embodiments, treatment may comprise treating primary tumours and new metastasis simultaneously.

In various embodiments, the CSF-1R mediated disease or condition is a bone, inflammatory, or autoimmune disease or condition. Examples of such diseases or conditions include but are not limited to periodontitis, histiocytosis X (also known as Lagerhans cell histiocytosis), osteoporosis, Paget's disease of bone (PDB), bone loss due to cancer therapy, periprosthetic osteolysis, glucocorticoid-induced osteoporosis, arthritis, rheumatoid arthritis, psiratic arthritis, osteoarthritis, inflammatory arthridities, inflammation, systemic lupus erythematosus (SLE), inflammatory bowel disease (IBD), Crohn's disease, ulcerative colitis (UC), asthma, and pigmented villonodular synovitis, atherosclerosis, chronic glomerular nephritis, bone resorption, chronic inflammation, endometriosis, osteolytic bone lesions, osteolytic bone disease, prostatitis, schistosomiasis, and osteoclastogenesis.

In some embodiments, the method is for reducing or preventing tumour growth and/or metastasis. In some embodiments, the method is for reducing or preventing osteoclastogenesis, bone resorption, and/or bone lesions. In some embodiments, the method is for inhibiting the growth of cancer cells.

In some embodiments, the disease or condition is cancer, osteoporosis, arthritis, atherosclerosis and chronic glomerular nephritis. In certain embodiments, the disease or condition is a cancer selected from the group consisting of myelocytic leukemia, idiopathic myelofibrosis, breast cancer, cervical cancer, ovarian cancer, endometrial cancer, prostate cancer, hepatocellular cancer, multiple myeloma, lung cancer, renal cancer, and bone cancer. In certain embodiments, the disease or condition is rheumatoid arthritis.

The present invention also relates to a method of inhibiting CSF-1R comprising contacting a cell with a compound of the formula (I), or a pharmaceutically acceptable salt, solvate, or stereoisomer thereof in an amount effective to inhibit CSF-1R. The cell may in vivo, in vitro, or ex vivo. In certain embodiments where the cell is in vivo, the cell may be contacted with the compound by administering the compound to a subject. Methods of inhibiting CSF-1R in a cell in vitro or ex vivo may be useful, for example, in a variety of diagnostic tests or laboratory research. For use in vitro or ex vivo, compound concentrations of from about 0.1 nM to 1 mM may be suitable depending on the application.

Pharmaceutical Compositions

The present invention further relates to a pharmaceutical composition comprising a compound of the formula (I) or a pharmaceutically acceptable salt, solvate, or stereoisomer thereof; and a pharmaceutically acceptable carrier.

The term "pharmaceutically acceptable carrier" refers to a carrier (e.g. adjuvant or vehicle) that may be administered to a subject together with the compound of the formula (I), or a pharmaceutically acceptable salt, solvate, or stereoisomer thereof, which is generally safe, non-toxic, and neither biologically nor otherwise undesirable, including carriers suitable veterinary as well as human pharmaceutical use.

Pharmaceutically acceptable carriers that may be used in the compositions include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives may also be advantageously used to enhance delivery. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

The compositions are formulated to allow for administration to a subject by any chosen route, including but not limited to oral or parenteral (including topical, subcutaneous, intramuscular and intravenous) administration. For example, the compositions may be formulated with an appropriate pharmaceutically acceptable carrier (including excipients, diluents, auxiliaries, and combinations thereof) selected with regard to the intended route of administration and standard pharmaceutical practice. For example, the compositions may be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of the composition. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Examples of dosage forms suitable for transdermal administration include, but are not limited, to transdermal patches, transdermal bandages, and the like.

Examples of dosage forms suitable for topical administration of the compositions include any lotion, stick, spray, ointment, paste, cream, gel, etc., whether applied directly to the skin or via an intermediary such as a pad, patch or the like. Examples of dosage forms suitable for suppository administration of the compositions include any solid dosage form inserted into a bodily orifice particularly those inserted rectally, vaginally and urethrally.

Examples of dosage of forms suitable for injection of the compositions include delivery via bolus such as single or multiple administrations by intravenous injection, subcutaneous, subdermal, and intramuscular administration or oral administration. Examples of dosage forms suitable for depot administration of the compositions include pellets or solid forms wherein the active(s) are entrapped in a matrix of biodegradable polymers, microemulsions, liposomes or are microencapsulated.

Examples of infusion devices for the compositions include infusion pumps for providing a desired number of doses or steady state administration, and include implantable drug pumps. Examples of implantable infusion devices for compositions include any solid form in which the active(s) are encapsulated within or dispersed throughout a biodegradable polymer or synthetic, polymer such as silicone, silicone rubber, silastic or similar polymer. Examples of dosage forms suitable for transmucosal delivery of the compositions include depositories solutions for enemas, pessaries, tampons, creams, gels, pastes, foams, nebulised solutions, powders and similar formulations containing in addition to the active ingredients such carriers as are known in the art to be appropriate. Such dosage forms include forms suitable for inhalation or insufflation of the compositions, including compositions comprising solutions and/or suspensions in pharmaceutically acceptable, aqueous, or organic solvents, or mixture thereof and/or powders. Transmucosal administration of the compositions may utilize any mucosal membrane but commonly utilizes the nasal, buccal, vaginal and rectal tissues. Formulations suitable for nasal administration of the compositions may be administered in a liquid form, for example, nasal spray, nasal drops, or by aerosol administration by nebulizer, including aqueous or oily solutions of the polymer particles. Formulations may be prepared as aqueous solutions for example in saline, solutions employing benzyl alcohol or other suitable preservatives, absorption promoters to enhance bio-availability, fluorocarbons, and/or other solubilising or dispersing agents known in the art.

Examples of dosage forms suitable for buccal or sublingual administration of the compositions include lozenges, tablets and the like. Examples of dosage forms suitable for opthalmic administration of the compositions include inserts and/or compositions comprising solutions and/or suspensions in pharmaceutically acceptable, aqueous, or organic solvents.

Examples of formulations of compositions may be found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C, Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of oral dosage forms, including those formulated as tablets or capsules. See, for example, The United States Pharmacopeia 23/National Formulary 18, The United States Pharmacopeial Convention, Inc., Rockville Md., 1995 (hereinafter "the USP").

The dosage forms described herein can be in the form of physically discrete units suitable for use as unitary dosages for the subjects to be treated, each unit containing a predetermined quantity of active material calculated to produce the desired therapeutic effect.

Dosage levels of the active ingredients in the pharmaceutical compositions may be varied so as to provide an amount of the active ingredient which is effective to achieve the desired therapeutic effect for a particular patient, composition, and mode of administration, without being toxic to the patient (an effective amount).

The selected dosage level will depend upon a variety of pharmacokinetic factors including the activity of the particular compositions employed, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

Depending on the cells being targeted or the type and severity of the disease or condition, dosages of from about 0.01 mg/kg to 500 mg/kg per day may be suitable, for example 0.1 mg/kg to 250 mg/kg, 0.1 mg/kg to 100 mg/kg, 0.1 mg/kg to 50 mg/kg, or 0.1 mg/kg to 20 mg/kg per day may be suitable.

Kits

The present invention also provides a kit comprising a compound of formula (I) or a pharmaceutically acceptable salt, solvate, or stereoisomer thereof; and optionally instructions for use. The present invention also provides a kit comprising a compound of the formula (I), or a pharmaceutically acceptable salt, solvate, or stereoisomer thereof; one or more additional therapeutic agents; and optionally instructions for use.

The compound of formula (I), or a pharmaceutically acceptable salt, solvate, or stereoisomer thereof is typically in the form of a pharmaceutical composition, and contained within a container. The instructions for use may describe the method(s) of treatment in which the compounds are administered. In various embodiments, the instructions for use describe methods of treating the diseases and conditions indicated herein.

The container may be any vessel or other sealed or sealable apparatus that can hold the pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form and is made of a pharmaceutically acceptable material, for example a paper or cardboard box, a glass or plastic bottle or jar, a re-sealable bag, or a blister pack with individual doses for pressing out of the pack according to a therapeutic schedule. The container employed typically depends on the dosage form involved. More than one container can be used together in a single package for a single dosage form.

The kits may also comprise a device to administer or to measure out a unit dose of the pharmaceutical composition. The device may include, for example, an inhaler if the composition is an inhalable composition; a syringe and needle if the composition is an injectable composition; a syringe, spoon, pump, or a vessel with or without volume markings if the composition is an oral liquid composition; or any other measuring or delivery device appropriate to the dosage formulation of the composition present in the kit.

In various embodiments, the kits may comprise, for example in a separate vessel or container, one or more additional therapeutic agent, typically in the form of a pharmaceutical composition comprising the additional therapeutic agent and a pharmaceutically acceptable carrier. The additional therapeutic agent may be selected from any of those indicated herein for co-administration with a compound of formula (I), or a pharmaceutically acceptable salt, solvate, or stereoisomer thereof.

Combination Therapy

The compound of formula (I) can be administered as the sole therapeutic agent or in combination with one or more other additional therapeutic agents, for example one or more anti-cancer agents.

The compounds can also be administered in combination with radiation therapy. The terms "radiation therapy" and "radiotherapy" are used interchangeably herein. Radiation therapy is a standard treatment for controlling unresectable or inoperable tumours and/or tumour metastases. The radiation dosage regimen is generally defined in terms of radiation absorbed dose (Gy), time and fractionation, and must be carefully defined by the oncologist. The amount of radiation a patient receives will depend on various considerations, but the two most important are the location of the tumour in relation to other critical structures or organs of the body, and the extent to which the tumour has spread. The type of radiation used may include X-rays, gamma rays, alpha particles, beta particles, photons, electrons, neutrons, radioisotopes, and other forms of ionizing radiation.

The compound may be administered simultaneously, sequentially, or separately with the one or more additional therapeutic agents and/or radiation therapy. The compound and one or more additional therapeutic agents may be administered as single formulation or as separate formulations.

In some embodiments, the one or more additional therapeutic agents are anti-cancer agents, for example one or more chemotherapeutic agents and/or one or more immunomodulatory agents.

Suitable anticancer agents will be apparent to those skilled in the art having regard, for example to the cancer to be treated. Numerous anticancer agents are known in the art. Examples of suitable anticancer agents include those listed in Cancer: Principles and Practice of Oncology, 7th Edtion, Devita et al, Lippincott Williams & Wilkins, 2005, which is incorporated herein by reference.

Examples of suitable anticancer agents also include those listed in the Merck Index, 14$^{th}$ Edition, 2006, which is incorporated herein by reference. Such anticancer agents include but are not limited to alkaloids and natural products, including camptothecin derivatives for example 9-aminocamptothecin, exatecan, irinotecan rubitecan and topotecan, podophyllum derivatives for example etoposide and teniposide, taxanes for example docetaxel, paclitaxel and paclitaxel poliglumex, vinca alkaloids for example vinblastine, vincristine, vindesine, vinflunine and vinorelbine, and others for example aplidine, elliptinium acetate, irofulven, ixabepilone, kahalalide F, midostaurin and trabectedin; alkylating agents, including alkyl sulfonates for example busulfan, improsulfan and piposulfan, aziridines for example carboquone, diaziquone and uredepa, ethylenimines and methylmelamines for example altretamine, triethylenemelamine, triethylenephosphoramide and triethylenethiophosphoramide, nitrogen mustards for example bendamustine, canfosfamide, chlorambucil, chlornaphazine, cyclophosamide, estramustine, glufosfamide, ifosfamide, mechlorethamine, mechlorethamine oxide hydrochloride, melphalan, perfosfamide, prenimustine, trichlormethine, trofosfamide, and uracil mustard, nitrosoureas for example carmustine, chlorozotocin, fotemustine, lomustine, nimustine and ranimustine, and others for example dacarbazine, etoglucid, mitobronitol, mitolactol, pipobroman, procarbazine and temozolomide; antibiotics and analogs, including actinomycins for example cactinomycin and dactinomycin, anthracyclines for example aclacinomycins, amrubicin, carubicin, daunorubicin, doxorubicin, epirubicin, idarabicin, pirarubicin, valrubicin and zorubicin, and others for example bleomycins, mitomycins, peplomycin, plicamycin, porfiromycin, streptozocin, temsirolimus and zinostatin; antimetabolites, including folic acid analogs and antagonists for example denopterin, edatrexate, methotrexate, nolatrexed, pemetrexed, piritrexi, pteropterin, raltitrexed and trimetrexate, purine analogs for example cladribine, clofarabine, fludarabine, 6-mercaptopurine, nelarabine, thiamiprine, thioguanine and tiazofurine, and pyrimidine analogs for example ancitabine, azacitidine 6-azauridine, capecitabine, carmofur, cytarabine, decitabine, doxifluridine, enocitabine, floxuridine, fluorouracil, gemcitabine, tegafur andtroxacitabine; enzymes for example L-asparaginase and ranpirnase; farnesyl transferase inhibitors for example lonafarnib, tipifarnib; immunomodulators for example aldesleukin, interferon-α, interferon-γ, lentinan, mepact, oregovomab, propagermanium, PSK®, roquinimex, sipuleucel-T, sizofiran, teceleukin and ubenimex; immunotoxins for example cintredekin besudotox and denileukin diftitox; monoclonal antibodies for example alemtuzumab, bevacizumab, cetuximab, edrecolomab, epratuzumab, gemtuzumab, ozogamicin, oregovomab, panitumumab, rituximab, tositumomab $^{131}$I and trastuzumab; oligonucleotides for example aprinocarsen and oblimersen sodium; platinum complexes for example carboplatin, cisplatin, lobaplatin, oxaliplatin, picoplatin and satraplatin; retinoids and analogs for example alitretinoin, bexarotene, fenretinidem, mofarotene and tarnibarotene; tyrosine kinase inhibitors for example canertinib, dasatinib, erlotinib, gefitinib, imatinib, lapatinib, sorafenib, sunitinib and vatalanib; and others for example amsacrine, arsenic trioxide, atrasentan, bisantrene, bortezomib, brostallicin, calcitriol, edotecarin, eflornithine, flavopiridol, gallium nitrate, hydroxyurea, liarozole, lonidamine, miltefosine, mitoguazone, mitoxantrone, nitracrine, pentostatin, perifosine, pixantrone, razoxane, seocalcitol, sobuzoxane, spirogermanium, tirapazamine and vorinostat. Such anticancer agents also include without limitation antineoplastic hormonal agents including androgens for example dromostanolone, epitiostanol, mepitiostane and testolactone; antiadrenals for example aminoglutethimide, mitotane, trilostane; antiandrogens, bicalutainide, flutamide and nilutamide; antiestrogens for example arzoxifene, droloxifene, fulvestrant, idoxifene, tamoxifen and toremifene; antiprogestins for example onapristone; aromatase inhibitors for example aminoglutethimide, anastrozole, exemestane, fadrozole, formestane, letrozole and vorozole; estrogens for example diethylstilbestrol, fosfestrol, hexestrol and polyestradiol phosphate; LH-RH analogs for example abarelix, buserelin, cetrorelix, goserelin, leuprolide and triptorelin; progestogens for example chlormadinone acetate, medroxyprogesterone and megestrol acetate; and somatostatin analogs for example lanreotide. Such anticancer agents also include without limitation antineoplastic photosensitisers for example 6-aminolevulinic acid, methyl aminolevulinate, motexafin lutetium, porfimer sodium, talaporfin and temoporfin.

Examples of suitable anticancer agents also include those described in WO 2007/121484, which is incorporated herein by reference, including but not limited to estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, and agents that interfere with cell cycle checkpoints.

In certain embodiments, the additional therapeutic agent is selected from cisplatin (Platinol), carboplatin (Paraplatin), oxaliplatin (Eloxatin), daunomycin/daunorubicin, (DanuoXome, Cerubidine), doxorubicin (Adriamycin, Rubex), epirubicin (Ellence), idarubicin (Idamycin), valrubicin (Valstar), mitoxantrone (Novantrone), paclitaxel (Taxol), docetaxel (Taxotere) and cyclophosphamide (Cytoxan), aspirin, sulindac, curcumin, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); thylenimines/methylmelamine such as triethylenemelamine (TEM), triethylene, thiophosphoramide (thiotepa), hexamethylmelamine (HMM, altretamine); alkyl sulfonates such as busulfan; triazines such as dacarbazine (OTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase. In some embodiments the chemotherapeutic agent is selected from the group consisting of taxanes e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In some embodiments the chemotherapeutic agent is selected from the group consisting oftaxanes (like e.g. taxol (paclitaxel), docetaxel (Taxotere), modified paclitaxel (e.g. Abraxane and Opaxio). In some embodiments the chemotherapeutic agent is selected from 5-fluorouracil (5-FU), leucovorin, irinotecan, or oxaliplatin. In some embodiments the chemotherapeutic agent is 5-fluorouracil, leucovorin and irinotecan (FOL- FIRI). In some embodiments the chemotherapeutic agent is 5-fluorouracil, and oxaliplatin (FOLFOX).

In some embodiments, the additional therapeutic agent is selected from a CTLA4 agent (e.g., ipilimumab (BMS)); GITR agent (e.g., MK-4166 (MSD)); vaccines (e.g., Nanovacc (MerckSerono), Stimuvax (MerckSerono), Sipuleucel-T (Dendron); or a SOC agent (e.g., radiation, docetaxel, Temozolomide (MSD), Gemcitibine, or Paclitaxel). In some embodiments, the additional therapeutic agent is an immune enhancer such as a vaccine, immune-stimulating antibody, immunoglobulin, agent or adjuvant including, but not limited to, sipuleucel-t (Provenge), BMS-663513 (Bristol-Myers Squibb), CP-870893 (Pfizer/VLST), anti-OX40 (AgonOX), or CDX-1127 (CellDex).

In some embodiments, the additional therapeutic agent is an anti-PD-1 or anti-PD-L1 agent. In certain embodiments, the anti-PD-1 or anti-PD-L1 is administered as an intravenous infusion.

In certain embodiments, the anticancer agent is an immunomodulatory agent. Immunomodulatory agents include agents that elicit or amplify an immune response (activation immunotherapy) and agents that reduce or suppress an immune response (suppression immunotherapy). Examples of immunomodulatory agents suitable for use in combination as described herein include, but are not limited to, antibodies, such as monoclonal antibodies, immune effector cells, adoptive cell transfers, vaccines, cytokines, and immune checkpoint inhibitors, such as antibodies targeted against CTLA4, PD-1 or PD-L1.

Antibodies include monoclonal antibodies, including monoclonal antibody drug conjugates, and polyclonal antibodies. Examples of such antibodies include, but not limited to, alemtuzumab, bevacizumab, brentuximab vedotin, cetuximab, gemtuzumab ozogamicin, ibritumomab tiuxetan, ofatumumab, panitumumab, rituximab, tositumomab, and trastuzumab.

Immune effector cells include lymphocytes, macrophages, dendritic cells, natural killer cells, lymphokine activated killer cells, cytotoxic T lymphocytes, and the like. Such cells are either activated in vivo by administering certain cytokines, such as interleukins, or they are isolated, enriched and transfused to the subject. The immune cells are highly cytotoxic to the cancer cells.

Adoptive cell transfer typically uses T-cell-based cytotoxic responses to attack cancer cells. T-cells having a natural or genetically engineered reactivity to a subject's cancer are generated in vitro and then transferred back to the subject. This process can be achieved by taking T-cells associated with a particular tumor of the subject that are trained to attack the cancerous cells. Such T-cells are referred to as tumor-infiltrating lymphocytes (TIL) and are encouraged to multiply in vitro using high concentrations of IL-2, anti-CD3, and allo-reactive feeder cells for example. The T-cells can be transferred back into the subject along with exogenous administration of IL-2 to further boost their anti-cancer activity.

Cancer vaccines include, but are not limited to, tumor cell vaccines, including autologous and allogeneic tumor cell vaccines; antigen vaccines; dendritic cell vaccines; anti-idiotype vaccines; DNA vaccines, and vector-based vaccines, including vector-based antigen vaccines and vector-based DNA vaccines. A non-limiting example of cancer vaccine is Sipuleucel-T (Provenge®), which is used to treat advanced prostate cancer.

Examples of cytokines include but are not limited to interleukins (ILs) and interferons (IFNs), such as IL-2, IFN-alpha, IFN-beta, and IFN-gamma.

Examples of immune checkpoint inhibitors include but are not limited to anti-CTLA4 antibodies (such as ipilimumab and tremelimumab), anti-PD-1 antibodies (such as nivolumab [also known as MDX-1106 or BMS-936558], MK3475, CT-011 and AMP-224), and antibodies against PDL1 (PD-1 ligand), LAG3 (lymphocyte activation gene 3), TIM3 (T cell membrane protein 3), B7-H3 and B7-H4 (see, for example, Pardoll, 2012 Nature Rev Cancer 12:252-264). Immune checkpoint inhibitors also include indoleamine dioxygenase (IDO) inhibitors. Examples include but are not limited to INCB-024360, indoximod, NLG-919 (WO 2009/73620, WO 2011/56652, WO 2012/142237) or F001287.

The additional therapeutic agents to be used in combination with the compounds of formula (I) as described herein can be used in therapeutic amounts indicated or approved for the particular agent, for example in the Physicians' Desk Reference (PDR) 47th Edition (1993), as would be known to those skilled in the art.

Preparation of Compounds of the Invention

The compounds of formula (I) described herein can be prepared from readily available starting materials using the following general methods and procedures. It will be appreciated that where typical or preferred process conditions (for example, reaction temperatures, times, mole ratios of reactants, solvents, pressures, etc.) are indicated, other process conditions can also be used unless otherwise stated. Optimum reaction conditions may vary with the particular reactants used.

Conventional protecting groups may be necessary to prevent certain functional groups from undergoing undesired reactions. Suitable protecting groups for various functional groups as well as suitable conditions for protecting and deprotecting particular functional groups are well known in the art (see, for example, T. W. Greene and G. M. Wuts, Protecting Groups in Organic Synthesis, Third Edition, Wiley, New York, 1999).

The starting materials for the following reactions are commercially available or can be prepared by known procedures or modifications thereof, for example those described in in standard reference texts such as Fieser and Fieser's Reagents for Organic Synthesis, Volumes 1-15 (John Wiley and Sons, 1991), Organic Reactions, Volumes 1-40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

The various starting materials, intermediates, and compounds may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of formula (I) wherein X is $NR^4$, O, S, Se, or Te, $R^2$ is G, and $J^1$ in G is O may be prepared by the general procedure outlined in Scheme 1.

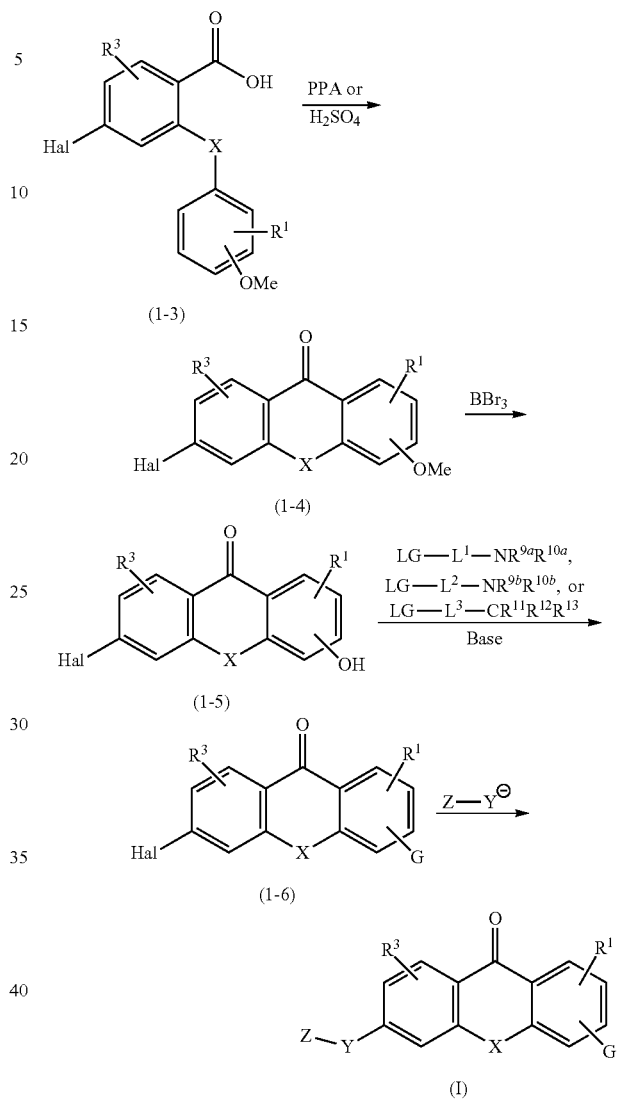

Treatment of acid (1-3), wherein Hal is a halogen such as F or Br, with a strong acid, for example polyphosphoric acid (PPA) or $H_2SO_4$ at 100° C., provides the corresponding tricyclic compound (1-4). Removal of the methyl ether of compound (1-4) by treatment with a strong Lewis acid, for example boron tribromide in dichloromethane, provides the corresponding alcohol (1-5). Alcohol (1-5) is then reacted with a compound of the formula LG-$L^1$-$NR^{9a}R^{10a}$, LG-$L^2$-$NR^{9b}R^{10b}$, or LG-$L^3$-$CR^{11}R^{12}R^{13}$, wherein LG is a suitable leaving group such as a halogen, in the presence of a base, for example NaOH in a mixture of water and dichloromethane, to provide the compound (1-6), wherein G is —O-$L^1$-$NR^{9a}R^{10a}$, —O-$L^2$-$NR^{9b}R^{10b}$, or —O-$L^3$-$CR^{11}R^{12}R^{13}$. It will be appreciated that when $R^4$ is a group other than H, the nitrogen atom may be need to be protected with a suitable protecting group prior to removal of the methyl group of the methyl ether. Reaction of compound (1-6) with an anion of the formula Z—Y$^-$, wherein Y is $CHR^6NR^5$, $CHR^6O$, $CHR^6S$, $NR^5$, O, and S, in for example dimethylsulfoxide (DMSO), provides the corresponding compound of formula (I). The anion of the formula Z—Y$^-$ is generated from a suitable precursor either prior to reaction with compound (1-6) or in situ during the reaction. In some embodiments, the precursor of the anion of the formula Z—Y⁻ is a compound of the formula Z—YH, for example a compound of the formula Z—CHR⁶OH or Z—OH, which may be deprotonated with a suitable base, for example NaOH. In some embodiments, the precursor is a silylated compound of the formula Z—Y—SiR₃, wherein each R is independently alkyl, for example a compound of the formula Z—S—Si(i-Pr)₃ or Z—CHR⁶S—Si(i-Pr)₃, which may be treated with a source of fluorine, for example CsF, to remove the silyl group and provide the anion of the formula Z—Y⁻.

Compound of formula (1-3) wherein Hal is F may be prepared as set out below in Scheme 2.

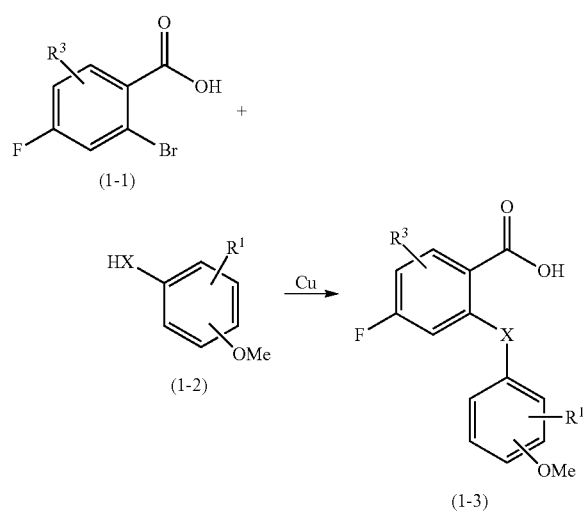

Carboxylic acid (1-1) is reacted with compound (1-2) in the presence of Cu, for example in 1,4-dioxane at 80° C., to provide fluoro acid (1-3). When X is a group other than O, the coupling reaction may be carried out in the presence of a base such as potassium carbonate. When X is O the coupling reaction is carried out using a preformed salt of compound (1-1) and a preformed salt of compound (1-2), for example a sodium or potassium salt of compound (1-1) and a sodium or potassium salt of compound (1-2). Salts of carboxylic acid (1-1) may be formed by, for example, treatment with aqueous potassium carbonate. Salts of compound (1-2) wherein X is O (i.e. phenoxide salts) may be formed by, for example, treatment with NaH, NaOH, KOH, or sodium dissolved in methanol.

Compounds of formula (1-3) wherein Hal is Br may be prepared as set our below in Scheme 3.

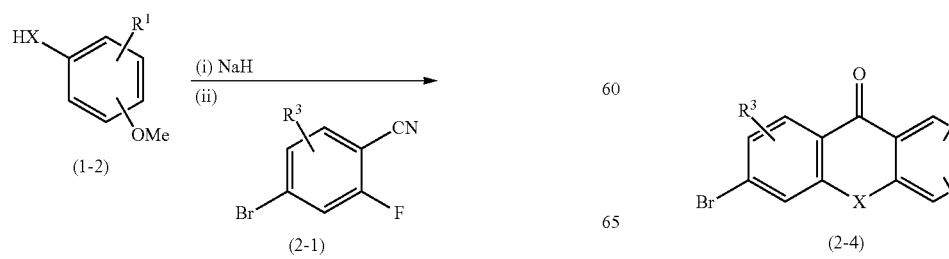

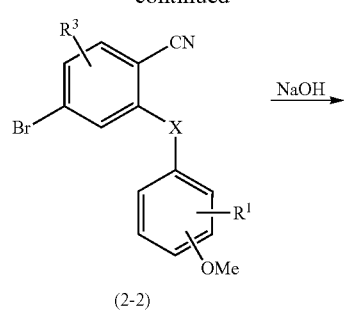

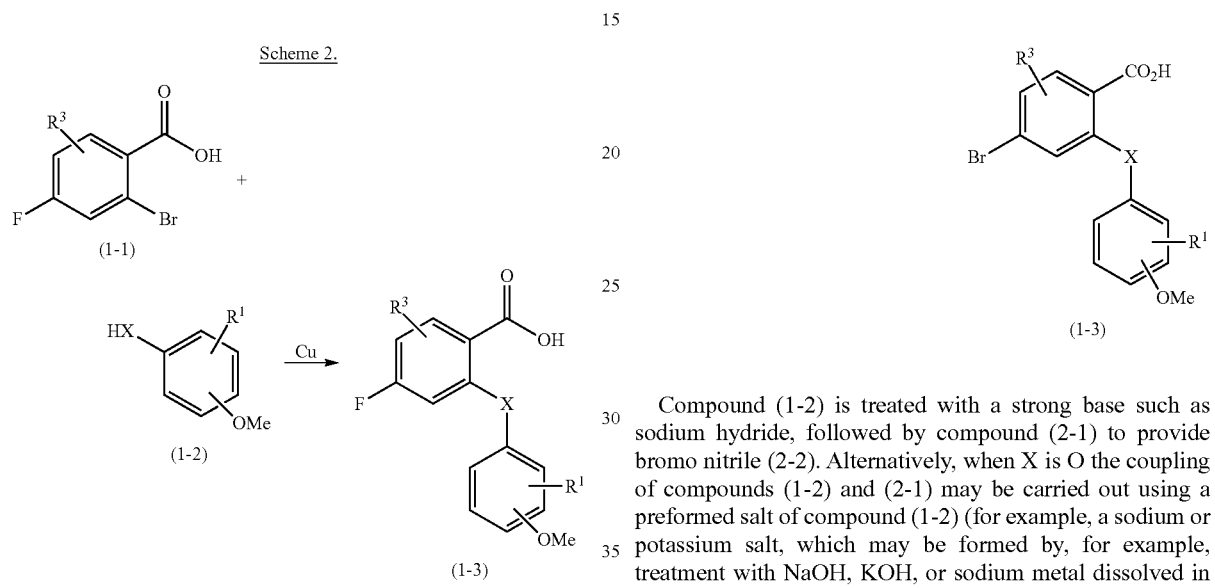

Compound (1-2) is treated with a strong base such as sodium hydride, followed by compound (2-1) to provide bromo nitrile (2-2). Alternatively, when X is O the coupling of compounds (1-2) and (2-1) may be carried out using a preformed salt of compound (1-2) (for example, a sodium or potassium salt, which may be formed by, for example, treatment with NaOH, KOH, or sodium metal dissolved in methanol). Hydrolysis of the nitrile using sodium hydroxide, for example, provides the corresponding bromo acid (1-3).

Compounds of formula (I) wherein X is NR⁴, O, S, Se, or Te, R² is G, J¹ in G is O may also be prepared by the general procedure outlined in Scheme 4.

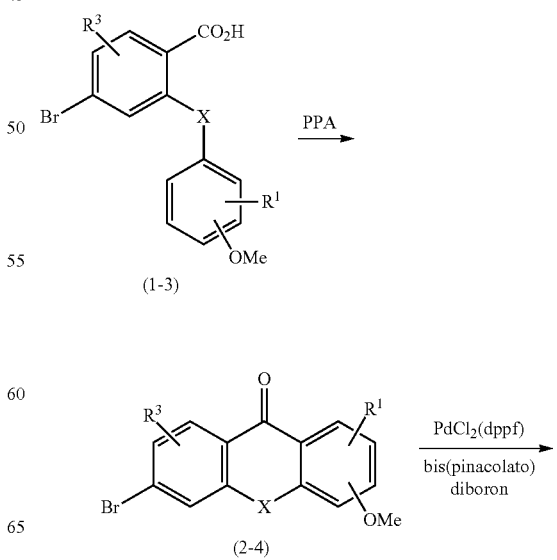

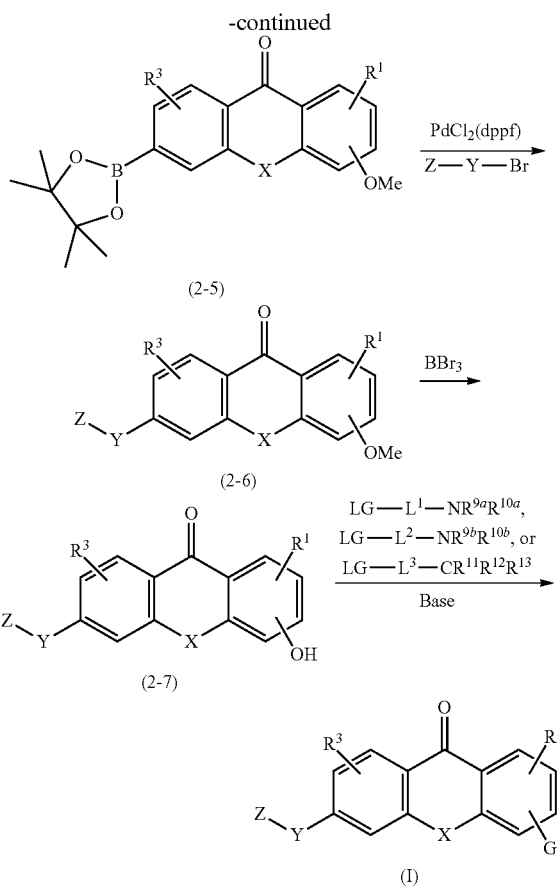

(2-5)

(2-6)

(2-7)

(I)

Ring closure of compound (1-3) using a strong acid, for example PPA at 100° C., provides compound (2-4). Treatment of compound (2-4) with bis(pinacolato)diboron in the presence of a palladium catalyst, such as $PdCl_2(dppf)$ wherein dppf is 1,1'-bis(diphenylphosphino) ferrocene, provides boronate (2-5). It will be appreciated that other boranes may be used, if desired, to provide different boronates. Treatment of boronate (2-5) with a bromide of the formula Z—Y—Br wherein Y is $CHR^6$ in the presence of a palladium catalyst, such as $PdCl_2(dppf)$, provides compound (2-6). Removal of the methyl ether to provide compound (2-7) and installation of the G group to provide the compound of formula (I) are carried out as described above with respect to Scheme 1.

Compounds of formula (I) wherein Y is CO may be prepared from corresponding compounds of formula (I) wherein Y is $CH_2$ by oxidation, for example by heating in air in a suitable solvent. Other suitable methods of oxidation will be apparent to those skilled in the art.

Compounds of formula (I) wherein $R^2$ is G and $J^1$ is a $NR^6$, S, $(C_{1-3}alkylene)O$, $(C_{1-3}alkylene)NR^6$, or $(C_{1-3}alkylene)S$ may be prepared by procedures analogous to those outlined in Schemes 1, 2, 3, and 4 by using a compound of the formula (1-2) wherein the OMe group is replaced by a $NR^6P^a$, $SP^a$, $(C_{1-3}alkylene)OP^a$, $(C_{1-3}alkylene)NR^6P^a$, or $(C_{1-3}alkylene)SP^a$, wherein $P^a$ is a suitable protecting group. The protecting group is removed at an appropriate point in the synthetic sequence for reaction with a compound of formula $LG-L^1-NR^{9a}R^{10a}$, $LG-L^2-NR^{9b}R^{10b}$, or $LG-L^3-CR^{11}R^{12}R^{13}$ to provide the corresponding G group.

Certain compounds of formula (I) wherein G is $-L^{10}-NR^{9a}R^{10a}$ or $-L^{20}-NR^{9b}R^{10b}$ may be prepared by following the general procedure set out in Scheme 5 below. Compound (2-10), wherein X is O, S, or $NR^4$, P is a suitable protecting group, and $L^a$ and $L^b$ are groups that in combination with the $CH_2$ produced on reduction of the amide of compound (2-11) correspond to $L^{10}$ and $L^{20}$ respectively, is reacted with an amine of the formula $HNR^{9a}R^{10a}$ or $HNR^{9b}R^{10b}$ to provide the corresponding amide (2-11). Reduction of the amide compound (2-11) with a suitable reducing agent, for example $LiAlH_4$ or $BH_3$, provides the corresponding amine (2-12), wherein G is $-L^a-CH_2NR^{9a}R^{10a}$ or $-L^b-CH_2NR^{9b}R^{10b}$. Removal of the protecting group provides compound (2-13) which is converted to compound (2-15) by a procedure analogous to that described above with respect to Scheme 3. Ring closure followed by reaction with an anion of the formula Z—Y⁻ by a procedure analogous to that described above with respect to Scheme 1 provides the corresponding compound of formula (I).

Scheme 5.

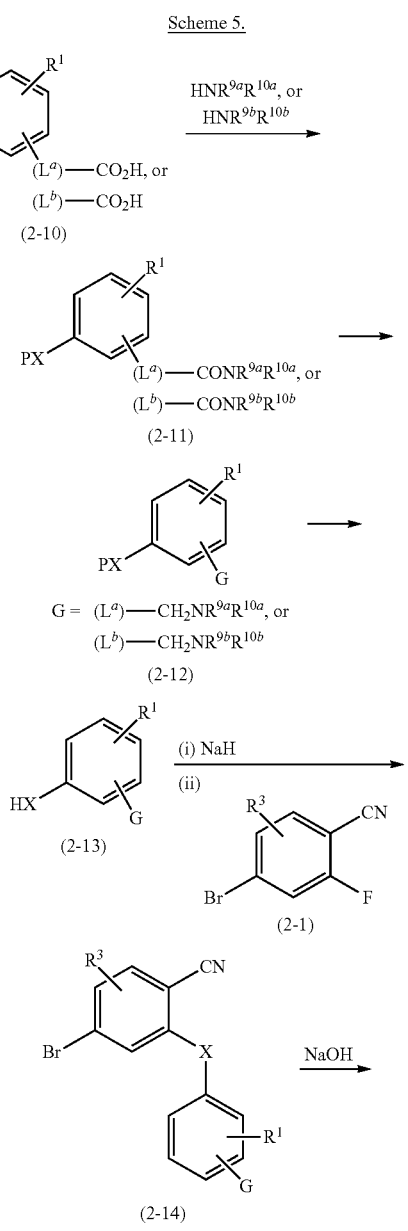

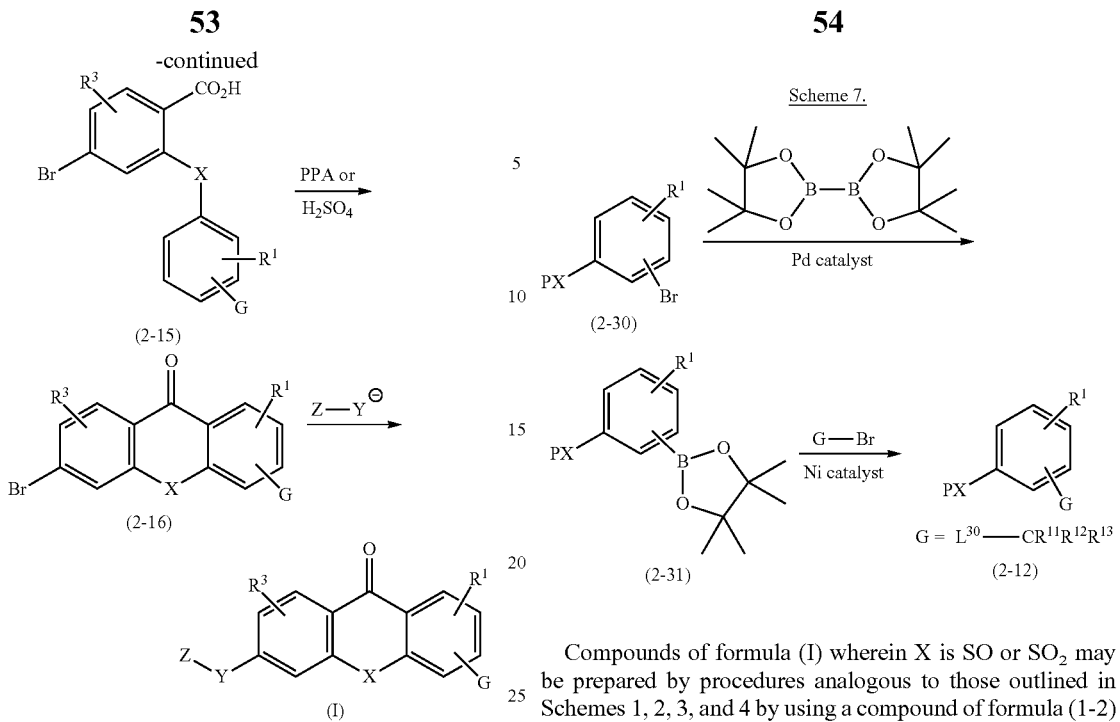

Compounds of formula (I) wherein G is -L$^{10}$-NR$^{9a}$R$^{10a}$ or -L$^{20}$-NR$^{9b}$R$^{10b}$ may also be prepared from a compound of the formula (2-20) wherein LG is a suitable leaving group (Scheme 6). Displacement of the leaving group by reaction with an amine of the formula amine of the formula HNR$^{9a}$R$^{10a}$ or HNR$^{9b}$R$^{10b}$ provides a compound of the formula (2-12) wherein the G group is -L$^{10}$-NR$^{9a}$R$^{10a}$ or -L$^{20}$-NR$^{9b}$R$^{10b}$, which is converted to a compound of formula (I) as described above with respect to Scheme 5.

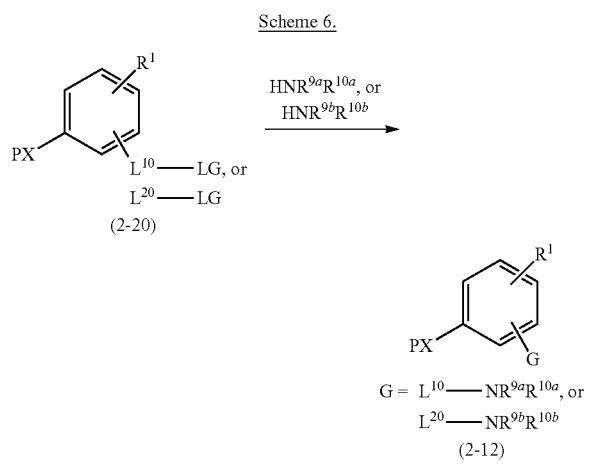

Compounds of formula (I) wherein G is -L$^{30}$-CR$^{11}$R$^{12}$R$^{13}$ may be prepared by, for example, the general procedure set out in Scheme 7 below. The compound of formula (2-12) formed is converted to a compound of formula (I) as described above with respect to Scheme 5. The general procedure may be suitable for installing other G groups. The Suzuki reaction based methodology is similar to that described by Gonzalez-Bobes and Fu. *J. Amer. Chem. Soc.*, 2006, 128, 5360-61.

Compounds of formula (I) wherein X is SO or SO$_2$ may be prepared by procedures analogous to those outlined in Schemes 1, 2, 3, and 4 by using a compound of formula (1-2) wherein X is S and oxidising the sulfide to the desired sulfoxide or sulfone at an appropriate point in the synthetic sequence with a suitable oxidising agent, for example m-chloroperoxybenzoic acid (mCPBA). Similarly, compounds of formula (I) wherein Y is SO, SO$_2$, CHR$^6$SO$_2$, or SO$_2$CHR$^6$ may be prepared from compounds of formula (I) or a precursor thereof wherein Y is S, CHR$^6$S, or SCHR$^6$ by oxidation of the sulfide to the desired sulfoxide or sulfone.

Compounds of formula (I) wherein Y is NR$^5$CO may be prepared via a nitrile intermediate as set out in Scheme 8 below. Addition of the nitrile may be achieved by displacement of the bromine in compound (1-6) by direct reaction with CuCN, or by palladium catalysed reaction with Zn(CN)$_2$. Subsequent hydrolysis of the nitrile (3-A) provides carboxylic acid (3-B). Reaction of acid (3-B) with an amine of the formula Z—NR$^5$H under suitable conditions then provides the desired amide.

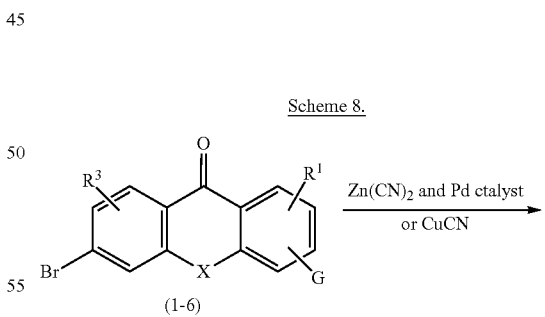

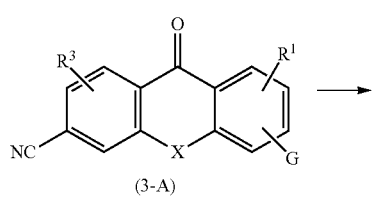

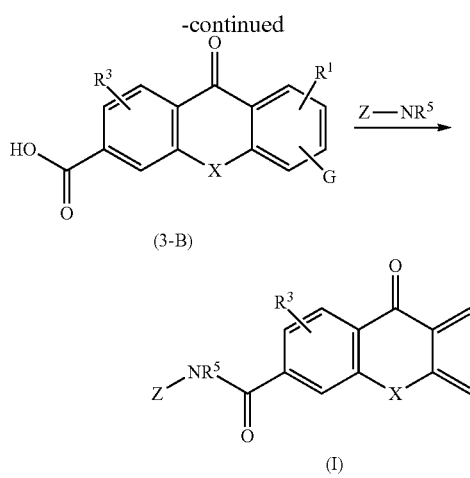

(3-B)

(I)

Compounds of formula (3-B) may be also be prepared by the general procedure outlined in Scheme 9. Reaction of bromide (1-6) with carbon monoxide under palladium catalysed conditions in the presence of methanol gives methyl ester (3-C), which is hydrolysed to carboxylic acid (3-B).

Scheme 9.

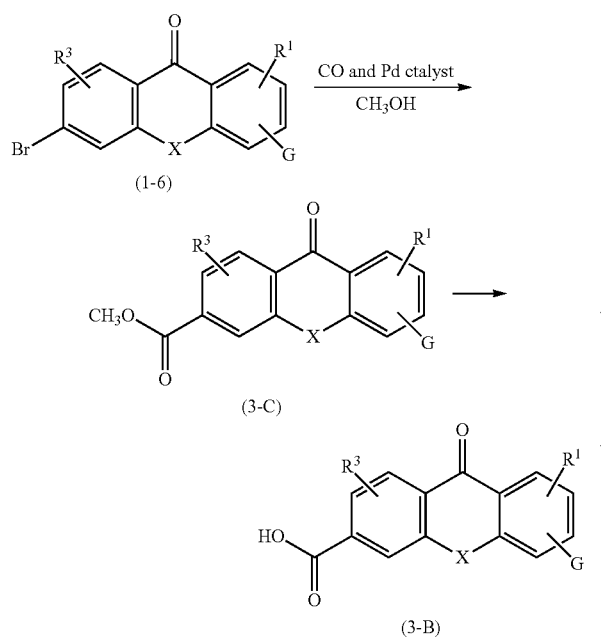

Certain compounds of formula (I) wherein Y is $CH_2$, $OCH_2$, or $SCH_2$ may be prepared by the general procedure outlined in Scheme 10 below. Reduction of carboxylic acid (3-B) (or the corresponding ester (3-C), not shown), for example by treatment with 1,1'-carbonyldiimidazole (CDI) followed by sodium borohydride, gives the hydroxymethyl group of compound (4-A), which on conversion to halide (4-B) (or some other suitable leaving group, such as a sulfonate) is reacted with a nucleophile of the formula $Z^-$, $Z-O^-$, or $Z-S^-$ to give the corresponding compounds of formula (I) wherein Y is $CH_2$, $OCH_2$, or $SCH_2$. Nucleophiles of the formula $Z^-$, $Z-O^-$, or $Z-S^-$ are generated prior to reaction with compound (4-B) or in situ during the reaction from a suitable precursor, for example a precursor of the formula ZH, Z—OH, or Z—SH by treatment with a suitable base.

Scheme 10.

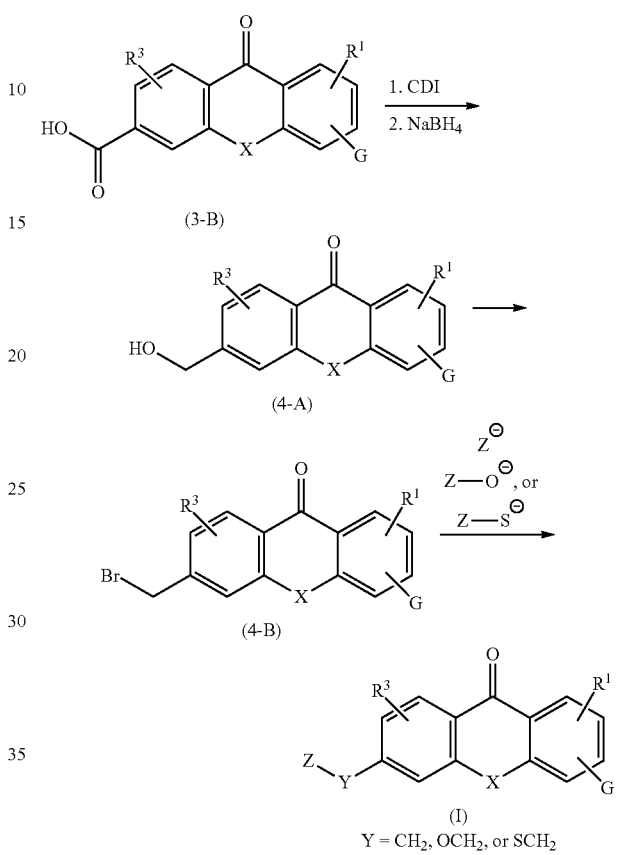

$Y = CH_2, OCH_2,$ or $SCH_2$

Compounds of formula (I) wherein Y is $CHR^6$, $OCHR^6$, or $SCHR^6$, wherein $R^6$ is a group other than hydrogen may be prepared by converting the carboxylic acid of compound (3-B) to a ketone bearing the $R^6$ group. The carboxylic acid is converted to a Weinreb amide and treated with a Grignard reagent of the formula $R^6MgBr$ or $R^6MgCl$. Reduction of the ketone provides a $CHR^6OH$ group which is then converted to the desired Y group via the corresponding bromide as illustrated in Scheme 10.

Alternatively, compounds of formula (I) wherein Y is $CHR^6$, $OCHR^6$, or $SCHR^6$ wherein $R^6$ is a group other than hydrogen may be prepared via the Pd-catalysed Heck reaction of bromide (1-6) with a suitable vinyl ether, for example $CH_2=CH$-OEt (to obtain a compound wherein $R^6$ is $CH_3$). Acid catalysed hydrolysis provides the corresponding ketone bearing $R^6$. Reduction of the ketone provides a $CHR^6OH$ group which is then converted to the desired Y group via the corresponding bromide as illustrated in Scheme 10.

Compounds of formula (I) wherein Y is $NR^5SO_2$ may be prepared as shown below in Scheme 11 from sulfonyl chloride (5-C). Compound (5-C) is in turn prepared by oxidation of thiol (5-B) group, which in turn is prepared by displacement of the fluorine atom of compound (5-A) with sodium hydrogen sulfide.

Scheme 11.

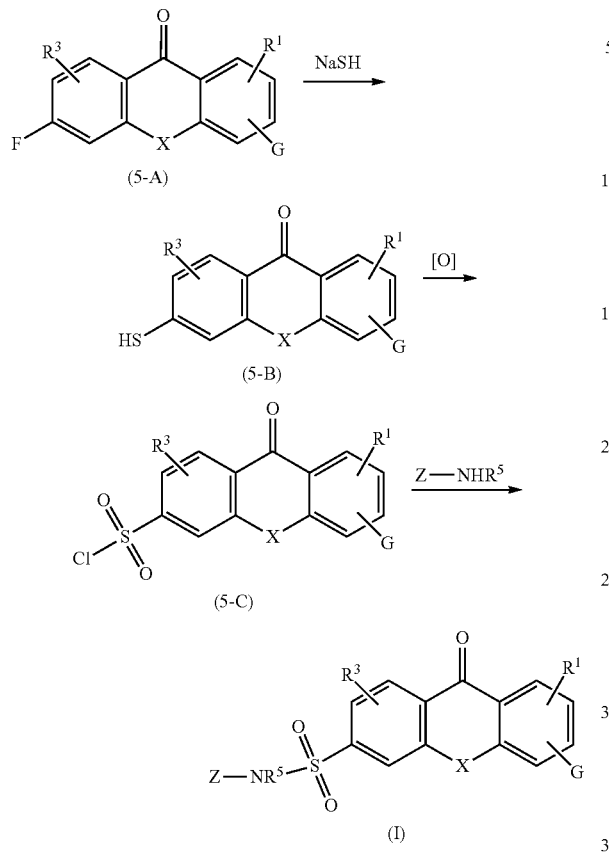

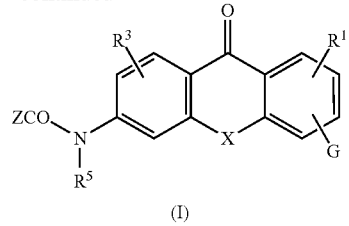

Compounds of formula (I) wherein $SO_2NR^5$ may be prepared as shown in Scheme 13 by reaction of amine (5-D) with a sulfonyl chloride of the formula $ZSO_2Cl$.

Scheme 13.

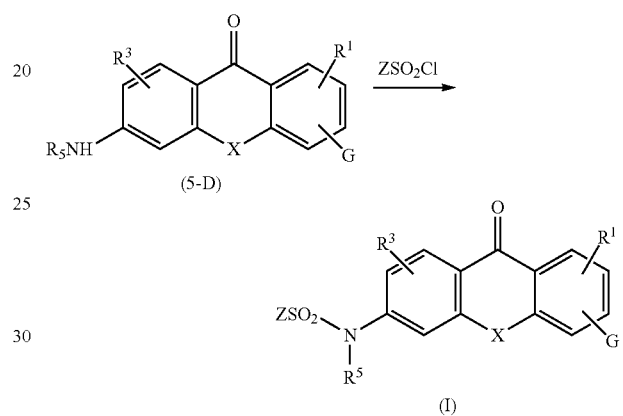

Compounds of formula (I) wherein X is $NG^1$ may be prepared by the general procedure outlined in Scheme 14.

Compounds of formula (I) wherein Y is $CONR^5$ may be prepared as shown below in Scheme 12. Reaction of (5-A) with an amine of the formula $R^5NH_2$ provides amine (5-D) which is reacted with a carboxylic acid of the formula $ZCO_2H$ (and a coupling agent), an acid chloride of the formula ZCOCl, or an anhydride of the formula $(ZCO)_2O$ to provide the compound of formula (I).

Scheme 14.

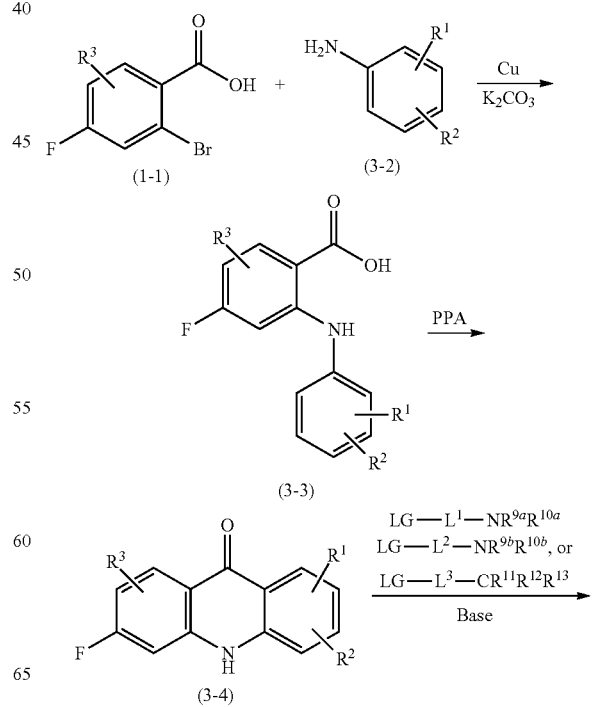

Scheme 12.

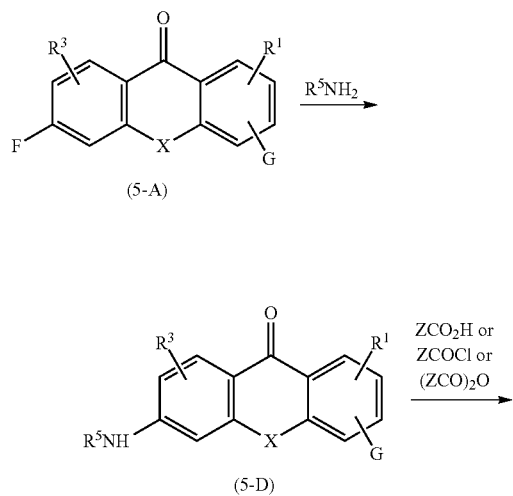

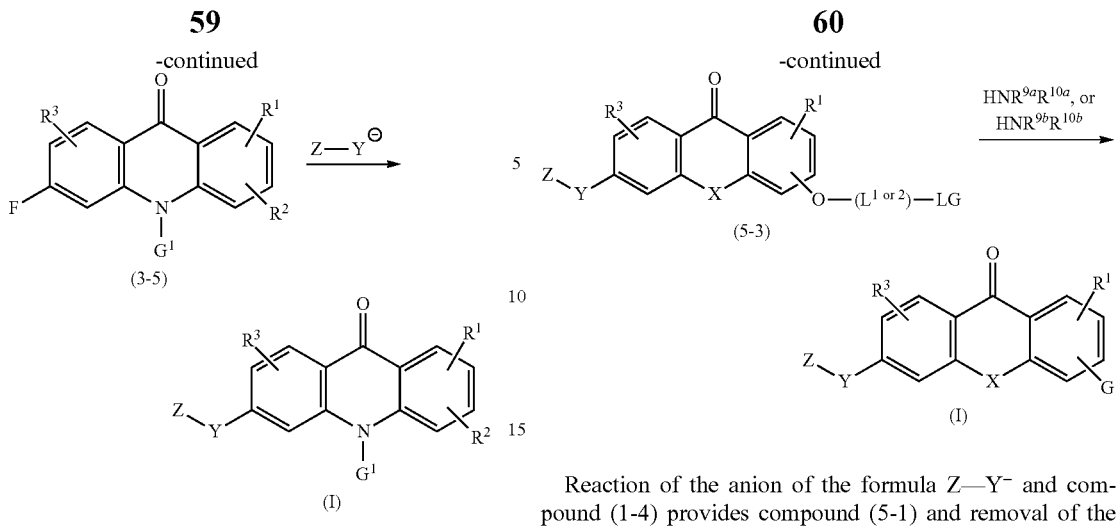

Coupling of compounds (1-1) and (3-2) to provide compound (3-3) and ring closure to provide acridinone (3-4) is carried out as described above with respect to Scheme 2. Treatment of compound (3-4) with a compound of the formula LG-L$^1$-NR$^{9a}$R$^{10a}$, LG-L$^2$-NR$^{9b}$R$^{10b}$, or LG-L$^3$-CR$^{11}$R$^{12}$R$^{13}$, in the presence of a base, for example potassium carbonate in acetone, provides the compound (3-5). Reaction of compound (3-5) with an anion of the formula Z—Y$^-$, wherein Y is CHR$^6$NR$^5$, CHR$^6$O, CHR$^6$S, NR$^5$, O, and S, as described above with respect to Scheme 1 provides the corresponding compound of formula (I). It will be appreciated that compounds of formula (I) wherein X is NG$^1$ having other Y groups may be prepared by procedures analogous to those described above with respect to compounds of formula (I) wherein X is a group other than NG$^1$.

It will be appreciated that, in various embodiments, the G or G$^1$ group in the compounds of formula (I) may be installed in a stepwise fashion involving two or more separate synthetic steps. For example, in certain compounds of formula (I) wherein G is —O-L$^1$-NR$^{9a}$R$^{10a}$ or —O-L$^2$-NR$^{9b}$R$^{10b}$ may be prepared by the general procedure outlined in Scheme 15.

Scheme 15.

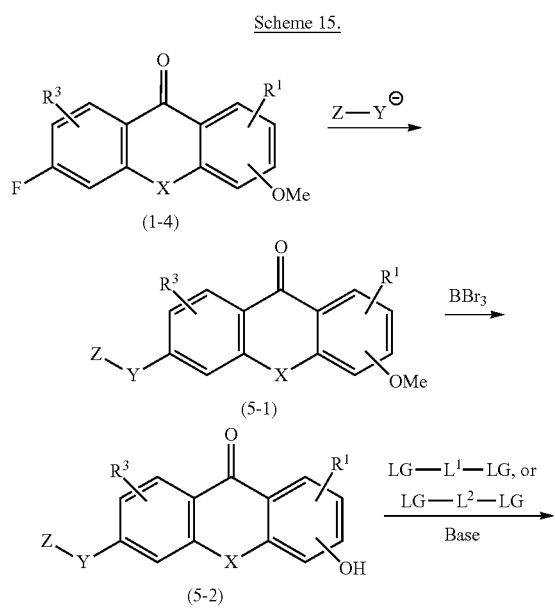

Reaction of the anion of the formula Z—Y$^-$ and compound (1-4) provides compound (5-1) and removal of the methyl group of the methyl ether provides compound (5-2). The reactions may be carried out as described with respect to Scheme 1 above. Treatment of alcohol (5-2) with a compound of the formula LG-L$^1$-LG or LG-L$^2$-LG, wherein each LG is independently a leaving group such as a halogen atom or a sulfonate, in the presence of base provides compound (5-3). The leaving group of compound (5-3) is then displaced with an amine of the formula HNR$^{9a}$R$^{10a}$ or HNR$^{9b}$R$^{10b}$ to provide the corresponding compound of formula (I).

It will be appreciated that, in various embodiments, the order of the steps set out in Scheme 15 to obtain the compound of formula (I) above can be altered, as shown in Schemes 16 and 17.

Scheme 16.

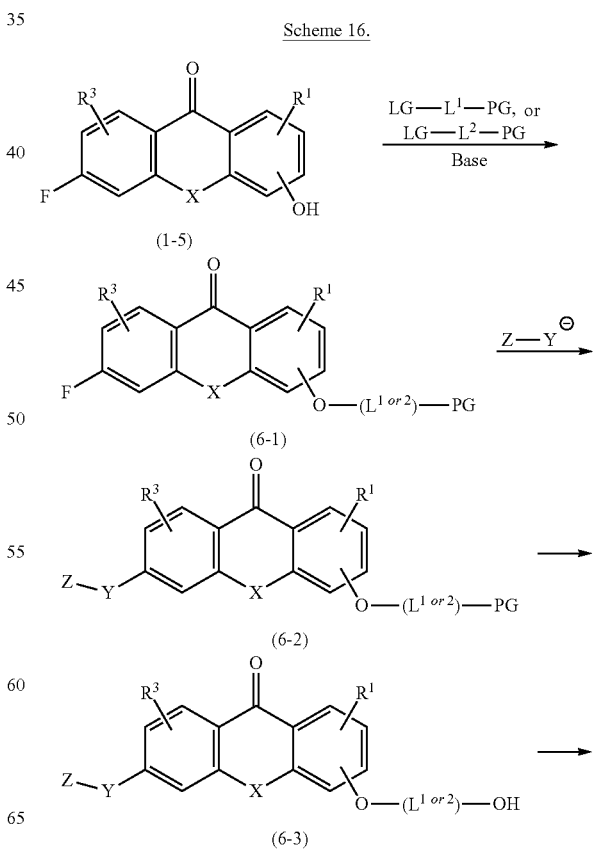

-continued

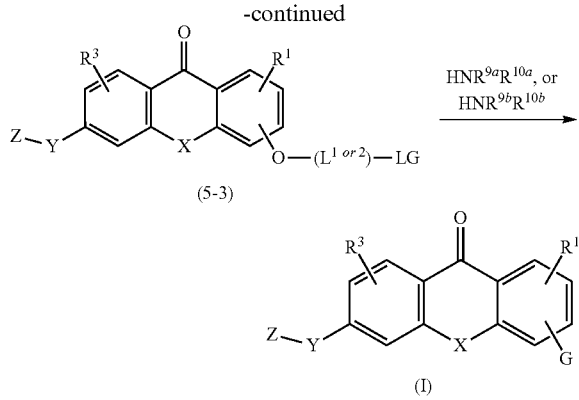

In various embodiments, as shown in Scheme 16, compound (1-5) may be treated with a compound of the formula LG-L$^1$-PG or LG-L$^2$-PG, wherein PG is a protected alcohol group such as an alcohol protected with a benzyl protecting group (CH$_2$Ph) to provide compound (6-1). Subsequent reaction with the anion of the formula Z—Y$^-$ provides compound (6-2). Removal of the protecting group from the protected alcohol provides alcohol (6-3). The alcohol group may be converted to a leaving group, such as a sulfonate, using procedures well known in the art, for example, by treatment with methylsulfonyl chloride in the presence of a base. The leaving group of compound (5-3) is then displaced with an amine of the formula HNR$^{9a}$R$^{10a}$ or HNR$^{9b}$R$^{10b}$ to provide the corresponding compound of formula (I).

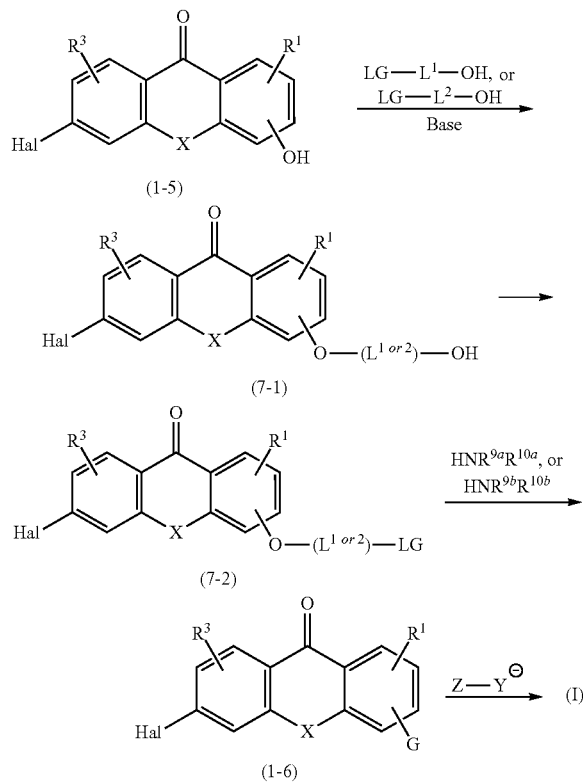

In other embodiments, as shown in Scheme 17, compound (1-5), wherein Hal is a halogen, for example Br, may be treated with a compound of the formula LG-L$^1$-OH or LG-L$^2$-OH to provide compound (7-1). The alcohol group may be converted to a leaving group, such as a sulfonate, using procedures well known in the art, for example, by treatment with methylsulfonyl chloride in the presence of a base, to provide compound (7-2). The leaving group of compound (7-2) is then displaced with an amine of the formula HNR$^{9a}$R$^{10a}$ or HNR$^{9b}$R$^{10b}$ to provide compound (1-6). Subsequent reaction with the anion of the formula Z—Y$^-$ as outlined in Scheme 1 provides the compound of formula (I).

It will also be appreciated that, in various embodiments, the —Y—Z group in the compounds of formula (I) may be installed in a stepwise fashion involving two or more separate synthetic steps. For example, certain compounds of formula (I) wherein Z is —W$^1$—Y$^1$—W$^2$, Y$^1$ is —(C$_{1-3}$alkylene)-J$^4$-* wherein * denotes the bond to W$^2$, and J$^4$ is CONR$^{14}$ may be prepared by the general procedure outlined in Scheme 18.

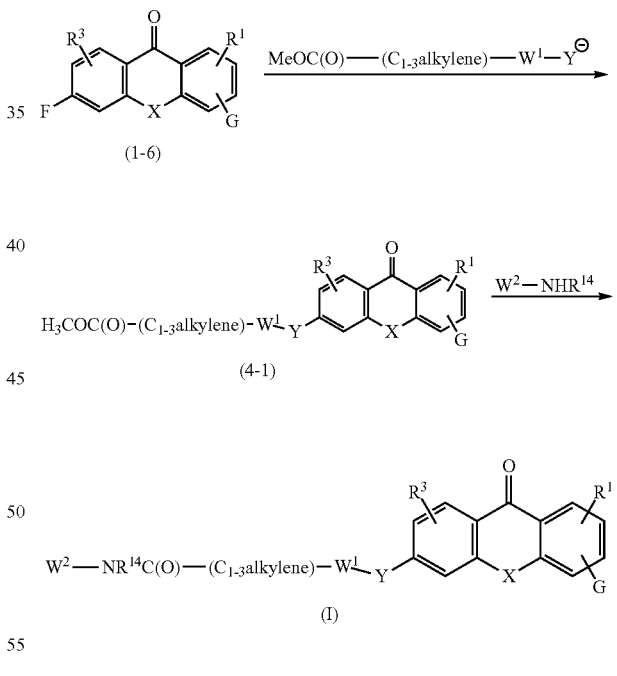

Compound (1-6) is reacted with the anion indicated to provide ester (4-1). Reaction of ester (4-1) and an amine of the formula W$^2$—NHR$^{14}$ provides the corresponding compound of formula (I).

Other suitable methods for preparing compounds of the invention will be apparent to those skilled in the art.

The following non-limiting examples are provided to illustrate the present invention and in no way limit the scope thereof.

EXAMPLES

Example 1

5-[2-(Dimethylamino)ethoxy]-3-phenoxy-9H-xanthen-9-one

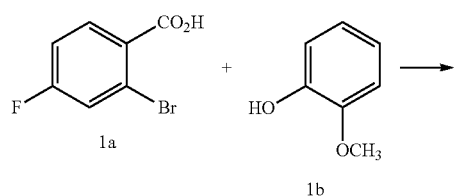
1a, 1b

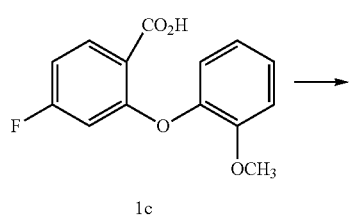
1c

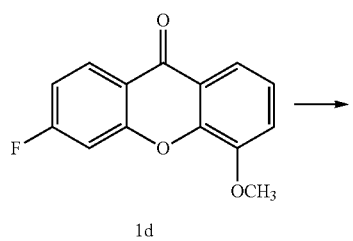
1d

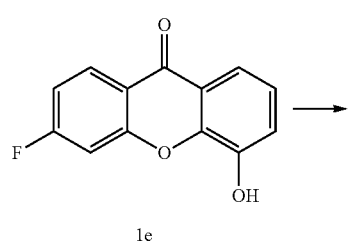
1e

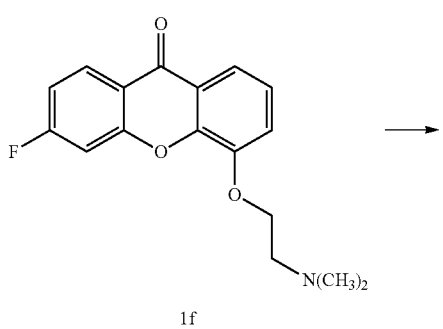
1f

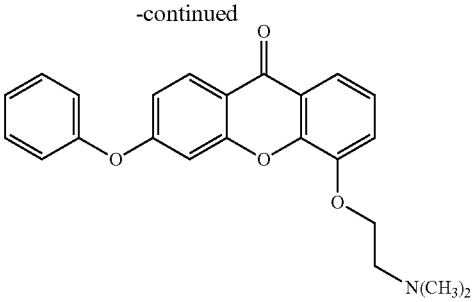
1

A stirred mixture of potassium 2-bromo-4-fluorobenzoate (5 g, 19.45 mmol), sodium 2-methoxyphenolate (3.85 g, 29.17 mmol), Cu (123 mg, 1.94 mmol), CuI (370 mg, 1.94 mmol) and tris-3,6-dioxaheptylamine (TDA-1) (0.63 mL, 1.94 mmol) in 1,4-dioxane (25 mL) was heated in a sealed tube at 80° C. for 16 h. It was cooled down to 18° C., and the solvent was removed under reduced pressure. 2N HCl (100 mL) was added and it was stirred at 18° C. for 1 h. The formed precipitate was filtered off and washed with $H_2O$ (500 mL) then hot $H_2O$ (300 mL), the resulting solid was dissolved in EtOAc (400 mL) and filtered over celite. The solvent was evaporated and the residue dried to give 4-fluoro-2-(2-methoxyphenoxy)benzoic acid (1c) (3.84 g, 75%) as an off white powder which was used in the following step without further purification: mp 123-126° C.; $^1$H NMR (DMSO-$d_6$) δ 12.88 (br. s, 1H), 7.88 (dd, J=6.9, 8.8 Hz, 1H), 7.18-7.32 (m, 2H), 6.94-7.06 (m, 3H), 6.35 (dd, J=2.5, 10.8 Hz, 1H), 3.75 (s, 3H); MS (ESI) m/z 263.1 (M+H$^+$); HRMS (ESI); Calcd for $C_{14}H_{12}FO_4$ (M+H$^+$) m/z 263.0703; found m/z 263.0709.

Polyphosphoric acid (PPA) (30 g) was added to 4-fluoro-2-(2-methoxyphenoxy)benzoic acid (1c) (3.68 g, 14.06 mmol) and the reaction mixture was heated at 100° C. for 3 h. It was then cooled to 18° C., ice was added and it was stirred for 30 min. The formed precipitate was filtered off, washed with $H_2O$ and dried to give 3-fluoro-5-methoxy-9H-xanthen-9-one (1d) (3.16 g, 92%) as a white powder: mp 183-185° C.; $^1$H NMR (DMSO-$d_6$) δ 8.25 (dd, J=6.6, 8.9 Hz, 1H), 7.72 (dd, J=1.5, 7.5 Hz, 1H), 7.67 (dd, J=2.4, 9.9 Hz, 1H), 7.53 (dd, J=1.4, 8.0 Hz, 1H), 7.42 (t, J=8.0 Hz, 1H), 7.37 (dt, J=2.4, 8.6 Hz, 1H), 3.99 (s, 3H); MS (ESI) m/z 224.3 (M+H$^+$); HRMS (ESI) Calcd for $C_{14}H_{10}FO_3$ (M+H$^+$) m/z 245.0603; found m/z 245.0613.

BBr$_3$ (1M in $CH_2Cl_2$, 8 mL, 8 mmol) was added at 0° C. to a solution of 3-fluoro-5-methoxy-9H-xanthen-9-one (1d) (1 g, 4.1 mmol) in $CH_2Cl_2$ (20 mL), and the reaction mixture was stirred at 18° C. for 16 h. It was cooled to 0° C., ice-water was added, it was partitioned between $CH_2Cl_2$ (250 mL) and $H_2O$ (100 mL), the organic phase was washed with $H_2O$ (3×50 mL) then brine, dried over $MgSO_4$, filtered and the solvent was removed under reduced pressure to give 3-fluoro-5-hydroxy-9H-xanthen-9-one (1e) (935 mg, 99%) as a white solid: mp 259-261° C.; $^1$H NMR (DMSO-$d_6$) δ 10.51 (s, 1H), 8.25 (dd, J=6.6, 8.9 Hz, 1H), 7.60 (dd, J=1.7, 7.7 Hz, 1H), 7.58 (dd, J=2.3 Hz, 1H), 7.33-7.38 (m, 2H), 7.28 (t, J=7.8 Hz, 1H); MS (ESI) m/z 231.1 (M+H$^+$); HRMS (ESI) Calcd for $C_{13}H_8FO_3$ (M+H$^+$) m/z 231.0447; found m/z 231.0451.

A mixture of 3-fluoro-5-hydroxy-9H-xanthen-9-one (1e) (400 mg, 1.74 mmol), 2-dimethylaminoethylchloride hydrochloride (1.5 g, 10.42 mmol), tetrabutylammonium bromide (55 mg, 0.17 mmol) and NaOH (834 mg, 20.85 mmol) in a 1:1 mixture of CH$_2$Cl$_2$/H$_2$O (40 mL) was stirred at 18° C. for 24 h. The reaction mixture was partitioned between CH$_2$Cl$_2$ (150 mL) and H$_2$O (50 mL), the organic phase was separated and washed with H$_2$O (3×50 mL) then brine (30 mL). It was dried over MgSO$_4$, filtered and the solvent was removed under reduced pressure. The residue was purified by column chromatography (SiO$_2$, EtOAc/MeOH/NEt$_3$) to give 5-[2-(dimethylamino)ethoxy]-3-fluoro-9H-xanthen-9-one (1f) (366 mg, 70%) as a white solid: mp 109-111° C.; $^1$H NMR (DMSO-d$_6$) δ 8.26 (dd, J=6.6, 8.8 Hz, 1H), 7.73 (d, J=8.0 Hz, 1H), 7.61 (dd, J=2.3, 9.8 Hz, 1H), 7.57 (d, J=8.0 Hz, 1H), 7.37-7.42 (m, 2H), 4.29 (t, J=5.8 Hz, 2H), 2.77 (t, J=5.8 Hz, 2H), 2.30 (s, 6H); MS (ESI) m/z 302.2 (100%, [M+H]+); HRMS (ESI) Calcd for C$_{17}$H$_7$FNO$_3$ (M+H)$^+$ m/z 302.1182; found m/z 302.1189.

A mixture of phenol (63 mg, 0.66 mmol), 5-[2-(dimethylamino)ethoxy]-3-fluoro-9H-xanthen-9-one (1f) (100 mg, 0.33 mmol) and K$_2$CO$_3$ (92 mg, 0.66 mmol) in anhydrous DMSO (2 mL) was heated at 80° C. in a sealed tube for 16 h. It was cooled down and partitioned between EtOAc (150 mL) and H$_2$O (50 mL). The organic phase was separated, washed with H$_2$O (3×50 mL) then brine (30 mL). It was dried over MgSO$_4$, filtered and the solvent was removed under reduced pressure. The residue was purified by column chromatography (Al$_2$O$_3$, hexanes/EtOAc, 1:1) to give 5-[2-(dimethylamino)ethoxy]-3-phenoxy-9H-xanthen-9-one (1) (121 mg, 98%) as a white solid: mp 151-152° C.; $^1$H NMR (DMSO-d$_6$) δ 8.19 (d, J=8.8 Hz, 1H), 7.71 (dd, J=1.4, 8.0 Hz, 1H), 7.50-7.56 (m, 3H), 7.31-7.39 (m, 2H), 7.23-7.26 (m, 2H), 7.12 (dd, J=2.4, 8.9 Hz, 1H), 6.91 (d, J=2.3 Hz, 1H), 4.23 (t, J=5.9 Hz, 2H), 2.71 (t, J=5.9 Hz, 2H), 2.23 (s, 6H); $^{13}$C NMR (DMSO-d$_6$) δ 174.9, 163.2, 156.8, 154.3, 147.5, 145.9, 130.5, 128.4, 125.5, 124.1, 122.0, 120.6, 117.6, 116.6, 116.3, 114.9, 104.3, 67.5, 57.4, 45.6; MS (ESI) m/z 376.2 (M+H$^+$); HPLC purity 99.4%. Anal. Calcd for C$_{23}$H$_{21}$NO$_4$: C, 73.6; H, 5.6; N, 3.7. Found: C, 73.5; H, 5.7; N, 3.8%.

Example 2

3-({5-[2-(Dimethylamino)ethoxy]-9-oxo-9H-xanthen-3-yl}oxy)-N-phenylbenzamide

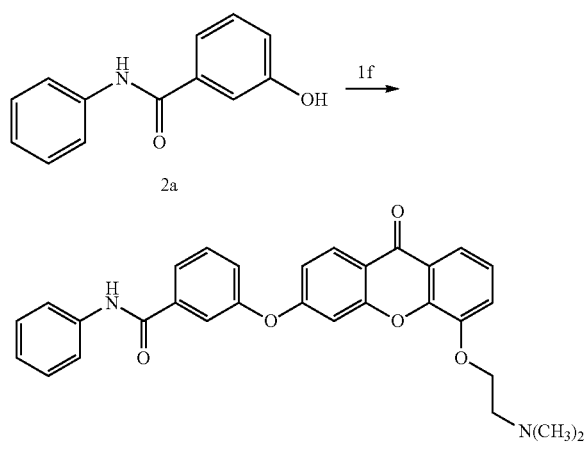

A mixture of 3-hydroxy-N-phenylbenzamide (2a) (141 mg, 0.66 mmol), 5-[2-(dimethylamino)ethoxy]-3-fluoro-9H-xanthen-9-one (1f) (100 mg, 0.33 mmol) and K$_2$CO$_3$ (92 mg, 0.66 mmol) in anhydrous DMSO (2 mL) was heated at 80° C. in a sealed tube for 16 h. It was cooled down and partitioned between EtOAc (150 mL) and H$_2$O (50 mL). The organic phase was separated, washed with H$_2$O (3×50 mL) then brine (30 mL). It was dried over MgSO$_4$, filtered and the solvent was removed under reduced pressure. The residue was triturated with EtOAc, filtered and washed with cold EtOAc to give 3-({5-[2-(dimethyl amino)ethoxy]-9-oxo-9H-xanthen-3-yl}oxy)-N-phenylbenzamide (2) (98 mg, 60%) as a white solid: mp 193-195° C.; $^1$H NMR (DMSO-d$_6$) δ 10.31 (s, 1H), 8.22 (d, J=8.8 Hz, 1H), 7.92 (dt, J=1.1, 8.1 Hz, 1H), 7.82 (t, J=1.9 Hz, 1H), 7.76 (dd, J=1.0, 8.6 Hz, 2H), 7.72 (dd, J=1.4, 8.0 Hz, 1H), 7.68 (t, J=8.0 Hz, 1H), 7.53 (dd, J=1.4, 8.1 Hz, 1H), 7.48 (ddd, J=0.8, 2.4, 8.1 Hz, 1H), 7.33-7.39 (m, 3H), 7.18 (dd, J=2.3, 8.8 Hz, 1H), 7.08-7.13 (m, 1H), 7.03 (d, J=2.3 Hz, 1H), 4.24 (t, J=6.0 Hz, 2H), 2.70 (t, J=6.0 Hz, 2H), 2.23 (s, 6H); $^{13}$C NMR (DMSO-d$_6$) δ 175.0, 164.3, 162.8, 156.8, 154.4, 147.5, 146.0, 138.9, 137.2, 130.7, 128.6, 128.5, 124.7, 124.1, 123.9, 123.7, 122.0, 120.5, 119.6, 117.7, 116.6 (2C), 115.0, 104.9, 67.5, 57.4, 45.6; MS (ESI) m/z 495.2 (M+H$^+$); HPLC purity 99.1%. Anal. Calcd for C$_{30}$H$_{26}$N$_2$O$_5$: C, 72.9; H, 5.3; N, 5.7. Found: C, 72.8; H, 5.2; N, 5.7%.

Example 3

5-[2-(Dimethylamino)ethoxy]-3-({6-[2-(4-methoxyphenyl)ethyl]-3-pyridinyl}oxy)-9H-xanthen-9-one

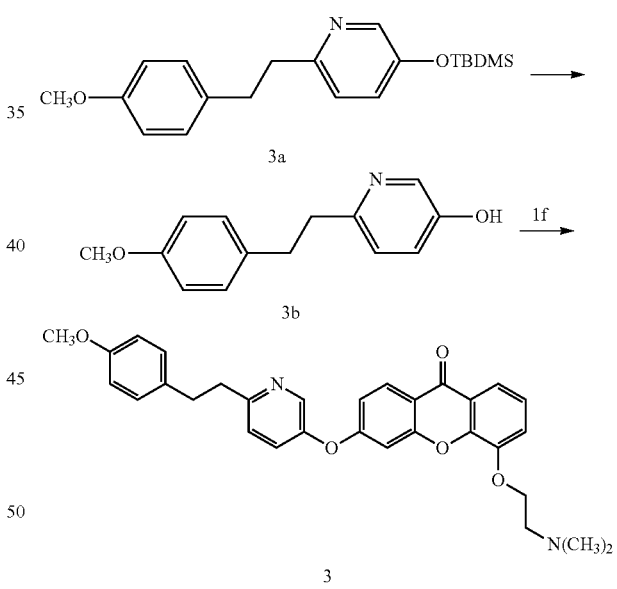

To a solution of 5-{[tert-butyl(dimethyl)silyl]oxy}-2-[2-(4-methoxyphenyl)ethyl]pyridine (3a) (*Eur. J. Med. Chem.* 2009, 44, 3560) (2.3 g, 6.7 mmol) in THF at 0° C. was added TBAF (1 M in THF, 10 mL, 10 mmol) and the mixture was stirred at 18° C. for 1 h. H$_2$O (50 mL) was then added and it was extracted with EtOAc (3×100 mL). The organic phase was dried over MgSO$_4$, filtered and the solvent was removed under reduced pressure. The residue was purified by column chromatography on SiO$_2$, using a gradient elution of hexanes/EtOAc, where the proportion of EtOAc was increased from 50-80%, to give 6-[2-(4-methoxyphenyl)ethyl]-3-pyridinol (3b) (1.2 g, 78%) as a white powder: mp 191-192° C.; $^1$H NMR (DMSO-d$_6$) δ 9.60 (br. s, 1H), 8.04

(dd, J=0.9, 2.6 Hz, 1H), 7.07-7.11 (m, 2H), 7.03 (dd, J=2.6, 8.4 Hz, 1H), 7.00 (dd, J=0.9, 8.4 Hz, 1H), 6.79-6.83 (m, 2H), 3.70 (s, 3H), 2.85 (s, 4H); $^{13}$C NMR (DMSO-d$_6$) δ 157.3, 151.6, 151.0, 136.9, 133.5, 129.2, 122.9, 122.4, 113.6, 54.9, 38.5, 34.5; MS (ESI) m/z 230.2 (M+H$^+$); HRMS (ESI) Calcd for C$_{14}$H$_{16}$NO$_2$ (M+H$^+$) m/z 230.1176; found m/z 230.1174.

A mixture of 6-[2-(4-methoxyphenyl)ethyl]-3-pyridinol (3b) (97 mg, 0.42 mmol), 5-[2-(dimethylamino)ethoxy]-3-fluoro-9H-xanthen-9-one (1f) (75 mg, 0.25 mmol) and K$_2$CO$_3$ (70 mg, 0.5 mmol) in anhydrous DMSO (2 mL) was heated at 80° C. in a sealed tube for 16 h. It was cooled down and partitioned between EtOAc (150 mL) and H$_2$O (50 mL). The organic phase was separated, washed with H$_2$O (3×50 mL) then brine (30 mL). It was dried over MgSO$_4$, filtered and the solvent was removed under reduced pressure. The residue was purified by column chromatography (Al$_2$O$_3$, EtOAc) to give 5-[2-(dimethylamino)ethoxy]-3-({6-[2-(4-methoxyphenyl)ethyl]-3-pyridinyl}oxy)-9H-xanthen-9-one (3) (124 mg, 97%) as a white solid: mp 109-111° C.; $^1$H NMR (DMSO-d$_6$) δ 8.48 (d, J=2.8 Hz, 1H), 8.21 (d, J=8.9 Hz, 1H), 7.71 (dd, J=1.4, 8.0 Hz, 1H), 7.62 (dd, J=2.9, 8.4 Hz, 1H), 7.54 (dd, J=1.4, 8.0 Hz, 1H), 7.35-7.40 (m, 2H), 7.11-7.16 (m, 3H), 6.97 (d, J=2.4 Hz, 1H), 6.83-6.87 (m, 2H), 4.24 (t, J=6.0 Hz, 2H), 3.71 (s, 3H), 3.02-3.07 (m, 2H), 2.94-2.99 (m, 2H), 2.71 (t, J=5.9 Hz, 2H), 2.23 (s, 6H); $^{13}$C NMR (DMSO-d$_6$) δ 175.0, 162.9, 158.0, 157.5, 156.8, 149.2, 147.5, 146.0, 141.8, 133.1, 129.2, 128.6, 128.5, 124.2, 124.1, 122.0, 117.7, 116.6 (2C), 114.7, 113.7, 104.5, 67.5, 57.4, 54.9, 45.6, 38.9, 34.2; MS (ESI) m/z 511.2 (M+H$^+$); HPLC purity 97%. Anal. Calcd for C$_{31}$H$_{30}$N$_2$O$_5$: C, 72.9; H, 5.9; N, 5.5. Found: C, 72.95; H, 6.0; N, 5.6%.

Example 4

4-[2-(Dimethylamino)ethoxy]-2-methyl-6-phenoxy-9H-xanthen-9-one

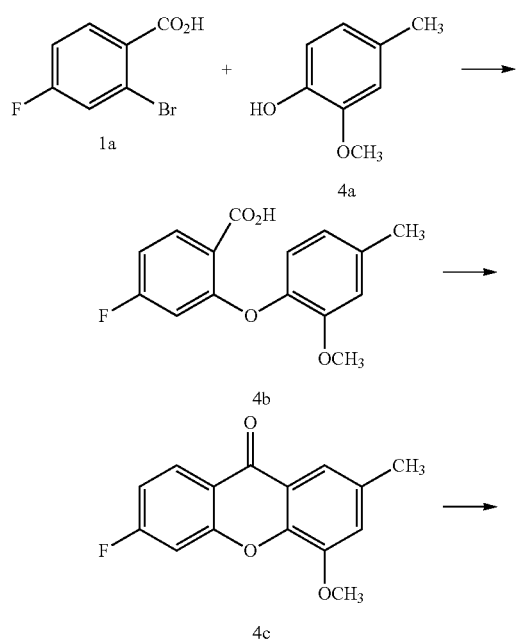

A mixture of potassium 2-bromo-4-fluorobenzoate (3.0 g, 11.67 mmol), sodium 2-methoxy-4-methylphenolate (2.8 g, 17.5 mmol), Cu (75 mg, 1.17 mmol) CuI (185 mg, 1.17 mmol) and tris-3,6-dioxaheptylamine (TDA-1) (0.38 mL, 1.17 mmol) in 1,4-dioxane (30 mL) was heated in a sealed tube at 80° C. for 16 h. It was cooled down to 18° C., and the solvent was removed under reduced pressure. H$_2$O (30 mL) was added, followed by 2N HCl (100 mL) and it was stirred at 18° C. for 1 h. The formed precipitate was filtered off and washed with H$_2$O (500 mL) then warm H$_2$O (300 mL), the resulting solid was dissolved in EtOAc (400 mL) and filtered over celite. The solvent was evaporated and the residue dried to give 4-fluoro-2-(2-methoxy-4-methylphenoxy)benzoic acid (4b) (2.56 g, 67%) which was used in the following step without further purification: $^1$H NMR (DMSO-d$_6$) δ 12.87 (br. s, 1H), 7.86 (dd, J=6.9, 8.7 Hz, 1H), 7.02 (d, J=1.4 Hz, 1H), 6.90-6.96 (m, 2H), 6.80 (dd, J=1.1, 8.0 Hz, 1H), 6.29 (dd, J=2.4, 10.9 Hz, 1H), 3.72 (s, 3H), 2.34 (s, 3H); MS (ESI) m/z 277.2 (M+H$^+$). 4-Fluoro-2-(2-methoxy-4-methylphenoxy)benzoic acid (4b) (0.93 g, 3.5 mmol) was added to PPA (2 mL) at 100° C. and the reaction was stirred for 10 mins, then poured into hot water. The resulting precipitate was collected by filtration and washed well with water to give 6-fluoro-4-methoxy-2-methyl-9H-xanthen-9-one (4c) (0.51 g, 55%): $^1$H NMR (DMSO-d$_6$) δ 8.24 (dd, J=8.9, 6.6 Hz, 1H), 7.63 (dd, J=9.9, 2.4 Hz, 1H), 7.50 (dd, J=1.8, 0.8 Hz, 1H), 7.36 (d, J=2.1 Hz, 1H), 7.33 (dd, J=8.7, 2.4 Hz, 1H), 3.97 (s, 3H), 2.45 (d, J=14.4 Hz, 3H); MS (APCI$^+$) 259.3 (M+H$^+$).

BBr$_3$ (1 M in CH$_2$Cl$_2$, 22 mL, 22 mmol) was added to a solution of 6-fluoro-4-methoxy-2-methyl-9H-xanthen-9-one (4c) (2.85 g, 11 mmol) in $CH_2Cl_2$ (50 mL), and the reaction was stirred at rt. After 16 h, water was added, and the biphasic suspension was stirred for an additional 1 h. The precipitate was then collected by filtration, and the aqueous layer extracted with EtOAc, washed brine, dried over $Na_2SO_4$, concentrated. The solids were combined then dissolved in boiling EtOH, and filtered. The blue solution was concentrated, and triturated with $Et_2O$ to give 6-fluoro-4-hydroxy-2-methyl-9H-xanthen-9-one (4d) (2.41 g, 90%) as a pale blue solid: mp ($CH_2Cl_2$/hexanes) 181-183° C.; $^1H$ NMR ($CDCl_3$) δ 8.35 (dd, J=8.9, 6.4 Hz, 1H), 7.69 (dd, J=1.9, 0.9 Hz, 1H), 7.28 (dd, J=7.8, 2.4 Hz, 1H), 7.13-7.07 (m, 2H), 4.02 (s, 3H), 2.47 (s, 3H). Anal. Calcd for $C_{15}H_{11}FO_3$: C, 69.8; H, 4.3. Found: C, 69.6; H, 4.2%.

A mixture of 6-fluoro-4-hydroxy-2-methyl-9H-xanthen-9-one (4d) (679 mg, 2.78 mmol), tetrabutylammonium bromide (89 mg, 10%), NaOH (1.33 mg, 12 equiv.) and 2-chloro-N,N-dimethylethylamine hydrochloride (4.8 g, 12 equiv.) in $CH_2Cl_2$ (40 mL) and $H_2O$ (40 mL) was stirred for 20 h at 20° C. The $CH_2Cl_2$ layer was separated and the aqueous layer was further extracted with $CH_2Cl_2$. The combined $CH_2Cl_2$ extracts were evaporated and the residue was chromatographed on $Al_2O_3$ eluting with a gradient of 0-2% $CH_2Cl_2$/MeOH to give 4-(2-(dimethylamino)ethoxy)-6-fluoro-2-methyl-9H-xanthen-9-one (4e) (659 mg, 75%) as a white solid: mp ($CH_2Cl_2$/hexanes) 110-111° C.; $^1H$ NMR ($CDCl_3$) δ 8.34 (dd, J=8.9, 6.4 Hz, 1H), 7.69 (dd, J=2.0, 0.9 Hz, 1H), 7.24 (dd, J=9.4, 2.3 Hz, 1H), 7.14-7.05 (m, 2H), 4.24 (t, J=5.8 Hz, 2H), 2.88 (t, J=5.8 Hz, 2H), 2.45 (s, 3H), 2.43 (s, 6H); MS ($APCI^+$) 316.2 ($M+H^+$). Anal. Calcd for $C_{18}H_{18}FNO_3$: C, 68.4; H, 5.7; N, 4.4. Found: C, 68.4; H, 5.7; N, 4.5%.

A mixture of 4-(2-(dimethylamino)ethoxy)-6-fluoro-2-methyl-9H-xanthen-9-one (4e), phenol, and $K_2CO_3$ in DMSO was heated at 85° C. for 16 h to give 4-[2-(dimethylamino)-ethoxy]-2-methyl-6-phenoxy-9H-xanthen-9-one (4): $^1H$ NMR ($CDCl_3$) δ 8.29 (d, J=8.8 Hz, 1H), 7.70 (br s, 1H), 7.45 (t, J=7.9 Hz, 2H), 7.26 (t, J=7.4 Hz, 1H), 7.14 (d, J=7.7 Hz, 1H), 7.07 (d, J=1.6 Hz, 1H), 7.03 (dd, J=8.8, 2.3, 1H), 6.96 (d, J=2.3 Hz, 1H), 4.22 (t, J=5.9 Hz, 2H), 2.85 (t, J=5.9 Hz, 2H), 2.44 (s, 3H), 2.38 (s, 6H).

Example 5

3-((5-(2-(Dimethylamino)ethoxy)-7-methyl-9-oxo-9H-xanthen-3-yl)oxy)-N-phenyl-benzamide

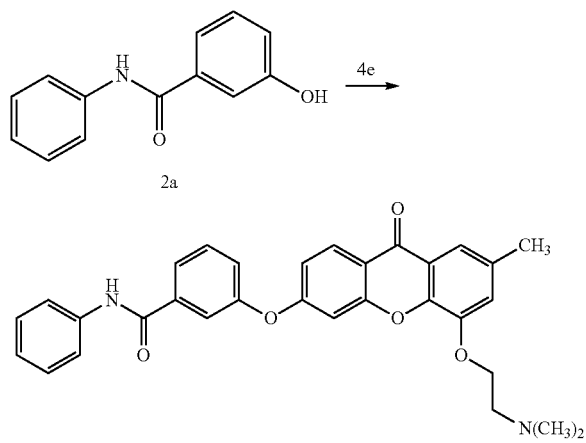

A mixture of 4-(2-(dimethylamino)ethoxy)-6-fluoro-2-methyl-9H-xanthen-9-one (4e) (50 mg, 0.159 mmol), 3-hydroxy-N-phenylbenzamide (2a) (37 mg, 0.174 mmol) and $K_2CO_3$ (26 mg, 0.19 mmol) were heated in DMSO (2 mL) at 85° C. for 16 h. The reaction contents were poured onto crushed ice and sat. $K_2CO_3$ and the white solution was extracted with EtOAc ×3, washed with brine, dried over $Na_2SO_4$, and concentrated. The crude residue was filtered through a pad of alumina, eluting with neat $CH_2Cl_2$ gave foreruns, the further elution with neat EtOAc gave 3-((5-(2-(dimethylamino)ethoxy)-7-methyl-9-oxo-9H-xanthen-3-yl)oxy)-N-phenylbenzamide (5) as a foamy-white solid. Recrystallization from (methanolic $HCl/Et_2O$) gave the hydrochloride (68 mg, 79%), as a white solid: mp (MeOH/$Et_2O$) 271-274° C.; $^1H$ NMR (DMSO-$d_6$) δ 10.33 (s, 1H), 9.96 (s, 1H), 8.24 (d, J=8.8 Hz, 1H), 7.93 (d, J=8.3 Hz, 1H), 7.82-7.79 (m, 1H), 7.76 (dd, J=8.6, 1.1 Hz, 2H), 7.68 (t, J=7.9 Hz, 1H), 7.60 (dd, J=1.9, 0.8 Hz, 1H), 7.50-7.45 (m, 2H), 7.35 (t, J=7.4 Hz, 2H), 7.18 (dd, J=8.8, 2.3 Hz, 1H), 7.15-7.07 (m, 2H), 4.51 (t, J=5.0 Hz, 2H), 3.65-3.48 (m, 2H), 2.86 (s, 6H), 2.44 (s, 3H). Anal Cald for $C_{31}H_{29}ClN_2O_5 \cdot 0.25H_2O$: C, 67.75; H, 5.4; Cl, 6.45; N, 5.1. Found: C, 67.6; H, 5.3; N, 5.1; Cl, 6.4%.

Example 6

1-(3-((5-(2-(Dimethylamino)ethoxy)-7-methyl-9-oxo-9H-xanthen-3-yl)oxy)phenyl)-3-phenylurea

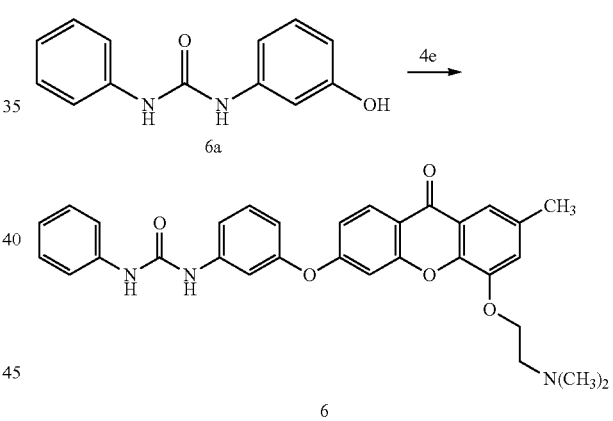

A mixture of 4-(2-(dimethylamino)ethoxy)-6-fluoro-2-methyl-9H-xanthen-9-one (4e) (50 mg, 0.159 mmol), 1-(3-hydroxyphenyl)-3-phenylurea (6a) (189 mg, 0.83 mmol), and $K_2CO_3$ (0.86 mmol) was heated in DMSO (2 mL) at 85° C. for 16 h. Workup gave a crude solid which was purified by flash column chromatography, eluting with EtOAc and then MeOH/$CH_2Cl_2$ (1:9), to give a white solid. Recrystallization from methanolic $HCl/Et_2O$ gave 1-(3-((5-(2-(dimethylamino)ethoxy)-7-methyl-9-oxo-9H-xanthen-3-yl)oxy)phenyl)-3-phenylurea hydrochloride (6) (130 mg, 92%) as a white solid: mp (MeOH/$Et_2O$) 226-229° C.; $^1H$ NMR (DMSO-$d_6$) δ 9.95 (s, 1H), 9.23 (s, 1H), 8.99 (s, 1H), 8.21 (d, J=8.8 Hz, 1H), 7.60 (s, 1H), 7.55-7.50 (m, 1H), 7.49-7.37 (m, 4H), 7.32-7.21 (m, 3H), 7.15 (dd, J=8.9, 2.3 Hz, 1H), 7.07 (d, J=2.3 Hz, 1H), 6.96 (t, J=7.3 Hz, 1H), 6.87-6.79 (m, 1H), 4.58-4.44 (m, 2H), 3.65-3.56 (m, 2H), 2.90 (s, 6H), 2.47 (s, 3H); Anal. Cald for $C_{31}H_{30}ClN_3O_5 \cdot 0.75H_2O$: C, 64.9; H, 5.5; Cl, 6.2; N, 7.3. Found: C, 65.1; H, 5.3; Cl, 6.3.

Example 7

4-(2-(Dimethylamino)ethoxy)-6-(3-methoxy-4-((4-methylbenzyl)oxy)phenoxy)-2-methyl-9H-xanthen-9-one

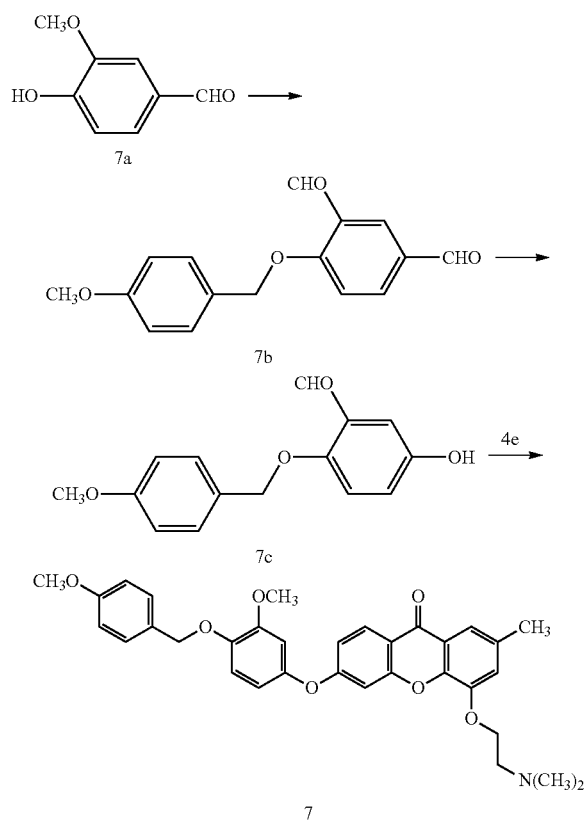

A mixture of vanillin (7a) (5 g 32.9 mmol), 4-methoxybenzyl chloride (6.18 g, 39 mmol), K₂CO₃ (5 g, 36.1 mmol), and KI (5 mg) in MEK (20 mL) was heated at 80° C. for 16 h.

The reaction was then cooled, diluted with EtOAc, filtered and concentrated to a yellow solid, that was triturated with hexanes to give 3-methoxy-4-((4-methoxybenzyl)oxy)benzaldehyde (7b) (8 g, 89%) as an off-white solid: ¹H NMR (DMSO-d₆) δ 9.83 (s, 1H), 7.54 (dd, J=8.24, 1.89 Hz, 1H), 7.42-7.37 (m, 3H), 7.27 (d, J=8.28 Hz, 1H), 6.96 (d, J=8.73 Hz, 2H), 5.12 (s, 2H), 3.82 (s, 3H), 3.76 (s, 3H).

77% m-CPBA (680 mg, 2.76 mmol) was added to 3-methoxy-4-((4-methoxybenzyl)oxy)-benzaldehyde (7b) (500 mg, 1.85 mmol) in CH₂Cl₂ (3 mL) with water bath cooling. The reaction was neutralised with sat. aq. NaHCO₃, and the aqueous layer was extracted with CH₂Cl₂. The combined organic layers were washed with sat. aq. NaHCO₃ and concentrated to give 3-methoxy-4-((4-methoxybenzyl) oxy)phenol (7c) (289 mg, 60%) as a tan solid. ¹H NMR (DMSO-d₆) δ 8.97 (s, 1H), 7.32 (d, J=8.7 Hz, 2H), 6.92 (d, J=8.7 Hz, 2H), 6.77 (d, J=8.6 Hz, 1H), 6.41 (d, J=2.7 Hz, 1H), 6.21 (dd, J=8.6, 2.7 Hz, 1H), 4.84 (s, 2H), 3.75 (s, 3H), 3.70 (s, 3H).

A mixture of 4-(2-(dimethylamino)ethoxy)-6-fluoro-2-methyl-9H-xanthen-9-one (4e) (76.3 mg, 0.24 mmol), 3-methoxy-4-((4-methoxybenzyl)oxy)phenol (7c) (70 mg, 0.27 mmol) and K₂CO₃ (41 mg, 0.289 mmol) were heated in DMSO at 85° C. for 16 h. This was then poured onto crushed ice, and the resulting precipitate was collected by filtration and washed well with water. The crude solid was purified by flash column chromatography, eluting with (MeOH/CH₂Cl₂, 5:95) to give a white solid. Recrystallization from CH₂Cl₂/hexanes, followed by (methanolic HCl/Et₂O) gave 4-(2-(dimethylamino)ethoxy)-6-(3-methoxy-4-((4-methylbenzyl)oxy)phenoxy)-2-methyl-9H-xanthen-9-one (7) (44 mg, 31%) as a white solid: mp (MeOH/Et₂O) 162-165° C. (powder to glue), 181-183° C. (glue to liquid); ¹H NMR (DMSO-d₆) δ 9.99 (s, 1H), 8.18 (d, J=8.9 Hz, 1H), 7.59 (dd, J=2.0, 0.9 Hz, 1H), 7.46 (d, J=2.0 Hz, 1H), 7.39 (d, J=8.9 Hz, 2H), 7.13 (d, J=8.8 Hz, 1H), 7.08 (dd, J=8.9, 2.3 Hz, 1H), 7.02-6.88 (m, 4H), 6.74 (dd, J=8.7, 2.8 Hz, 1H), 5.02 (s, 2H), 4.52 (t, J=5.1 Hz, 2H), 3.77 (s, 3H), 3.76 (s, 3H), 3.58 (d, J=6.3 Hz, 2H), 2.89 (s, 6H), 2.44 (s, 3H); HRMS (ESI) Calcd for C₃₃H₃₄NO₇: m/z 556.2330; found m/z 556.2348 (M+H⁺).

Example 8

4-(2-(Dimethylamino)ethoxy)-6-((6-methoxypyridin-3-yl)oxy)-2-methyl-9H-xanthen-9-one

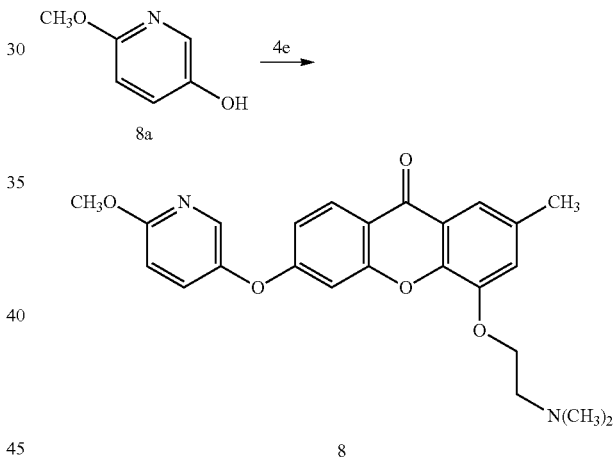

4-(2-(Dimethylamino)ethoxy)-6-fluoro-2-methyl-9H-xanthen-9-one (4e) (40 mg, 0.127 mmol), 3-hydroxy-6-methoxypyridine (20.6 mg, 0.164 mmol) and K₂CO₃ (24.5 mg, 0.177 mmol) were heated in DMSO at 85° C. for 16 h. This was then poured onto crushed ice, and the resulting precipitate was collected by filtration and washed well with water. The crude solid was purified by flash column chromatography, eluting with MeOH/CH₂Cl₂ (5:95) to give 4-(2-(dimethylamino)ethoxy)-6-((6-methoxypyridin-3-yl) oxy)-2-methyl-9H-xanthen-9-one (8) as a white solid. Recrystallization from (methanolic HCl/Et₂O) gave the hydrochloride (53 mg, 85%): mp (MeOH/Et₂O) 215-218° C.; ¹H NMR (DMSO-d₆) δ 9.97 (s, 1H), 8.20 (d, J=8.9 Hz, 1H), 8.18 (dd, J=3.0, 0.6 Hz, 1H), 7.71 (dd, J=8.9, 3.0 Hz, 1H), 7.59 (dd, J=2.0, 1.0 Hz, 1H), 7.46 (d, J=2.0 Hz, 1H), 7.11 (dd, J=8.9, 2.4 Hz, 1H), 7.02 (d, J=2.3 Hz, 1H), 6.99 (dd, J=8.9, 0.6 Hz, 1H), 4.51 (t, J=5.1 Hz, 2H), 3.90 (s, 3H), 3.57-3.50 (m, 2H), 2.86 (s, 6H), 2.44 (s, 3H); HRMS (ESI) Calcd for C₂₄H₂₅N₂O₅: m/z 421.1758; found m/z 421.1761 (M+H⁺). HPLC Purity 98.3%.

Example 9

6-((5,6-Dimethoxypyridin-3-yl)oxy)-4-(2-(dimethylamino)ethoxy)-2-methyl-9H-xanthen-9-one

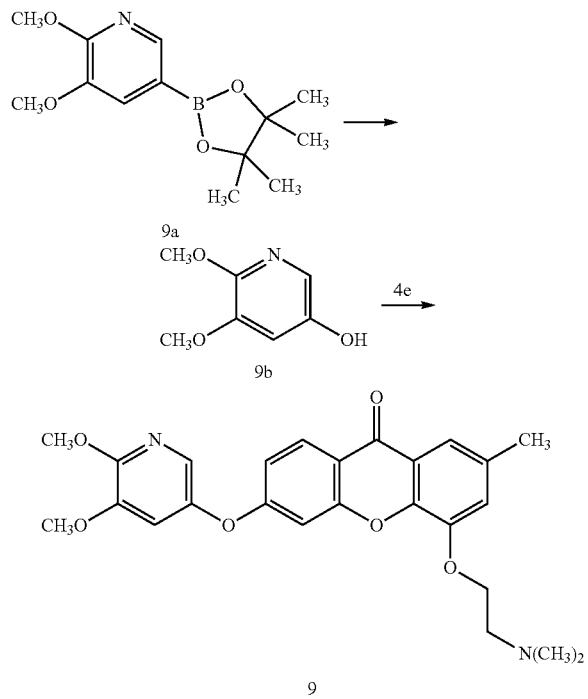

Commercially available 2,3-dimethoxy-5-(4,4,5,5-tetramethyl-1,3,2-dioxaborolan-2-yl)-pyridine (9a) was oxidized with oxone/KHCO$_3$ to give 5,6-dimethoxypyridin-3-ol (9b) in 71% yield. $^1$H NMR (CDCl$_3$) δ 7.34 (d, J=2.5 Hz, 1H), 6.74 (d, J=2.5 Hz, 1H), 4.79 (s, 1H), 3.96 (s, 3H), 3.86 (s, 3H); MS (APCI) m/z: 157 (M+H$^+$).

The coupling reaction of compounds 4e and 9b with K$_2$CO$_3$ in DMSO at 85° C. for 16 h gave 6-((5,6-dimethoxypyridin-3-yl)oxy)-4-(2-(dimethylamino)ethoxy)-2-methyl-9H-xanthen-9-one (9) in 83% yield: mp (CH$_2$Cl$_2$/hexanes) 173-175° C.; $^1$H NMR (CDCl$_3$) δ 8.30 (d, J=8.8 Hz, 1H), 7.70 (dd, J=1.9, 0.9 Hz, 1H), 7.65 (d, J=2.4 Hz, 1H), 7.07 (d, J=1.9 Hz, 1H), 7.03 (dd, J=8.8, 2.4 Hz, 1H), 6.91 (dd, J=5.9, 2.4 Hz, 1H), 4.07 (s, 3H), 3.88 (s, 3H), 4.22 (t, J=6.0 Hz, 1H), 2.85 (t, J=5.9 Hz, 1H), 2.45 (s, 3H), 2.38 (s, 6H), HPLC 99.7%. MS (APCI) m/z: 451 (M+H$^+$).

Example 10

4-(2-(Dimethylamino)ethoxy)-6-((6-((4-methoxybenzyl)oxy)pyridin-3-yl)oxy)-2-methyl-9H-xanthen-9-one

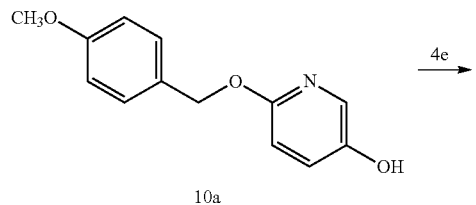

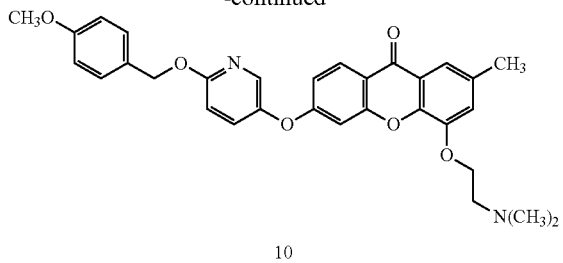

4-(2-(Dimethylamino)ethoxy)-6-fluoro-2-methyl-9H-xanthen-9-one (4e) (40 mg, 0.127 mmol), 6-((4-methoxybenzyl)oxy)pyridin-3-ol (10a) [WO 2006044707] (29.3 mg, 0.164 mmol), and K$_2$CO$_3$ (24.5 mg, 0.177 mmol) were heated in DMSO at 85° C. for 16 h. This was then poured onto crushed ice, and the resulting precipitate was collected by filtration and washed well with water. The crude solid was purified by flash column chromatography, eluting with (MeOH/CH$_2$Cl$_2$, $_{5:95}$) to give a white solid.

Recrystallization from (CH$_2$Cl$_2$/hexanes) gave 4-(2-(dimethylamino)ethoxy)-6-((6-((4-methoxybenzyl)oxy)pyridin-3-yl)oxy)-2-methyl-9H-xanthen-9-one (10) (38 mg, 50%) as a white solid: mp (CH$_2$Cl$_2$/hexanes) 144-146° C.; $^1$H NMR (DMSO-d$_6$) δ 8.22-8.15 (m, 2H), 7.72 (dd, J=8.9, 3.0 Hz, 1H), 7.51 (dd, J=2.0, 1.0 Hz, 1H), 7.42 (d, J=8.7 Hz, 2H), 7.39 (d, J=2.0 Hz, 1H), 7.12 (dd, J=8.9, 2.4 Hz, 1H), 7.00 (d, J=9.0 Hz, 1H), 6.96 (d, J=8.9 Hz, 2H), 6.93 (d, J=2.4 Hz, 1H), 5.29 (s, 2H), 4.23 (t, J=6.0 Hz, 2H), 3.77 (s, 3H), 2.72 (t, J=6.0 Hz, 2H), 2.42 (s, 3H), 2.24 (s, 6H); HRMS (ESI$^+$) Calcd for C$_{31}$H$_{31}$N$_2$O$_6$: 527.2177; found (M+H$^+$) 527.2169. HPLC Purity 98.1%.

Example 11

4-(2-(Dimethylamino)ethoxy)-6-((6-((6-methoxypyridin-3-yl)methoxy)pyridin-3-yl)oxy)-2-methyl-9H-xanthen-9-one

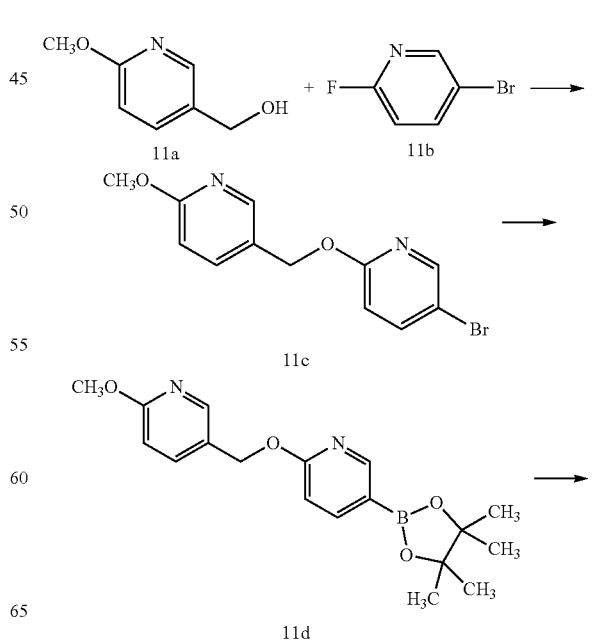

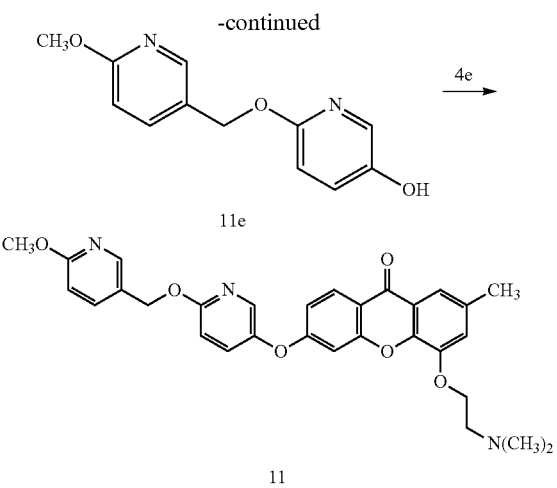

A mixture of (6-methoxypyridin-3-yl)methanol (11a) (1.20 g, 8.6 mmol), 5-bromo-2-fluoropyridine (11b) and NaH (226 mg, 10.3 mmol, 1.2 eq) in DMF (6 mL) was stirred at 20° C. for 20 min, then the reaction mixture was heated at 50° C. for 20 h. The mixture was cooled to 20° C., diluted with $H_2O$ (50 mL) and stirred for 1 h. The resulting precipitate was filtered, washed with water, and dried under vacuum to give 5-bromo-2-((6-methoxypyridin-3-yl)methoxy)pyridine (11c) (2.0 g, 79%): $^1$H NMR (CDCl$_3$) δ 8.25 (d, J=2.1 Hz, 1H), 8.20 (dd, J=2.5, 0.4 Hz, 1H), 7.68 (dd, J=8.6, 2.6 Hz, 1H), 7.65 (dd, J=8.8, 2.6 Hz, 1H), 6.75 (d, J=8.5 Hz, 1H), 6.67 (dd, J=8.8, 0.6 Hz, 1H), 5.27 (s, 2H), 3.94 (s, 3H); MS (APCI) m/z: 295 and 297 (M+H$^+$).

A mixture of compound 1c (1.0 g, 3.39 mmol), bispinacalatodiborane (1.032 g, 4.07 mmol 1.2eq) and KOAc (732 mg, 7.54 mmol, 2.2 eq) in 1,4-dioxane (20 mL) was degassed by bubbling with N$_2$ then PdCl$_2$(dppf)-CH$_2$Cl$_2$ (230 mg, 0.3 mmol, 8 mol %) was added. The mixture was degassed again and the reaction mixture was heated at 80° C. for 20 h. After cooling, the solvent was removed under vacuum. The residue was chromatographed on SiO$_2$ eluting with a gradient of 0-20% hexanes/EtOAc, to give the unstable boronate (11d), which was directly subjected to oxidation with oxone/KHCO$_3$ in acetone/H$_2$O to give 6-((6-methoxypyridin-3-yl)methoxy)pyridin-3-ol (11e) in 57% yield over two steps: $^1$H NMR (DMSO-d$_6$) δ 8.23 (d, J=1.9 Hz, 1H), 7.77 (dd, J=8.5, 2.4 Hz, 1H), 7.69 (dd, J=3.0, 0.4 Hz, 1H), 7.18 (dd, J=8.8, 3.0 Hz, 1H), 6.81 (d, J=8.5 Hz, 1H), 6.69 (d, J=8.9 Hz, 1H), 5.17 (s, 2H), 3.84 (s, 3H); MS (APCI) m/z: 233 (M+H$^+$).

A mixture of 4-(2-(dimethylamino)ethoxy)-6-fluoro-2-methyl-9H-xanthen-9-one (4e) (100 mg, 0.32 mmol), 11e (88.4 mg, 0.38 mmol) and K$_2$CO$_3$ (112 mg, 0.81 mmol) in DMSO (3 mL) was heated at 80° C. for 60 h. The reaction mixture was then diluted with H$_2$O (50 mL), extracted into EtOAc (4×20 mL), and dried (Na$_2$SO$_4$). Evaporation of the solvents under vacuum, and chromatography of the residue on SiO$_2$, eluting with a gradient of CH$_2$Cl$_2$/MeOH 0-2% gave 4-(2-(dimethylamino)ethoxy)-6-((6-((6-methoxypyridin-3-yl)methoxy)pyridin-3-yl)oxy)-2-methyl-9H-xanthen-9-one (11) (131 mg, 78%): Mp (CH$_2$Cl$_2$/hexanes) 105-107° C.; $^1$H NMR (CDCl$_3$) δ 8.31-8.24 (m, 2H), 8.06 (dd, J=3.0, 0.4 Hz, 1H), 7.73 (dd, J=8.5, 2.4 Hz, 1H), 7.70 (dd, J=1.9, 0.9 Hz, 1H), 7.42 (dd, J=8.9, 3.0 Hz, 1H), 7.08 (d, J=1.9 Hz, 1H), 7.01 (dd, J=8.9, 2.4 Hz, 1H), 6.92 (d, J=2.3 Hz, 1H), 6.86 (dd, J=8.93, 0.42 Hz, 1H), 6.78 (dd, J=8.6, 0.4 Hz, 1H), 4.23 (t, J=5.9 Hz, 1H), 3.95 (s, 2H), 2.85 (t, J=5.9 Hz, 1H), 2.45 (s, 3H), 2.39 (s, 6H). Anal. Calcd for C$_{30}$H$_{29}$N$_3$O$_6$1.25H$_2$O: C, 65.5; H, 5.8; N, 7.6. Found: C, 65.6; H, 5.5; N, 7.4%.

Example 12

4-(2-(Dimethylamino)ethoxy)-6-((5-methoxy-6-((4-methoxybenzyl)oxy)pyridin-3-yl)oxy)-2-methyl-9H-xanthen-9-one

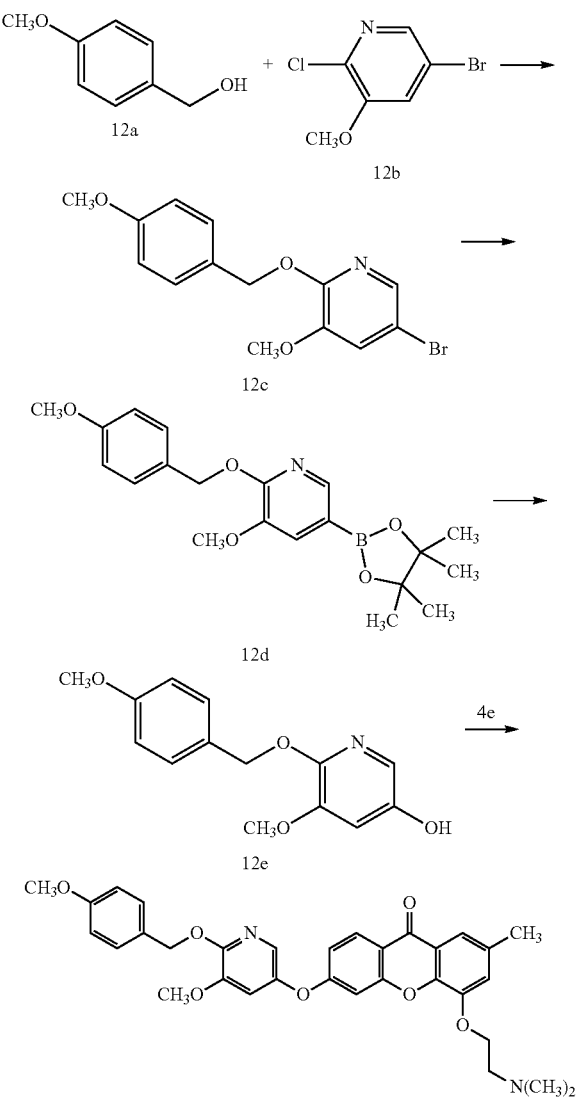

Using the method described in example 11, reaction of (4-methoxyphenyl)methanol (12a) and 5-bromo-2-chloro-3-methoxypypyridine (12b) gave 5-bromo-3-methoxy-2-((4-methoxybenzyl)oxy)pyridine (12c) in 48% yield. Boronation of 12c as in Example 11 gave 3-methoxy-2-((4-methoxybenzyl)oxy)-5-(4,4,5,5-tetramethyl-1,3,2-dioxaborolan-2-yl)pyridine (12d) in 86% yield.

Oxidation of compound 12d with oxone/KHCO$_3$ in acetone/H$_2$O gave 5-methoxy-6-((4-methoxybenzyl)oxy)pyridin-3-ol (12e) in 69% yield. $^1$H NMR (CDCl$_3$) δ 7.41 (d, J=8.8 Hz, 2H), 7.33 (d, J=2.5 Hz, 1H), 6.88 (d, J=8.7 Hz, 2H), 6.73 (d, J=2.5 Hz, 1H), 5.33 (s, 2H, 4.62 (s, 1H), 3.82 s, 3H), 3.79 (s, 3H).

Using the method described in example 11, reaction of compound 12e with compound 4e gave 4-(2-(dimethylamino)ethoxy)-6-((5-methoxy-6-((4-methoxybenzyl)oxy)pyridin-3-yl)oxy)-2-methyl-9H-xanthen-9-one (12) in 43% yield: mp (CH$_2$Cl$_2$/MeOH) 150-152° C.; $^1$H NMR (CDCl$_3$) δ 8.29 (d, J=8.9 Hz, 1H), 7.70 (dd, J=1.8, 0.8 Hz, 1H), 7.64 (d, J=2.4 Hz, 1H), 7.47 (d, J=8.7 Hz, 2H), 7.07 (d, J=1.9 Hz, 1H), 7.03 (dd, J=8.9, 2.3 Hz, 1H), 6.94-6.89 (m, 4H), 5.43 (s, 2H), 4.22 (t, J=5.9 Hz, 2H), 3.84 (s, 3H), 3.81 (s, 3H), 2.85 (t, J=5.9 HZ, 2H), 2.45 (s, 3H), 2.39 (s, 6H); HPLC purity 97%.

Example 13

4-(2-(Dimethylamino)ethoxy)-2-methyl-6-((6-((6-(trifluoromethyl)pyridin-3-yl)meth-oxy)pyridin-3-yl)oxy)-9H-xanthen-9-one

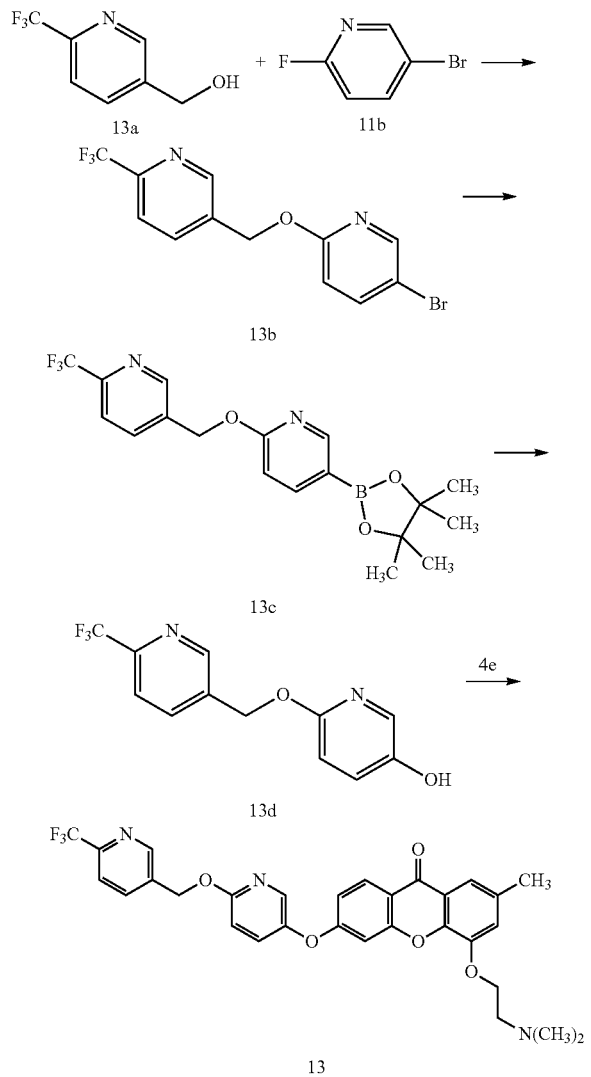

Reaction of (6-(trifluoromethyl)pyridin-3-yl)methanol (13a) and 5-bromo-2-fluoro-pyridine (11b) as in Example 11 gave 5-bromo-2-((6-(trifluoromethyl)pyridin-3-yl)methoxy)pyridine (13b) in 76% yield. This was used directly for boronation, as in example 11, followed by oxidation, to give 6-((6-(trifluoromethyl)pyridin-3-yl)methoxy)pyridin-3-ol (13d) in 72% yield over two steps. $^1$H NMR (DMSO-d$_6$) δ 9.38 (s, 1H), 8.82 (d, J=1.2 Hz, 1H), 8.11 (dm, J=8.1 Hz, 1H), 7.91 (d, J=8.1 Hz, 1H), 7.67 (dd, J=2.9, 0.4 Hz, 1H), 7.22 (dd, J=3.0, 8.8 Hz, 1H), 6.78 (d, J=8.7 Hz, 1H), 5.440 (s, 2H).

Using the method described in example 11, the coupling reaction of 13d and compound 4e in DMSO gave 4-(2-(dimethylamino)ethoxy)-2-methyl-6-((6-((6-(trifluoromethyl)pyridin-3-yl)methoxy)pyridin-3-yl)oxy)-9H-xanthen-9-one (13) in 77% yield: mp (CH$_2$Cl$_2$/hexanes) 158-160° C.; $^1$H NMR (DMSO-d$_6$) δ 8.90 (d, J=1.1 Hz, 1H), 8.20-8.18 (m, 2H), 7.96 (d, J=8.1 Hz, 1H), 7.78 (dd, J=8.9, 2.9 Hz, 1H), 7.51 (dd, J=1.7, 0.7 Hz, 1H), 7.39 (d, J=1.8 Hz, 1H), 7.13-1.07 (m, 2H), 6.95 (d, J=2.3 Hz, 1H), 5.55 (s, 2H), 4.24 (t, J=6.0 Hz, 2H), 2.73 (t, J=5.9 Hz, 2H), 2.41 (s, 3H), 2.26 (s, 6H); HPLC purity 96.7%.

Example 14

4-(2-(Dimethylamino)ethoxy)-6-((6-((4-methoxybenzyl)amino)pyridin-3-yl)oxy)-2-methyl-9H-xanthen-9-one

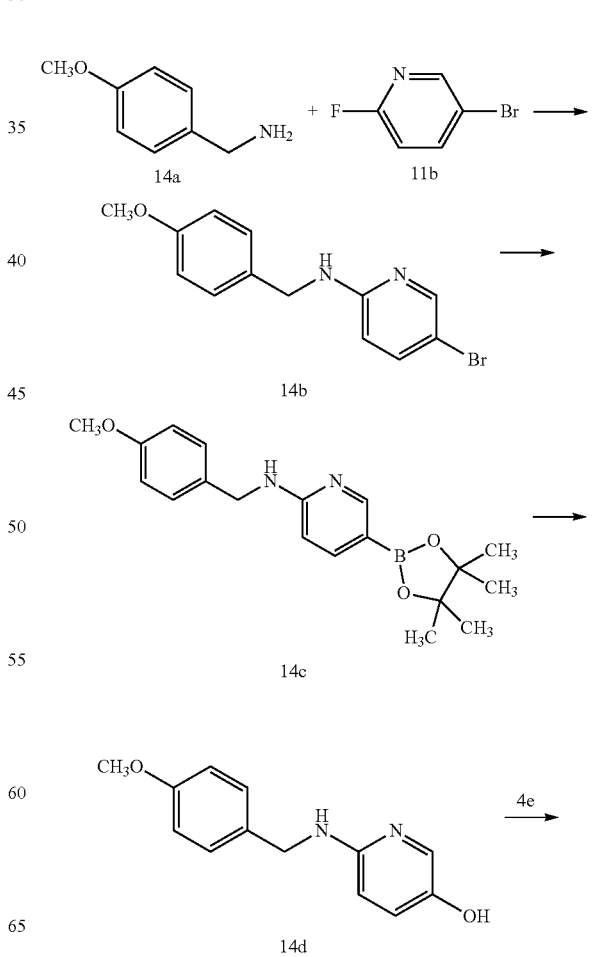

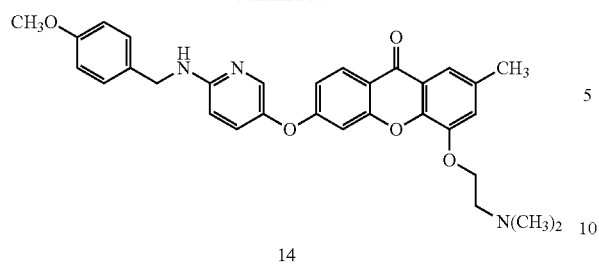

Reaction of (4-methoxyphenyl)methanamine (14a) and compound 11b gave 5-bromo-N-(4-methoxybenzyl)pyridin-2-amine (14b) in 59% yield. Boronation of 14b, as in example 11, followed by oxidation with oxone gave 6-((4-methoxybenzyl)amino)pyridin-3-ol (14d) in 44% yield: $^1$H NMR (CDCl$_3$) δ 7.77 (d, J=3.0 Hz, 1H), 7.20-7.25 (m, 2H), 7.08 (dd, J=8.9, 3.0 Hz, 1H), 6.86 (d, J=8.7 Hz, 1H), 6.34 (d, J=8.9 Hz, 1H), 4.60 (br s, 1H), 4.35 (brs, 2H), 3.79 (s, 3H).

Using the method described in example 11, reaction of compound 14d with compound 4e gave 4-(2-(dimethylamino)ethoxy)-6-((6-((4-methoxybenzyl)amino)pyridin-3-yl)oxy)-2-methyl-9H-xanthen-9-one (14) in 25% yield: mp (CH$_2$Cl$_2$/hexanes) 177-179° C.; $^1$H NMR (DMSO-d$_6$) δ 8.15 (d, J=8.9 Hz, 1H), 7.95 (d, J=2.8 Hz, 1H), 6.90 (d, J=8.7 Hz, 2H), 6.81 (d, J=2.4 Hz, 1H), 6.63 (d, J=9.0 Hz, 1H), 4.42 (d, J=5.8 Hz, 2H), 4.23 (t, J=6.0 Hz, 2H), 3.73 (s, 3H), 2.73 (t, J=6.0 Hz, 2H), 2.41 (s, 3H), 2.25 (s, 6H); HPLC purity 98%; MS (APCI) m/z: 562 (M+H$^+$).

Example 15

4-(2-(Dimethylamino)ethoxy)-2-methyl-6-((6-((4-(trifluoromethoxy)benzyl)amino)-pyridin-3-yl)oxy)-9H-xanthen-9-one

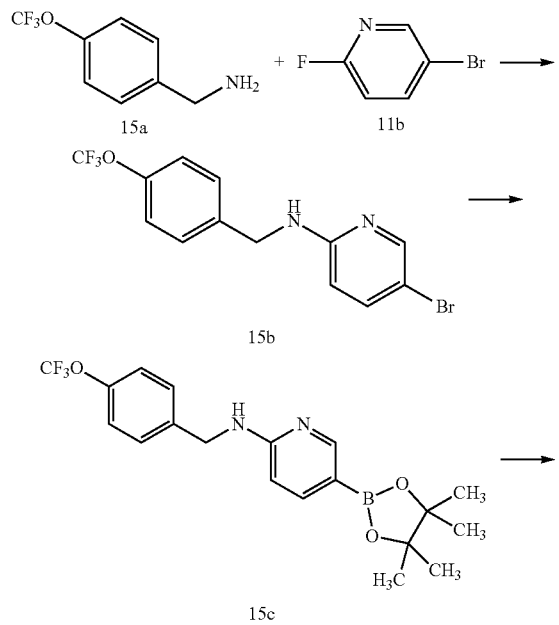

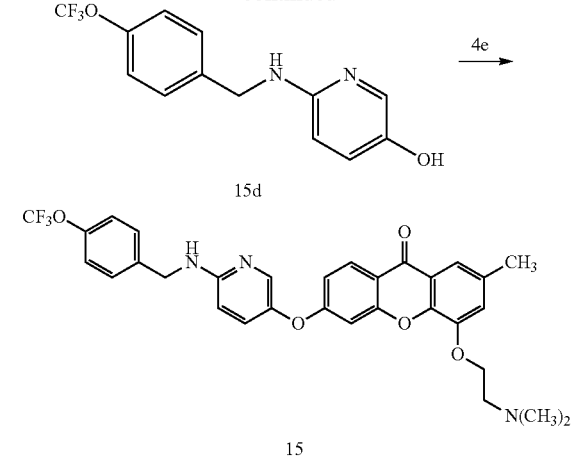

The condensation of (4-(trifluoromethoxy)phenyl)methanamine (15a) with compound 11b gave 5-bromo-N-(4-(trifluoromethoxy)benzyl)pyridin-2-amine (15b) in 45% yield: $^1$H NMR (CDCl$_3$) δ 8.14 (d, J=2.0 Hz, 1H), 7.47 (dd, J=2.5, 8.8 Hz, 1H), 7.36 (d, J=8.7 Hz, 2H), 7.18 (d, J=7.9 Hz, 2H), 6.29 (dd, J=8.82, 0.54 Hz, 1H), 4.89 (br, 1H), 4.51 (d, J=6.0 Hz, 2H); MS (APCI) m/z: 347 and 349 (M+H$^+$).

Boronation of compound 15b as in example 11, followed by oxidation gave 6-((4-(trifluoromethoxy)benzyl)amino)pyridin-3-ol (15d) in 48% yield over two steps: $^1$H NMR (CDCl$_3$) δ 7.76 (d, J=2.8 Hz, 1H), 7.35 (d, J=8.6 Hz, 2H), 7.16 (d, J=8.0 Hz, 2H), 7.09 (dd, J=8.9, 2.9 Hz, 1H), 6.32 (d, J=8.9 Hz, 1H), 4.77 (b, 1H), 4.43 (s, 2H); MS (APCI) m/z: 285 (M+H$^+$).

The coupling reaction of compound 15d with compound 4e as in example 11 gave 4-(2-(dimethylamino)ethoxy)-2-methyl-6-((6-(4-(trifluoromethoxy)phenethyl)pyridin-3-yl)oxy)-9H-xanthen-9-one (15) in 22% yield: mp (CH$_2$Cl$_2$/hexanes) 89-91° C.; $^1$H NMR (CDCl$_3$) δ 8.27 (d, J=8.9 Hz, 1H), 8.03 (d, J=2.8 Hz, 1H), 7.69 (dd, J=1.9, 0.9 Hz, 1H), 7.43 (d, J=8.7 Hz, 2H), 7.27 (d, J=8.9, 2.8 Hz, 1H), 7.21 (d, J=7.9 Hz, 2H), 7.07 (d, J=1.9 Hz, 1H), 7.01 (dd, J=8.9, 2.4 Hz, 1H), 6.92 (d, J=2.3 Hz, 1H), 6.47 (d, J=8.9 Hz, 1H), 5.03 (t, J=5.9 Hz, 2H), 4.58 (d, J=5.9 Hz, 1H), 4.23 (t, J=6.0 Hz, 1H), 2.61 (s, 6H), 2.39 (s, 3H).

Example 16

4-(2-(Dimethylamino)ethoxy)-6-((6-(((6-methoxypyridin-3-yl)methyl)amino)pyridin-3-yl)oxy)-2-methyl-9H-xanthen-9-one

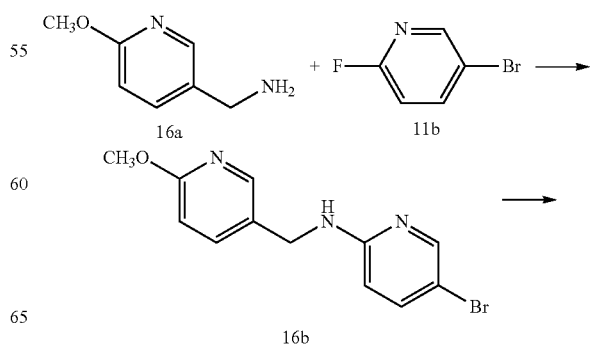

-continued

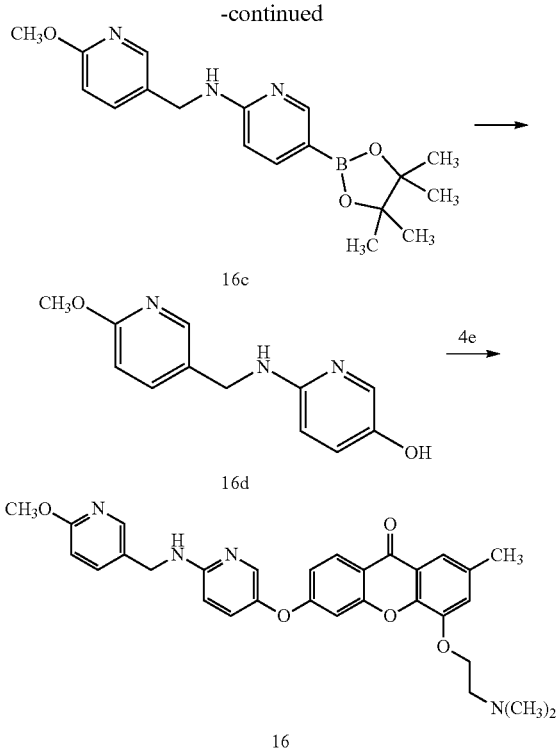

16c

16d

16

A mixture of (6-methoxypyridin-3-yl)methanamine (16a) (0.60 g, 4.34 mmol), compound 11b (1.50 g, 8.52 mmol), and KHCO$_3$ in DMSO (10 mL) was heated at 70° C. for 20 h, cooled to room temperature, and diluted with water. The resulting precipitate was filtered and washed with water, then dissolved in CH$_2$Cl$_2$ (dried Na$_2$SO$_4$). Evaporation of the solvents gave the crude compound which was purified by column chromatography on SiO$_2$, eluting with hexanes/EtOAc 0-50% to give 5-bromo-N-((6-methoxypyridin-3-yl) methyl)pyridin-2-amine (16b) (1.04 g, 81% yield): $^1$H NMR (CDCl$_3$) δ 8.13 (d, J=2.4 Hz, 2H), 7.57 (dd, J=8.5, 2.5 Hz, 1H), 7.47 (dd, J=8.80, 2.5 Hz, 1H), 6.72 (d, J=8.5 Hz, 1H), 6.31 (dd, J=8.8, 0.5 Hz, 1H), 4.79 (brs, 1H), 4.42 (d, J=5.8' Hz, 2H), 3.92 (s, 3H); MS (APCI) m/z: 294 and 296 (M+H$^+$).

Boronation of 16b as in example 11 and oxidation of the boronated product 16c gave 6-(((6-methoxypyridin-3-yl) methyl)amino)pyridin-3-ol (16d) in 47% yield over two steps: $^1$H NMR (CDCl$_3$) δ 8.12 (d, J=1.9 Hz, 1H), 7.76 (d, J=2.8 Hz, 1H), 7.57 (dd, J=8.5, 2.4 Hz, 1H), 7.08 (dd, J=8.9, 2.9 Hz, 1H), 6.71 (d, J=8.5 Hz, 1H), 6.35 (d, J=8.9 Hz, 1H), 4.55 (brs, 1H), 4.36 (s, 2H), 3.90 (s, 3H); MS (APCI) m/z: 232.3 (M+H$^+$).

The coupling reaction of compound 16d with compound 4e as in example 11 gave 4-(2-(dimethylamino)ethoxy)-6-((6-(((6-methoxypyridin-3-yl)methyl)amino)pyridin-3-yl) oxy)-2-methyl-9H-xanthen-9-one (16) in 16% yield: mp (diisopropyl ether) 156-159° C.; $^1$H NMR (CDCl$_3$) δ 8.27 (d, J=8.9 Hz, 1H), 8.19 (d, J=2.1 Hz, 1H), 8.04 (d, J=2.7 Hz, 1H), 7.69 (dd, J=1.8, 0.8 Hz, 1H), 7.64 (dd, J=8.5, 2.4 Hz, 1H), 7.26 (dd, J=8.8, 2.9 Hz, 1H), 7.07 (d, J=1.8 Hz, 1H), 7.00 (dd, J=8.9, 2.3 Hz, 1H), 6.91 (d, J=2.3 Hz, 1H), 6.76 (d, J=8.5 Hz, 1H), 6.48 (d, J=8.9 Hz, 1H), 4.88 (t, 1H), 4.49 (d, J=5.7 Hz, 2H), 4.23 (t, J=6.0 Hz, 2H), 3.93 (s, 3H) 2.86 (t, J=6.0 Hz, 2H), 2.44 (s, 3H), 2.39 (s, 6H); HPLC purity 90%.

Example 17

6-((6-Aminopyridin-3-yl)oxy)-4-(2-(dimethylamino) ethoxy)-2-methyl-9H-xanthen-9-one

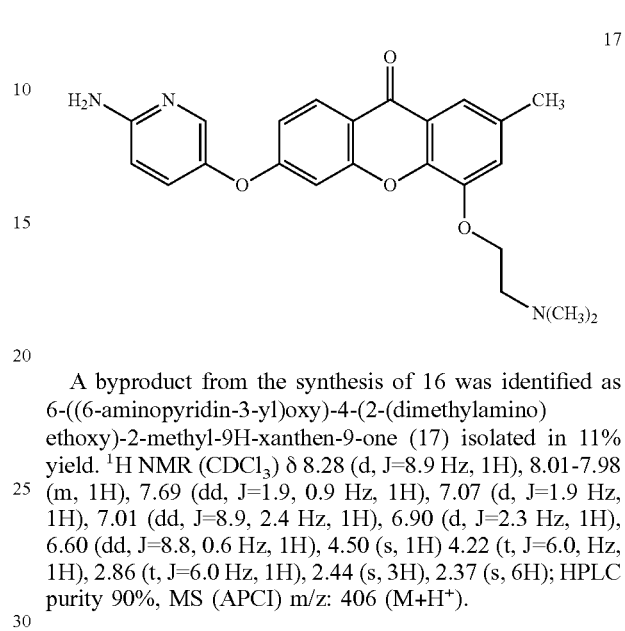

17

A byproduct from the synthesis of 16 was identified as 6-((6-aminopyridin-3-yl)oxy)-4-(2-(dimethylamino) ethoxy)-2-methyl-9H-xanthen-9-one (17) isolated in 11% yield. $^1$H NMR (CDCl$_3$) δ 8.28 (d, J=8.9 Hz, 1H), 8.01-7.98 (m, 1H), 7.69 (dd, J=1.9, 0.9 Hz, 1H), 7.07 (d, J=1.9 Hz, 1H), 7.01 (dd, J=8.9, 2.4 Hz, 1H), 6.90 (d, J=2.3 Hz, 1H), 6.60 (dd, J=8.8, 0.6 Hz, 1H), 4.50 (s, 1H) 4.22 (t, J=6.0, Hz, 1H), 2.86 (t, J=6.0 Hz, 1H), 2.44 (s, 3H), 2.37 (s, 6H); HPLC purity 90%, MS (APCI) m/z: 406 (M+H$^+$).

Example 18

4-(2-(Dimethylamino)ethoxy)-6-((6-(4-methoxyphenethyl)pyridin-3-yl)oxy)-2-methyl-9H-xanthen-9-one

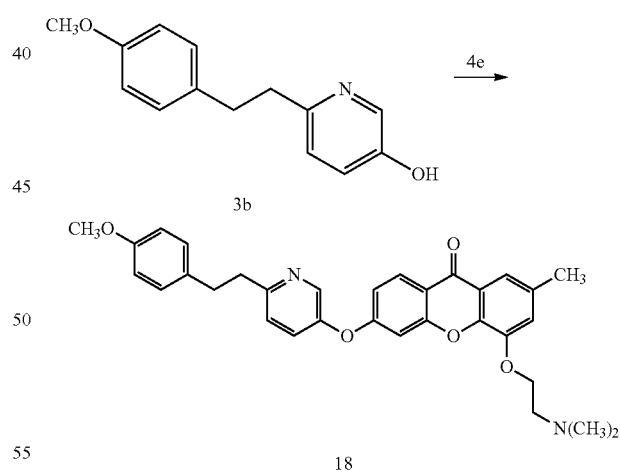

3b

18

The coupling reaction of 3b with compound 4e as in example 3 gave 4-(2-(dimethylamino)ethoxy)-6-((6-(4-methoxyphenethyl)pyridin-3-yl)oxy)-2-methyl-9H-xanthen-9-one (18) in 86% yield: mp (CH$_2$Cl$_2$/hexanes) 134-136° C.; $^1$H NMR (CDCl$_3$) δ 8.46 (d, J=2.6 Hz, 1H), 8.31 (d, J=8.8 Hz, 1H), 7.70 (dd, J=1.9, 0.9 Hz, 1H), 7.34 (dd, J=8.4, 2.8 Hz, 1H), 7.14 (dd, J=8.7, 2.4 Hz, 1H), 7.08 (d, J=1.8 Hz, 1H), 7.02 (dd, J=8.8, 2.3 Hz, 1H), 6.97 (d, J=2.3 Hz, 1H), 6.85 (d, J=8.7 Hz, 1H), 4.22 (t, J=5.9 Hz, 2H), 3.80 (s, 3H), 3.14-3.10 (m, 2H), 3.06-3.01 (m, 2H), 2.84 (t, J=5.9

Hz, 2H), 2.84 (s, 3H), 2.31 (s, 6H). Anal. Calcd for $C_{32}H_{32}N_2O_5$: C, 73.3; H, 6.1; N, 5.3. Found: C, 73.3; H, 6.2; N, 5.4%.

Example 19

4-(2-(Dimethylamino)ethoxy)-6-((6-methoxypyridin-3-yl)methyl)-2-methyl-9H-xanthen-9-one

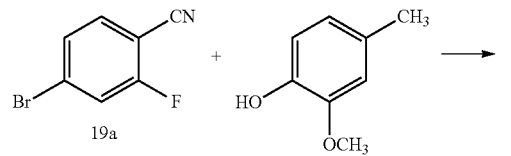
19a    4a

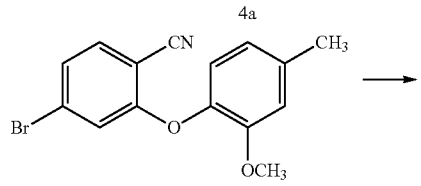
19b

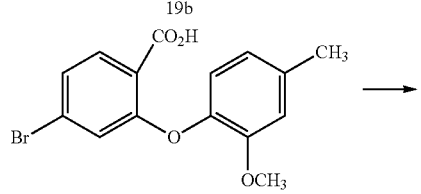
19c

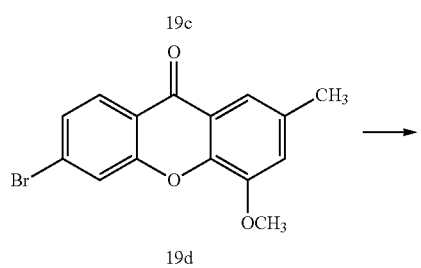
19d

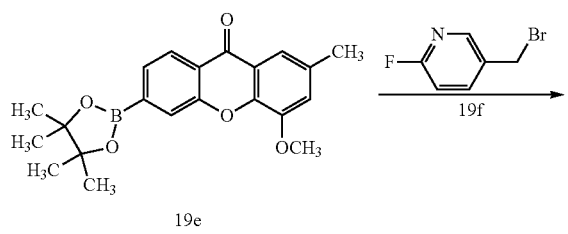
19e    19f

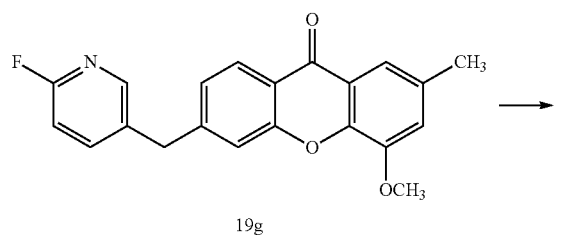
19g

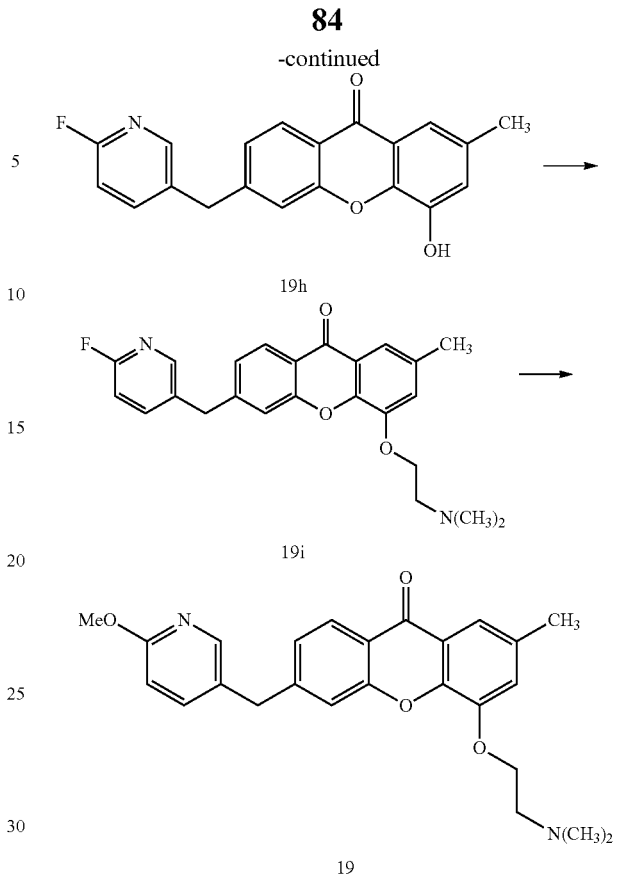
19h

19i

19

According to the method of U.S. Pat. No. 7,553,850B2, a stirred solution of 2-methoxy-4-methylphenol (4a) (8.3 g, 60 mmol) in dry DMF (40 mL) was treated with NaH (60% in oil, 2.4 g, 60 mmol) and after 10 min, 4-bromo-2-fluorobenzonitrile (19a) (10 g, 50 mmol) was added. The mixture was heated under reflux overnight, cooled, and poured into 2 M NaOH solution to give 4-bromo-2-(2-methoxy-4-methylphenoxy)benzonitrile (19b): mp (MeOH) 121-122° C.; $^1$H NMR (CDCl$_3$) δ 7.46 (d, J=8.3 Hz, 1H), 7.19 (dd, J=8.3, 1.7 Hz, 1H), 7.00 (d, J=8.0 Hz, 1H), 6.84 (d, J=1.4 Hz, 1H), 6.80 (ddd, J=8.1, 1.9, 0.7 Hz, 1H), 6.78 (d, J=1.7 Hz, 1H), 3.77 (s, 3H), 2.39 (s, 3H). Anal. Calcd for $C_{15}H_{12}BrNO_2$: C, 56.6; H, 3.8; N, 4.4. Found: C, 56.5; H, 3.7; N, 4.4%.

Hydrolysis of 19b with aq. NaOH in EtOH gave 4-bromo-2-(2-methoxy-4-methylphenoxy)benzoic acid (19c): mp (aq. MeOH) 171-173° C.; $^1$H NMR (CDCl$_3$) δ 10.40 (br, 1H, OH), 8.03 (d, J=8.4 Hz, 1H), 7.30 (dd, J=8.4, 1.8 Hz, 1H), 7.09 (d, J=8.2 Hz, 1H), 6.90 (d, J=1.8 Hz, 1H), 6.86-6.83 (m, 2H), 3.77 (s, 3H), 2.41 (s, 3H). Anal. Calcd for $C_{15}H_{13}BrO_4$: C, 53.4; H, 3.9. Found: C, 53.5; H, 3.8%.

Ring closure of 19c with PPA at 100° C. gave 6-bromo-4-methoxy-2-methyl-9H-xanthen-9-one (19d): mp (MeOH—CH$_2$Cl$_2$) 223-235° C.; $^1$H NMR (CDCl$_3$) δ 8.19 (d, J=8.5 Hz, 1H), 7.81 (d, J=1.7 Hz, 1H), 7.67 (dd, J=1.9, 0.9 Hz, 1H), 7.49 (dd, J=8.5, 1.8 Hz, 1H), 7.07 (d, J=1.9, 1H), 4.01 (s, 3H), 2.46 (s, 3H); Anal. Calcd for $C_{15}H_{11}BrO_3$: C, 56.5, H, 3.5. Found: C, 56.6; H, 3.4%.

A mixture of 19d (1.0 g, 3.13 mmol), bis(pinacolato)diboron (874 mg, 11 eq) and KOAc (307 mg, 3.13 mmol) in 1,4-dioxane (20 mL) was degassed with N$_2$, then PdCl$_2$(dppf).CH$_2$Cl$_2$ (127 mg, 0.5 mol %) was added degassed, flushed with nitrogen and heated at 80° C. for 20 h. The reaction mixture was cooled to 20° C. and H$_2$O (10 mL), K₂CO₃ and 5-(bromomethyl)-2-fluoropyridine (19f) (715 mg, 3.76 mmol) in DMF (6 mL) was added. PdCl₂(dppf).CH₂Cl₂ (127 mg, 0.5 mol %) was added, the mixture was degassed, flushed with nitrogen, and the resulting mixture heated at 80° C. for 20 h. The reaction mixture was cooled to 20° C. and diluted with H₂O (100 mL), extracted into EtOAc (50 mL×3), and dried (Na₂SO₄). Evaporation of the solvents and the chromatography of the residue on SiO₂, eluting with a gradient of hexanes/EtOAc 0-30% gave 6-((6-fluoropyridin-3-yl)methyl)-4-methoxy-2-methyl-9H-xanthen-9-one (19g) (630 mg, 22% yield): $^1$H NMR (CDCl₃) δ 8.28 (d, J=8.2 Hz, 1H), 8.14 (d, J=2.1 Hz, 1H), 7.69 (dd, J=1.9, 0.9 Hz, 1H), 7.60 (dt, J=7.9, 2.5 Hz, 1H), 7.35 (brs, 1H), 7.21 (dd, J=8.2, 1.6 Hz, 1H), 7.06 (d, J=1.9 Hz, 1H), 6.89 (dd, J=8.4, 3.0 Hz, 1H), 4.12 (s, 2H), 4.01 (s, 3H), 2.46 (s, 3H); MS (APCI) m/z: 350 (M+H⁺).

Demethylation of 19g with CH₂Cl₂/BBr₃ gave 6-((6-fluoropyridin-3-yl)methyl)-4-hydroxy-2-methyl-9H-xanthen-9-one (19h) in 29% yield: $^1$H NMR (DMSO-d₆) δ 10.31 (s, 1H), 8.27 (d, J=2.0 Hz, 1H), 8.10 (d, J=8.1 Hz, 1H), 7.94 (dt, J=8.2, 2.5 Hz, 1H), 7.52 (d, J=1.1 Hz, 1H), 7.39-7.35 (m, 2H), 7.16-7.13 (m, 2H), 4.19 (s, 2H), 2.34 (s, 3H); MS (APCI) m/z: 336 (M+H⁺).

Compound 19h was coupled with 2-chloro-N,N-dimethylethylamine in the presence of the phase transfer catalyst tert-butylammonium bromide to give 4-(2-(dimethylamino)ethoxy)-6-((6-fluoropyridin-3-yl)methyl)-2-methyl-9H-xanthen-9-one (19i) in 63% yield: mp (CH₂Cl₂/hexanes) 119-121° C.; $^1$H NMR (CDCl₃) δ 8.26 (d, J=8.2 Hz, 1H), 8.13 (d, J=2.1 Hz, 1H), 7.68 (dd, J=1.7, 0.8 Hz, 1H), 7.59 (dt, J=8.1, 8, 2.5 Hz, 1H), 7.31 (brs, 1H), 7.18 (dd, J=8.2, 1.5 Hz, 1H), 7.07 (d, J=1.8 Hz, 1H), 6.89 (dd, J=8.4, 2.9 Hz, 1H), 4.23 (t, J=5.9 Hz, 1H), 2.87 (t, J=5.9 Hz, 1H), 2.43 (s, 3H), 2.40 (s, 6H); MS (APCI) m/z: 407 (M+H⁺).

A mixture of NaOMe (freshly made by dissolving Na in MeOH) in MeOH and compound 19i (16 mg, 0.039 mmol) was stirred under N₂ at 20° C. for 4 days, and the reaction mixture was evaporated to dryness. The residue was stirred in cold H₂O (20 mL), and the resulting precipitate was filtered, washed with H₂O, and dried in a 100° C. oven to give 4-(2-(dimethylamino)ethoxy)-6-((6-methoxypyridin-3-yl)methyl)-2-methyl-9H-xanthen-9-one (19) (915 mg, 91% yield): mp (H₂O) 133-135° C.; $^1$H NMR (CDCl₃) δ 8.24 (d, J=8.2 Hz, 1H), 8.08 (d, J=2.1 Hz, 1H), 7.70 (dd, J=1.9, 0.8 Hz, 1H), 7.39 (dd, J=8.5, 2.5 Hz, 1H), 7.33 (d, J=1.0 Hz, 1H), 7.19 (dd, J=8.2, 1.5 Hz, 1H), 7.08 (d, J=1.8 Hz, 1H), 6.71 (d, J=8.8 Hz, 1H), 4.24 (t, J=5.9 Hz, 2H), 4.03 (s, 2H), 3.93 (s, 3H), 2.87 (t, J=5.9 Hz, 2H), 2.44 (s, 3H), 2.41 (s, 6H); HPLC purity 98%; HRMS (ESI) Calcd. for C₂₅H₂₆N₂O₄ m/z 419.1965; found 419.1969.

Example 20

(2-(Dimethylamino)ethoxy)-6-(6-((4-methoxybenzyl)oxy)nicotinoyl)-2-methyl-9H-xanthen-9-one

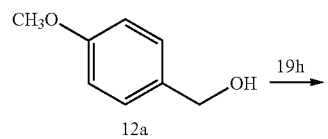

-continued

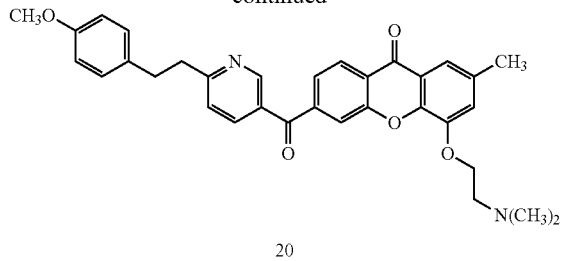

20

4-(2-(Dimethylamino)ethoxy)-6-((6-fluoropyridin-3-yl)methyl)-2-methyl-9H-xanthen-9-one (19h) (74 mg, 0.18 mmol) and 4-methoxybenzyl alcohol (12a) (75 mg, 0.36 mmol) were dissolved in dry DMF (6 mL), cooled in ice and then NaH (13 mg, 0.54 mmol) was added. The resulting blue reaction mixture was stirred at 20° C. for 1 h, followed by 3 h at 50° C. in air, by which time the blue colour had disappeared. The reaction mixture was cooled to 20° C., diluted with water, extracted into EtOAc (30 mL×3), and dried (Na₂SO₄).

Evaporation of the solvents and chromatography of the residue on neutral Al₂O₃, eluting with CH₂Cl₂/MeOH 0-2% gave 4-(2-(dimethylamino)ethoxy)-6-(6-((4-methoxybenzyl)oxy)nicotinoyl)-2-methyl-9H-xanthen-9-one (20) (13 mg, 13% yield): mp (diisopropylether) 135-137° C.; $^1$H NMR (CDCl₃) δ 8.68 (dd, J=2.4, 0.5 Hz, 1H), 8.45 (d, J=8.2 Hz, 1H), 8.15 (dd, J=8.7, 2.4 Hz, 1H), 7.94 (d, J=1.2 Hz, 1H), 7.73-6.89 (m, 2H), 7.42 (d, J=8.7 Hz, 2H), 7.13 (d, J=1.8 Hz, 1H), 6.94-6.89 (m, 3H), 5.42 (s, 2H), 4.26 (t, J=5.8 Hz, 2H), 3.83 (s, 3H), 2.88 (t, J=5.8 Hz, 2H), 2.47 (s, 3H), 2.41 (s, 6H); HPLC purity 95%; HRMS calcd. for C₃₂H₃₁N₂O₆ m/z 539.2117, found 531.2159.

Example 21

3-(5-((5-(2-(Dimethylamino)ethoxy)-7-methyl-9-oxo-9H-xanthen-3-yl)oxy)pyridin-2-yl)-N-(pyridin-3-yl)propanamide

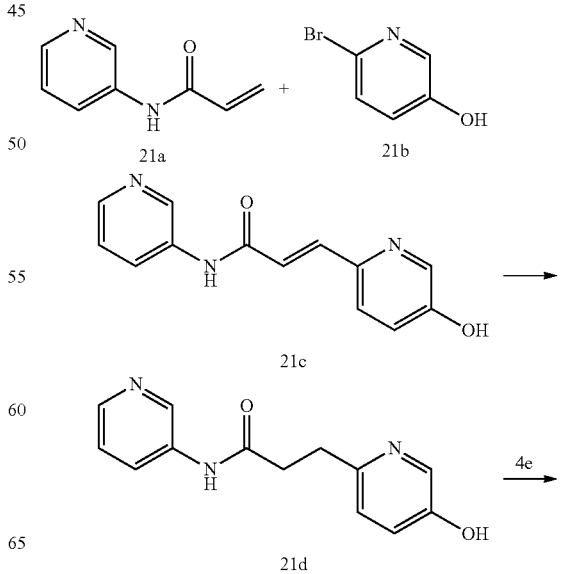

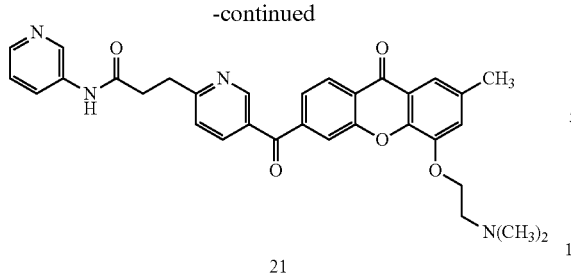

21

In a sealed tube N-(pyridin-3-yl)acrylamide (21a) (Reactive Polymers, 1995, 24, 139) (1,047 g, 7.11 mmol), 5-hydroxy-2-bromomopyridine (21b) (1.86 g, 10.7 mmol, 1.5 eq), tolylphosphine (973 mg, 3.2 mmol, 0.45 eq), and Et$_3$N (1.5 mL, 16 mmol, 2.25 eq) in DMF (12 mL) was degassed and flushed with N$_2$. PdCl$_2$(dppf).CH$_2$Cl$_2$ (116 mg, 0.02 eq) was added and the mixture was degassed again, stirred 10 min at 20° C. and then 3 days at 140° C. After cooling to 20° C. the reaction mixture was diluted with H$_2$O, and the resulting precipitate was collected, washed with water, and chromatographed on SiO$_2$ eluting with CH$_2$Cl$_2$/MeOH 0-6%. Further product was eluted with 4-6% MeOH/EtOAc. The combined fractions were evaporated to dryness and trituration of the residue with MeOH gave (E)-3-(5-hydroxypyridin-2-yl)-N-(pyridin-3-yl)acrylamide (21c) (651 mg, 58% yield): $^1$H NMR (DMSO-d$_6$) δ 10.44 (S, 1H), 10.38 (S, 1H), 8.82 (d, J=2.11 Hz, 1H), 8.27 (dd, J=4.68, 1.48 Hz, 1H), 8.21 (d, J=2.9 Hz, 1H), 8.14 (ddd, J=8.3, 2.5, 1.5 Hz, 1H), 7.52 (dd, J=18.5, 11.8 Hz, 2H), 7.37 (ddd, J=8.4, 4.7, 0.9 Hz, 1H), 7.20 (dd, J=8.4, 2.9 Hz, 1H), 7.08 (d, J=15.3 Hz, 1H): MS (APCI) m/z: 242 (M+H$^+$).

Hydrogenation of compound 21c with H$_2$/Pd/C/in MeOH gave 3-(5-hydroxypyridin-2-yl)-N-(pyridin-3-yl)propanamide (21d) in quantitative yield: $^1$H NMR (DMSO-d$_6$) δ 10.14 (s, 1H), 9.63 (s, 1H), 8.71 (d, J=2.2 Hz, 1H), 8.23 (dd, J=4.5, 1.5 Hz, 1H), 8.03-8.02 (m, 1H), 8.01 (dd, J=2.5, 1.54 Hz, 1H), 7.31 (dd, J=8.3, 4.7 Hz, 1H), 7.30-7.05 (m, 2H), 2.95 (t, J=7.6 Hz, 2H), 2.72 (t, J=7.6 Hz, 2H); MS (APCI) m/z: 244 (M+H$^+$).

The coupling reaction of compound 21d and compound 4e as in example 11 gave 3-(5-((5-(2-(dimethylamino)ethoxy)-7-methyl-9-oxo-9H-xanthen-3-yl)oxy)pyridin-2-yl)-N-(pyridin-3-yl)propanamide (21) in 83% yield: $^1$H NMR (CDCl$_3$) δ 9.33 (br, 1H), 8.59 (d, J=1H), 8.46 (d, J=2.7 Hz, 1H), 8.34-8.31 (m, 2H), 8.19 (brd, J=8.2 Hz, 1H), 7.70 (d, J=0.9 Hz, 1H), 7.43 (dd, J=8.4, 2.8 Hz, 1H), 7.33 (d, J=8.5 Hz, 1H), 7.24 (d, J=4.7 Hz, 1H), 7.08 (d, J=1.8 Hz, 1H), 7.05-7.00 (m, 2H), 4.22 (t, J=5.9 Hz, 2H), 3.31-3.29 (m, 2H), 3.00-2.92 (m, 2H), 2.83 (t, J=5.8 Hz, 2H), 2.41 (s, 3H), 2.19 (s, 6H); HPLC purity 98%; MS (APCI) m/z: 539 (M+H$^+$). HCl salt: mp (MeOH/EtOAc) 236-238° C.

Example 22

N-Cyclopentyl-3-(5-((5-(2-(dimethylamino)ethoxy)-7-methyl-9-oxo-9H-xanthen-3-yl)-oxy)pyridin-2-yl)propanamide

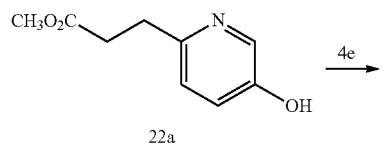

22a

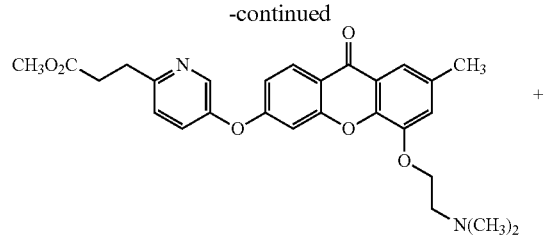

The coupling reaction of methyl 3-(5-hydroxypyridin-2-yl)propanoate (22a) (Brit. UK Pat. Appl., 2498976, 7 Aug. 2013) and compound 4e in DMSO/K$_2$CO$_3$ at 125° C. as in example 11 gave methyl 3-(5-((5-(2-(dimethylamino)ethoxy)-7-methyl-9-oxo-9H-xanthen-3-yl)oxy)pyridin-2-yl)propanoate (22b) in 100% yield: $^1$H NMR (DMSO-d$_6$) δ 8.45 (d, J=2.5 Hz, 1H), 8.20 (d, J=8.86 Hz, 1H), 7.65 (dd, J=8.48, 2.88 Hz, 1H), 7.51 (dd, J=1.85, 0.86 Hz, 1H), 7.44 (d, J=8.51 Hz, 1H), 7.39 (d, J=1.82 Hz, 1H), 7.13 (dd, J=8.88, 2.36 Hz, 1H), 6.97 (d, J=2.34 Hz, 1H), 4.23 (t, J=5.98, 5.98 Hz, 1H), 3.08 (t, J=7.32, 7.32 Hz, 1H), 2.80 (t, J=7.35, 7.35 Hz, 1H), 2.71 (t, J=5.96, 5.96 Hz, 1H).

A mixture of compound 22b (250 mg, 0.52 mmol) and cyclopentylamine 22c (4 mL, excess) was heated at 125° C. for 20 h. Excess cyclopentylamine was removed under vacuum and the reaction mixture was cooled to 20° C., and diluted with water. The resulting precipitate was collected by filtration, washed with water, EtOAc, and then hexanes to give N-cyclopentyl-3-(5-((5-(2-(dimethylamino)ethoxy)-7-methyl-9-oxo-9H-xanthen-3-yl)oxy)pyridin-2-yl)propanamide (22) (194 mg, 70% yield): mp (EtOAc/hexanes) 149-152° C.; $^1$H NMR (CDCl$_3$) δ 8.40 (d, J=2.7 Hz, 1H), 8.31 (d, J=8.7 Hz, 1H), 7.70 (dd, J=1.8, 0.8 Hz, 1H), 7.39 (dd, J=8.43, 2.81 Hz, 1H), 7.29 (d, J=8.5 Hz, 1H), 7.08 (d, J=1.8 Hz, 1H), 6.00 (d, J=7.61 Hz, 1H), 4.24-4.15 (m, 3H), 3.17 (t, J=7.1 Hz, 2H), 2.84 (t, J=5.9 Hz, 2H), 2.66 (t, J=7.1 Hz, 2H), 2.44 (s, 3H), 2.38 (s, 6H), 1.98-1.90 (m, 2H), 1.72-1.56 (m, 4H), 1.37-1.33 (m, 2H): MS (APCI) m/z: 530 (M+H$^+$).

Example 23

4-(2-(Dimethylamino)ethoxy)-2-methyl-6-((6-(3-oxo-3-(pyrrolidin-1-yl)propyl)pyridin-3-yl)oxy)-9H-xanthen-9-one

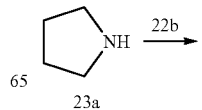

23a

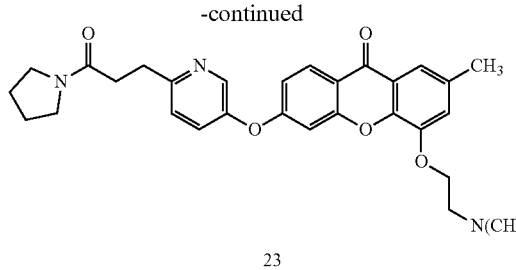

23

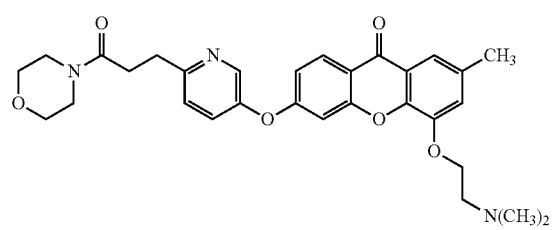

24

Reaction of compound 22b and pyrrolidine at 75° C. gave 4-(2-(dimethylamino)ethoxy)-2-methyl-6-((6-(3-oxo-3-(pyrrolidin-1-yl)propyl)pyridin-3-yl)oxy)-9H-xanthen-9-one (23) in 72% yield: $^1$H NMR (CDCl$_3$) δ 8.40 (dd, J=2.5, 0.7 Hz, 1H), 8.30 (d, J=8.8 Hz, 1H), 7.70 (dd, J=1.8, 0.8 Hz, 1H), 7.39-7.34 (m, 2H), 7.08 (d, J=1.9 Hz, 1H), 7.02 (dd, J=8.8, 2.3 Hz, 1H), 6.98 (d, J=2.3 Hz, 1H), 4.22 (t, J=5.9 Hz, 2H), 3.48 (t, J=5.1 Hz, 2H), 3.45 (t, J=5.1 Hz, 2H), 3.21 (t, J=7.4 Hz, 2H), 2.84 (t, J=5.9 Hz, 2H), 2.45 (s, 3H), 2.41 (s, 6H) 2.80 (t, J=7.4 Hz, 2H), 1.99-1.91 (m, 2H), 1.89-1.82 (m, 2H); HPLC purity 92.8%; MS (APCI) m/z: 515 (M+H$^+$).

Example 24

4-(2-(Dimethylamino)ethoxy)-2-methyl-6-((6-(3-morpholino-3-oxopropyl)pyridin-3-yl)oxy)-9H-xanthen-9-one

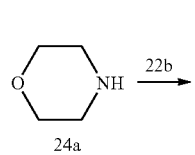

24a

Reaction of compound 22b with morpholine at 125° C. gave 4-(2-(dimethylamino)ethoxy)-2-methyl-6-((6-(3-morpholino-3-oxopropyl)pyridin-3-yl)oxy)-9H-xanthen-9-one (24) in 46% yield after converting to the methanesulfonate: mp (CH$_2$Cl$_2$/EtOAc) 189-191° C.; $^1$H NMR (DMSO-d$_6$) δ 9.58 (br, 1H), 8.45 (d, J=2.8 Hz, 1H), 8.22 (d, J=8.8 Hz, 1H), 7.64 (dd, J=8.5, 2.9 Hz, 1H), 7.61 (brs, 1H), 7.47 (d, J=2.3 Hz, 1H), 7.46 (d, J=8.9 Hz, 1H), 7.12 (dd, J=8.8, 2.4 Hz, 1H), 7.09 (d, J=2.2 Hz, 1H), 4.52 (brm, 1H), 3.62 (br, 2H), 3.57-3.53 (m, 4H), 3.48-3.43 (m, 4H), 3.04 (t, J=7.4 Hz, 2H), 2.94 (brs, 6H), 2.79 (t, J=7.4 Hz, 2H), 2.45 (brs, 3H), 2.29 (s, 3H); HPLC purity 96.7%.

Example 25

N-Cyclopentyl-2-((5-((5-(2-(dimethylamino)ethoxy)-7-methyl-9-oxo-9H-xanthen-3-yl)oxy)pyridin-2-yl)amino)acetamide

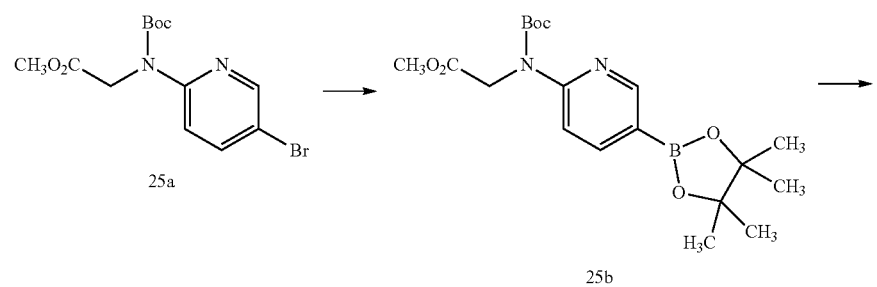

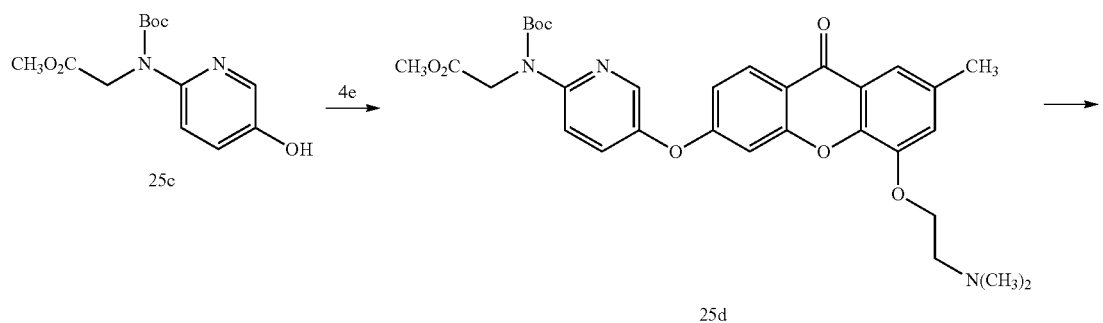

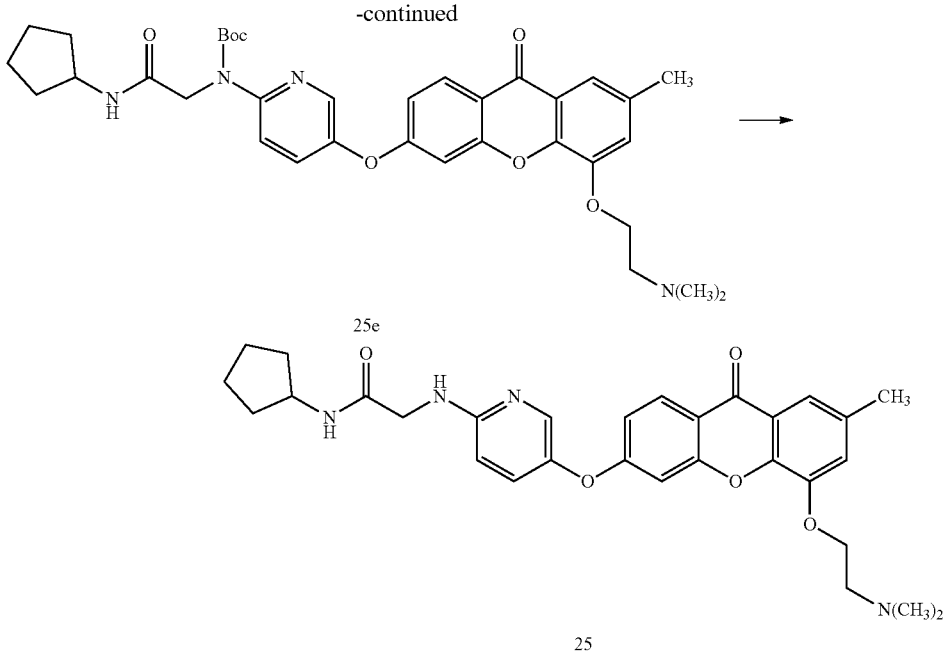

Boronation of methyl N-(5-bromopyridin-2-yl)-N-(tert-butoxycarbonyl)glycinate (25a) (WO 2003088897) as in example 11, followed by oxidation of the resulting methyl N-(tert-butoxycarbonyl)-N-(5-(4,4,5,5-tetramethyl-1,3,2-dioxaborolan-2-yl)pyridin-2-yl)glycinate (25b) with oxone gave methyl N-(tert-butoxycarbonyl)-N-(5-hydroxypyridin-2-yl)glycinate (25c) in 100% yield.

The coupling reaction of compound 25c with compound 4e as in example 11 gave methyl N-(tert-butoxycarbonyl)-N-(5-((5-(2-(dimethylamino)ethoxy)-7-methyl-9-oxo-9H-xanthen-3-yl)oxy)pyridin-2-yl)glycinate (25d): $^1$H NMR (CDCl$_3$) δ 8.30 (d, J=8.82 Hz, 1H), 8.18 (d, J=2.5 Hz, 1H), 7.96 (d, J=8.4 Hz, 1H), 7.69 (dd, J=1.8, 0.8 Hz, 1H), 7.45 (dd, J=9.1, 2.9 Hz, 1H), 7.07 (d, J=1.9 Hz, 1H), 7.03 (dd, J=8.8, 2.4 Hz, 1H), 6.98 (d, J=2.3 Hz, 1H), 4.73 (s, 2H), 4.22 (t, J=6.0 Hz, 2H), 3.78 (s, 3H), 2.86 (t, J=6.0 Hz, 2H), 2.44 (s, 3H), 2.38 (s, 6H), 1.54 (s, 9H); MS (APCI) m/z: 578 (M+H$^+$).

Reaction of compound 25d with cyclopentylamine at 125° C. as in example 22 gave tert-butyl (2-(cyclopentylamino)-2-oxoethyl)(5-((5-(2-(dimethylamino)ethoxy)-7-methyl-9-oxo-9H-xanthen-3-yl)oxy)pyridin-2-yl)carbamate (25e). Treatment with CH$_2$Cl$_2$/TFA gave N-cyclopentyl-2-((5-((5-(2-(dimethylamino)ethoxy)-7-methyl-9-oxo-9H-xanthen-3-yl)oxy)pyridin-2-yl)amino)acetamide (25) as an oil, which was converted to the solid methanesulfonate with methane sulfonic acid in CH$_2$Cl$_2$ (46% yield over two steps): $^1$H NMR (DMSO-d$_6$) δ 9.60 (br, 1H), 8.18 (d, J=8.9 Hz, 1H), 7.94 (d, J=2.8 Hz, 1H), 7.84 (d, J=7.3 Hz, 1H), 7.59 (dd, J=1.78, 0.8 Hz, 1H), 7.46 (d, J=1.8 Hz, 1H), 7.41 (dd, J=9.0, 2.8 Hz, 1H), 7.09 (dd, J=8.9, 2.4 Hz, 1H), 6.93 (d, J=2.3 Hz, 1H), 6.73 (d, J=9.0 Hz, 1H), 4.52-450 (m, 2H), 4.07-3.98 (m, 1H), 3.87 (s, 2H), 3.62 (brs, 2H), 2.93. (s, 6H), 2.43 (s, 3H), 2.29 (s, 3H), 1.84-1.76 (m 2H), 1.68-1.58 (m, 2H), 1.55-1.46 (m, 2H), 1.42-1.34 (s, 2H); HPLC purity 94%; MS (APCI) m/z: 531 (M+H$^+$).

Example 26

N-(2-(5-((5-(2-(Dimethylamino)ethoxy)-7-methyl-9-oxo-9H-xanthen-3-yl)oxy)pyridin-2-yl)ethyl)cyclopentanecarboxamide

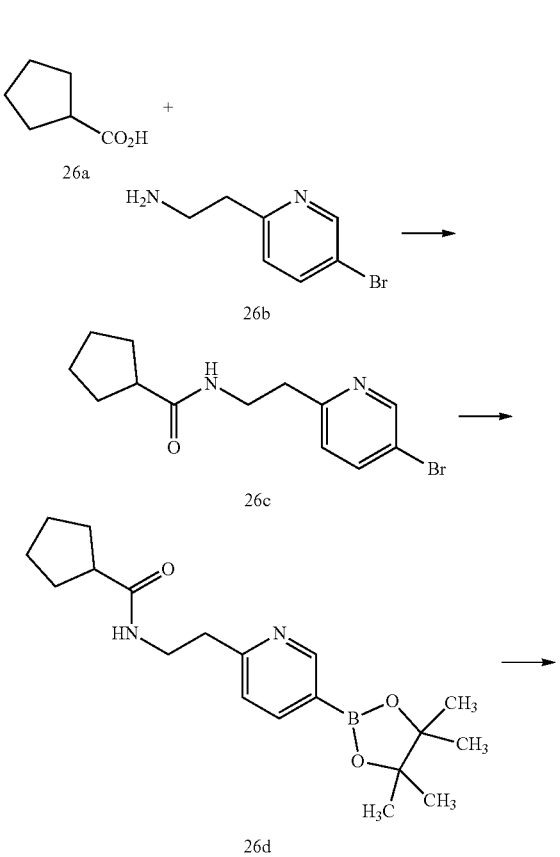

93

-continued

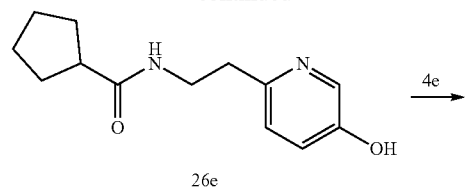

26e

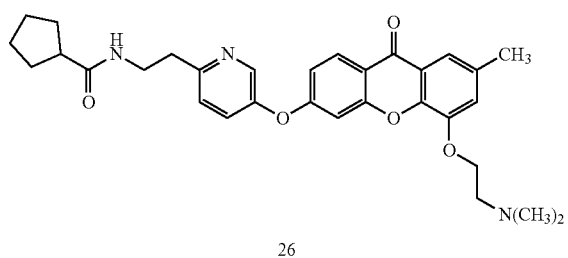

26

To a solution of cyclopentanecarboxylic acid (26a) (956 mg, 8.37 mmol) in dry $CH_2Cl_2$ (6 mL) at 0° C. was added EDCI (1.605 g, 8.37 mmol) and HOBT (1.28 h, 8.37 mmol). The reaction mixture was allowed to warm 20 OC and stirred for 20 h. A solution of 2-(5-bromopyridin-2-yl)ethan-1-amine (26b) [WO 2004041210] (377 mg, 1.9 mmol) in $CH_2Cl_2$ (5 mL) was added, and the mixture stirred at 20° C. for 5 h. After dilution with aq. $K_2CO_3$ the organic layer was separated, and the aqueous layer was further extracted with $CH_2Cl_2$ ×2. The combined organic fractions were dried ($Na_2SO_4$), and the solvent was removed under vacuum. Chromatography of the residue on neutral $Al_2O_3$, eluting with 50% $CH_2Cl_2$/hexanes, followed by $CH_2Cl_2$/EtOAc 5-10% gave N-(2-(5-bromopyridin-2-yl)ethyl)cyclopentanecarboxamide (26c) (324 mg 71% yield): mp ($CH_2Cl_2$/hexanes) 140-141° C.; $^1$H NMR ($CDCl_3$) δ 8.59 (d, J=2.3 Hz, 1H), 7.74 (dd, J=8.3, 2.4 Hz, 1H), 7.08 (d, J=8.3 Hz, 1H), 6.21 (brs, 1H), 3.66-3.69 (m, 2H), 2.95 (t, J=6.3 Hz, 2H), 2.51-2.43 (m, 1H), 1.86-1.78 (m, 2H), 1.76-1.67 9m, 4H), 1.59-1.52 (m, 2H); MS (APCI) m/z: 297 and 299 (M+H$^+$).

Boronation of compound 26c, followed by oxidation gave N-(2-(5-hydroxypyridin-2-yl)ethyl)cyclopentanecarboxamide (26e) in 78% yield over two steps: $^1$H NMR (DMSO-$d_6$) δ 9.62 (s, 1H), 8.03 (br d, J=27 Hz, 1H), 7.06 (dd, J=8.4, 2.8 Hz, 1H), 7.02 (d, J=8.2 Hz, 1H), 3.23-3.28 (m, 2H), 2.72 (t, J=7.4 Hz, 2H), 2.51-2.44 (m, 1H), 1.71-1.24 (m, 8H); MS (APCI) m/z: 235 (M+H$^+$).

The coupling reaction of compound 26e with compound 4e gave N-(4-((5-(2-(dimethyl-amino)ethoxy)-7-methyl-9-oxo-9H-xanthen-3-yl)oxy)phenethyl)cyclopentanecarboxamide (26) in 100% yield: mp ($CH_2Cl_2$/EtOAc/hexanes) 182-184° C.; $^1$H NMR (DMSO-$d_6$) δ 9.61 (br s, 1H), 8.52 (d, J=2.8 Hz, 1H), 8.21 (d, J=9.4 Hz, 1H), 7.87 (t, J=5.7 Hz, 1H), 7.71 (dd, J=8.5, 2.8 Hz, 1H), 7.60 (s, 1H), 7.48-7.44 (m, 2H), 7.14-7.11 (m 2H), 4.52 (t, J=4.9 Hz, 2H), 3.62-3.60 (m, 3H), 3.45-3.41 (m, 2H), 2.94-2.92 (m, 8H), 2.44 (s, 3H), 2.31 (s, 6H), 1.72-1.66 (m, 2H), 160-1.55 (m, 4H), 1.53-1.46 (m, 2H); HPLC purity 99%. MS (APCI) m/z: 530 (M+H$^+$).

94

Example 27

N-(2-(5-((5-(2-(Dimethylamino)ethoxy)-7-methyl-9-oxo-9H-xanthen-3-yl)oxy)pyridin-2-yl)ethyl)pyrrolidine-1-carboxamide To a solution of compound 26b (509 mg, 2.53 mmol) and DIPEA (2.2 mL 5 eq) in dry $CH_2Cl_2$ (10 mL) at 0° C. was added pyrrolidine-1-carbonylchloride (27a) (1.6 mL, 5 eq). The reaction mixture was stirred for 20 h, and allowed to warm to room temperature. The solvent was evaporated under vacuum and the residue was diluted with a solution of $K_2CO_3$ and stirred overnight. The resulting precipitate was collected, washed with water, and dried to give N-(2-(5-bromopyridin-2-yl)ethyl)pyrrolidine-1-carboxamide (27b) (500 mg, 66% yield), which was used directly without further purification: ¹H NMR (CDCl₃) δ 8.58 (s, 1H), 7.73 (dd, J=8.13, 1.89 Hz, 1H), 7.10 (d, J=8.20 Hz, 1H), 5.01 (s, 1H), 3.64-3.60 (m, 2H), 3.39 (m, 4H), 2.97 (t, J=6.2 Hz, 1H), 1.88 (m, 4H).

Boronation of compound 27b, and oxidation of the boronate (27c) gave N-(2-(5-hydroxypyridin-2-yl)ethyl)pyrrolidine-1-carboxamide (27d) in 39% yield over three steps: ¹H NMR (DMSO-d₆) δ 9.61 (s, 1H), 8.03 (d, J=2.6 Hz, 1H), 7.07 (dd, J=8.4, 2.8 Hz, 1H), 7.03 (d, J=8.30 Hz, 1H), 6.10 (t, J=5.5 Hz, 1H), 3.30-3.24 (m, 2H), 3.18-3.15 (m, 4H), 2.76-2.72 (m, 2H), 1.78-1.77 (m, 4H); MS (APCI) m/z: 236 (M+H⁺).

The coupling reaction of compound 27d and compound 4e gave N-(2-(5-((5-(2-(dimethyl-amino)ethoxy)-7-methyl-9-oxo-9H-xanthen-3-yl)oxy)pyridin-2-yl)ethyl)pyrrolidine-1-carboxamide (27): ¹H NMR (CDCl₃) δ 8.41 (d, J=2.8 Hz, 1H), 8.32 (d, J=8.7 Hz, 1H), 7.70 (dd, J=1.8, 0.8 Hz), 7.41 (dd, J=2.3, 8.8 Hz, 1H), 7.29 (s, 1H), 7.00 (d, J=2.2 Hz, 1H), 5.20 (t, J=5.1 Hz, 1H), 4.23 (t, J=5.9, Hz, 2H), 3.69-350 (m, 2H), 3.33 (t, J=6.6 Hz, 4H), 3.06 (t, J=6.3 Hz, 2H), 2.84 (t, J=5.9 Hz, 2H), 2.45 (s, 3H), 2.38 (s, 6H), 1.90-1.88 (m, 4H); MS (APCI) m/z: 531 (M+H⁺). Anal. Calcd for C₃₀H₃₄N₄O₅·0.5H₂O: C, 66.8, H, 6.5, N, 10.4. Found: C, 66.5; H, 6.5; N, 10.3%.

Example 28

3-(5-((5-(2-Aminoethoxy)-7-methyl-9-oxo-9H-xanthen-3-yl)oxy)pyridin-2-yl)-N-cyclopentylpropanamide

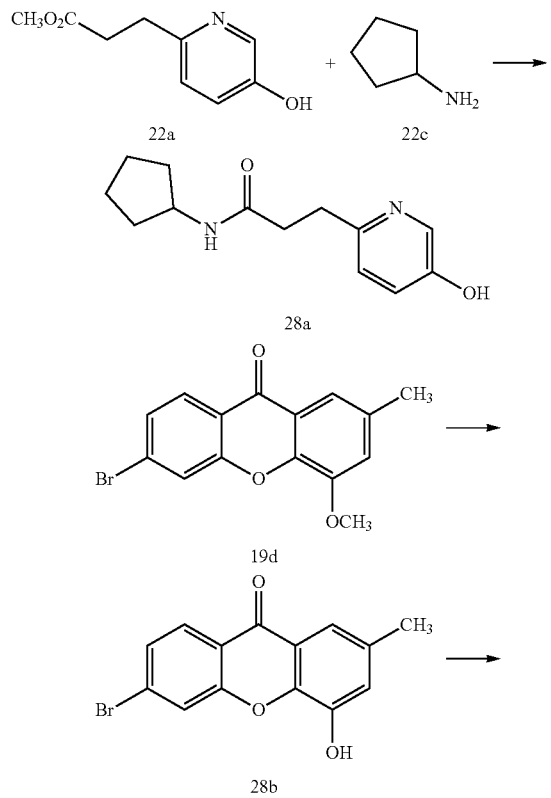

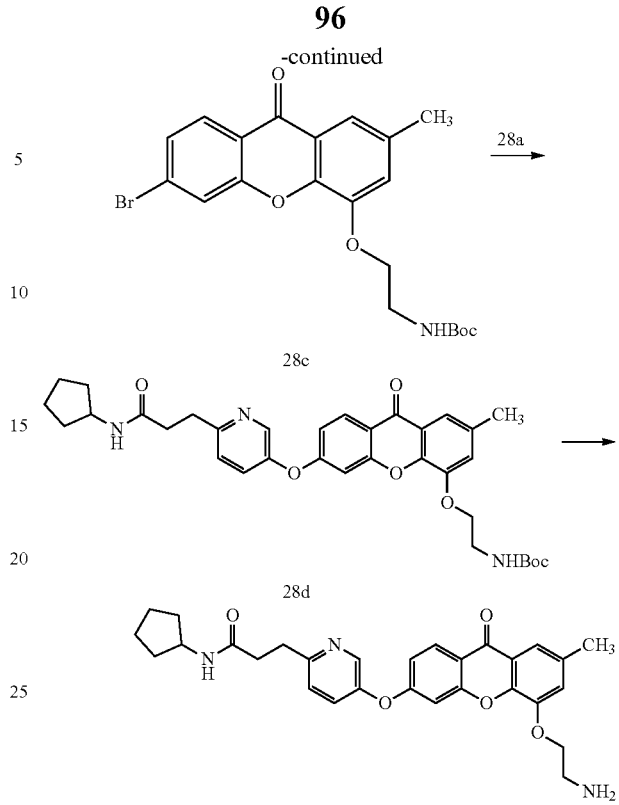

A mixture of compound 22a (685 mg, 3.78 mmol) and cyclopentylamine (1 mL, excess) was heated in a sealed tube at 122° C. for 20 h. Excess cyclopentylamine was removed under vacuum, and the residue was stirred in H₂O for 1 h. The resulting precipitate was collected, washed with water, and recrystallized from CH₂Cl₂/hexanes to give N-cyclopentyl-3-(5-hydroxypyridin-2-yl)propanamide (28a) (604 mg, 68% yield): mp (CH₂Cl₂/hexanes) 126-128° C., ¹H NMR (CDCl₃) δ 8.14 (d, J=2.2 Hz, 1H), 7.09 (dd, J=8.3, 2.4 Hz, 1H), 7.04 (d, J=8.4 Hz, 1H), 6.22 (d, J=7.3 Hz, 1H), 4.18-4.10 (m, 1H), 3.02 (t, J=7.1 Hz, 2H), 2.58 (t, J=7.1H, 2H), 1.93-1.85 (m, 2H), 1.64-1.52 (m, 4H), 1.43-1.26 (m, 2H).

Demethylation of 6-bromo-4-methoxy-2-methyl-9H-xanthen-9-one (19d) with BBr₃ in CH₂Cl₂ gave 6-bromo-4-hydroxy-2-methyl-9H-xanthen-9-one (28b) in quantitative yield: ¹H NMR (DMSO-d₆) δ 10.40 (s, 1H), 8.08 (d, J=8.5 Hz, 1H), 7.93 (d, J=1.8 Hz, 1H), 7.63 (dd, J=8.5, 1.8 Hz, 1H), 7.40 (dd, J=2.0, 0.8 Hz, 1H), 7.16 (d, J=2.0 Hz, 1H), 2.36 (s, 3H).

A mixture of 28b (1.1 g, 3.6 mmol), tert-butyl (2-bromoethyl)carbamate (968 mg, 4.31 mmol), NaOH (1.45 g, 3.62 mmol), and Bu₄N⁺Br⁻ (116 mg, 10 mol %) in CH₂Cl₂/H₂O (60 mL/60 mL) was stirred at 20° C. for 20 h. The reaction mixture was diluted with CH₂Cl₂ (30 mL), the organic layer was separated, and the aqueous layer further extracted with CH₂Cl₂ (2×30 mL). The combined organic fractions were washed with water and dried (Na₂SO₄). Evaporation of the solvent, and chromatography of the residue on neutral Al₂O₃, eluting with hexanes/EtOAc 0-10%, gave tert-butyl (2-((6-bromo-2-methyl-9-oxo-9H-xanthen-4-yl)oxy)ethyl)carbamate (28c) (1.365 g, 85%): ¹H NMR (CDCl₃) δ 8.19 (d, J=8.5 Hz, 1H), 7.80 (d, J=1.7 Hz, 1H), 7.70 (dd, J=1.7, 0.8 Hz, 1H), 7.50 (dd, J=8.5, 1.8 Hz, 1H) 7.10 (d, J=1.1 Hz, 1H), 5.17 (br, 1H), 4.20 (t, J=5.1 Hz, 2H), 3.68-3.64 (m, 2H), 2.44 (s, 3H), 1.48 (s, 9H).

Following the method of *J. Org. Chem.* 2010, 75, 1791, a mixture of compound 28c (208 mg, 0.39 mmol), compound 28a (110 mg, 4.6 mmoL), picolinic acid (5 mg, 10 mol %), CuI (4 mg, 5 mol %), and $K_3PO_4$ (166 mg, 0.78 mmol) in DMSO (3 mL) was heated in a sealed tube for 20 h at 80° C. under nitrogen. After cooling to room temperature the mixture was diluted with $H_2O$/aqueous $NH_3$, and stirred for 2 h. The resulting precipitate was collected, washed with water, and chromatographed on neutral $Al_2O_3$, eluting with $CH_2Cl_2$/EtOAc 0-50%, to give tert-butyl (2-((6-((6-(3-(cyclopentylamino)-3-oxopropyl)pyridin-3-yl)oxy)-2-methyl-9-oxo-9H-xanthen-4-yl)oxy)ethyl)carbamate (28d) (150 mg, 64%): $^1$H NMR (CDCl$_3$) δ 8.41 (d, J=2.7 Hz, 1H), 8.32 (d, J=9.3 Hz, 1H), 7.72 (dd, J=1.7, 0.8 Hz, 1H), 7.41 (dd, J=8.4, 2.8 Hz, 1H), 7.30 (d, J=8.4 Hz, 1H), 5.94 (br 1H), 5.11 (br, 1H), 4.23-4.17 (m, 2H), 3.66-3.61 (m, 2H), 3.18 (t, J=7.1 Hz, 2H), 2.66 (t, J=7.1 Hz, 2H), 2.44 (s, 3H), 1.98-1.90 (m, 2H), 1.67-1.56 (m, 4H), 1.36-1.28 (m, 2H).

3-(5-((5-(2-aminoethoxy)-7-methyl-9-oxo-9H-xanthen-3-yl)oxy)pyridin-2-yl)-N-cyclopentylpropanamide (28) (99 mg, 74% yield): mp ($CH_2Cl_2$/hexanes) 221-223° C.; $^1$H NMR (CDCl$_3$) δ 8.40 (d, J=2.7 Hz, 1H), 8.32 (d, J=8.8 Hz, 1H), 7.70 (dd, J=1.9, 0.8 Hz, 1H), 7.40 (dd, J=8.4, 2.81 Hz, 1H), 7.30 (d, J=8.4 Hz, 1H), 7.08 (s, J=1.8 Hz, 1H), 7.03 (dd, J=8.8, 2.3 Hz, 1H), 6.97 (d, J=2.3 Hz, 1H), 5.96 (d, J=7.3 Hz, 1H), 4.23-4.14 (m, 1H), 4.15 (t, J=5.2 Hz, 2H), 2.67 (t, J=7.1 Hz, 2H), 1.97 (s, 3H), 1.98-1.90 (m, 2H), 1.65-1.50 (m, 4H), 1.36-1.28 (m, 2H); MS (APCI) m/z: 502 (M+H$^+$). Anal. Calcd for $C_{29}H_{31}N_3O_5 \cdot 0.75H_2O$: C, 67.6; H, 6.4; N, 8.2. Found: C, 67.6; H, 6.6; N, 8.1%.

Example 29

N-Cyclopentyl-3-(5-((7-methyl-5-(2-(methylamino)ethoxy)-9-oxo-9H-xanthen-3-yl)oxy)pyridin-2-yl)propanamide

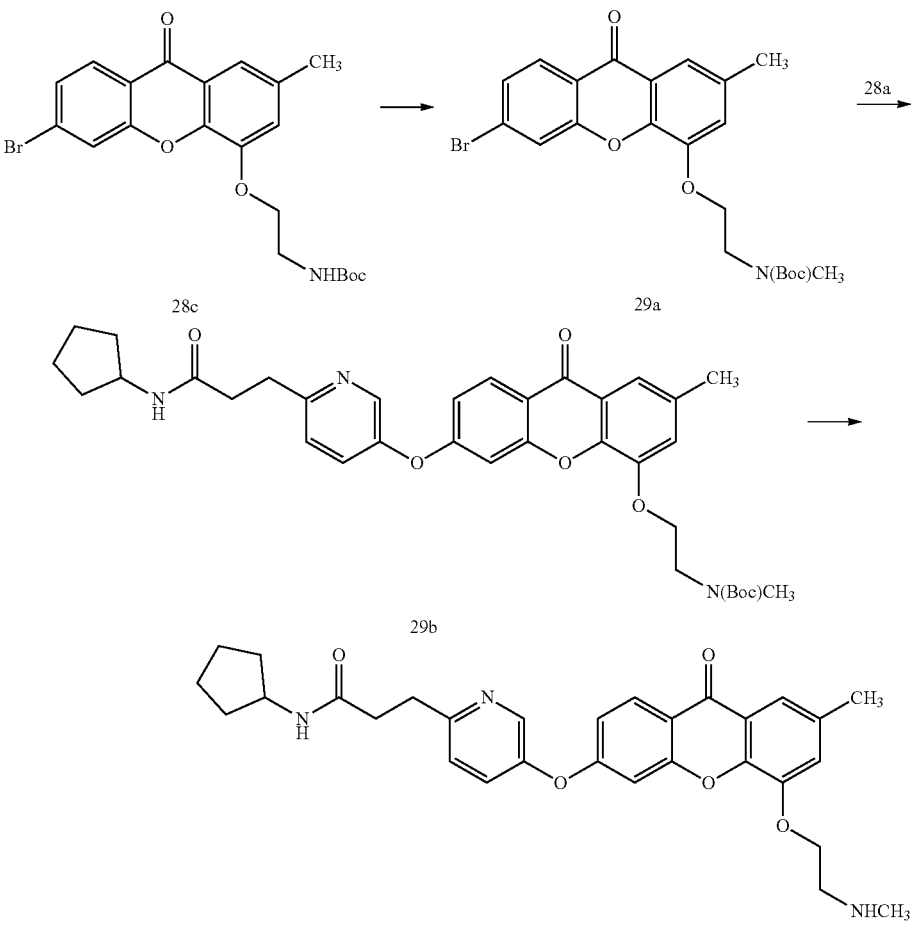

A solution of compound 28d (149 mg, 0.24 mmol) in dry $CH_2Cl_2$ (20 mL) was treated with TFA (1 mL, excess), and the reaction mixture was stirred at room temperature for 20 h before being carefully poured on to ice/aqueous $NH_3$. The $CH_2Cl_2$ was then removed under vacuum at room temperature. The resulting precipitate was filtered, washed with water and chromatographed on neutral alumina, eluting with $CH_2Cl_2$/MeOH 0-2% with a trace of aqueous $NH_3$, to give A solution of compound 28c (265 mg, 0.5 mmol) in DMF (3 mL) at 0° C. was treated with NaH (57 mg, 2.375 mmol). The reaction mixture was stirred at 20° C. for 1 h and MeI (1 mL, excess) was added and the stirring was continued for 20 h. The resulting reaction mixture was diluted with water and aqueous $KHCO_3$, and the resulting precipitate was collected, washed with water, and chromatographed on neutral $Al_2O_3$, eluting with $CH_2Cl_2$/hexanes 0-75%, to give tert-butyl (2-((6-bromo-2-methyl-9-oxo-9H-xanthen-4-yl)oxy)ethyl)(methyl)carbamate (29a) in 74% yield: $^1$H NMR (CDCl$_3$) δ 8.19 (d, J=8.5 Hz, 1H), 7.72 (br, 1H), 7.68 (br, 1H), 7.50 (dd, J=8.5, 1.8 Hz, 1H), 7.08 (br, 1H), 4.27 (br, 2H), 3.73 (br, 2H), 3.13 (s, 3H), 2.45 (s, 3H), 1.47 (s, 9H).

Following the method of *J. Org. Chem.* 2010, 75, 1791 as in Example 28, copper catalysed coupling of compound 29a with compound 28a gave tert-butyl (2-((6-((6-(3-(cyclopentylamino)-3-oxopropyl)pyridin-3-yl)oxy)-2-methyl-9-oxo-9H-xanthen-4-yl)oxy)ethyl)(methyl)carbamate (29b) which was used directly for next step without purification: MS (APCI) m/z: 616 (M+H$^+$). Deprotection of compound 29b with TFA/CH$_2$Cl$_2$ at 20° C. gave N-cyclopentyl-3-(5-((7-methyl-5-(2-(methylamino)ethoxy)-9-oxo-9H-xanthen-3-yl)oxy)pyridin-2-yl)propanamide (29) in 69% yield over two steps: mp (CH$_2$Cl$_2$/hexanes) 222-224° C.; $^1$H NMR (CDCl$_3$) δ 8.40 (d, J=2.7 Hz, 1H), 8.32 (d, J=8.7 Hz, 1H), 7.70 (dd, J=1.9, 0.8 Hz, 1H), 7.40 (dd, J=8.4, 2.8 Hz, 1H), 7.30 (d, J=8.50 Hz, 1H), 7.09 (d, J=1.8 Hz, 1H), 7.02 (dd, J=8.7, 2.4 Hz, 1H), 6.99 (d, J=2.2 Hz, 1H), 5.96 (d, J=7.5 Hz, 1H), 4.24 (t, J=5.2 Hz, 2H), 4.24-4.15 (m, 1H), 3.18 (t, J=7.1 Hz, 12H), 3.08 (t, J=5.2 Hz, 1H), 2.66 (t, J=7.2 Hz, 1H), 2.54 (s, 3H), 2.44 (s, 3H), 1.98-1.90 (m, 2H), 1.65-1.57 (m, 4H), 1.36-1.29 (m, 2H); MS (APCI) m/z: 516 (M+H$^+$). Anal. Calcd for C$_{30}$H$_{33}$N$_3$O$_5$: C, 68.9; H, 6.4; N, 8.1. Found: C, 68.8; H, 6.4; N, 8.1%.

Example 30

4-[3-(Dimethylamino)propoxy]-2-methyl-6-phenoxy-9H-xanthen-9-one

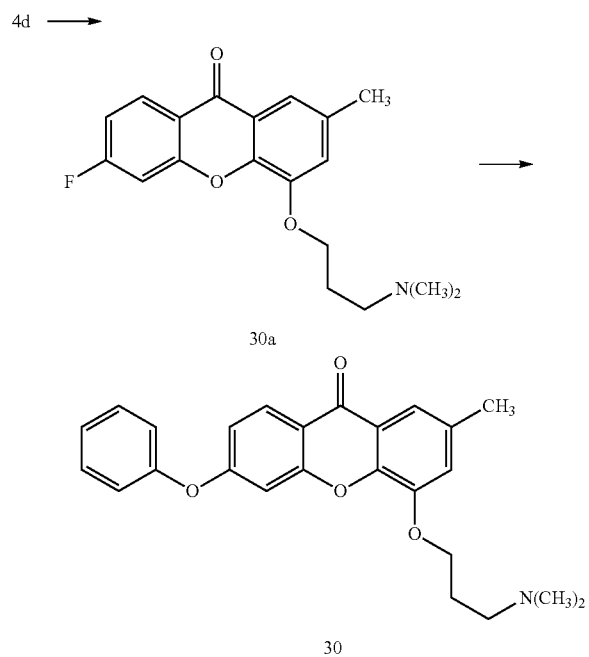

A mixture of 6-fluoro-4-hydroxy-2-methyl-9H-xanthen-9-one (4d) (50 mg, 0.20 mmol), 3-chloro-N,N-dimethylpropylamine (99 mg, 0.80 mmol) and K$_2$CO$_3$ (30 mg, 0.42 mmol) in MEK (5 mL) was heated at 80° C. for 2 h, then cooled, filtered, washed with EtOAc, and concentrated. The crude solid was filtered through a plug of alumina, using gradient elution from CH$_2$Cl$_2$ to EtOAc/CH$_2$C$_2$(1:4) to give 4-(3-(dimethylamino)propoxy)-6-fluoro-2-methyl-9H-xanthen-9-one (30a) (50 mg, 69%), as a white solid: $^1$H NMR (CDCl$_3$) δ 8.35 (dd, J=8.9, 6.4 Hz, 1H), 7.68 (dd, J=1.9, 0.9 Hz, 1H), 7.26 (dd, J=9.4, 2.4 Hz, 1H), 7.14-7.07 (m, 2H), 4.21 (t, J=6.5 Hz, 2H), 2.55 (t, J=7.1 Hz, 2H), 2.44 (s, 3H), 2.30 (s, 6H), 2.10 (quintet, J=6.8 Hz, 2H); MS (APCI) m/z 330.2 (M+H$^+$).

Reaction of 4-(3-(dimethylamino)propoxy)-6-fluoro-2-methyl-9H-xanthen-9-one (30a) and phenol with K$_2$CO$_3$ in DMSO at 85° C. gave 4-[3-(dimethylamino)propoxy]-2-methyl-6-phenoxy-9H-xanthen-9-one (30): $^1$H NMR (CDCl$_3$) δ 8.31 (d, J=8.8 Hz, 1H), 7.74 (br s, 1H), 7.48 (t, J=7.6 Hz, 2H), 7.30 (m, 1H), 7.17 (d, J=7.6 Hz, 2H), 7.07 br s, 1H), 7.05 (d, J=8.8 Hz, 1H), 6.94 (br s, 1H), 4.27 (br s, 2H), 3.33 (t, J=7.4 Hz, 2H), 2.88 (s, 6H), 2.50 (m, 2H), 2.46 (s, 3H).

Example 31

3-((5-(3-(Dimethylamino)propoxy)-7-methyl-9-oxo-9H-xanthen-3-yl)oxy)-N-phenylbenzamide

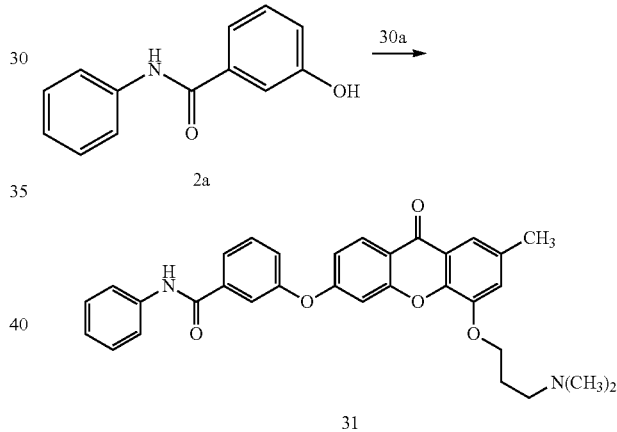

A mixture of 4-(3-(dimethylamino)propoxy)-6-fluoro-2-methyl-9H-xanthen-9-one (30a) (50 mg, 0.152 mmol), 3-hydroxy-N-phenylbenzamide (2a) (36 mg, 0.167 mmol) and K$_2$CO$_3$ (25.2 mg, 0.182 mmol) was heated in DMSO (2 mL) at 85° C. for 16 h. Workup and purification as in example 5 gave a foamy white semi-solid. Recrystallization from methanolic HCl/Et$_2$O gave the hydrochloride of 3-((5-(3-(dimethylamino)propoxy)-7-methyl-9-oxo-9H-xanthen-3-yl)oxy)-N-phenylbenzamide (31) (54 mg, 61%), as a white solid: mp (MeOH/Et$_2$O) 169-173° C.; $^1$H NMR (DMSO-d$_6$) δ 10.35 (s, 1H), 10.19 (b s, 1H), 8.23 (d, J=8.8 Hz, 1H), 7.94 (d, J=8.2 Hz, 1H), 7.83-7.80 (m, 1H), 7.77 (dd, J=8.5, 0.9 Hz, 2H), 7.68 (t, J=7.9 Hz, 1H), 7.55 (dd, J=1.8, 0.8 Hz, 1H), 7.47 (ddd, J=8.1, 2.4, 0.9 Hz, 1H), 7.41-7.32 (m, 2H), 7.17 (dd, J=8.8, 2.4 Hz, 2H), 7.14-7.08 (m, 2H), 4.25 (t, J=6.1 Hz, 2H), 3.31-3.16 (m, 2H), 2.78 (d, J=4.1 Hz, 6H), 2.43 (s, 3H), 2.26-2.18 (m, 2H). Anal. Calcd for C$_{32}$H$_{31}$ClN$_2$O$_5$.0.75H$_2$O: C, 67.1; H, 5.7; Cl, 6.2; N, 4.9. Found: C, 66.8; H, 5.6; N, 4.9; Cl, 6.2%.

Example 32

1-(3-((5-(3-(Dimethylamino)propoxy)-7-methyl-9-oxo-9H-xanthen-3-yl)oxy)phenyl)-3-phenylurea

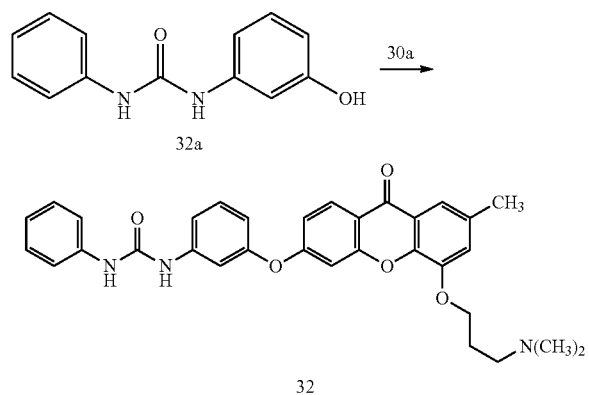

A mixture of 4-(3-(dimethylamino)propoxy)-6-fluoro-2-methyl-9H-xanthen-9-one (30a) (90 mg, 0.276 mmol), 1-(3-hydroxyphenyl)-3-phenylurea (32a) (189 mg, 0.80 mmol), and K$_2$CO$_3$ (118 mg, 0.86 mmol) was heated in DMSO (2 mL) at 85° C. for 16 h. Workup as in example 6 gave a crude solid, which was purified by flash column chromatography on silica. After initial elution with neat EtOAc, elution with MeOH/CH$_2$Cl$_2$ (1:9) gave a brown oil. Recrystallization from (methanolic HCl/Et$_2$O) gave the hydrochloride of 1-(3-((5-(3-(dimethylamino)propoxy)-7-methyl-9-oxo-9H-xanthen-3-yl)oxy)phenyl)-3-phenylurea (32) (52 mg, 39%), as a white solid: mp (MeOH/Et$_2$O) 200-203° C.; $^1$H NMR (DMSO-d$_6$) δ 9.50 (s, 1H), 9.12 (s, 1H), 8.90 (s, 1H), 8.21 (d, J=8.9 Hz, 1H), 7.55 (dd, J=1.9, 0.9 Hz, 1H), 7.52 (t, J=2.2, 2.2 Hz, 1H), 7.45-7.38 (m, 3H), 7.37 (d, J=1.8 Hz, 1H), 7.29-7.21 (m, 3H), 7.14 (dd, J=8.8, 2.3 Hz, 1H), 7.07 (d, J=2.3 Hz, 1H), 6.96 (dt, J=7.4, 1.1 Hz, 1H), 6.83 (ddd, J=8.1, 2.4, 0.8 Hz, 1H), 4.24 (t, J=6.0 Hz, 2H), 3.30-3.20 (m, 2H), 2.80 (s, 6H), 2.43 (s, 3H), 2.24-2.16 (m, 2H). Anal. Calcd for C$_{32}$H$_{32}$ClN$_3$O$_5$H$_2$O: C, 64.9; H, 5.8; Cl, 6.0; N, 7.1. Found: C, 65.0; H, 5.5; N, 7.1; Cl, 6.2%.

Example 33

2-Methyl-4-(3-morpholinopropoxy)-6-phenoxy-9H-xanthen-9-one

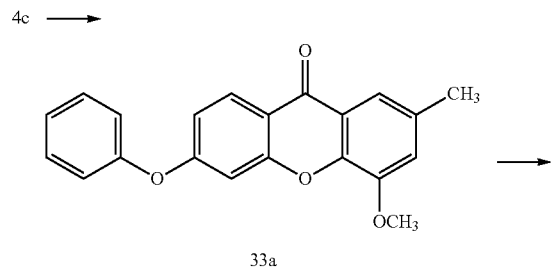

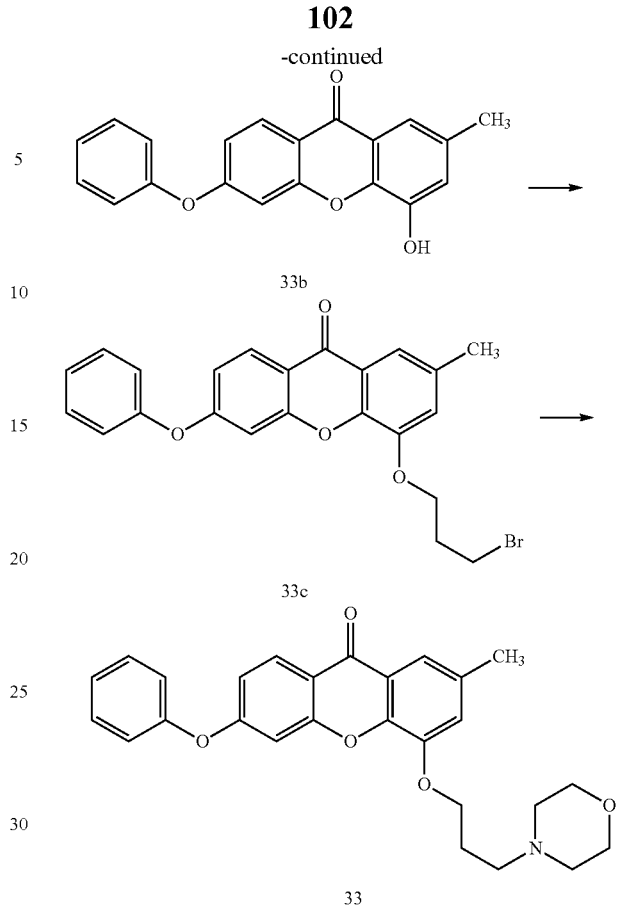

6-Fluoro-4-methoxy-2-methyl-9H-xanthen-9-one (4c) (200 mg, 0.77 mmol), phenol (80 mg, 0.82 mmol) and K$_2$CO$_3$ (128 mg, 0.93 mmol) were heated in DMSO at 85° C. for 16 h. The reaction mixture was poured onto crushed ice, and the resulting precipitate was collected by filtration and washed well with water to give 4-methoxy-2-methyl-6-phenoxy-9H-xanthen-9-one (33a) (120 mg, 47%): $^1$H NMR (CDCl$_3$) δ 8.30 (d, J=8.9 Hz, 1H), 7.69 (dd, J=1.9, 0.9 Hz, 1H), 7.44 (t, J=7.5 Hz, 2H), 7.30-7.23 (m, 1H), 7.14 (dd, J=8.6, 1.1 Hz, 2H), 7.06 (dd, J=8.9, 2.3 Hz, 1H), 7.04 (d, J=1.9 Hz, 1H), 6.96 (d, J=2.3 Hz, 1H), 3.99 (s, 3H), 2.46 (s, 3H).

BBr$_3$ (1 M in CH$_2$Cl$_2$, 1.1 mL, 1.08 mmol) was added to a solution of 4-methoxy-2-methyl-6-phenoxy-9H-xanthen-9-one (33a) (120 mg, 0.36 mmol) in CH$_2$Cl$_2$ (5 mL) and the reaction was stirred at rt overnight. After removal of the CH$_2$Cl$_2$ the residue was diluted with water, and the resulting precipitate was collected by filtration, then washed with water to give 4-hydroxy-2-methyl-6-phenoxy-9H-xanthen-9-one (33b) (86 mg, 75%), as a white solid: $^1$H NMR (CDCl$_3$) δ 8.31 (d, J=8.9 Hz, 1H), 7.64 (dd, J=2.0, 0.8 Hz, 1H), 7.50-7.43 (m, 2H), 7.29 (d, J=7.4 Hz, 1H), 7.18-7.12 (m, 3H), 7.05 (dd, J=8.9, 2.3 Hz, 1H), 6.89 (d, J=2.3 Hz, 1H), 5.66 (s, 1H), 2.42 (s, 3H); MS (APCI) m/z: 319.1 (M+H$^+$).

A mixture of 4-hydroxy-2-methyl-6-phenoxy-9H-xanthen-9-one (33b) (40 mg, 0.126 mmol), 1,3-dibromopropane (128 μL, 1.26 mmol), and K$_2$CO$_3$ (19 mg, 0.138 mmol) was heated in MEK (3 mL) at 80° C. for 48 h. The reaction was cooled, diluted with EtOAc, filtered and concentrated. The crude residue was filtered through a silica gel pad, with gradient elution from neat CH$_2$Cl$_2$ to EtOAc/CH$_2$C$_2$(1:4)

giving 4-(3-bromopropoxy)-2-methyl-6-phenoxy-9H-xanthen-9-one (33c) (46 mg, 84%), as a white solid: $^1$H NMR (CDCl$_3$) δ 8.30 (d, J=8.8 Hz, 1H), 7.71 (dd, J=1.9, 0.9 Hz, 1H), 7.46 (t, J=7.5 Hz, 2H), 7.29-7.24 (m, 1H), 7.15 (dd, J=8.6, 1.1 Hz, 2H), 7.09 (d, J=1.9 Hz, 1H), 7.04 (dd, J=8.8, 2.3 Hz, 1H), 6.98 (d, J=2.3 Hz, 1H), 4.27 (t, J=5.9 Hz, 2H), 3.68 (t, J=6.3 Hz, 2H), 2.47-2.38 (m, 5H); MS (APCI) m/z: 439.1 and 441.1 (M+H$^+$).

A mixture of 4-(3-bromopropoxy)-2-methyl-6-phenoxy-9H-xanthen-9-one (33c) (37 mg, 0.084 mmol) and morpholine (29 mg, 0.34 mmol) was heated in DMF at 90° C. for 3 h, then cooled, diluted with EtOAc, washed with brine, dried over Na$_2$SO$_4$ and concentrated.

The crude solid was purified by flash column chromatography, eluting with (MeOH/CH$_2$Cl$_2$, 2:98) to give crude 2-methyl-4-(3-morpholinopropoxy)-6-phenoxy-9H-xanthen-9-one (33) as a white solid: $^1$H NMR (DMSO-d$_6$) δ 8.19 (d, J=8.8 Hz, 1H), 7.56-7.49 (m, 3H), 7.38-7.30 (m, 2H), 7.28-7.22 (m, 2H), 7.11 (dd, J=8.9, 2.4 Hz, 1H), 6.91 (d, J=2.3 Hz, 1H), 4.19 (t, J=6.5, Hz, 2H), 3.63-3.49 (m, 4H), 2.45 (t, J=7.1 Hz, 2H), 2.42 (s, 3H), 2.39-2.30 (m, 4H), 2.00-1.90 (m, 2H). Recrystallization from methanolic HCl/Et$_2$O gave a white solid (31 mg, 78%): mp 272-275° C.; $^1$H NMR (DMSO-d$_6$) δ 10.20 (s, 1H), 8.20 (d, J=8.9 Hz, 1H), 7.58-7.48 (m, 3H), 7.40-7.35 (m, 1H), 7.33 (t, J=7.4 Hz, 1H), 7.24 (d, J=7.6 Hz, 2H), 7.11 (dd, J=8.9, 2.3 Hz, 1H), 7.06-6.99 (m, 1H), 4.44-4.11 (m, 2H), 4.12-3.85 (m, 2H), 3.79-3.61 (m, 2H), 3.58-3.43 (m, 2H), 3.21-3.02 (m, 2H), 2.43 (s, 3H), 2.30-2.20 (m, 2H); HRMS (ESI) Calcd for C$_{27}$H$_{28}$NO$_5$: m/z 446.1962; found m/z 446.1969 (M+H$^+$); HPLC purity 97.5%.

Example 34

4-(4-(Dimethylamino)butoxy)-2-methyl-6-phenoxy-9H-xanthen-9-one

A mixture of 4-hydroxy-2-methyl-6-phenoxy-9H-xanthen-9-one (33b) (40 mg, 0.126 mmol), 1,4-dibromobutane (131 μL, 1.10 mmol), and K$_2$CO$_3$ (17 mg, 0.12 mmol) was heated in MEK (3 mL) at 80° C. for 48 h. The reaction was cooled, diluted with EtOAc, filtered and concentrated. The crude residue was filtered through a silica gel pad, gradient elution from neat CH$_2$Cl$_2$ to EtOAc/CH$_2$Cl$_2$ (1:8) to give 4-(4-bromobutoxy)-2-methyl-6-phenoxy-9H-xanthen-9-one (34a) (44 mg, 90%) as a white solid: $^1$H NMR (CDCl$_3$) δ 8.29 (d, J=8.8 Hz, 1H), 7.69 (dd, J=1.9, 0.9 Hz, 1H), 7.51-7.41 (m, 2H), 7.29-7.24 (obs CDCl$_3$, m, 2H), 7.15 (dd, J=8.6, 1.1 Hz, 1H), 7.07-7.01 (m, 2H), 6.99 (d, J=2.2 Hz, 1H), 4.16 (t, J=6.0 Hz, 2H), 3.55 (t, J=6.4 Hz, 2H), 2.42 (s, 3H), 2.17-2.05 (m, 4H); MS (APCI) m/z: 453 and 455.1 (M+H$^+$).

A mixture of 4-(4-bromobutoxy)-2-methyl-6-phenoxy-9H-xanthen-9-one (34a) (30 mg, 0.066 mmol) and dimethylamine (12 mg, 0.26 mmol) were stirred in DMF at rt for 3 h, then diluted with EtOAc, washed with brine, dried over Na$_2$SO$_4$ and concentrated. The crude solid was purified by flash column chromatography, eluting with (MeOH/CH$_2$Cl$_2$, 5:95) to give 4-(4-(dimethylamino)butoxy)-2-methyl-6-phenoxy-9H-xanthen-9-one (34) as a white solid (29 mg, 99%): $^1$H NMR (DMSO-d$_6$) δ 8.19 (d, J=8.8 Hz, 1H), 7.56-7.48 (m, 3H), 7.36-7.31 (m, 2H), 7.25 (dd, J=8.6, 1.0 Hz, 2H), 7.13 (dd, J=8.8, 2.3 Hz, 1H), 6.86 (d, J=2.3 Hz, 1H), 4.15 (t, J=6.5 Hz, 2H), 2.41 (s, 3H), 2.25 (t, J=7.2 Hz, 2H), 2.08 (s, 6H), 1.86-1.74 (m, 2H), 1.62-1.52 (m, 2H). Recrystallization from methanolic HCl/Et$_2$O gave the hydrochloride (26 mg, 90%) as a white solid: mp 208-211° C.; $^1$H NMR (DMSO-d$_6$) δ 9.77 (s, 1H), 8.20 (d, J=8.9 Hz, 1H), 7.59-7.49 (m, 3H), 7.37-7.31 (m, 2H), 7.24 (dd, J=8.6, 1.0 Hz, 2H), 7.12 (dd, J=8.9, 2.3 Hz, 1H), 6.95 (d, J=2.3 Hz, 1H), 4.19 (t, J=5.5 Hz, 2H), 3.20-3.04 (m, 2H), 2.71 (s, 6H), 2.42 (s, 3H), 1.90-1.80 (m, 4H); MS (ESI) Calcd for C$_{26}$H$_{28}$NO$_4$: m/z 418.2013; found m/z 418.2015 (M+H$^+$); HPLC purity 98.7%.

Example 35

2-Methyl-4-((1-methylpiperidin-4-yl)methoxy)-6-phenoxy-9H-xanthen-9-one

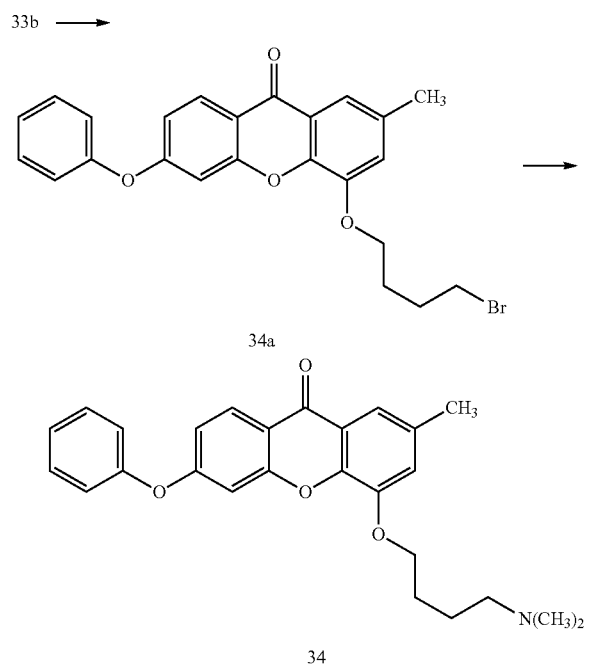

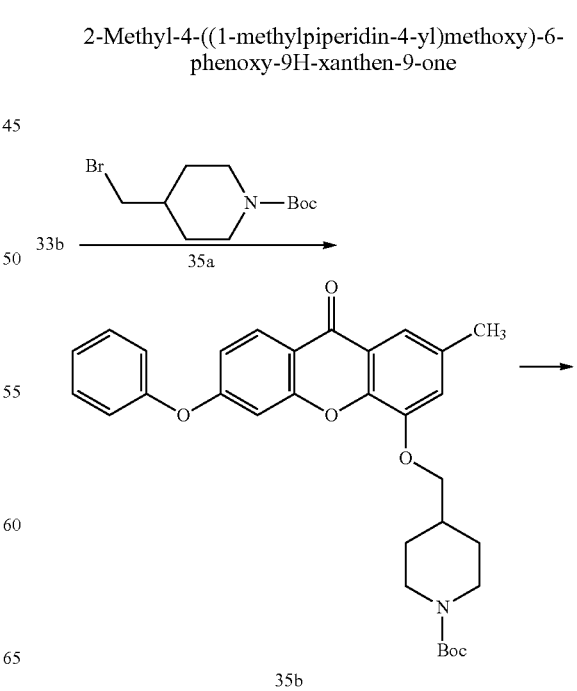

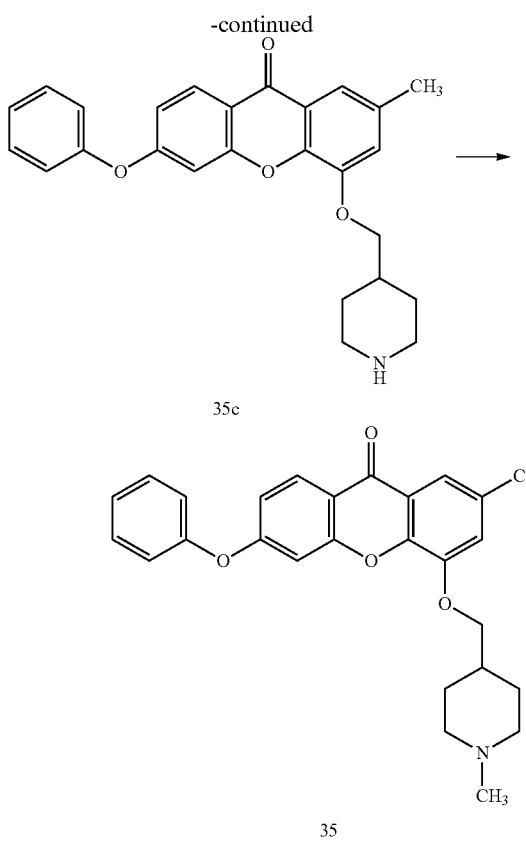

35c

35

A mixture of 4-hydroxy-2-methyl-6-phenoxy-9H-xanthen-9-one (33b) (100 mg, 0.31 mmol), 4-bromomethyl-1-(tert-butoxycarbonyl)piperidine (35a) (262 mg, 0.94 mmol), K$_2$CO$_3$ (47.8 mg, 0.35 mmol), and KI (5 mg) in MEK (3 mL), was heated at 70° C. for 16 h. The reaction was then cooled to room temperature, diluted with EtOAc, filtered and concentrated. The crude residue was filtered through a pad of silica gel, eluting with neat EtOAc to give 2-methyl-4-((1-(tert-butoxycarbonyl)piperidin-4-yl)methoxy)-6-phenoxy-9H-xanthen-9-one (35b) (159 mg, 99%), that was used directly as is in the next step.

The crude 2-methyl-4-((1-(tert-butoxycarbonyl)piperidin-4-yl)methoxy)-6-phenoxy-9H-xanthen-9-one (35b) was dissolved in MeOH (10 mL), cooled in an ice bath, and HCl$_{(gas)}$ was bubbled through for 15 s. After stirring for an additional 5 mins, the reaction was concentrated to afford a residue, which was triturated with Et$_2$O to give the hydrochloride of 2-methyl-6-phenoxy-4-(piperidin-4-ylmethoxy)-9H-xanthen-9-one (35c) as a crude solid (130 mg, 93%); MS (APCI) m/z: 416.2 (M+H$^+$).

A portion of this solid (30 mg, 0.07 mmol), 37% formaldehyde (46 mg, 0.58 mmol), acetic acid (10.8 mg, 0.18 mmol) and NaBH$_3$CN (20 mg, 0.32 mmol) were combined and stirred at rt for 16 h. The reaction was then neutralised with conc. aq. NH$_3$, and then concentrated. The crude residue was filtered through a pad of alumina, with gradient elution from neat CH$_2$Cl$_2$, to neat EtOAc to give a white solid. Recrystallization from methanolic HCl/Et$_2$O gave 2-methyl-4-((1-methylpiperidin-4-yl)methoxy)-6-phenoxy-9H-xanthen-9-one (35) as the hydrochloride (10 mg, 33%): mp 244-247° C.; $^1$H NMR (DMSO-d$_6$) δ 10.05 (s, 1H), 8.19 (d, J=9.3 Hz, 1H), 7.58-7.48 (m, 3H), 7.39 (d, J=1.6 Hz, 1H), 7.32 (t, J=7.4 Hz, 1H), 7.23 (d, J=7.9 Hz, 2H), 7.11-7.05 (m, 2H), 4.06 (d, J=6.2 Hz, 2H), 3.43 (d, J=11.5 Hz, 2H), 2.97 (q, J=10.6 Hz, 2H), 2.73 (d, J=4.7 Hz, 3H), 2.42 (s, 3H), 2.02 (d, J=13.6 Hz, 2H), 1.70-1.65 (m, 2H); HRMS (ESI) Calcd for C$_{27}$H$_{28}$NO$_4$: m/z 430.2013; found m/z 430.2015 (M+H$^+$); HPLC purity 98.6%.

Example 36

2-Methyl-4-(2-(1-methylpiperidin-4-yl)ethoxy)-6-phenoxy-9H-xanthen-9-one

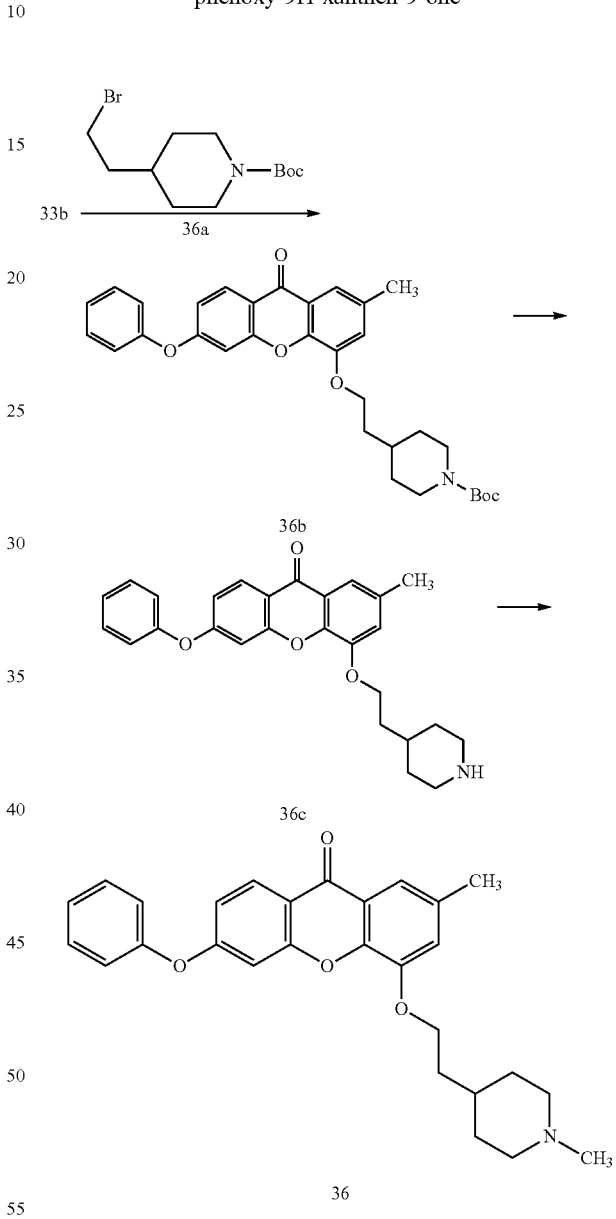

A mixture of 4-hydroxy-2-methyl-6-phenoxy-9H-xanthen-9-one (33b) (100 mg, 0.31 mmol), 4-bromoethyl-1-(tert-butoxycarbonyl)piperidine (36a) (275 mg, 0.92 mmol), K$_2$CO$_3$ (47.8 mg, 0.35 mmol), and KI (5 mg) in MEK (3 mL), were heated at 70° C. for 16 h. The reaction was then cooled to room temperature, diluted with EtOAc, filtered and concentrated. The crude residue was filtered through a pad of silica gel, eluting with neat EtOAc to give impure 2-methyl-4-(2-(1 (tert-butoxycarbonyl)piperidin-4-yl)ethoxy)-6-phenoxy-9H-xanthen-9-one (36b) (181 mg, >100%), that was used directly in the next step.

The impure solid 36b was dissolved in MeOH (10 mL), cooled in an ice bath, then $HCl_{(gas)}$ was bubbled through for 15 s. After stirring for an additional 5 mins the reaction was concentrated to afford a residue, which was triturated with $Et_2O$ to give (36c) as a crude solid (130 mg, 100%): MS ($APCI^+$) 430.2 ($M+H^+$). This was combined with 37% formaldehyde (46 mg, 0.58 mmol), acetic acid (10.8 mg, 0.18 mmol) and $NaBH_3CN$ (20 mg, 0.32 mmol) and stirred at rt for 16 h. The reaction was then neutralised with conc. $NH_{3(aq)}$, and concentrated. The crude residue was filtered through a pad of alumina, gradient elution from neat $CH_2Cl_2$, to neat EtOAc to give a white solid. Recrystallization from methanolic $HCl/Et_2O$ gave the hydrochloride of 2-methyl-4-(2-(1-methylpiperidin-4-yl)ethoxy)-6-phenoxy-9H-xanthen-9-one (36): mp 212-214° C.; $^1$H NMR (DMSO-$d_6$) δ 9.95 (s, 1H), 8.19 (d, J=8.9 Hz, 1H), 7.60-7.47 (m, 3H), 7.37 (d, J=1.8 Hz, 1H), 7.33 (t, J=7.4 Hz, 1H), 7.25 (d, J=7.6 Hz, 2H), 7.10 (dd, J=8.9, 2.3 Hz, 1H), 6.94 (d, J=2.3 Hz, 1H), 4.21 (t, J=6.1 Hz, 2H), 3.41-3.36 (m, 2H), 3.20-3.08 (m, 1H), 2.89 (q, J=11.8 Hz, 2H), 2.70 (s, 3H), 2.42 (s, 3H), 1.96 (d, J=12.9 Hz, 2H), 1.83-1.68 (m, 2H), 1.49 (q, J=10.4 Hz, 2H); HRMS (ESI) Calcd for $C_{28}H_{30}NO_4$: m/z 444.2169; found m/z 430.2169 ($M+H^+$); HPLC purity 99.9%.

Example 37

N-Cyclopentyl-3-(5-((7-methyl-9-oxo-5-(2-(pyrrolidin-1-yl)ethoxy)-9H-xanthen-3-yl)oxy)pyridin-2-yl)propanamide The reaction of compound 28b with 1-(2-chloroethyl)pyrrolidine (37a) under phase-transfer alkylation conditions, using tert-butylammonium bromide as in example 1 gave 6-bromo-2-methyl-4-(2-(pyrrolidin-1-yl)ethoxy)-9H-xanthen-9-one (37b) in 63% yield. $^1$H NMR ($CDCl_3$) δ 8.19 (d, J=8.5 Hz, 1H), 7.77 (d, J=1.7 Hz, 1H), 7.68 (dd, J=1.9, 0.9 Hz, 1H), 7.49 (dd, J=8.5, 1.8 Hz, 1H), 7.10 (d, J=1.9 Hz, 1H), 4.28 (t, J=6.0 Hz, 2H), 3.04 (t, J=6.0 Hz, 2H), 2.74-2.70 (m, 4H), 2.45 (s, 3H), 1.88-1.82 (m, 4H).

Following the method of J. Org. Chem. 2010, 75, 1791 as in example 28, the copper catalysed coupling reaction of compound 37b with compound 28a gave N-cyclopentyl-3-(5-((7-methyl-9-oxo-5-(2-(pyrrolidin-1-yl)ethoxy)-9H-xanthen-3-yl)oxy)pyridin-2-yl)propanamide (37) in 83% yield: mp ($CH_2Cl_2$/hexanes); $^1$H NMR ($CDCl_3$) δ 8.40 (d, J=2.6 Hz, 1H), 8.31 (d, J=8.8 Hz, 1H), 7.69 (dd, J=1.9, 0.9 Hz, 1H), 7.39 (dd, J=8.4, 2.8 Hz, 1H), 7.29 (d, J=8.4 Hz, 1H), 7.09 (d, J=1.9 Hz, 1H), 7.02 (dd, J=8.8, 2.3 Hz, 1H), 6.97 (d, J=2.3 Hz, 1H), 5.98 (d, J=7.8 Hz, 1H), 4.27 (t, J=6.2 Hz, 2H), 3.17 (t, J=7.1 Hz, 2H), 3.00 (t, J=6.2 Hz, 2H), 2.68-2.64 (m, 6H), 2.44 (s, 3H), 1.98-1.90 (m 2H), 1.82-1.79 (m, 2H), 1.65-1.59 (m, 4H), 1.37-1.28 (m, 2H); MS (APCI) m/z 556 ($M+H^+$). Anal. Calcd for $C_{33}H_{37}N_3O_5$: C, 71.3; H, 6.7; N, 7.6. Found: C, 71.0; H, 6.6; N, 7.7%.

Example 38

N-Cyclopentyl-3-(5-((7-methyl-9-oxo-5-(2-(piperidin-1-yl)ethoxy)-9H-xanthen-3-yl)oxy)pyridin-2-yl)propanamide

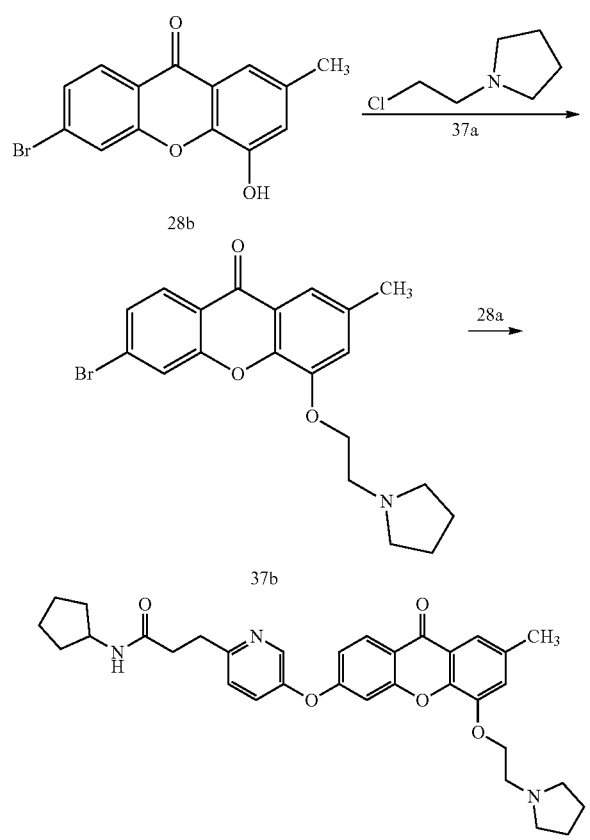

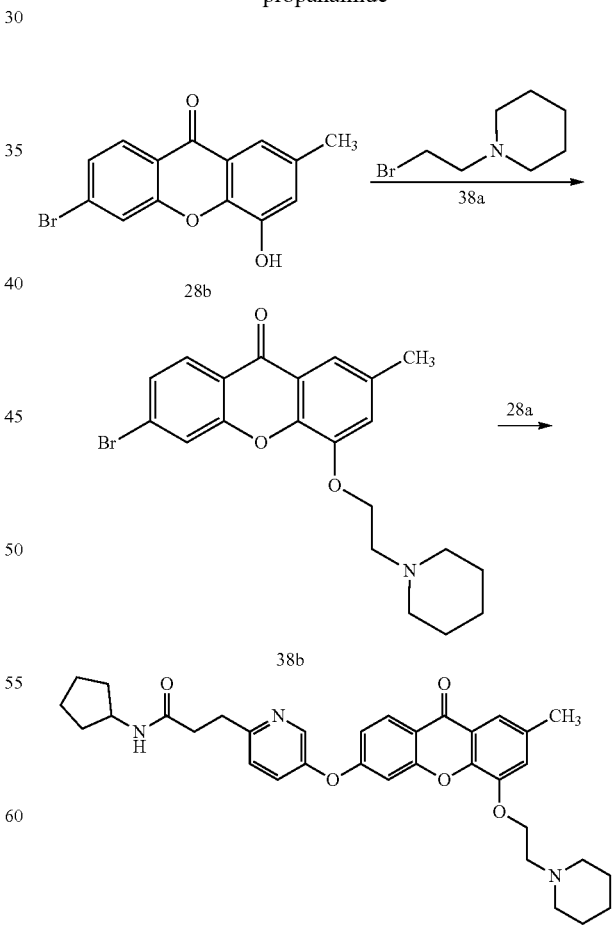

The reaction of compound 28b and 1-(2-bromoethyl) piperidine (38a) under phase-transfer alkylation conditions as in example 37 gave 6-bromo-2-methyl-4-(2-(piperidin-1-yl)ethoxy)-9H-xanthen-9-one (38b) in 84% yield; $^1$H NMR (CDCl$_3$) δ 8.18 (d, J=8.5 Hz, 1H), 7.77 (d, J=1.7 Hz, 1H), 7.67 (d, J=0.9 Hz, 1H), 7.49 (dd, J=8.5, 1.8 Hz, 1H), 7.11 (d, J=1.8 Hz, 1H), 4.27 (t, J=6.1 Hz, 2H), 2.91 (t, J=6.1 Hz, 2H) 2.59 (brm, 4H), 1.67-1.61 (m, 4H), 1.51-1.45 (m, 2H).

Following the method of *J. Org. Chem.* 2010, 75, 1791 as in example 28, the copper catalysed coupling reaction of compound 38b with compound 28a gave N-cyclopentyl-3-(5-((7-methyl-9-oxo-5-(2-(piperidin-1-yl)ethoxy)-9H-xanthen-3-yl)oxy)pyridin-2-yl)propanamide (38) in 94% yield: mp (CH$_2$Cl$_2$/hexanes) 186-188° C.; $^1$H NMR (CDCl$_3$) δ 8.40 (d, J=2.7 Hz, 1H), 8.31 (d, J=8.8 Hz, 1H), 7.69 (dd, J=1.8, 0.8 Hz, 1H), 7.39 (dd, J=8.4, 2.8 Hz, 1H), 7.29 (d, J=8.4 Hz, 1H), 7.10 (d, J=1.9 Hz, 1H), 7.02 (dd, J=8.8, 2.3 Hz, 1H), 6.96 (d, J=2.3 Hz, 1H), 5.97 (d, J=7.2 Hz, 1H), 4.26 (t, J=6.2 Hz, 2H), 4.24-4.15 (m, 1H), 3.17 (t, J=7.1, Hz, 2H), 2.87 (t, J=6.2 Hz, 2H), 2.66 (t, J=7.1 Hz, 2H), 2.55 (brm, 4H), 2.44 (s, 3H), 1.98-1.90 (m, 2H), 1.65-1.60 (m, 8H), 1.48-1.42 (m, 2H), 1.37-1.29 (m, 2H). MS (APCI) 570 (M+H$^+$). Anal. Calcd for C$_{34}$H$_{39}$N$_3$O$_5$: C, 71.7; H, 6.9; N, 7.4. Found: C, 71.4; H, 6.9; N, 7.3%.

Example 39

2-Chloro-4-[2-(dimethylamino)ethoxy]-6-phenoxy-9H-xanthen-9-one

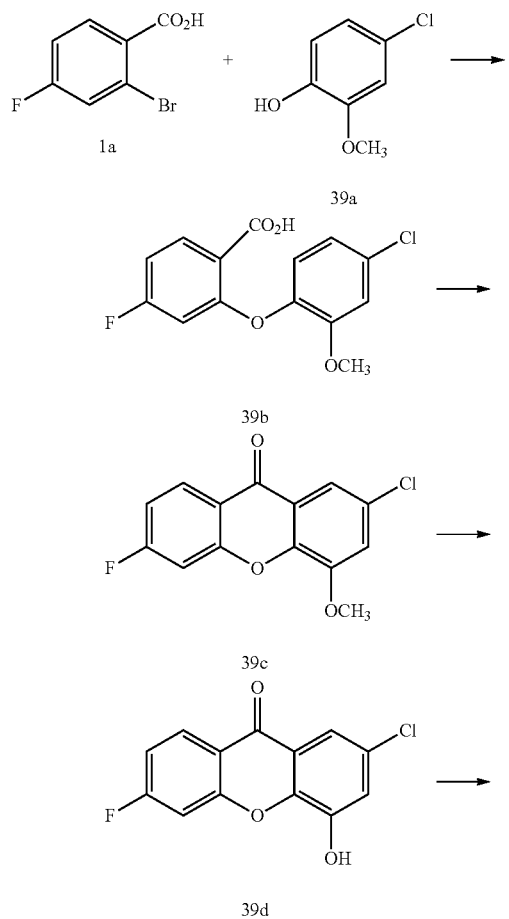

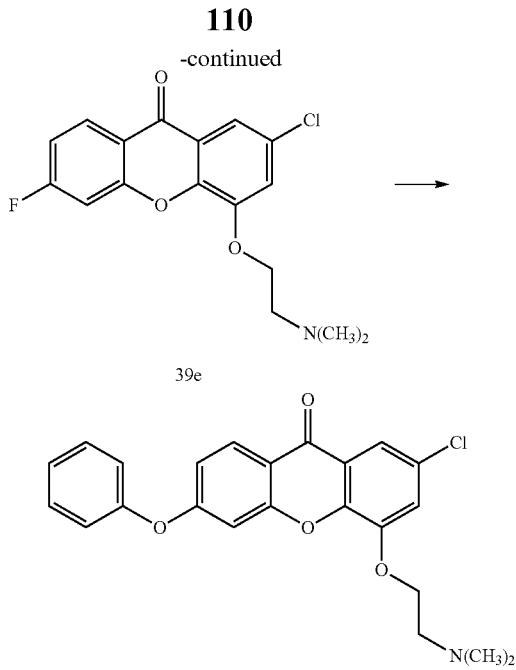

A mixture of potassium 2-bromo-4-fluorobenzoate (2.5 g, 9.72 mmol), sodium 2-methoxy-4-chlorophenolate (2.63 g, 14.58 mmol), Cu (62 mg, 0.97 mmol) CuI (185 mg, 0.97 mmol) and tris-3,6-dioxaheptylamine (TDA-1) (0.31 mL, 0.97 mmol) in 1,4-dioxane (30 mL) was heated in a sealed tube at 80° C. for 16 h. It was cooled down to 18° C., and the solvent was removed under reduced pressure. H$_2$O (30 mL) was added, followed by 2N HCl (100 mL) and it was stirred at 18° C. for 1 h. The formed precipitate was filtered off and washed with H$_2$O (500 mL) then hot H$_2$O (300 mL), the resulting solid was dissolved in EtOAc (400 mL) and filtered over celite. The solvent was evaporated and the residue dried to give crude 2-(4-chloro-2-methoxyphenoxy)-4-fluorobenzoic acid (39b) (1.56 g) which was used in the following step without further purification; mp 154-157° C.; HRMS (ESI) Calcd for C$_{14}$H$_{11}$ClFO$_4$ m z 297.0313; found m/z 297.0324 (M+H$^+$).

Polyphosphoric acid (19 g) was added to 2-(4-chloro-2-methoxyphenoxy)-4-fluorobenzoic acid (39b) (1.56 g, 5.28 mmol) and the reaction mixture was heated at 100° C. for 3 h. It was then cooled to 18° C., ice was added and it was stirred for 30 min. The formed precipitate was filtered off, washed with H$_2$O and dried to give 2-chloro-6-fluoro-4-methoxy-9H-xanthen-9-one (39c) (1.02 g, 70%) as a white powder: mp 194-196° C.; $^1$H NMR (DMSO-d$_6$) δ 8.19 (dd, J=6.6, 8.8 Hz, 1H), 7.62 (dd, J=2.1, 9.8 Hz, 1H), 7.56 (d, J=2.2 Hz, 1H), 7.52 (d, J=2.2 Hz, 1H), 7.35 (dt, J=2.2, 8.6 Hz, 1H), 3.99 (s, 3H); HRMS (ESI) Calcd for C$_{14}$H$_9$ClFO$_3$ (M+H$^+$)$^+$ m/z 279.0214; found m/z 279.0220 (M+H$^+$).

BBr$_3$ (1M in CH$_2$Cl$_2$, 7 mL, 7 mmol) was added at 0° C. to a solution of 2-chloro-6-fluoro-4-methoxy-9H-xanthen-9-one (39c) (935 mg, 3.35 mmol) in CH$_2$Cl$_2$ (20 mL), and the reaction mixture was stirred at 18° C. for 16 h. It was cooled to 0° C., ice-water was added, it was partitioned between CH$_2$Cl$_2$ (250 mL) and H$_2$O (100 mL), the organic phase was washed with H$_2$O (3×50 mL) then brine (30 mL), dried over MgSO$_4$, filtered and the solvent was removed under reduced pressure to give an off white solid. The aqueous phase was further extracted with EtOAc (3×100 mL), the combined organic fractions were washed with H$_2$O (50 mL) then brine (30 mL), it was dried over MgSO$_4$, filtered, the solvent was removed under reduced pressure and the solids combined to give 2-chloro-6-fluoro-4-hydroxy-9H-xanthen-9-one (39d) (754 mg, 85%) as an off-white solid: mp 296-300° C.; $^1$H NMR (DMSO-d$_6$) δ 11.12 (br. s, 1H), 8.24 (dd, J=6.5, 8.9 Hz, 1H), 7.60 (dd, J=2.3, 9.8 Hz, 1H), 7.52 (d, J=2.5 Hz, 1H), 7.37 (dt, J=2.4, 8.7 Hz, 1H), 7.30 (d, J=2.5 Hz, 1H); HRMS (ESI) Calcd for C$_{13}$H$_7$ClFO$_3$ m/z 265.0051; found m/z 265.0056 (M+H$^+$).

A mixture of 2-chloro-6-fluoro-4-hydroxy-9H-xanthen-9-one (39d) (516 mg, 1.95 mmol), dimethylaminoethyl chloride hydrochloride (1.68 g, 11.7 mmol), tetrabutylammonium bromide (63 mg, 0.19 mmol) and NaOH (936 mg, 23.4 mmol) in a 1:1 mixture of CH$_2$Cl$_2$/H$_2$O (50 mL) was stirred at 18° C. for 24 h. The reaction mixture was partitioned between CH$_2$Cl$_2$ (150 mL) and H$_2$O (50 mL), the organic phase was separated and washed with H$_2$O (3×50 mL) then brine (30 mL). It was dried over MgSO$_4$, filtered and the solvent was removed under reduced pressure. The residue was purified by column chromatography (SiO$_2$, EtOAc/MeOH/NEt$_3$) to give 2-chloro-4-[2-(dimethylamino)ethoxy]-6-fluoro-9H-xanthen-9-one (39e) (566 mg, 85%) as a white solid: mp 139-140° C.; $^1$H NMR (DMSO-d$_6$) δ 8.24 (dd, J=6.5, 8.9 Hz, 1H), 7.60-7.63 (m, 3H), 7.38 (dt, J=2.4, 8.6 Hz, 1H), 4.31 (t, J=5.8 Hz, 2H), 2.75 (t, J=5.8 Hz, 2H), 2.28 (s, 6H); HRMS (ESI) Calcd for C$_{17}$H$_{16}$ClFNO$_3$ m/z 336.0786; found m/z 336.0801 (M+H$^+$).

A mixture of phenol (87 mg, 0.92 mmol), 2-chloro-4-[2-(dimethylamino)ethoxy]-6-fluoro-9H-xanthen-9-one (39e) (154 mg, 0.46 mmol) and K$_2$CO$_3$ (127 mg, 0.92 mmol) in anhydrous DMSO (2 mL) was heated at 80° C. in a sealed tube for 16 h. After cooling, and partitioning between EtOAc (150 mL) and H$_2$O (50 mL), the organic phase was separated, washed with H$_2$O (3×50 mL) and brine (30 mL). After drying over MgSO$_4$, the solution was filtered and the solvent was removed under reduced pressure. The residue was purified by recrystallization from EtOAc to give 2-chloro-4-[2-(dimethylamino)ethoxy]-6-phenoxy-9H-xanthen-9-one (39) (61 mg, 16%) as a white solid: mp 135-137° C.; $^1$H NMR (DMSO-d$_6$) δ 8.18 (d, J=8.9 Hz, 1H), 7.62 (d, J=2.4 Hz, 1H), 7.60 (d, J=2.4 Hz, 1H), 7.51-7.55 (m, 2H), 7.34 (t, J=7.4 Hz, 1H), 7.23-7.26 (m, 2H), 7.14 (dd, J=2.3, 8.8 Hz, 1H), 6.92 (d, J=2.3 Hz, 1H), 4.27 (t, J=5.8 Hz, 2H), 2.71 (t, J=5.8 Hz, 2H), 2.23 (s, 6H); $^{13}$C NMR (DMSO-d$_6$) δ 173.9, 163.4, 156.7, 154.2, 148.7, 144.9, 130.6, 128.6, 128.5, 125.6, 122.5, 120.6, 117.4, 116.1, 115.3, 115.2, 104.4, 68.0, 57.3, 45.5; MS (ESI) m/z 410.2 (M+H$^+$); Anal. Calcd for C$_{23}$H$_{20}$ClNO$_2$: C, 67.4; H, 4.9; N, 3.4. Found: C, 67.45; H, 4.8; N, 3.4%.

Example 40

3-({7-Chloro-5-[2-(dimethylamino)ethoxy]-9-oxo-9H-xanthen-3-yl}oxy)-N-phenylbenzamide

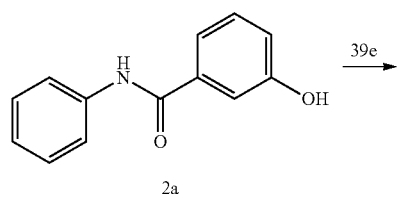

2a

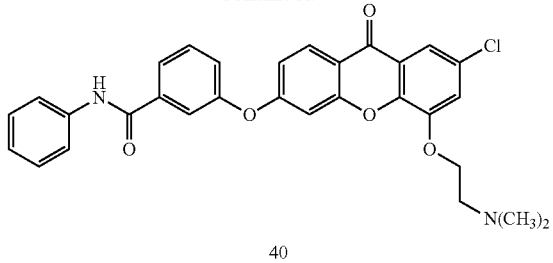

40

A mixture of 3-hydroxy-N-phenylbenzamide (2a) (190 mg, 0.90 mmol), 2-chloro-4-[2-(dimethylamino)ethoxy]-6-fluoro-9H-xanthen-9-one (39e) (150 mg, 0.45 mmol) and K$_2$CO$_3$ (125 mg, 0.90 mmol) in anhydrous DMSO (2 mL) was heated at 80° C. in a sealed tube for 16 h. The mixture was cooled and partitioned between EtOAc (150 mL) and H$_2$O (50 mL). The organic phase was separated, washed with H$_2$O (3×50 mL) and brine (30 mL). It was dried over MgSO$_4$, filtered and the solvent was removed under reduced pressure. The aqueous phase was further extracted with CH$_2$Cl$_2$ (3×100 mL), dried and evaporated and the combined solids were recrystallized from EtOAc to give 3-({7-chloro-5-[2-(dimethylamino)ethoxy]-9-oxo-9H-xanthen-3-yl}oxy)-N-phenylbenzamide (40) (100 mg, 43%) as a white solid: mp 205-208° C.; $^1$H NMR (DMSO-d$_6$) δ 10.3 (s, 1H), 8.21 (d, J=8.8 Hz, 1H), 7.92 (ddd, J=1.0, 1.5, 7.7 Hz, 1H), 7.82 (t, J=2.0 Hz, 1H), 7.74-7.77 (m, 2H), 7.68 (t, J=8.0 Hz, 1H), 7.63 (d, J=2.4 Hz, 1H), 7.60 (d, J=2.4 Hz, 1H), 7.48 (ddd, J=0.9, 2.5, 8.2 Hz, 1H), 7.32-7.37 (m, 2H), 7.19 (dd, J=2.4, 8.9 Hz, 1H), 7.08-7.13 (m, 1H), 7.03 (d, J=2.3 Hz, 1H), 4.27 (t, J=5.9 Hz, 2H), 2.70 (t, J=5.9 Hz, 2H), 2.22 (s, 6H); $^{13}$C NMR (DMSO-d$_6$) δ 173.9, 164.2, 163.0, 156.7, 154.3, 148.7, 144.9, 138.8, 137.2, 130.7, 128.6, 124.8, 123.9, 123.7, 122.5, 120.5, 119.6, 117.5, 116.4, 115.4, 115.3, 104.9, 68.0, 57.3, 45.5; MS (ESI) m/z 592.2 (M+H). Anal. Calcd for C$_{30}$H$_{25}$ClN$_2$O$_5$: C, 68.1; H, 4.8; N, 5.3. Found: C, 67.95; H, 4.65; N, 5.3%.

Example 41

2-Chloro-4-[2-(dimethylamino)ethoxy]-6-({6-[2-(4-methoxyphenyl)ethyl]-3-pyridinyl}oxy)-9H-xanthen-9-one

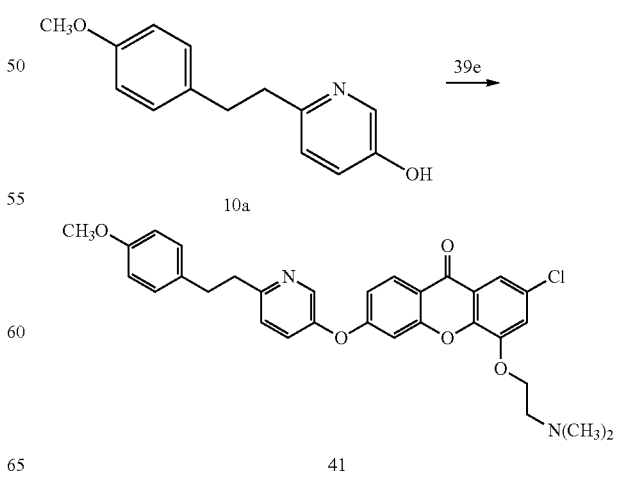

A mixture of 6-[2-(4-methoxyphenyl)ethyl]-3-pyridinol (10a) (205 mg, 0.89 mmol), 2-chloro-4-[2-(dimethylamino) ethoxy]-6-fluoro-9H-xanthen-9-one (39e) (150 mg, 0.44 mmol) and $K_2CO_3$ (125 mg, 0.89 mmol) in anhydrous DMSO (2 mL) was heated at 80° C. in a sealed tube for 16 h. It was cooled down and partitioned between EtOAc (150 mL) and $H_2O$ (50 mL). The organic phase was separated, washed with $H_2O$ (3×50 mL) then brine (30 mL). It was dried over $MgSO_4$, filtered and the solvent was removed under reduced pressure. The residue was purified by column chromatography ($Al_2O_3$, EtOAc) followed by trituration in EtOAc to give 2-chloro-4-[2-(dimethylamino)ethoxy]-6-({6-[2-(4-methoxyphenyl)ethyl]-3-pyridinyl}oxy)-9H-xanthen-9-one (41) (145 mg, 60%) as a white solid: mp 92-94° C.; $^1$H NMR (DMSO-$d_6$) δ 8.47 (d, J=2.8 Hz, 1H), 8.20 (d, J=8.9 Hz, 1H), 7.60-7.63 (m, 3H), 7.35 (d, J=8.5 Hz, 1H), 7.11-7.17 (m, 3H), 6.97 (d, J=2.3 Hz, 1H), 6.83-6.86 (m, 2H), 4.28 (t, J=5.9 Hz, 2H), 3.71 (s, 3H), 3.02-3.07 (m, 2H), 2.94-2.98 (m, 2H), 2.70 (t, J=5.8 Hz, 2H), 2.22 (s, 6H); $^{13}$C NMR (DMSO-$d_6$) δ 173.9, 163.1, 158.1, 157.5, 156.7, 149.1, 148.7, 144.9, 141.7, 133.1, 129.2, 128.6, 128.5, 124.1, 122.5, 117.5, 116.4, 115.3, 115.0, 113.7, 104.6, 68.0, 57.3, 54.9, 45.5, 38.9, 34.2; MS (ESI) m/z 229.2 (M+H$^+$). Anal. Calcd for $C_{31}H_{29}ClN_2O_5$: C, 68.3; H, 5.4; N, 5.1. Found: C, 68.15; H, 5.3; N, 5.2%.

Example 42

3-(5-((7-Bromo-5-(2-(dimethylamino)ethoxy)-9-oxo-9H-xanthen-3-yl)oxy)pyridin-2-yl)-N-cyclopentylpropanamide

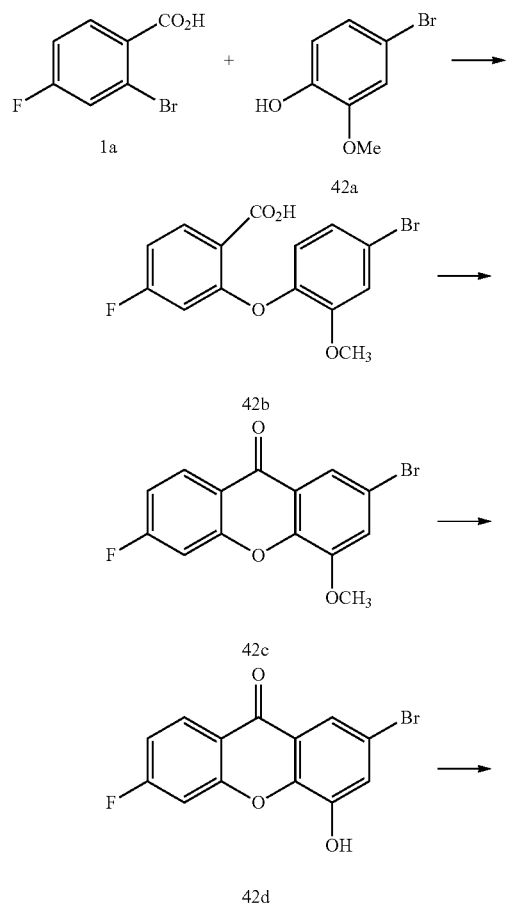

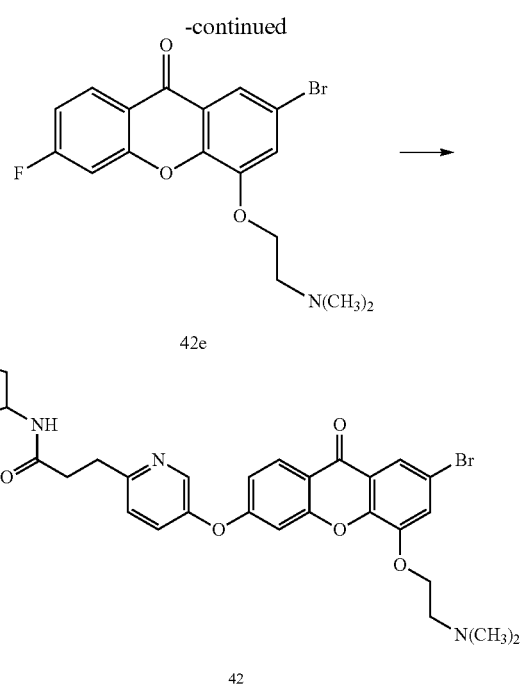

Reaction of 4-bromo-2-methoxyphenol (42a) and compound 1a as in Example 39 gave 2-(4-bromo-2-methoxyphenoxy)-4-fluorobenzoic acid (42b) in 20% yield: $^1$H NMR (DMSO-$d_6$) δ 12.92 (br, 1H), 7.89 (dd, J=8.7, 6.8 Hz, 1H), 7.37 (d, J=2.2 Hz, 1H), 7.15 (dd, J=8.5, 2.3 Hz, 1H) 7.03-6.98 (m, 1H), 6.96 (d, J=8.5 Hz, 1H), 6.52 (dd, J=10.5, 2.4 Hz, 1H), 3.78 (s, 3H); MS (APCI) m/z: 241 (M+H$^+$).

Ring closure of compound 42b with PPA as in Example 39 gave 2-bromo-6-fluoro-4-methoxy-9H-xanthen-9-one (42c) in 84% yield: $^1$H NMR (CDCl$_3$) δ 8.35 (dd, J=8.9, 6.4 Hz, 1H), 8.03 (d, J=2.2 Hz, 1H), 7.33 (d, J=2.2 Hz, 1H), 7.29 (dd, J=9.3, 2.4 Hz, 1H), 7.14 (ddd, J=8.4, 8.1, 2.4 Hz, 1H), 4.03 (s, 3H).

Demethylation of compound 42c with BBr$_3$ in CH$_2$Cl$_2$ as in Example 39 gave 2-bromo-6-fluoro-4-hydroxy-9H-xanthen-9-one (42d) in 86% yield: $^1$H NMR (DMSO-$d_6$) δ 11.11 (br s, 1H), 8.24 (dd, J=8.74, 6.65 Hz, 1H), 7.65 (d, J=2.12 Hz, 1H), 7.60 (dd, J=9.71, 2.02 Hz, 1H), 7.42 (d, J=1.95 Hz, 1H), 7.37 (dt, J=8.73, 8.68, 2.14 Hz, 1H).

Phase transfer coupling of compound 42d with 2-dimethylaminoethylchloride hydrochloride as in Example 1 gave 2-bromo-4-(2-(dimethylamino)ethoxy)-6-fluoro-9H-xanthen-9-one (42e) in 62% yield: mp (CH$_2$Cl$_2$/hexanes) 149-151° C.; $^1$H NMR (CDCl$_3$) δ 8.34 (dd, J=8.9, 6.4 Hz, 1H), 8.02 (d, J=2.2 Hz, 1H), 7.34 (d, J=2.2 Hz, 1H), 7.25 (d, J=9.1, 2.4 Hz, 1H), 7.13 (ddd, J=8.8, 8.2, 2.4 Hz, 1H); MS (APCI) m/z: 380 (M+H$^+$).

Coupling of compound 42e with compound 28a in DMSO as in Example 1 gave 3-(5-((7-bromo-5-(2-(dimethylamino)ethoxy)-9-oxo-9H-xanthen-3-yl)oxy)pyridin-2-yl)-N-cyclopentylpropanamide (42) in 99% yield: mp (CH$_2$Cl$_2$/hexanes) 212-215° C.; $^1$H NMR (CDCl$_3$) δ 8.40 (d, J=2.7 Hz, 1H), 8.30 (d, J=8.8 Hz, 1H), 8.02 (d, J=2.2 Hz, 1H), 7.39 (dd, J=8.4, 2.8 Hz, 1H), 7.33 (d, J=2.2 Hz, 1H), 7.30 (d, J=8.44 Hz, 1H), 7.03 (dd, J=8.8, 2.3 Hz, 1H), 6.99 (d, J=2.3 Hz, 1H), 5.93 (d, J=7.1 Hz, 1H), 4.22 (t, J=5.8 Hz, 1H), 4.23-4.15 (m, 1H), 3.18 (t, J=6.8 Hz, 1H), 2.85 (t, J=5.5 Hz, 1H), 2.66 (t, J=7.3 Hz, 1H); MS (APCI) m/z: 594 (M+H$^+$).

Anal. Calcd for $C_{30}H_{32}BrN_3O_5$: C, 60.6; H, 5.5; N, 7.1. Found C, 60.7; H, 5.5; N, 6.9%.

Example 43

N-Cyclopentyl-3-(5-((5-(2-(dimethylamino)ethoxy)-7-methyl-9-oxo-9H-xanthen-3-yl)thio)pyridin-2-yl)propanamide

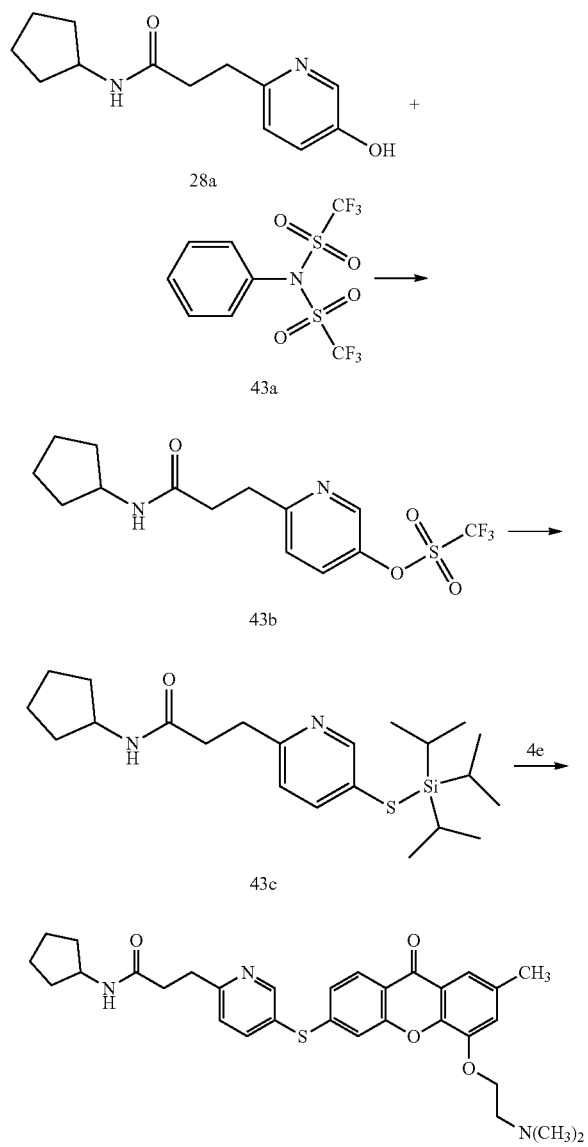

To a suspension of compound 28a (246 mg, 1.05 mmol), N-phenyltriflimide (43a) (390 mg, 1.09 mmol, 1.05 eq) in $CH_2Cl_2$ (6 mL) was added $Et_3N$ (0.16 mL, 1.15 mmol, 11 eq) at 0° C. The reaction mixture was stirred for 3 hr allowing it to warm up to 20° C., then it was concentrated, diluted with water and stirred for 1 hr. The resulting precipitate was filtered, washed with water and vacuum dried at 20° C. to give 6-(3-(cyclopentylamino)-3-oxopropyl)pyridin-3-yl trifluoromethanesulfonate (43b) in 89.4% yield: $^1$H NMR (CDCl$_3$) δ 8.47 (d, J=2.8 Hz, 1H), 7.53 (dd, J=8.6, 2.9 Hz, 1H), 7.33 (d, J=8.6 Hz, 1H), 5.63 (d, J=6.4 Hz, 1H), 3.17 (t, J=7.1 Hz, 1H), 2.63 (t, J=7.1 Hz, 1H), 4.19-4.10 (m, 1H), 3.17 (t, J=7.1 Hz, 2H), 2.63 (t, J=7.1 Hz, 2H), 1.95-1.87 (m, 2H), 1.63-1.54 (m, 4H), 1.31-1.22 (m, 2H); MS m/z 367 (M+H$^+$).

To a suspension of compound 43b (107 mg, 0.29 mmol) and $Cs_2CO_3$ (127 mg, 0.43 mmol, 1.5 eq) in toluene under $N_2$ was added Pd(Ph$_3$)$_4$ (20 mg, 0.07 eq) and triisopropylsilyl thiol (0.06 mL, 1.1 eq). The reaction mixture was heated at 130° C. for 2 hr, cooled to 20° C., diluted with water and extracted into EtOAc. The organic layer was washed with aq. $K_2CO_3$ and dried over $Na_2SO_4$ to give crude N-cyclopentyl-3-(5-((triisopropylsilyl)thio)-pyridin-2-yl)propanamide (43c).

Crude 43c was treated with $Cs_2CO_3$ (190 mg, 0.58 mmol, 2 eq), CsF (66 mg, 0.43 mmol, 1.5 eq), 4e (73 mg, 0.23 mmol, 0.8 eq) and DMSO (3 mL) under $N_2$. The reaction mixture was heated for 20 hr at 80° C. then cooled to 20° C., diluted with water and stirred for 1 hr.

The resulting precipitate was collected by filtration, washed with water, aq. $K_2CO_3$, and again with water. Chromatography of the collected solid on neutral $Al_2O_3$, eluting with a gradient of hexanes/EtOAc (0-100%) gave N-cyclopentyl-3-(5-((5-(2-(dimethylamino)ethoxy)-7-methyl-9-oxo-9H-xanthen-3-yl)thio)pyridin-2-yl)propanamide (43) (38 mg, 30%): mp (CH$_2$Cl$_2$/hexanes) 202-204° C.; $^1$H NMR (CDCl$_3$) δ 8.68 (d, J=2.1 Hz, 1H), 8.07 (d, J=8.4 Hz, 1H), 7.99 (dd, J=8.1, 2.3 Hz, 1H), 7.80 (d, J=7.2 Hz, 1H), 7.48 (s, 1H), 7.45 (d, J=8.1 Hz, 1H), 7.38 (d, J=1.6 Hz, 1H), 7.19 (dd, J=8.4, 1.7 Hz, 1H), 7.12 (d, J=1.6 Hz, 1H), 4.22 (t, J=5.8 Hz, 2H), 4.02-3.93 (m, 1H), 3.04 (t, J=7.6 Hz, 2H), 2.72 (t, J=5.8 Hz, 2H) 2.50 (t, J=8.1 Hz, 2H), 2.41 (s, 3H), 2.25 (s, 6H), 1.79-1.71 (m, 2H), 1.64-1.54 (m, 2H), 1.51-1.42 (m, 2H), 1.50-1.42 (m, 2H), 1.35-1.27 (m, 2H); MS m/z 546 (M+H$^+$). Anal. Calcd for $C_{31}H_{35}N_3O_4S$: C, 68.2; H, 6.5; N, 7.7; S, 5.9. Found: C, 68.3; H, 6.6; N, 7.7; S, 5.8%.

Example 44

N-Cyclopentyl-3-(5-((7-(2-(dimethylamino)ethoxy)-9-oxo-9H-xanthen-3-yl)oxy)-pyridin-2-yl)propanamide

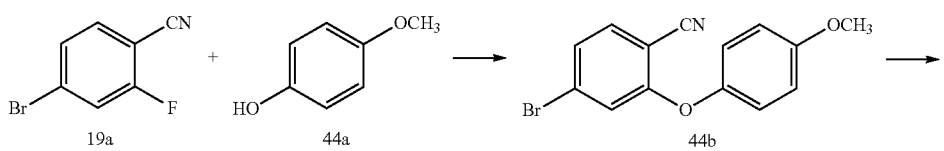

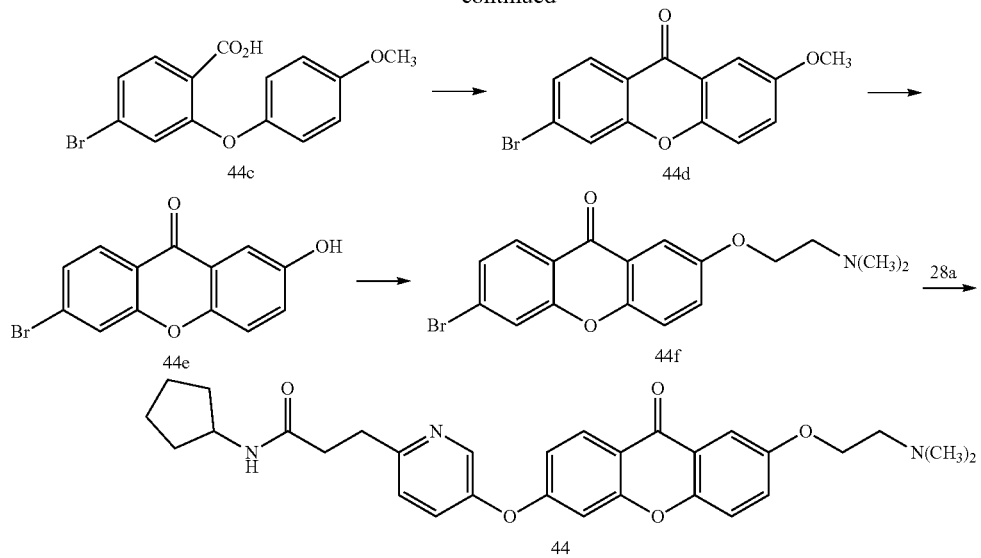

Using a modification of the method of example 19, a mixture of 4-methoxyphenol (44a) (6.2 g, 50 mmol) and KOH (2.8 g, 50 mmol) in 1,4-dioxane (50 mL) was stirred at 20° C. until all the KOH pellets disappeared. Then 4-bromo-2-fluorobenzonitrile (19a) (11.0 g, 55.0 mmol) was added and the reaction mixture was refluxed for 20 hr. A further portion of compound 44a (3.1 g) and KOH (1.4 g) was added, and refluxing was continued for 20 more hours. The reaction mixture was concentrated and stirred in ice/$H_2O$. The resulting precipitate was collected by filtration, washed with water, and dried to give 4-bromo-2-(4-methoxyphenoxy)benzonitrile (44b) (16.0 g, 95%): $^1$H NMR (CDCl$_3$) δ 7.48 (d, J=8.3 Hz, 1H), 7.22 (dd, J=8.3, 1.7 Hz, 1H), 7.06-7.04 (m, 2H), 6.97-6.93 (m, 2H), 6.89 (d, J=1.71 Hz, 1H), 3.84 (s, 3H).

Compound 44b (15.0 g, 49 mmol) was suspended in solution of KOH (11 g, 196 mmol) in $H_2O$ (100 mL) and EtOH (100 mL). The reaction mixture was refluxed for 48 hr, cooled to 20° C. and the ethanol was removed under vacuum. The aqueous layer was filtered and then acidified with conc. HCl to give a precipitate which was collected, washed with water, and dried in an oven to give clean 4-bromo-2-(4-methoxyphenoxy)benzoic acid (44c) (14.98 g, 94%): $^1$H NMR (CDCl$_3$) δ 8.02 (d, J=8.4 Hz, 1H), 7.30 (dd, J=8.4, 1.8 Hz, 1H), 7.08-7.02 (m, 2H), 6.99-6.95 (m, 2H), 6.92 (d, J=1.8 Hz, 1H); MS m/z 323 (M+H$^+$).

Ring closure of compound 44c with PPA at 100° C. gave 6-bromo-2-methoxy-9H-xanthen-9-one (44d) in 88% yield: $^1$H NMR (CDCl$_3$) δ 8.18 (d, J=8.5 Hz, 1H), 7.48 (dd, J=8.5, 1.7 Hz, 1H), 7.66 (m, 2H), 7.41 (d, J=9.1 Hz, 1H), 7.33 (dd, J=9.1, 3.1 Hz, 1H), 3.91 (s, 3H); MS (ESI) m/z 305 (M+H$^+$).

Demethylation of compound 44d with CH$_2$Cl$_2$/BBr$_3$ gave 6-bromo-2-hydroxy-9H-xanthen-9-one (44e) in 76% yield: $^1$H NMR (DMSO-d$_6$) δ 8.06 (d, J=8.5 Hz, 1H), 7.61 (d, J=8.3 Hz, 1H), 7.52 (d, J=9.0 Hz, 1H), 7.45 (d, J=2.0 Hz, 1H), 7.31 (dd, J=7.3, 2.1 Hz, 1H); MS m/z 291 (M+H$^+$).

Phase transfer coupling of compound 44e with 2-dimethylaminoethylchloride as in example 1 gave 6-bromo-2-(2-(dimethylamino)ethoxy)-9H-xanthen-9-one (44f) in 79% yield: $^1$H NMR (CDCl$_3$) δ 8.20 (d, J=8.54 Hz, 1H), 7.69 (dd, J=3.7, 2.2 Hz, 2H), 7.49 (dd, J=8.5, 1.8 Hz, 1H), 7.40-7.38 (m, 2H), 4.18 (t, J=5.5 Hz, 1H), 2.78 (t, J=5.5 Hz, 1H), 2.36 (m, 6H); MS m/z 362 (M+H$^+$).

Following the method of *J. Org. Chem.* 2010, 75, 1791 as in Example 28, the copper catalysed coupling of compound 28a with compound 44f gave N-cyclopentyl-3-(5-((7-(2-(dimethylamino)ethoxy)-9-oxo-9H-xanthen-3-yl)oxy)pyridin-2-yl)propanamide (44) in 38% yield: mp (i-Pr$_2$O/MeOH) 164-167° C.; $^1$H NMR (CDCl$_3$) δ 8.40 (d, J=2.7 Hz, 1H), 8.33 (d, J=8.9 Hz, 1H), 7.70 (t, J=1.6 Hz, 1H), 7.40 (dd, J=8.4, 2.8 Hz, 1H), 7.36 (d, J=1.7 Hz, 2H), 7.30 (d, J=8.4 Hz, 1H), 7.02 (dd, J=8.9, 2.3 Hz, 1H), 6.89 (d, J=2.3 Hz, 1H), 5.93 (d, J=7.0 Hz, 1H), 4.23-4.15 (m, 3H), 3.17 (t, J=7.8 Hz, 1H), 2.78 (t, J=5.5 Hz, 1H), 2.67 (t, J=7.1 Hz, 1H), 2.36 (s, 6H), 1.98-1.90 (m, 2H), 1.65-1.58 (m, 4H), 1.36-1.28 (m, 2H); MS m/z 516 (M+H$^+$). Anal. Calcd for $C_{30}H_{33}N_3O_5$: C, 69.9; H, 6.4; N, 8.1. Found C, 69.7; H, 6.5; N, 8.0%.

Example 45

N-Cyclopentyl-3-(5-((7-(2-(dimethylamino)ethoxy)-5-methyl-9-oxo-9H-xanthen-3-yl)oxy)pyridin-2-yl)propanamide

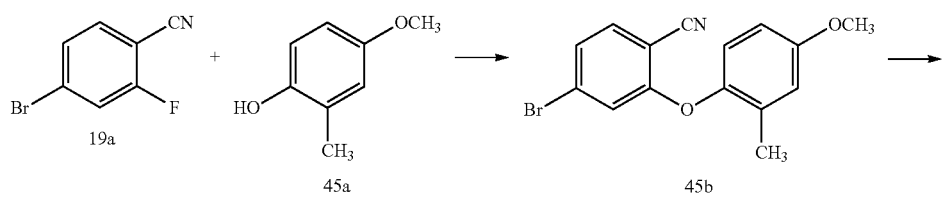

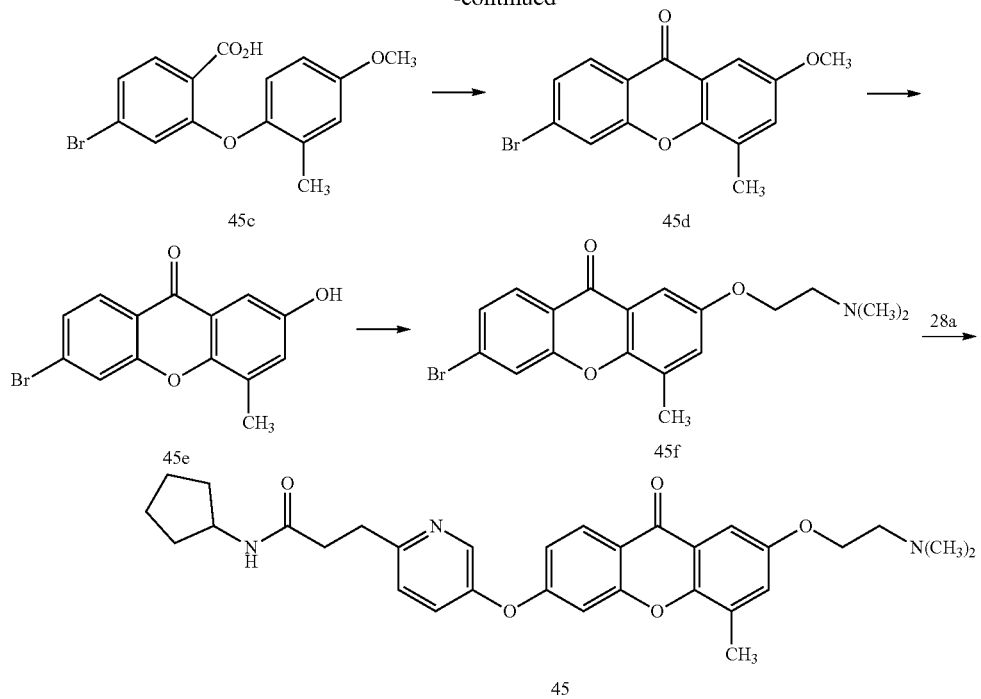

Coupling of the potassium salt of 4-methoxy-2-methylphenol (45a) with 4-bromo-2-fluorobenzonitrile (19a) as in Example 44 gave 4-bromo-2-(4-methoxy-2-methylphenoxy)benzonitrile (45b) in 90% yield: $^1$H NMR (CDCl$_3$) δ 7.49 (d, J=8.2 Hz, 1H), 7.21 (dd, J=8.2, 1.6 Hz, 1H), 6.96 (d, J=8.7 Hz, 1H), 6.83 (d, J=2.8 Hz, 1H), 6.78 (dd, J=8.7, 3.0 Hz, 1H), 6.75 (d, J=1.6 Hz, 1H), 3.82 (s, 3H), 2.16 (s, 3H).

Hydrolysis of 45b with KOH in aq. EtOH as in Example 44 gave 4-bromo-2-(4-methoxy-2-methylphenoxy)benzoic acid (45c) in 83% yield: $^1$H NMR (DMSO-d$_6$) δ 13.03 (br 1H), 7.71 (d, J=8.30 Hz, 1H), 7.32 (dd, J=8.3, 1.9 Hz, 1H), 6.93-6.91 (m 2H) 6.82 (dd, J=8.8, 3.00 Hz, 1H), 6.70 (d, J=1.8 Hz, 1H), 3.76 (s, 3H), 2.10 (s, 3H) PPA ring closure of compound 45c as in Example 44 gave 6-bromo-2-methoxy-4-methyl-9H-xanthen-9-one (45d) in 57% yield: $^1$H NMR (CDCl$_3$) δ 8.20 (d, J=8.5 Hz, 1H), 7.75 (d, J=1.8 Hz, 1H), 7.54 (d, J=3.1 Hz, 1H), 7.49 (dd, J=8.5, 1.77 Hz, 1H), 7.20 (dd, J=3.1, 0.8 Hz, 1H), 3.90 (s, 3H), 2.52 (s, 3H); MS (APCI) m/z: 319 (M+H$^+$).

Demethylation of compound 45d with BBr$_3$/CH$_2$Cl$_2$ as in Example 44 gave 6-bromo-2-hydroxy-4-methyl-9H-xanthen-9-one (45e) in 99% yield: $^1$H NMR (DMSO-d$_6$) δ 9.86 (brs, 1H), 8.05 (d, J=8.5 Hz, 1H), 7.97 (d, J=1.7 Hz, 1H), 7.61 (dd, J=8.5, 1.8 Hz, 1H), 7.30 (d, J=2.9 Hz, 1H), 7.21 (dd, J=3.0, 0.7 Hz, 1H), 2.46 (s, 3H).

Phase transfer coupling of N-dimethylaminoethylchloride with compound 45e as in Example 44 gave 6-bromo-2-(2-(dimethylamino)ethoxy)-4-methyl-9H-xanthen-9-one (45f) in 66% yield: $^1$H NMR (CDCl$_3$) δ 8.20 (d, J=8.5 Hz, 1H), 7.75 (d, J=1.7 Hz, 1H), 7.54 (d, J=3.1 Hz, 1H), 7.49 (dd, J=8.5, 1.77 Hz, 1H) 4.16 (t, J=5.54 Hz, 2H), 2.77 (t, J=5.5 Hz, 1H), 2.51 (s, 3H), 2.35 (s, 6H); MS (APCI) m/z: 375 (M+H$^+$).

Copper catalysed reaction of compound 45f with compound 28a as in Example 44 gave N-cyclopentyl-3-(5-((7-(2-(dimethylamino)ethoxy)-5-methyl-9-oxo-9H-xanthen-3-yl)oxy)pyridin-2-yl)propanamide (45) in 78% yield: mp (CH$_2$Cl$_2$/hexanes) 169-170° C.; $^1$H NMR (CDCl$_3$) δ 8.41 (d, J=2.7 Hz, 1H), 8.32 (d, J=8.8 Hz, 1H), 7.55 (d, J=3.1 Hz, 1H), 7.40 (dd, J=8.4, 2.8 Hz, 1H), 7.31 (d, J=8.4 Hz, 1H), 7.23 (dd, J=3.1, 0.7 Hz, 1H), 7.02 (dd, J=8.9, 2.3 Hz, 1H), 6.9 (d, J=2.3 Hz, 1H), 5.93 (d, J=6.9 Hz, 1H), 4.16 (t, J=5.6 Hz, 2H), 3.18 (t, J=7.1 Hz, 2H), 2.77 (t, J=5.5 Hz, 2H), 2.67 (t, J=7.1 Hz, 2H) 2.48 (s, 3H), 2.35 (s, 6H), 1.98-1.89 (m, 2H), 1.65-1.56 (m, 4H), 1.36-1.27 (m, 2H); MS (APCI) m/z: 530 (M+H$^+$).

Example 46

N-Cyclopentyl-3-(5-((7-(2-(dimethylamino)ethoxy)-5-methoxy-9-oxo-9H-xanthen-3-yl)oxy)pyridin-2-yl)propanamide

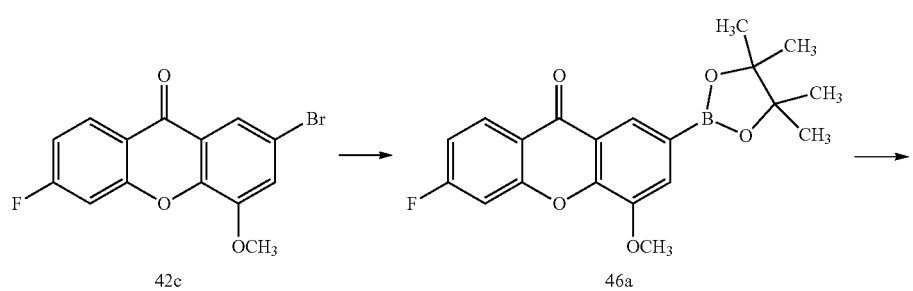

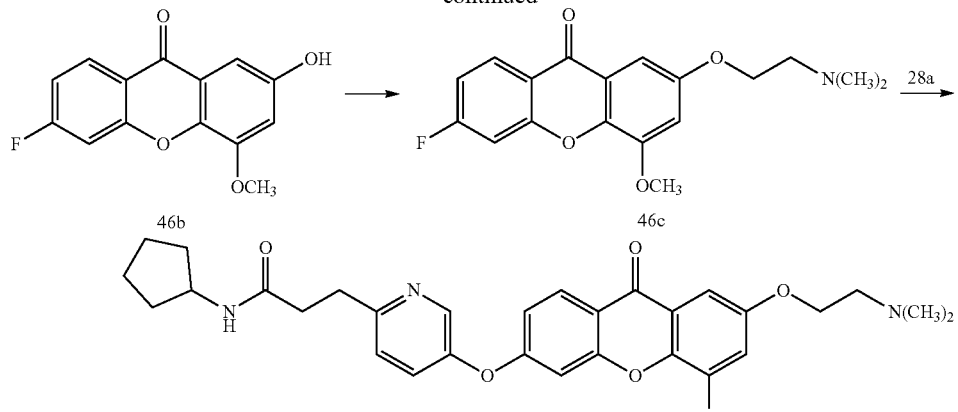

A suspension of compound 42c (500 mg, 1.55 mmol), KOAc (456 mg, 4.65 mmol, 3 eq) and bis(pinacolato)diboron (792 mg, 3.1 mmol, 2 eq) in 1,4-dioxane (6 mL) was degassed with $N_2$. Then $PdCl_2(dppf)$ (63 mg, 5 mol %) was added and the reaction mixture was heated to 80° C. under $N_2$ for 20 hr. The reaction mixture was cooled to 20° C., filtered, and the filter cake was further washed with EtOAc. The combined washings were evaporated. The filter cake was washed with aq. $KHCO_3$ and acetone. This $KHCO_3$/acetone washings and the residue obtained from EtOAc evaporation were combined and treated with oxone (953 mg, 1.55 mmol), $KHCO_3$ (2 g, 20 mmol) in $H_2O$ (30 mL) and acetone (30 mL) at 20° C. The reaction mixture was stirred 20 hr at 20° C. and filtered. The filtrate was extracted with EtOAc (50 mL×3), and dried ($Na_2SO_4$). Evaporation of the solvents and the chromatography of the residue on $SiO_2$/EtOAc/hexanes (0-75%) gave fractions containing the mass of 261, which were combined and the solvent was evaporated. The residue was stirred in $CH_2Cl_2$ for 30 min, filtered and the collected solid was triturated with diisopropyl ether to give 6-fluoro-2-hydroxy-4-methoxy-9H-xanthen-9-one (46b) (100 mg, 25%): $^1$H NMR (DMSO-$d_6$) δ 10.42 (s, 1H), 8.22 (dd, J=8.9, 6.6 Hz, 1H), 7.61 (dd, J=10.9, 2.3 Hz, 1H), 7.33 (dt, J=8.7, 2.4 Hz, 1H), 7.02 (d, J=2.7 Hz, 1H), 6.96 (d, J=2.7 Hz, 1H), 3.94 (s, 3H).

Phase transfer reaction of compound 46b with 2-dimethylaminoethylchloride hydrochloride as in Example 1 gave 2-(2-(dimethylamino)ethoxy)-6-fluoro-4-methoxy-9H-xanthen-9-one (46c) in 40% yield: $^1$H NMR (CDCl$_3$) δ 8.36 (dd, J=8.9, 6.4 Hz, 1H), 7.29-7.25 (m, 2H), 7.11 (dt, J=8.8, 2.4 Hz, 1H), 6.96 (d, J=2.8 Hz, 1H), 4.18 (t, J=5.4 Hz, 2H), 3.99 (s, 3H), 2.77 (t, J=5.4 Hz, 2H), 2.36 (s, 6H).

Coupling reaction of compound 46c with compound 28a gave N-cyclopentyl-3-(5-((7-(2-(dimethylamino)ethoxy)-5-methoxy-9-oxo-9H-xanthen-3-yl)oxy)pyridin-2-yl)propanamide (46) in 69% yield: mp (CH$_2$Cl$_2$/hexanes) 172-174° C.; $^1$H NMR (CDCl$_3$) δ 8.40 (d, J=2.7 Hz, 1H), 8.33 (d, J=8.9 Hz, 1H), 7.39 (dd, J=8.4, 2.8 Hz, 1H), 7.06 (dd, J=8.9, 2.3 Hz, 1H), 6.95 (d, J=2.3 Hz, 1H), 6.94 (d, J=2.8 Hz, 1H), 5.96 (d, J=6.3 Hz, 1H), 4.24-4.16 (m, 1H), 4.17 (t, J=5.5 Hz, 2H), 3.99 (s, 3H), 3.17 (t, J=7.1 Hz, 1H), 2.77 (t, J=5.4 Hz, 1H), 2.67 (t, J=7.1 Hz, 1H), 2.35 (s, 6H), 1.98-1.90 (m, 2H), 1.68-1.56 (m, 4H), 1.37-1.29 (m, 2H); MS (APCI) m/z: 546 (M+H$^+$).

Example 47

N-Cyclopentyl-3-(5-((6-(2-(dimethylamino)ethoxy)-9-oxo-9H-xanthen-3-yl)oxy)pyridine-2-yl)propanamide

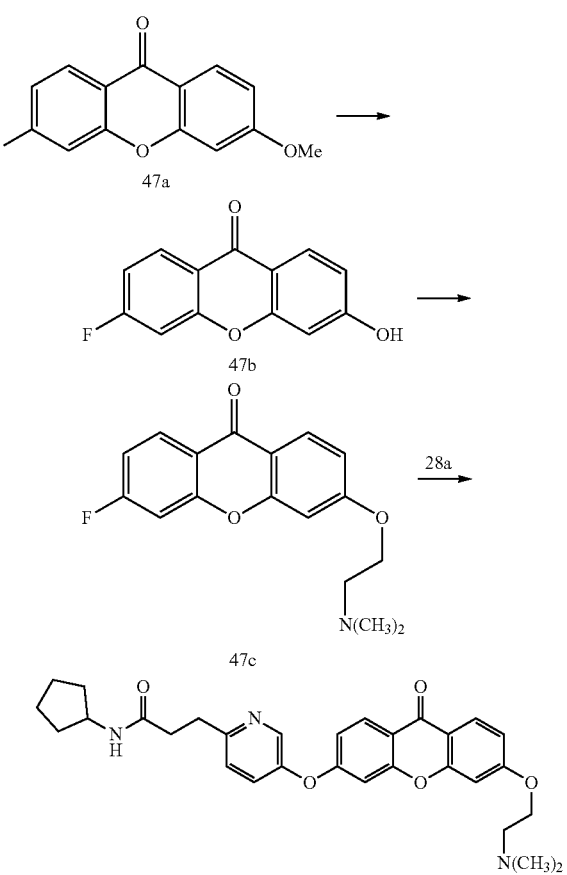

A mixture of 3-fluoro-6-methoxy-9H-xanthen-9-one (47a) (U.S. Pat. No. 8,350,041B2) 427 mg, 1.75 mmol) and a solution of 48% HBr in HOAc (15 mL) was heated in a sealed tube for 20 h at 120° C. Then the reaction mixture was cooled to 20° C. and the excess reagent was evaporated, the resulting residue was stirred in H₂O for 2 hr, filtered washed with more H₂O, dried in the oven to give 3-fluoro-6-hydroxy-9H-xanthen-9-one (47b) (391 mg, 97%): ¹H NMR (DMSO-d₆) δ 11.01 (s, 1H), 8.21 (dd, J=8.9, 6.6 Hz, 1H), 8.04 (d, J=8.7 Hz, 1H), 7.55 (dd, J=9.9, 2.41 Hz, 1H), 7.32 (dt, J=8.7, 2.4 Hz, 1H), 6.92 (dd, J=8.7, 2.2 Hz, 1H), 6.87 (d, J=2.2 Hz, 1H); MS (APCI) m/z 231.1 (M+H⁺).

A coupling reaction of 3-fluoro-6-hydroxy-9H-xanthen-9-one (47b) with N-dimethylaminoethyl chloride gave 3-(2-(dimethylamino)ethoxy)-6-fluoro-9H-xanthen-9-one (47c) in 77% yield: mp (CH₂Cl₂/hexanes) 105-107° C.; ¹H NMR (CDCl₃) δ 8.33 (dd, J=8.8, 6.4 Hz, 1H), 8.23 (d, J=8.9 Hz, 1H), 7.15-7.11 (m, 1H), 7.08 (dd, J=8.7, 2.40 Hz, 1H), 6.99 (dd, J=8.9, 2.4 Hz, 1H), 6.89 (d, J=2.3 Hz, 1H), 4.19 (t, J=5.6 Hz, 2H), 2.80 (t, J=5.64 Hz, 2H), 2.37 (s, 3H); MS (APCI) m/z 302.2 (M+H⁺).

Using the synthetic method described in example 28, the reaction of 3-(2-(dimethyl-amino)ethoxy)-6-fluoro-9H-xanthen-9-one (47c) with compound 28a in DMSO gave N-cyclopentyl-3-(5-((6-(2-(dimethylamino)ethoxy)-9-oxo-9H-xanthen-3-yl)oxy)pyridyl-2-yl)propanamide in 84% yield: mp (CH₂Cl₂/hexanes) 161-163° C.; ¹H NMR (CDCl₃) δ 8.40 (d, J=2.6 Hz, 1H), 8.30 (d, J=8.8 Hz, 1H), 8.23 (d, J=8.9 Hz, 1H), 7.40 (dd, J=8.4, 2.8 Hz, 1H), 7.29 (d, J=8.4 Hz, 1H), 6.99 (dt, J=9.1, 2.4 Hz, 2H), 6.88 (d, J=2.3 Hz, 1H), 6.84 (d, J=2.3 Hz, 1H), 5.95 (d, J=6.9 Hz, 1H), 4.23-4.15 (m, 1H), 4.17 (t, J=5.6 Hz, 1H), 3.17 (t, J=7.1 Hz, 1H), 2.79 (t, J=5.6 Hz, 1H), 2.66 (t, J=7.1 Hz, 1H), 2.36 (s, 6H), 1.98-1.90 (m, 2H), 1.66-1.55 (m, 4H), 1.36-1.25 (m, 2H); MS (APCI) m/z 516.3 (M+H⁺).

Example 48

4-(2-(Dimethylamino)ethoxy)-2-methyl-6-phenoxy-9H-thioxanthen-9-one

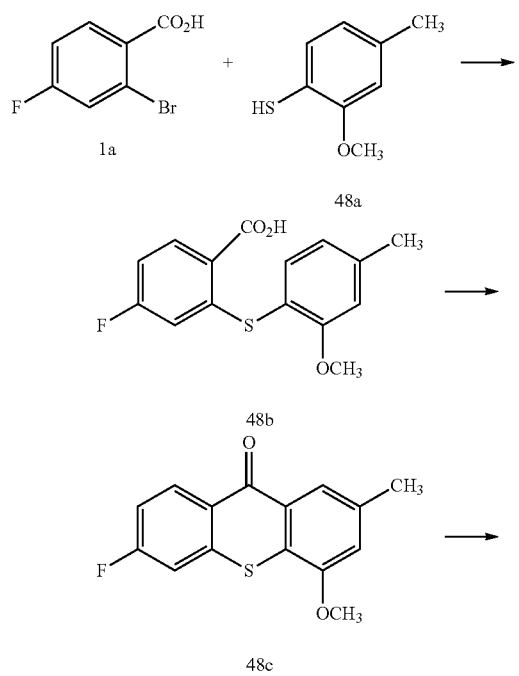

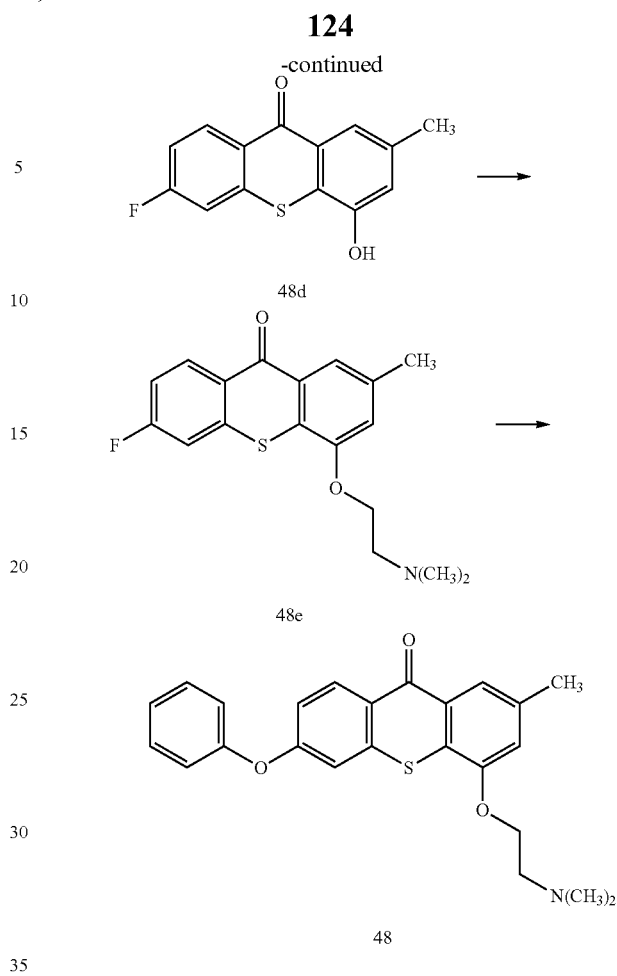

Using the method of *Synthesis,* 2007, 3519, a mixture of 2-bromo-4-fluorobenzoic acid (1a) (3.11 g, 14.20 mmol), 2-methoxy-4-methylbenzenethiol (48a) (WO2013/087647) (2.63 g, 17.05 mmol), K₂CO₃ (2.00 g, 14.47 mmol), copper powder (90 mg, 1.42 mmol) and Cu₂O (100 mg, 0.70 mmol) in 2-ethoxyethanol (5 mL) was stirred at 130° C. for 2 h before the solvent was removed. The residue was dissolved in water and the solution was washed with ethyl acetate twice. The aqueous phase was acidified with 2N HCl to pH 2 to give a white precipitate, which was collected by filtration, and washed with warm water to give 4-fluoro-2-((2-methoxy-4-methylphenyl)thio)benzoic acid (48b) (3.55 g, 86%) as a white solid: mp 220-222° C.; ¹H NMR (DMSO-d₆) δ 13.22 (s, 1H), 8.00 (dd, J=6.3, 8.7, 1H), 7.40 (d, J=7.6, 1H), 7.06 (s, 1H), 7.00 (dt, J=2.6, 8.3, 1H), 6.91 (dd, J=0.2, 7.7, 1H), 6.20 (dd, J=2.5, 10.7, 1H), 3.74 (s, 3H), 2.40 (s, 3H); HRMS (ESI) found m/z 315.0452 (M+Na); calculated for C₁₅H₁₃FNaO₃S 315.0462. Anal. Calcd for C₁₅H₁₃FO₃S.0.25H₂O: C, 60.7; H, 4.6; S, 10.8. Found: C, 60.6; H, 4.5; S, 10.75%. 4-Fluoro-2-((2-methoxy-4-methylphenyl)thio)benzoic acid (48b) (3.54 g, 12.11 mmol) was treated with 20 g of PPA at 110° C. for 3 h before ice was added. The sticky mixture was stirred until a white suspension formed. The solid was collected by filtration, washed with water and dried under vacuum to give 6-fluoro-4-methoxy-2-methyl-9H-thioxanthen-9-one (48c) (3.2 g, 96%) as an off-white solid: mp 178-180° C.; ¹H NMR (CDCl₃) δ 8.63 (dd, J=6.0, 9.0, 1H), 8.06 (dd, J=0.8, 1.6, 1H), 7.30 (dd, J=2.4, 8.8, 1H), 7.19-7.14 (m, 1H), 6.98 (d, J=1.4, 1H), 4.02 (s, 3H), 2.50 (s, 3H); MS (APCI) m/z 275.1

(M+H⁺). Anal. Calcd for C₁₅H₁₁FO₂S: C, 65.7; H, 4.0; S, 11.7. Found: C, 65.7; H, 4.1; S, 11.6%.

To a suspension of 6-fluoro-4-methoxy-2-methyl-9H-thioxanthen-9-one (48c) (3.00 g, 10.94 mmol) in CH₂Cl₂ (60 ml) in ice bath was added 1M solution of BBr₃ in CH₂Cl₂ (33 mL, 33.00 mmol). The mixture was allowed to warm up to room temperature and stirred for 5 h. Ice was added to quench the reaction and the mixture was distributed between water and CH₂Cl₂. The aqueous phase was washed with CH₂Cl₂ twice. The combined organic phase was washed with water, brine and dried over anhydrous Na₂SO₄. The resultant crude material was purified by silica gel column chromatography using mixtures of ethyl acetate and hexanes (v/v 1:4 and 1:2). The product off the column was further purified by recrystallization from CH₂Cl₂ and heptane to give 6-fluoro-4-hydroxy-2-methyl-9H-thioxanthen-9-one (48d) (560 mg, 20%) as a yellow solid: mp 270-273° C.; ¹H NMR (CDCl₃) δ 11.02 (s, 1H), 8.49 (dd, J=6.1, 9.0, 1H), 7.83 (dd, J=2.5, 9.5, 1H), 7.79 (dd, J=0.9, 1.6, 1H), 7.43-7.38 (m, 1H), 7.06 (d, J=1.2, 1H), 2.40 (s, 3H); MS (APCI) m/z 259.1 (M–H). Anal. Calcd for C₁₄H₉FO₂S: C, 64.6; H, 3.5; S, 12.3. Found: C, 64.35; H, 3.5; S, 12.3%.

A mixture of 6-fluoro-4-hydroxy-2-methyl-9H-thioxanthen-9-one (48d) (375 mg, 1.44 mmol), 2-dimethylaminoethyl chloride hydrochloride (1.25 g, 8.64 mmol), tetrabutylammonium bromide (46 mg, 0.14 mmol), and KOH (970 mg, 17.29 mmol) in CH₂Cl₂ (20 mL) and water (20 mL) was stirred at room temperature overnight. The aqueous phase was washed with CH₂Cl₂ twice. The combined organic phase was washed with water, brine and dried over anhydrous Na₂SO₄. The resultant crude material was purified by alumina (90 standardised) column chromatography using mixtures of ethyl acetate and hexanes (v/v 1:2 and 1:1) to give 4-(2-(dimethylamino)ethoxy)-6-fluoro-2-methyl-9H-thioxanthen-9-one (48e) (367 mg, 77%) as a pale yellow solid: mp 113-114° C.; ¹H NMR (CDCl₃) δppm 8.49 (dd, J=6.0, 8.8, 1H), 7.88-7.85 (m, 2H), 7.41 (dt, J=2.4, 8.4, 1H), 7.34 (d, J=0.8, 1H), 4.30 (t, J=5.8, 2H), 2.74 (t, J=5.6, 2H), 2.46 (s, 3H), 2.28 (s, 6H); MS (APCI) m/z 332.2 (M+H⁺). Anal. Calcd for C₁₈H₁₈FNO₂S: C, 65.2; H, 5.5; N, 4.2; S, 9.7. Found: C, 64.4; H, 5.5; N, 4.2; S, 9.7%.

A mixture of 4-(2-(dimethylamino)ethoxy)-6-fluoro-2-methyl-9H-thioxanthen-9-one (48e) (65 mg, 0.20 mmol), phenol (37 mg, 0.39 mmol), K₂CO₃ (54 mg, 0.39 mmol) in DMSO (2 mL) was stirred at 80° C. overnight. The resultant mixture was distributed between water and ethyl acetate. The aqueous phase was extracted with ethyl acetate twice. The combined organic phase was washed with water, brine and dried over anhydrous Na₂SO₄. The crude material obtained was purified by alumina (90 active neutral) column chromatography using mixtures of methanol and CH₂Cl₂ (v/v 1:200 and 1:100) to give 4-(2-(dimethylamino)ethoxy)-2-methyl-6-phenoxy-9H-thioxanthen-9-one (48) (50 mg, 62%) as a white solid: HPLC purity 98%; mp 141-142° C.; ¹H NMR (CDCl₃) δ 8.57 (d, J=8.8, 1H), 8.06 (dd, J=0.8, 1.6, 1H), 7.46-7.41 (m, 2H), 7.26-7.25 (m, 1H), 7.14-7.06 (m, 4H), 6.96 (d, J=1.4, 1H), 4.25 (t, J=5.8, 2H), 2.85 (t, J=5.8, 2H), 2.48 (s, 3H), 2.39 (s, 6H); MS (APCI) m/z 406.2 (M+H⁺). Anal. Calcd for C₂₄H₂₃NO₃S: C, 71.1; H, 5.7; N, 3.45; S, 7.9. Found: C, 70.8; H, 5.7; N, 3.5; S, 7.4%.

Example 49

3-((5-(2-(Dimethylamino)ethoxy)-7-methyl-9-oxo-9H-thioxanthen-3-yl)oxy)-N-phenylbenzamide

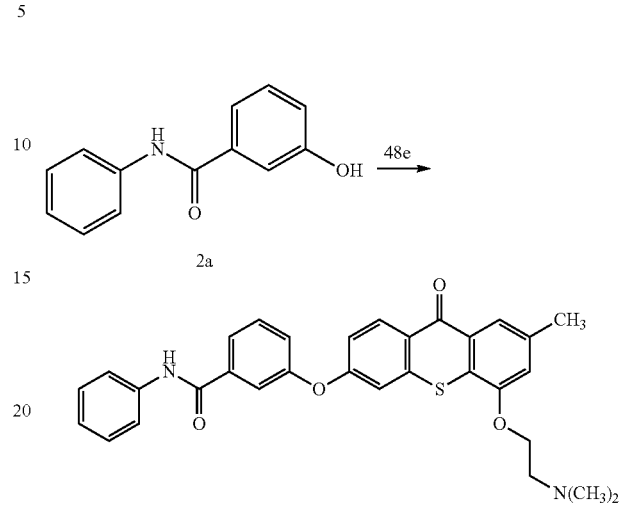

A mixture of 4-(2-(dimethylamino)ethoxy)-6-fluoro-2-methyl-9H-thioxanthen-9-one (48e) (65 mg, 0.20 mmol), 3-hydroxy-N-phenylbenzamide (2a) (84 mg, 0.39 mmol), K₂CO₃ (54 mg, 0.39 mmol in DMSO (2 mL) was stirred at 80° C. overnight. The resultant mixture was distributed between water and ethyl acetate. The aqueous phase was extracted with ethyl acetate twice. The combined organic phase was washed with water, brine and dried over anhydrous Na₂SO₄. The crude material obtained was purified by alumina (90 active neutral) column chromatography using a mixtures of methanol and CH₂Cl₂ (v/v 1:100) to give 3-((5-(2-(dimethylamino)ethoxy)-7-methyl-9-oxo-9H-thioxanthen-3-yl)oxy)-N-phenylbenzamide (49) (66 mg, 66%) as a white solid: HPLC purity 97%; mp 125-127° C.; ¹H NMR (CDCl₃) δ 8.58 (dd, J=0.8, 8.5, 1H), 8.05 (dd, J=0.8, 1.6, 1H), 7.91 (s, 1H), 7.76-7.73 (m, 1H), 7.66-7.63 (m, 3H), 7.55 (t, J=7.9, 1H), 7.39-7.35 (m, 2H), 7.31-7.28 (m, 1H), 7.18-7.14 (m, 1H), 7.11-7.07 (m, 2H), 6.95 (d, J=1.4, 1H), 4.24 (t, J=5.8, 2H), 2.84 (t, J=5.8, 2H), 2.48 (s, 3H), 2.39 (s, 6H); MS (APCI) m/z 525.2 (M+H⁺). Anal. Calcd for C₃₁H₂₈N₂O₄S.0.25H₂O: C, 70.4; H, 5.4; N, 5.3; S, 6.1. Found: C, 70.15; H, 5.2; N, 5.3; S, 5.75%.

Example 50

4-(2-(Dimethylamino)ethoxy)-6-((6-(4-methoxyphenethyl)pyridin-3-yl)oxy)-2-methyl-9H-thioxanthen-9-one

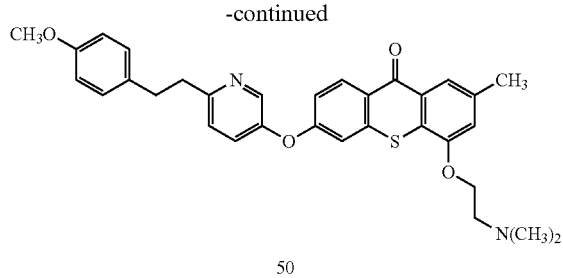

50

A mixture of 4-(2-(dimethylamino)ethoxy)-6-fluoro-2-methyl-9H-thioxanthen-9-one (48e) (100 mg, 0.30 mmol), 6-[2-(4-methoxyphenyl)ethyl]-3-pyridinol (3b) (97 mg, 0.42 mmol), K₂CO₃ (83 mg, 0.60 mmol in DMSO (2 mL) was stirred at 80° C. overnight. The resultant mixture was distributed between water and ethyl acetate. The aqueous phase was extracted with ethyl acetate twice. The combined organic phase was washed with water, brine and dried over anhydrous Na₂SO₄. The crude material obtained was purified by alumina (90 standardised) column chromatography using mixtures of ethyl acetate and hexanes (v/v 1:2 and 1:1) to give 4-(2-(dimethylamino)ethoxy)-6-((6-(4-methoxyphenethyl)pyridin-3-yl)oxy)-2-methyl-9H-thioxanthen-9-one (50) (108 mg, 66%) as a white solid: HPLC purity 95%; mp 120-121° C.; $^1$H NMR (CDCl₃) δ 8.60 (dd, J=0.4, 8.6, 1H), 8.44 (d, J=2.5, 1H), 8.06 (q, J=0.8, 1H), 7.33 (dd, J=2.8, 8.4, 1H), 7.15-7.11 (m, 3H), 7.10-7.06 (m, 2H), 6.97 (d, J=1.4, 1H), 6.86-6.83 (m, 2H), 4.25 (t, J=5.8, 2H), 3.80 (s, 2H), 3.14-3.10 (m, 2H), 3.06-3.02 (m, 2H), 2.85 (t, J=5.8, 2H), 2.49 (s, 3H), 2.40 (s, 6H); MS (APCI) m/z 541.3 (M+H⁺). Anal. Calcd for $C_{32}H_{32}N_2O_4S \cdot 0.25H_2O$: C, 70.5; H, 6.1; N, 5.1; S, 5.9. Found: C, 70.6; H, 6.0; N, 5.2; S, 5.8%.

Example 51

N-Cyclopentyl-3-(5-((5-(2-(dimethylamino)ethoxy)-7-methyl-9-oxo-9H-thioxanthen-3-yl)oxy)pyridin-2-yl)propanamide

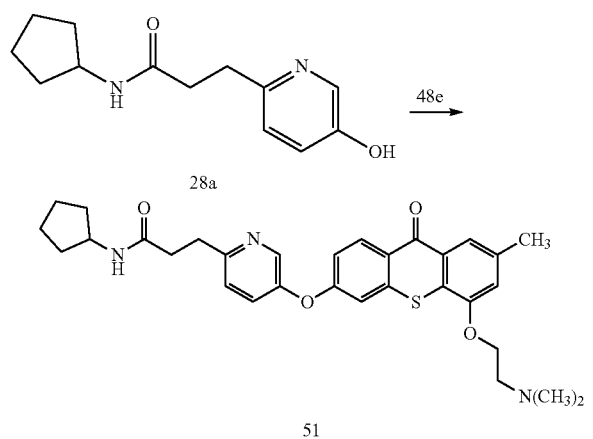

The coupling reaction of 4-(2-(dimethylamino)ethoxy)-6-fluoro-2-methyl-9H-thioxanthen-9-one (48e) and compound 28a as in example 50 gave N-cyclopentyl-3-(5-((5-(2-(dimethylamino)ethoxy)-7-methyl-9-oxo-9H-thioxanthen-3-yl)oxy)pyridin-2-yl)propanamide (51) in 100% yield: mp (CH₂Cl₂/hexanes) 173-175° C.; $^1$H NMR (CDCl₃) δ 8.61 (dd, J=8.6, 0.6 Hz, 1H), 8.41 (d, J=2.6 Hz, 1H), 8.08 (d, J=0.6 Hz, 1H), 7.40 (dd, J=8.4, 2.8 Hz, 1H), 7.31 (d, J=8.5 Hz, 1H), 7.10 (dd, J=10.0, 3.7 Hz, 1H), 6.99 (d, J=1.1 Hz, 1H), 5.96 (d, J=6.4 Hz, 1H), 4.27 (t, J=5.8 Hz, 1H), 3.19 (t, J=7.1 Hz, 1H), 2.87 (t, J=7.1 Hz), (t, J=5.8 Hz, 1H), 2.69 (t, J=7.1 Hz, 1H), 2.51 (s, 3H), 2.41 (s, 6H), 2.00-1.92 (m, 2H), 1.68-1.59 (m, 4H), 1.38-1.28 (m, 2H); MS (APCI) m/z: 546 (M+H⁺). HPLC 97.6%.

Example 52

10-(3-(Dimethylamino)propyl)-2-methyl-6-(phenylthio)acridin-9(10H)-one

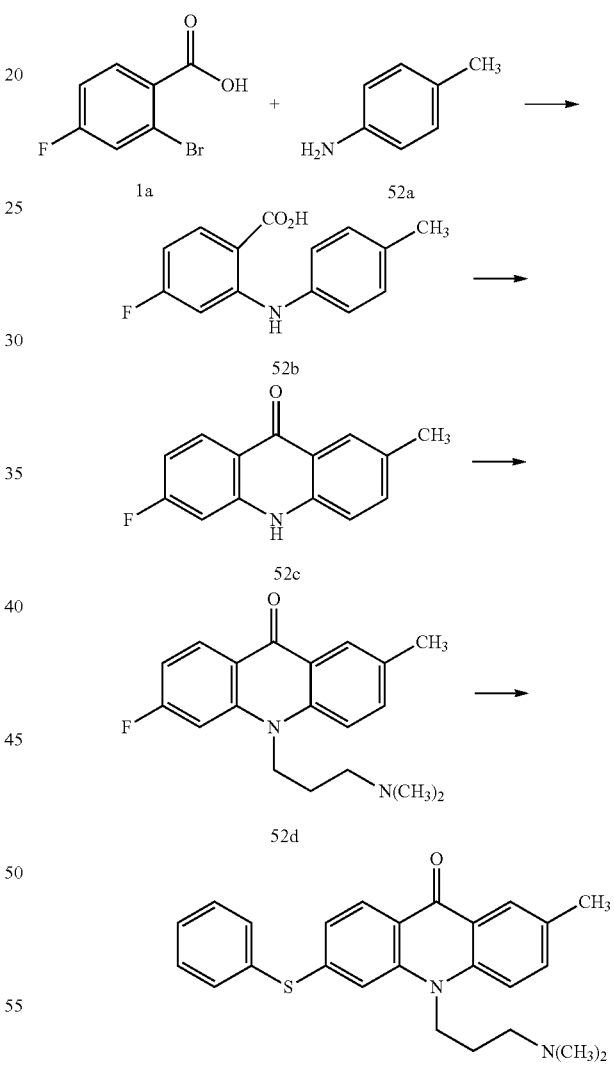

A mixture of 2-bromo-4-fluorobenzoic acid (1a) (4.38 g, 20 mmol) and 4-methylaniline (52a) (2.57 g, 24 mmol), Cu powder (128 mg, 2 mmol), Cu₂O (143 mg, 1 mmol), and K₂CO₃ (2.76 g, 20 mmol) in 2-ethoxyethanol (6 mL) was heated under reflux under nitrogen overnight. After cooling, the mixture was diluted with water and filtered through celite. Acidification with dilute aq. HCl gave 4-fluoro-2-((4- methylphenyl)amino)benzoic acid (52b) (1.86 g, 38%): mp (aq. MeOH) 221-223° C.; $^1$H NMR (DMSO-$d_6$) δ 13.11 (br s, 1H), 9.76 (br s, 1H), 7.94 (dd, J=8.9, 7.0 Hz, 1H), 7.21 (d, J=8.3 Hz, 2H), 7.16 (d, J=8.4 Hz, 2H), 6.71 (dd, J=12.4, 2.5 Hz, 1H), 6.53 (td, J=8.5, 2.5 Hz), and 2.30 (s, 3H); MS (APCI) m/z 246.2 (M+H$^+$).

Ring closure of (52b) (1.72 g, 7 mmol) in PPA at 120° C. for 2 h, followed by pouring into water gave 6-fluoro-2-methylacridin-9(10H)-one (52c) (1.51 g, 95%): mp (EtOH) >340° C.; $^1$H NMR (DMSO-$d_6$) δ 11.75 (br s, 1H), 8.27 (dd, J=9.0, 6.6 Hz, 1H), 8.01 (br s, 1H), 7.57 (dd, J=8.5, 2.0 Hz, 1H), 7.44 (d, J=8.4 Hz, 1H), 7.21 (dd, J=10.5, 2.3 Hz, 1H), 7.07 (td, J=8.8, 2.4 Hz, 1H); MS (APCI) m/z 228.2 (M+H$^+$).

A mixture of 52c (1.36 g. 6 mmol), 3-chloro-N,N-dimethylpropylamine hydrochloride (1.89 g, 12 mmol), and $K_2CO_3$ (0.83 g, 6 mmol) in acetone (30 mL) was heated under reflux for 2 days. The solvent was removed under vacuum and the residue was dissolved in dilute aq. HCl, and filtered. The solution was neutralized with aq. $NH_3$ and extracted with EtOAc to give 10-(3-(dimethylamino)propyl)-6-fluoro-2-methylacridin-9(10H)-one (52d) (0.853 g, 46%): mp (MeOH) 136-138° C.; $^1$H NMR (CDCl$_3$) δ 8.58 (dd, J=8.9, 7.0 Hz, 1H), 8.36 (br s, 1H), 7.54 (dd, J=8.8, 2.1 Hz, 1H), 7.52 (d, J=8.8 Hz, 1H), 6.99 (ddd, J=8.9, 7.8, 2.2 Hz, 1H), 4.40 (t, J=7.5 Hz, 2H), 2.48 (s, 3H), 2.43 (t, J=6.4 Hz, 2H), 2.32 (s, 6H), 2.03 (m 2H); MS (APCI) m/z 313.2 (M+H$^+$). Anal. Calcd for $C_{19}H_{21}FN_2O$: C, 73.1; H, 6.8; N, 9.0; F, 6.1. Found: C, 73.0; H, 7.0; N, 9.0; F, 6.4%.

A mixture of 52d (0.22 g, 0.7 mmol), thiophenol (0.16 g, 1.4 mmol), and $K_2CO_3$ (0.30 g, 2.1 mmol) in dry DMSO (4 mL) was flushed with nitrogen and heated at 85° C. for 16 h. The cooled mixture was diluted with water, and the yellow precipitate was collected and dissolved in dilute aqueous methanesulfonic acid. After washing with EtOAc, the aqueous layer was made basic with dil aq. $NH_3$ and extracted into EtOAc to give 10-(3-(dimethyl-amino)propyl)-2-methyl-6-(phenylthio)acridin-9(10H)-one (52) (0.258 g, 91%): mp (i-Pr$_2$O) 107-109° C.; $^1$H NMR (CDCl$_3$) δ 8.41 (d, J=8.4 Hz, 1H), 8.30 (br d, J=1.1 Hz, 1H), 7.58-7.55 (m, 2H), 7.49 (td, J=8.8, 2.14 Hz, 1H), 7.45-7.41 (m, 4H), 7.24 (d, J=1.4 Hz, 1H), 7.03 (dd, J=8.5, 1.5 Hz, 1H), 4.21 (t, J=7.6 Hz, 2H), 2.44 (s, 3H), 2.29 (t, J=7.6 Hz, 2H), 2.26 (s, 6H), 1.87 (m 2H); MS (APCI) m/z 403.1 (M+H$^+$). Anal. Calcd for $C_{25}H_{26}N_2OS$: C, 74.6; H, 6.5; N, 7.0. Found: C, 74.5; H, 6.5; N, 7.0%.

Example 53

4-(2-(Dimethylamino)ethoxy)-2-methyl-6-(pyridin-3-yloxy)-9H-xanthen-9-one

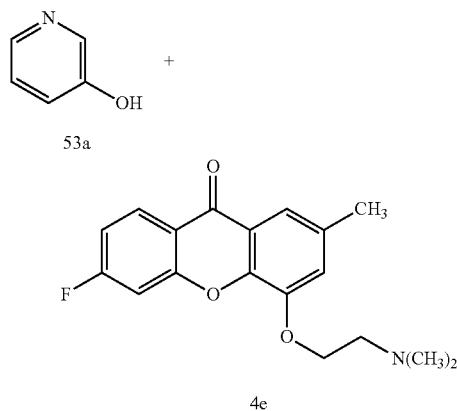

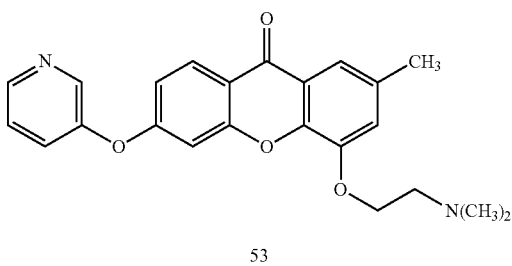

The coupling reaction of 3-hydroxypyridine (53a) and compound 4e as in Example 11 gave 4-(2-(dimethylamino)ethoxy)-2-methyl-6-(pyridin-3-yloxy)-9H-xanthen-9-one (53) in 85% yield: mp (CH$_2$Cl$_2$/hexanes) 132-133° C.; $^1$H NMR (CDCl$_3$) δ 8.54-8.52 (m, 2H), 8.33 (d, J=8.8 Hz, 1H), 7.70 (dd, J=1.9, 0.8 Hz, 1H), 7.47 (ddd, J=8.3, 2.7, 1.5 Hz, 1H), 7.39 (dd, J=8.6, 5.0 Hz, 1H), 7.08 (d, J=1.8 Hz, 1H), 7.05 (dd, J=8.8, 2.3 Hz, 1H), 7.00 (d, J=2.3 Hz, 1H), 4.22 (t, J=5.9 Hz, 1H), 2.85 (t, J=5.9 Hz, 1H), 2.45 (s, 3H), 2.38 (s, 3H); HPLC 98.9%; HRMS Calcd. for $C_{2-3}H_{22}N_2O_4$: m/z 391.16523 (M+H$^+$); found m/z 391.16623.

Example 54

4-(2-(Dimethylamino)ethoxy)-2-methyl-6-((6-(3-(4-methylpiperazin-1-yl)-3-oxopropyl)pyridin-3-yl)oxy)-9H-xanthen-9-one

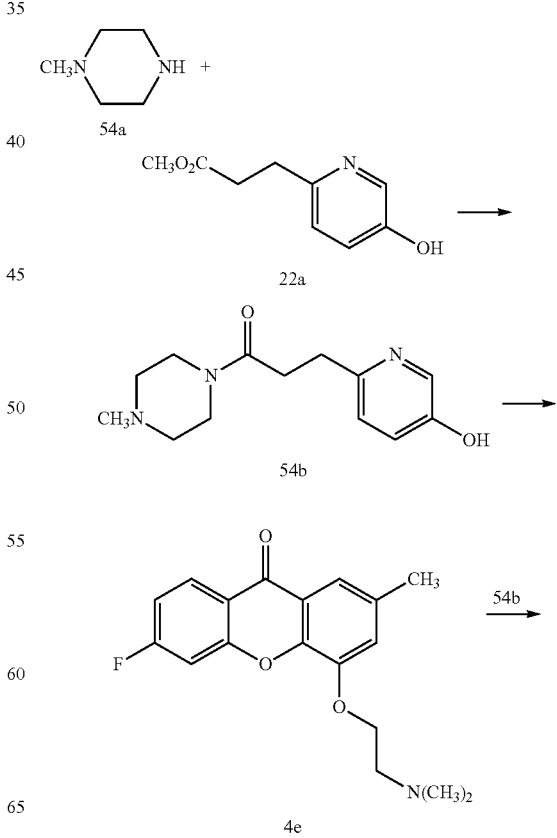

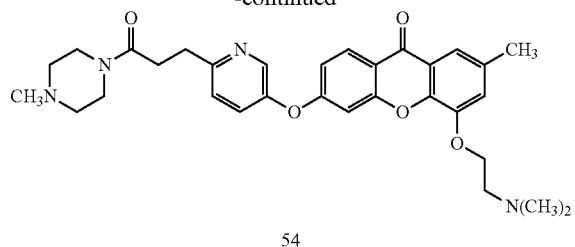

54

A mixture of compound 22a (253 mg, 1.34 mmol) and excess N-methylpiperazine (54a) was heated for 20 h at 122° C. Excess reagent was removed under vacuum and the resulting residue was stirred in CH$_2$Cl$_2$/diisopropylether/hexanes/EtOAc over three days. The resulting semisolid was filtered to give crude 3-(5-hydroxypyridin-2-yl)-1-(4-methylpiperazin-1-yl)propan-1-one (54b) which was used directly.

The coupling reaction of compound 4e and compound 54b as in Example 11 gave 4-(2-(dimethylamino)ethoxy)-2-methyl-6-((6-(3-(4-methylpiperazin-1-yl)-3-oxopropyl)pyridin-3-yl)oxy)-9H-xanthen-9-one (54) in 60% yield: mp (diisopropyl ether) 118-120° C.; $^1$H NMR (CDCl$_3$) δ 8.41 (d, J=2.7 Hz, 1H), 8.31 (d, J=8.8 Hz, 1H), 7.70 (brs, 1H), 7.38 (dd, J=8.4, 2.7 Hz, 1H), 7.33 (d, J=8.4 Hz, 1H), 7.08 (d, J=1.8 Hz, 1H), 7.03 (dd, J=8.8, 2.3 Hz, 1H), 6.98 (d, J=2.3 Hz, 1H), 4.23 (t, J=5.9 Hz, 1H), 3.67-3.64 (m, 2H), 3.55-3.52 (m, 2H), 3.19 (t, J=7.4 Hz, 1H), 2.89-2.83 (m, 4H), 2.44 (s, 3H), 2.39-2.36 (m, 4H), 2.38 (s, 6H), 2.30 (s, 3H), HPLC 98.5%, MS (APCI) m/z: 545.3 (M+H$^+$). Anal. Calcd for C$_{31}$H$_{36}$N$_4$O$_5$: C, 68.4; H, 6.7; N, 10.3. Found: C, 68.1; H, 6.8; N, 10.2%.

Example 55

N-Cyclopentyl-3-(5-((5-(2-(diethylamino)ethoxy)-7-methyl-9-oxo-9H-xanthen-3-yl)oxy)pyridin-2-yl)propanamide

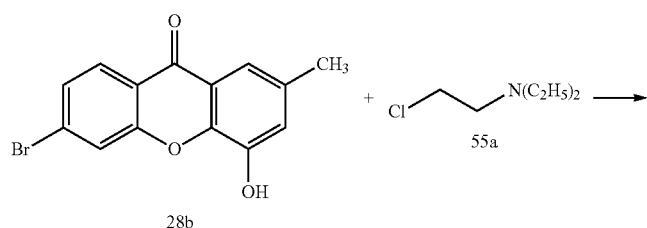

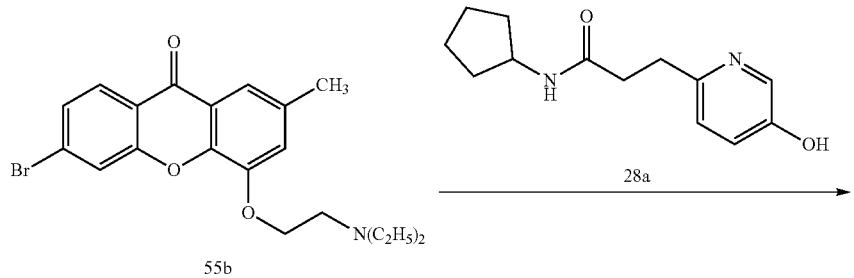

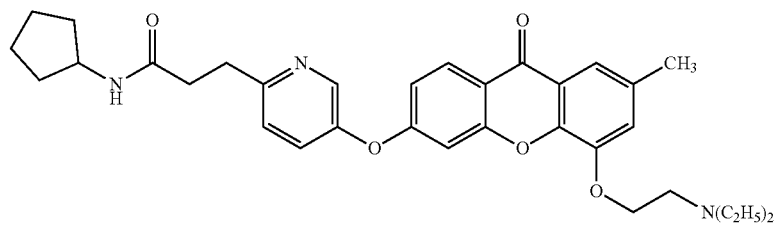

55

A mixture of 6-bromo-4-hydroxy-2-methyl-9H-xanthen-9-one (28b) (305 mg, 1 mmol), 2-chloro-N,N-diethylethylamine hydrochloride (55a) (1.85 g, 10 mmol), KOH (1.5 g, 10.8 mmol) and tetrabutylammonium bromide (150 mg) in $CH_2Cl_2$ (30 mL) and $H_2O$ (30 mL) was stirred for 1 h at 20° C. The organic layer was separated and the aqueous layer was further extracted with $CH_2Cl_2$. The combined $CH_2Cl_2$ extracts were washed with brine and dried ($Na_2SO_4$). Chromatography on neutral alumina, eluting with hexanes/EtOAc 0-50%, followed by $CH_2Cl_2$/EtOAc 0-20%, then with $CH_2Cl_2$/MeOH 0-2%, gave 6-bromo-4-(2-(diethylamino)ethoxy)-2-methyl-9H-xanthen-9-one (55b) (140 mg, 35% yield): $^1$H NMR (CDCl$_3$) δ 8.19 (d, J=8.5 Hz, 1H), 7.74 (d, J=1.8 Hz, 1H), 7.67 (dd, J=1.8, 0.8 Hz, 1H), 7.49 (dd, J=8.5, 1.8 Hz, 1H), 7.09 (d, J=1.9 Hz, 1H), 4.21 (t, J=6.1 Hz, 2H), 3.03 (t, J=6.1 Hz, 2H), 2.72 (q, J=7.1 Hz, 4H), 1.14 (t, J=7.1 Hz, 6H).

Following the method of Example 28, the coupling reaction of compound 28a and compound 55b gave N-cyclopentyl-3-(5-((5-(2-(diethylamino)ethoxy)-7-methyl-9-oxo-9H-xanthen-3-yl)oxy)pyridin-2-yl)propanamide (55) in 66% yield: mp ($CH_2Cl_2$/hexanes) 160-161° C.; $^1$H NMR (CDCl$_3$) δ 8.40 (d, J=2.7 Hz, 1H), 8.31 (d, J=8.8 Hz, 1H), 7.68 (dd, J=1.8, 0.8 Hz, 1H), 7.39 (dd, J=8.4, 2.8 Hz, 1H), 7.29 (d, J=8.5 Hz, 1H), 7.07 (d, J=1.8 Hz, 1H), 7.01 (dd, J=8.8, 2.3 Hz, 1H), 6.95 (d, J=2.3 Hz, 1H), 5.94 (d, J=6.4 Hz, 1H), 4.24-4.15 (m, 3H), 3.17 (t, J=7.1 Hz, 2H), 2.98 (t, J=6.3 Hz, 2H), 2.67 (q, J=7.3 Hz, 6H), 2.44 (s, 3H), 1.98-1.90 (m, 2H), 1.65-1.58 (m, 4H), 1.37-1.28 (m, 2H), 1.09 (t, J=7.1 Hz, 6H). Anal. Calcd. for $C_{33}H_{39}N_3O_5$: C, 71.1; H, 7.0; N, 7.5. Found: C, 70.6; H, 7.1; N, 7.5%.

Example 56

N-Cyclopentyl-3-[5-({7-methyl-5-[2-(4-morpholinyl)ethoxy]-9-oxo-9H-xanthen-3-yl}oxy)-2-pyridinyl]propanamide

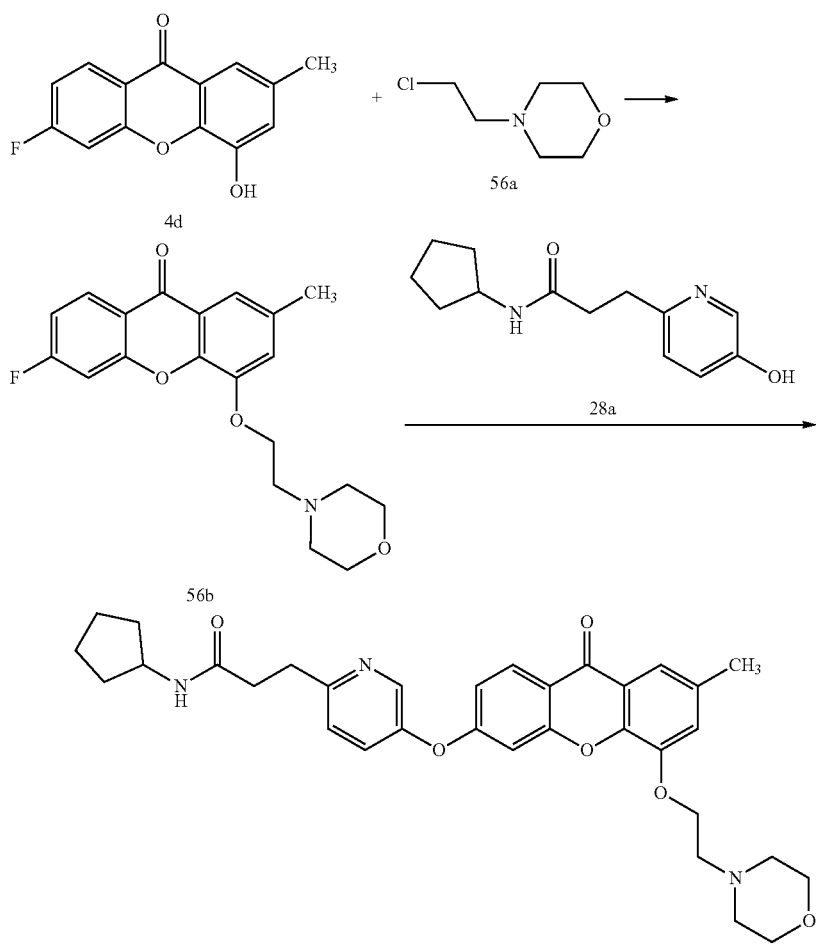

The reaction of 4d with 4-(2-chloroethyl)morpholine (56a) under phase transfer alkylation conditions, as in Example 1, using tetrabutylammoniun bromide as catalyst, gave 6-fluoro-2-methyl-4-[2-(4-morpholinyl)ethoxy]-9H-xanthen-9-one (56b): $^1$H NMR (DMSO-d$_6$) δ 8.25 (dd, J=8.9, 6.6 Hz, 1H), 7.59 (dd, J=9.8, 2.4 Hz, 1H), 7.52 (br, 1H), 7.43 (d, J=1.8 Hz, 1H), 7.35 (td, J=8.6, 2.4 Hz, 1H), 4.31 (t, J=5.9 Hz, 2H), 3.59 (t, J=4.6 Hz, 4H), 2.82 (t, J=5.9 Hz, 2H), 2.57-2.54 (m, 4H), 2.42 (s, 3H).

The coupling reaction of 28a with 56b as in Example 11 gave N-cyclopentyl-3-[5-({7-methyl-5-[2-(4-morpholinyl)ethoxy]-9-oxo-9H-xanthen-3-yl}oxy)-2-pyridinyl]propanamide (56): mp 182-185° C.; $^1$H NMR (DMSO-d$_6$) δ 8.44 (d, J=2.8 Hz, 1H), 8.19 (d, J=8.9 Hz, 1H), 7.78 (d, J=7.2 Hz, 1H), 7.64 (dd, J=2.9, 8.5 Hz, 1H), 7.52 (dd, J=0.9, 1.9 Hz, 1H), 7.40 (d, J=1.8 Hz, 1H), 7.38 (d, J=8.5 Hz, 1H), 7.13 (dd, J=2.4, 8.8 Hz, 1H), 6.95 (d, J=2.4 Hz, 1H), 4.27 (t, J=5.9 Hz, 2H), 3.94-4.04 (m, 1H), 3.54 (t, J=4.6 Hz, 4H), 3.00 (t, J=7.7 Hz, 2H), 2.78 (t, J=5.9 Hz, 2H), 2.41 (s, 3H), 1.72-1.80 (m, 2H), 1.55-1.65 (m, 2H), 1.42-1.53 (m, 2H), 1.28-1.36 (m, 2H); MS (APCI) m/z: 572.3 (M+H⁺). Anal. Calcd. for $C_{33}H_{37}N_3O_6H_2O$: C, 67.2; H, 6.7; N, 7.1. Found: C, 67.4; H, 6.4; N, 7.2%.

Example 57

N-Cyclopentyl-3-[5-({5-[2-(diisopropylamino)ethoxy]-7-methyl-9-oxo-9H-xanthen-3-yl}oxy)-2-pyridinyl]propanamide ethoxy]-6-fluoro-2-methyl-9H-xanthen-9-one (57b) in 30% yield: ¹H NMR (DMSO-d₆) δ 8.25 (dd, J=8.9, 6.6 Hz, 1H), 7.52-7.49 (m, 2H), 7.38 (d, J=1.9 Hz, 1H), 7.35 (td, J=8.7, 2.4 Hz), 4.08 (t, J=6.7 Hz, 2H), 3.06 (pentet, J=6.5 Hz, 2H), 2.90 (t, J=6.7 Hz, 2H), 2.42 (s, 3H), 1.02 (d, J=6.5 Hz, 12H); MS (APCI) m/z: 372.2 (M+H⁺).

The coupling reaction of 28a and 57b as in Example 11 gave N-cyclopentyl-3-[5-({5-[2-(diisopropylamino)ethoxy]-7-methyl-9-oxo-9H-xanthen-3-yl}oxy)-2-pyridinyl]propanamide (57) in 60% yield: mp 154-156° C.; ¹H NMR (DMSO-d₆) δ 8.45 (d, J=2.8 Hz, 1H), 8.19 (d, J=8.9 Hz, 1H), 7.79 (d, J=7.2 Hz, 1H), 7.65 (dd, J=8.5, 2.9 Hz, 1H), 7.48 (m, 1H), 7.40 (d, J=8.5 Hz, 1H), 7.33 (d, J=1.8 Hz, 1H), 7.14 (dd, J=8.9, 2.4 Hz, 1H), 6.85 (d, J=2.4 Hz, 1H), 4.02 (t, J=6.60 Hz, 1H), 3.98 (septet, J=6.9 Hz, 1H), 3.08-2.97 (m, 4H), 2.85 (t, J=6.5 Hz, 1H), 2.41 (s, 3H), 1.80-1.72 (m, 2H), 1.62-1.55 (m, 2H), 1.53-1.44 (m, 2H),

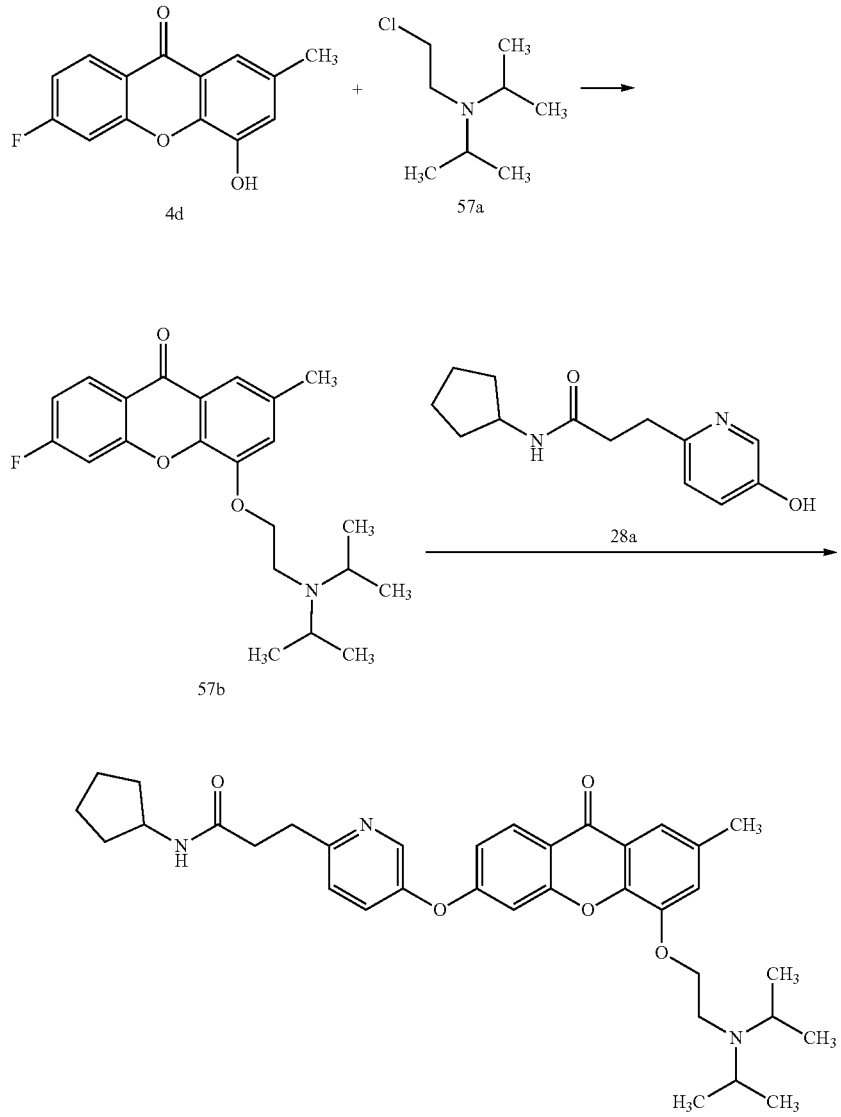

1.37-1.28 (m, 2H), 0.98 (d, J=6.5 Hz, 12H); MS (APCI) m/z: 586.3 (M+H⁺). Anal. Calcd. for $C_{35}H_{43}N_3O_5$: C, 71.8; H, 7.4; N, 7.2. Found: C, 71.9; H, 7.2; N, 7.0%.

The reaction of compound 4d with 2-(diisopropylamino)ethylchloride (57a) under phase transfer alkylation conditions as in Example 1, gave 4-[2-(diisopropylamino)

Example 58

N-Cyclopentyl-3-(5-((7-methyl-5-(2-(4-methylpiperazin-1-yl)ethoxy)-9-oxo-9H-xanthen-3-yl)oxy)pyridin-2-yl)propanamide

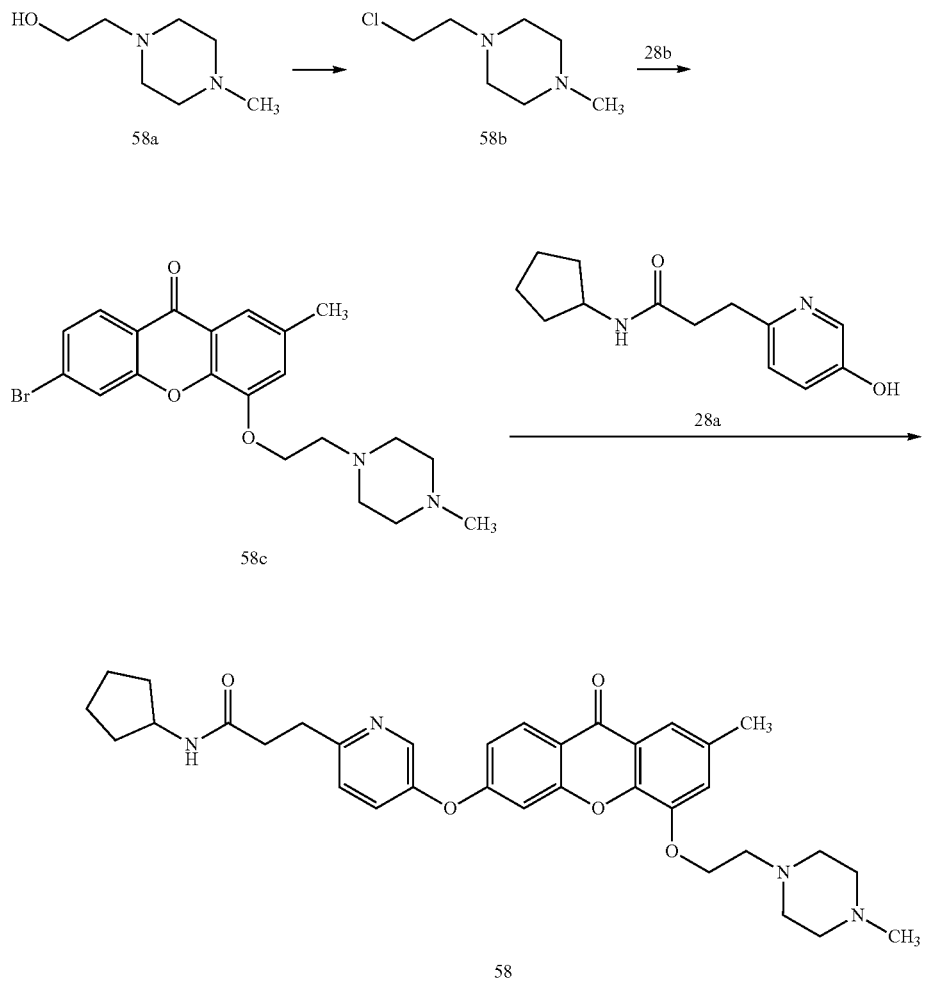

1-(2-Chloroethyl)-4-methylpiperazine (58b) was prepared by refluxing 2-(4-methylpiperazin-1-yl)ethanol (58a) (1.1 g, 7.33 mmol) with thionyl chloride (10 mL). The reaction mixture was cooled to 20° C., and poured into ice/water. The aqueous solution was then treated with 6-bromo-4-hydroxy-2-methyl-9H-xanthen-9-one (28b) (260 mg, 0.85 mmol), tetrabutylammonium bromide (100 mg), KOH (1.12 g, 20 mmol), and $CH_2Cl_2$ (50 mL), and the mixture was stirred for 3 days. The $CH_2Cl_2$ layer was separated, and the aqueous layer was further extracted with $CH_2Cl_2$. The combined $CH_2Cl_2$ extracts were dried ($Na_2SO_4$) and the solvent was removed. Chromatography on neutral alumina eluting with 0-20% hexanes/EtOAc followed by 0-1% $CH_2Cl_2$/MeOH gave crude material which was re-columned in $SiO_2$ eluting with 20% hexanes/EtOAc to remove impurities, then with 0-4% $CH_2Cl_2$/MeOH to elute 6-bromo-2-methyl-4-(2-(4-methylpiperazin-1-yl)ethoxy)-9H-xanthen-9-one (58c): MS (APCI) m/z: 431 and 433 (M+H$^+$). This was used directly without further purification.

Following the method of Example 28, copper catalysed coupling reaction of compound 58c with compound 28a gave N-cyclopentyl-3-(5-((7-methyl-5-(2-(4-methylpiperazin-1-yl)ethoxy)-9-oxo-9H-xanthen-3-yl)oxy)pyridin-2-yl)propanamide (58) in 46% yield: mp (MeOH/EtOAc) 168° C. (dec): $^1$H NMR (CDCl$_3$) δ 8.40 (d, J=2.7 Hz, 1H), 8.31 (d, J=8.8 Hz, 1H), 7.70 (d, J=1.0 Hz, 1H), 7.39 (dd, J=8.4, 2.8 Hz, 1H), 7.30 (d, J=8.4 Hz, 1H), 7.08 (d, J=1.8 Hz, 1H), 7.02 (dd, J=8.8, 2.3 Hz, 1H), 6.95 (d, J=2.3 Hz, 1H), 6.02 (d, J=6.7 Hz, 1H), 4.26 (t, J=6.0 Hz, 2H), 4.23-4.15 (m, 1H), 3.18 (t, J=7.2 Hz, 1H), 2.92 (t, J=6.0 Hz, 1H), 2.66 (t, J=7.2 Hz, 1H), 2.65 centred (brm, 4H), 2.47 centred (brm, 4H) 2.44 (s, 3H), 2.29 (s, 3H), 1.98-1.90 (m, 2H), 1.65-1.55 (brm, 4H), 1.37-1.29 (m, 2H), HPLC 96.7%. Anal Calcd. for $C_{34}H_{40}N_4O_5 \cdot 2H_2O \cdot 2.7$ HCl: C, 56.7; H, 6.6; N, 7.7; Cl, 13.1. Found: C, 56.0, H, 6.7; N, 7.4; Cl, 12.8%.

Example 59

N-Cyclopentyl-3-(5-((7-methyl-9-oxo-5-(2-(4-(2,2,2-trifluoroethyl)piperazin-1-yl)ethoxy)-9H-xanthen-3-yl)oxy)pyridin-2-yl)propanamide

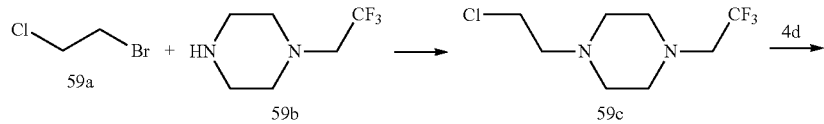

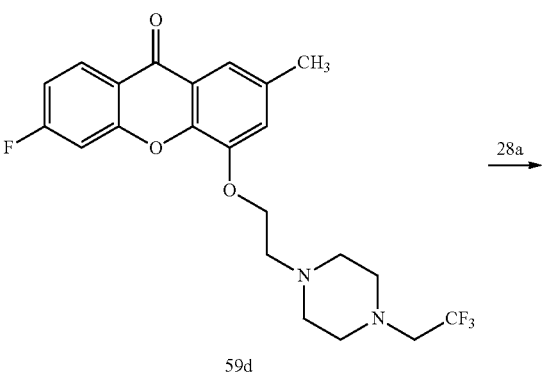

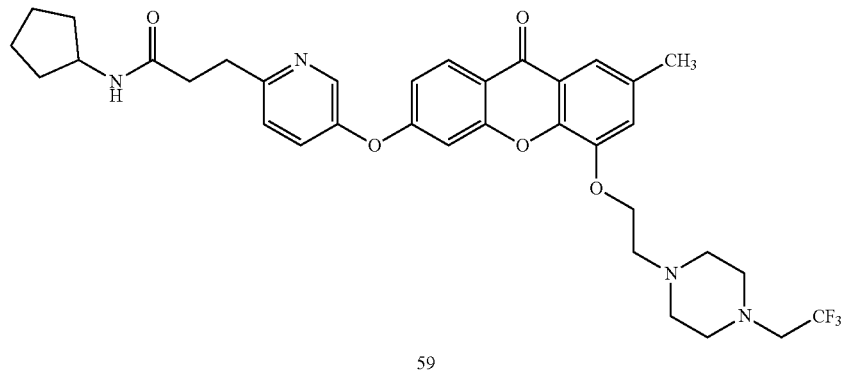

A mixture of 1-bromo-2-chloroethane (59a) (0.64 g, 4.46 mmol), 1-(2,2,2-trifluoroethyl)-piperazine (59b) (0.5 g, 2.97 mmol), K$_2$CO$_3$ (0.82 g, 593 mmol) in acetone (5 mL) was stirred at room temperature for 24 h. The solids were removed by filtration, and the solvent was evaporated to give crude 1-(2-chloroethyl)-4-(2,2,2-trifluoroethyl)piperazine (59c): $^1$H NMR (CDCl$_3$) δ 3.58 (t, J=7.0 Hz, 2H), 2.97 (q, J=9.6 Hz, 2H), 2.73 (t, J=7.0 Hz, 2H), 2.72-2.68 (m, 4H), 2.58-2.54 (m, 4H).

The reaction of 4d with crude 59c as in Example 1 gave 6-fluoro-2-methyl-4-(2-(4-(2,2,2-trifluoroethyl)piperazin-1-yl)ethoxy)-9H-xanthen-9-one (59d): $^1$H NMR (DMSO-d$_6$) δ 8.25 (dd, J=8.9, 6.6 Hz, 1H), 7.59 (dd, J=9.8, 2.4 Hz, 1H), 7.53 (br, 1H), 7.43 (d, J=1.8 Hz, 1H), 7.35 (dt, J=8.7, 2.4 Hz, 1H), 4.29 (t, J=5.9 Hz, 1H), 3.14 (q, J=10.3 Hz, 2H), 2.82 (t, J=5.9 Hz, 2H), 2.65-2.55 (m, 8H), 2.42 (s, 3H).

The coupling reaction of 28a with 59d as in Example 11 gave N-cyclopentyl-3-(5-((7-methyl-9-oxo-5-(2-(4-(2,2,2-trifluoroethyl)piperazin-1-yl)ethoxy)-9H-xanthen-3-yl)oxy)pyridin-2-yl)propanamide (59) in 79% yield: mp 189-191° C.; $^1$H NMR (CDCl$_3$) δ 8.40 (d, J=2.7 Hz, 1H), 8.31 (d, J=8.8 Hz, 1H), 7.71-7.69 (m, 1H), 7.39 (dd, J=8.4, 2.8 Hz, 1H), 7.29 (d, J=8.44 Hz, 1H), 7.08 (d, J=1.8 Hz, 1H), 7.01 (dd, J=8.8, 2.3 Hz, 1H), 5.95 (d, J=7.2 Hz, 1H), 4.26 (t, J=6.0 Hz, 2H), 4.19 (dd, J=13.73, 6.6 Hz, 1H), 3.17 (t, J=7.1 Hz, 2H), 2.98 (q, J=9.6 Hz, 2H), 2.92 (t, J=6.1 Hz, 2H), 2.74-2.64 (m, 10H), 2.44 (s, 3H), 1.98-1.89 (m, 2H), 1.65-1.57 (m, 2H), 1.37-1.28 (m, 2H); MS (APCI) m/z: 653.3 (M+H$^+$).

Example 60

N-Cyclopentyl-3-(5-((7-methyl-5-((1-methylpiperidin-3-yl)oxy)-9-oxo-9H-xanthen-3-yl)oxy)pyridin-2-yl)propanamide eluting with CH₂Cl₂/MeOH (3%)/aq. NH₃ followed by preparative plate chromatography (SiO₂/CH₂Cl₂/MeOH (3%)/aq NH₃) gave partially clean 6-bromo-2-methyl-4-((1-methylpiperidin-3-yl)oxy)-9H-xanthen-9-one (60c) which was used directly without further purification.

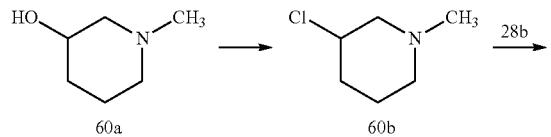

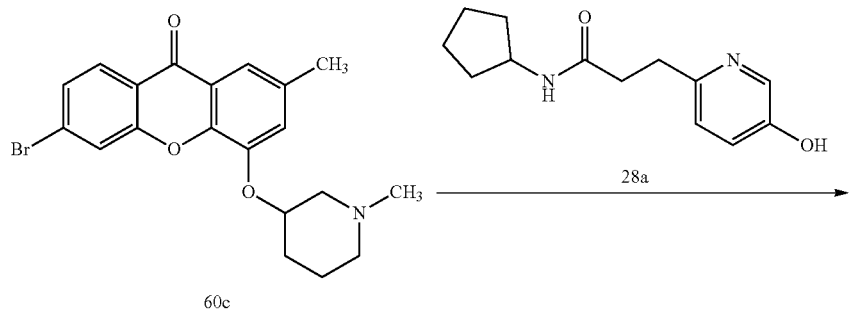

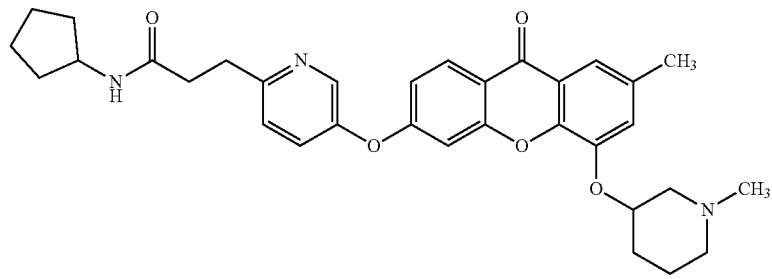

To a solution of 3-hydroxy-1-methylpiperidine (60a) (2.65 g, 23 mmol) and a trace of DMF in CH₂Cl₂ (20 mL) at 0° C. was added SOCl₂ (25 mL) dropwise. The reaction mixture was allowed to warm to 20° C. and was refluxed for 3 h. Excess SOCl₂ was removed under vacuum and the resulting residue was dried under high vacuum. The residue was dissolved in H₂O, cooled in ice, and basified with aq. KOH. 6-Bromo-4-hydroxy-2-methyl-9H-xanthen-9-one (28b) (500 mg, 1.6 mmol), KOH (1.2 g) in H₂O (300 mL), KI (100 mg), tetrabutylammonium bromide (150 mg) and CH₂Cl₂ (200 mL) were added, and the resulting mixture was stirred overnight. The organic layer was separated, washed with water, and dried (Na₂SO₄). Chromatography on SiO₂, The coupling reaction of compound 60c with compound 28a as in Example 28 gave N-cyclopentyl-3-(5-((7-methyl-5-((1-methylpiperidin-3-yl)oxy)-9-oxo-9H-xanthen-3-yl)oxy)-pyridin-2-yl)propanamide (60): mp (CH₂Cl₂/hexanes) 212-215° C.: $^1$H NMR (CDCl₃) δ 8.39 (d, J=2.7 Hz, 1H), 8.31 (d, J=9.5 Hz, 1H), 7.68 (dd, J=1.8, 0.8 Hz, 1H), 7.38 (dd, J=8.4, 2.8 Hz, 1H), 7.28 (d, J=8.5 Hz, 1H), 7.07 (d, J=1.9 Hz, 1H), 7.00-6.97 (m, 2H), 5.96 (brd, J=7.6 Hz, 1H), 4.23-4.15 (m, 1H), 4.09-4.05 (m, 2H), 3.16, t, J=7.2 Hz, 2H), 3.16-3.11 (m, 1H), 2.84-2.78 (m, 1H), 2.66 (t, J=7.1 Hz, 2H), 2.55 (s, 3H), 2.44 (s, 3H), 2.38-2.31 (m, 1H), 2.14-2.05 (m, 1H), 1.96-1.72 (m, 5H), 1.65-1.56 (m, 3H), 1.38-1.28 (m, 3H); HPLC 92%; MS (APCI) m/z: 556.4 (M+H⁺).

Example 61
N-Cyclopentyl-3-(5-((5-(2-((3S,5R)-3,5-dimethylpiperazin-1-yl)ethoxy)-7-methyl-9-oxo-9H-xanthen-3-yl)oxy)pyridin-2-yl)propanamide
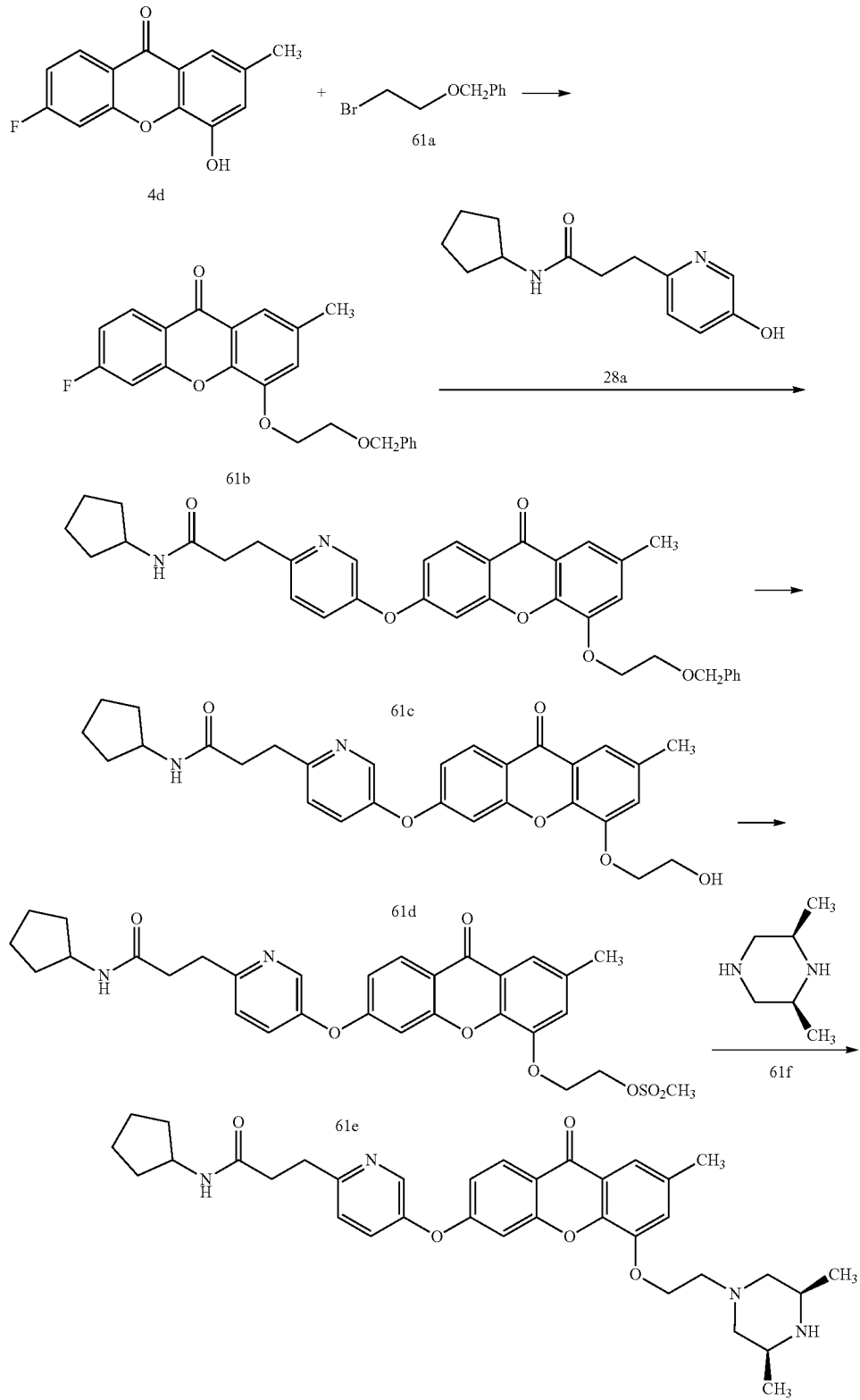

A mixture of compound 4d (496 mg, 2.03 mmol), benzyl 2-bromoethyl ether (61a) (436 mg, 4.06 mmol) and Cs$_2$CO$_3$ (1.32 g, 4.06 mmol) in DMSO (3 mL) was heated 1 h at 80° C. The reaction mixture was cooled to 20° C., diluted with water and stirred for 30 min. The resulting precipitate was collected, washed with water, and oven dried.

Chromatography on SiO$_2$, eluting with hexanes/EtOAc 5-10% gave 4-(2-(benzyloxy)ethoxy)-6-fluoro-2-methyl-9H-xanthen-9-one (61b) (629 mg, 82%): $^1$H NMR (CDCl$_3$) δ 8.35 (dd, J=8.9, 6.4 Hz, 1H), 7.70 (dd, J=1.9, 0.9 Hz, 1H), 7.44-7.28 (m 5H), 7.24 dd, J=9.5, 2.4 Hz, 1H), 7.12-7.08 (m, 2H), 4.71 (s, 2H), 4.35-4.33 (m 2H), 3.98-3.95 (m, 2H), 2.44 (s, 3H).

The coupling reaction of 61b with compound 28a as in Example 11 gave 3-(5-((5-(2-(benzyloxy)ethoxy)-7-methyl-9-oxo-9H-xanthen-3-yl)oxy)pyridin-2-yl)-N-cyclopentyl-propanamide (61c) in 94% yield: mp (CH$_2$Cl$_2$/hexanes) 183-185° C.; $^1$H NMR (CDCl$_3$) δ 8.40 (d, J=2.6 Hz, 1H), 8.32 ((dd, J=8.8, 1.9 Hz, 1H), 7.70 (dd, J=1.9, 0.8 Hz, 1H), 7.40-7.52 (m, 8H), 7.09 (d, 1.9 Hz, 1H), 7.03 (dd, J=8.8, 2.3 Hz, 1H), 6.98 (d, J=2.3 Hz, 1H), 5.95 (d, J=6.9 Hz, 1H), 4.66 (s, 2H), 4.33-4.31 (m, 2H), 4.23-4.14 (m, 2H), 3.93-3.90 (m, 2H), 3.16 (t, J=7.2 Hz, 2H), 2.64 (t, J=7.2 Hz, 1H), 2.43 (s, 3H), 1.97-1.89 (m, 2H), 1.66-1.56 (m, 4H), 1.36-1.27 (m, 2H). This was used directly.

Hydrogenation of 61c with 10% Pd/C in THF/MeOH gave N-cyclopentyl-3-(5-((5-(2-hydroxyethoxy)-7-methyl-9-oxo-9H-xanthen-3-yl)oxy)pyridin-2-yl)propanamide (61d) in 16.5% yield: $^1$H NMR (CDCl$_3$) δ 8.45 (d, J=2.8 Hz, 1H), 8.20 (d, J=8.8 Hz, 1H), 7.80 (d, J=7.2 Hz, 1H), 7.65 (dd, J=8.5, 2.9 Hz, 1H), 7.51 (brd, J=0.9 Hz, 1H), 7.39 (d, J=8.5 Hz, 1H), 7.37 (d, J=1.8 Hz, 1H), 7.14 (dd, J=8.8, 2.4 Hz, 1H), 6.98 (d, J=2.3 Hz, 1H), 4.92 (t, J=5.5 Hz, 1H), 4.18 (t, J=5.0 Hz, 2H), 4.02-3.94 (m, 1H), 3.81-3.77 (m, 2H) 3.01 (t, J=7.7 Hz, 2H), 2.52-2.48 (m, 2H), 2.41 (s, 3H), 1.80-1.72 (m, 2H), 1.65-1.55 (m, 2H), 1.52-1.45 (m, 2H), 1.29-1.28 (m, 2H); MS (APCI) m/z: 503 (M+H$^+$).

Compound 61d was reacted with methanesulfonyl chloride and triethylamine in dry CH$_2$Cl$_2$ at 0° C. to give 2-((6-((6-(3-(cyclopentyl amino)-3-oxopropyl)pyridin-3-yl) oxy)-2-methyl-9-oxo-9H-xanthen-4-yl)oxy)ethyl methanesulfonate (61e): $^1$H NMR (CDCl$_3$) δ 8.40 (d, J=2.6 Hz, 1H), 8.31 (d, J=8.8 Hz, 1H), 7.76 (dd, J=1.8, 0.8 Hz, 1H), 7.40 (dd, J=8.4, 2.8 Hz, 1H), 7.31 (d, J=8.4 Hz, 1H), 7.08 (d, J=1.8 Hz, 1H), 7.03 (dd, J=8.9, 2.3 Hz, 1H), 6.87 (d, J=2.3 Hz, 1H), 5.97 (d, J=6.9 Hz, 1H), 4.69-4.67 (m, 2H), 4.41-4.38 (m, 2H), 4.24-4.15 (m, 1H), 3.18 (t, J=7.2 Hz, 2H), 3.13 (s, 3H), 2.65 (t, J=7.2 Hz, 2H), 2.46 (s, 3H), 1.98-1.90 (m, 2H), 1.63-1.58 (m, 4H), 1.38-1.29 (m, 2H). This was used directly without further purification.

Reaction of crude 61e with (2S,6R)-2,6-dimethylpiperazine (61f) in DMSO gave N-cyclopentyl-3-(5-((5-(2-((3S,5R)-3,5-dimethylpiperazin-1-yl)ethoxy)-7-methyl-9-oxo-9H-xanthen-3-yl)oxy)pyridin-2-yl)propanamide (61) in 58% yield: mp (CH$_2$Cl$_2$/hexanes) 196-199° C.; $^1$H NMR (CDCl$_3$) δ 8.40 (d, J=2.7 Hz, 1H), 8.32 (d, J=8.8 Hz, 1H), 7.70 (dd, J=1.88, 0.84 Hz, 1H), 7.39 (dd, J=8.4, 2.8 Hz, 1H), 7.29 (d, J=8.5 Hz, 1H), 7.08 (d, J=1.9 Hz, 1H), 7.03 (dd, J=8.8, 2.3 Hz, 1H), 6.94 (d, J=2.1 Hz, 1H), 5.97 (d, J=6.6 Hz, 1H), 4.26 (t, J=6.0 Hz, 2H), 4.24-4.15 (m, 1H), 3.17 (t, J=7.1 Hz, 2H), 2.95-2.88 (m, 6H), 2.66 (t, J=7.1 Hz, 2H), 2.44 (s, 3H), 1.98-1.90 (m, 2H), 1.83 (t, J=11.0 Hz, 2H), 1.68-1.55 (m, 4H), 1.37-1.28 (m, 2H), 1.03 (d, J=6.2 Hz, 6H); HPLC 97.6%. HRMS Calcd. for C$_{35}$H$_{42}$N$_4$O$_5$: m/z 599.32413 (M+H$^+$); found m/z 599.32518.

Example 62

N-Cyclopentyl-3-(5-((7-methyl-9-oxo-5-(2-((3S,5R)-3,4,5-trimethylpiperazin-1-yl)ethoxy)-9H-xanthen-3-yl)oxy)pyridin-2-yl)propanamide

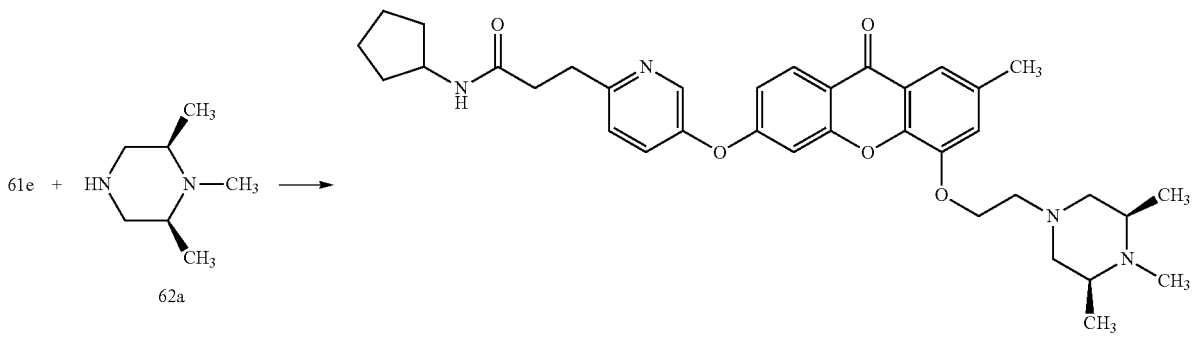

Similarly to Example 61, reaction of crude 61e with (2S,6R)-1,2,6-trimethylpiperazine (62a) (WO 2012/082689) in DMSO gave N-cyclopentyl-3-(5-((7-methyl-9-oxo-5-(2-((3S,5R)-3,4,5-trimethylpiperazin-1-yl)ethoxy)-9H-xanthen-3-yl)oxy)pyridin-2-yl)propanamide (62) in 90% yield: mp (CH$_2$Cl$_2$/hexanes) 180-182° C.; $^1$H NMR (CDCl$_3$) δ 8.39 (d, J=2.5 Hz, 1H), 8.32 (d, J=8.8 Hz, 1H), 7.70 (dd, J=1.9, 0.8 Hz, 1H), 7.39 (dd, J=8.44, 2.8 Hz, 1H), 7.29 (d, J=8.5 Hz, 1H), 7.08 (d, J=1.9 Hz, 1H), 7.02 (dd, J=8.8, 2.3 Hz, 1H), 6.95 (d, J=2.3 Hz, 1H), 5.98 (d, J=7.3 Hz, 1H), 4.25 (t, J=5.9 Hz, 2H), 4.23-4.10 (m, 1H), 3.17 (t, J=7.1 Hz, 2H), 2.90-2.84 (m, 4H), 2.66 (t, J=7.2 Hz, 2H), 2.44 (s, 3H), 2.31-2.33 (m, 2H), 2.26 (s, 3H), 2.11 (t, J=10.9 Hz, 2H), 1.98-1.90 (m, 2H), 1.65-1.54 (m, 4H), 1.36-1.25 (m, 2H), 1.06 (d, J=6.2 Hz, 6H). HPLC 98%, HRMS Calcd. for C$_{36}$H$_{44}$N$_4$O$_5$: m/z 613.33978 (M+H$^+$); found m/z 613.34109.

Example 63

N-Cyclopentyl-3-(5-((5-(3-(dimethylamino)propoxy)-7-methyl-9-oxo-9H-xanthen-3-yl)oxy)pyridin-2-yl)propanamide

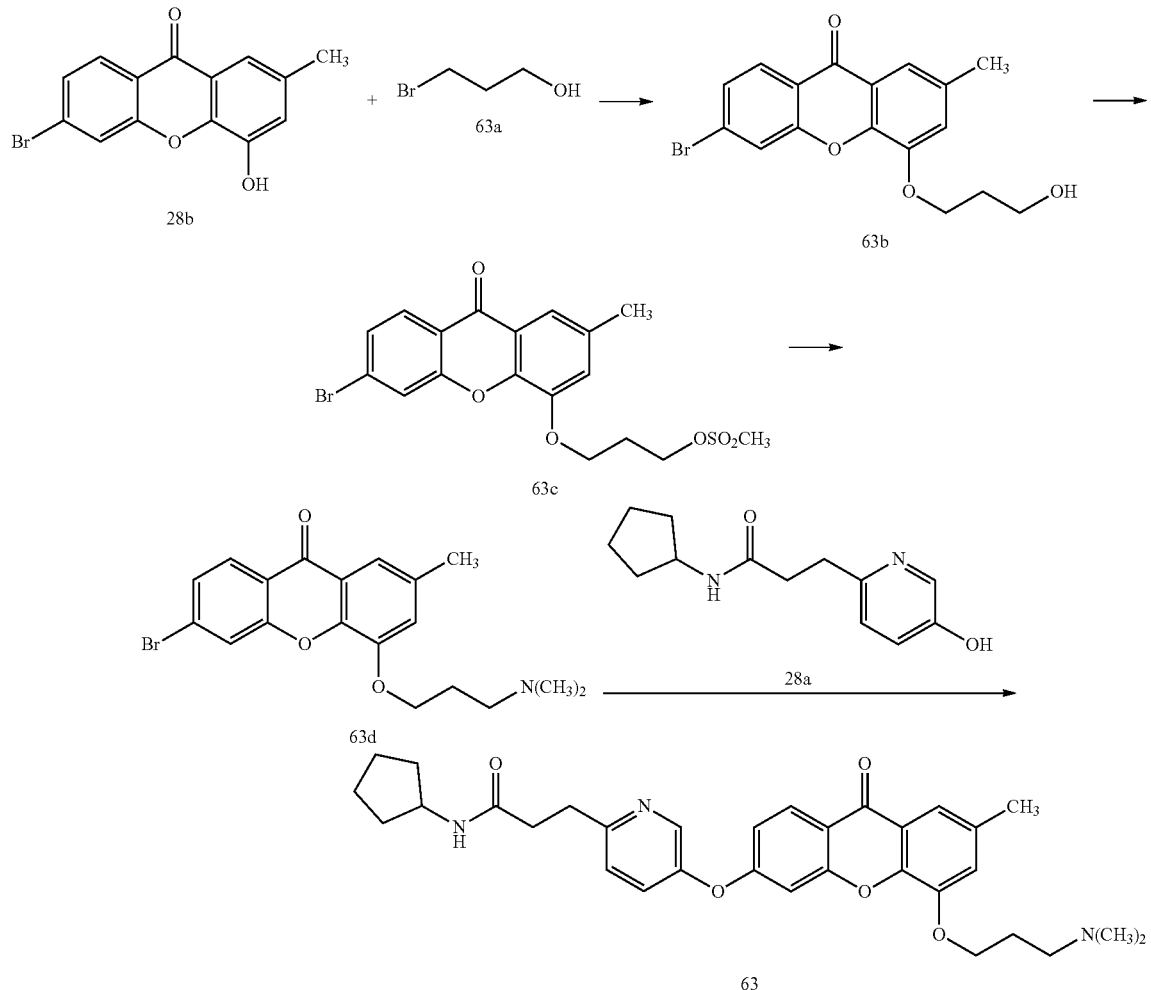

A mixture of 6-bromo-4-hydroxy-2-methyl-9H-xanthen-9-one (28b) (510 mg, 1.67 mmol) 3-bromopropanol (63a) (1.16 g, 8.35 mmol), KOH (935 mg, 16.7 mmol), tetrabutylammonium bromide (100 mg, 0.31 mmol) in 1:1 $CH_2Cl_2$/$H_2O$ 100 mL) was stirred at 20° C. for 20 h. The $CH_2Cl_2$ layer was separated, and the aqueous layer was further extracted with $CH_2Cl_2$. The combined organic fractions were washed with brine, and dried ($Na_2SO_4$). Chromatography on $SiO_2$, eluting with 0-50% $CH_2Cl_2$/hexanes, followed by $CH_2Cl_2$/EtOAc 0-5%, gave a product which was recrystallized from $CH_2Cl_2$/MeOH to give 6-bromo-4-(3-hydroxypropoxy)-2-methyl-9H-xanthen-9-one (63b) (485 mg 79%): mp 170-171° C.; $^1$H NMR (CDCl$_3$) δ 8.18 (d, J=8.5 Hz, 1H), 7.76 (d, J=1.7 Hz, 1H), 7.67 (dd, J=1.9, 0.9 Hz, 1H), 7.49 (dd, J=8.5, 1.8 Hz, 1H), 7.09 (d, J=1.8 Hz, 1H), 4.32 (t, J=5.9 Hz, 2H), 4.01-3.97, 2H), 2.44 (s, 3H), 2.30 (t, J=5.5 Hz, 1H), 2.22-2.17 (m, 2H); MS (APCI) m/z: 363 and 365 (M+H$^+$).

To a solution of 63b (456 mg, 1.25 mmol) and triethylamine (0.31 ml, 1.5 mmol) in dry $CH_2Cl_2$ (20 mL) at 0° C. was added methanesulphonyl chloride (0.17 mL) dropwise. The reaction mixture was stirred at 0° C. for 3 h, then the $CH_2Cl_2$ was washed with water, and dried ($Na_2SO_4$), to give crude 3-((6-bromo-2-methyl-9-oxo-9H-xanthen-4-yl)oxy)propyl methanesulfonate (63c), which was used directly.

Reaction of compound 63c and dimethylamine in DMSO gave 6-bromo-4-(3-(dimethyl-amino)propoxy)-2-methyl-9H-xanthen-9-one (63d) in 48% yield: $^1$H NMR (CDCl$_3$) δ 8.19 (d, J=8.5 Hz, 1H), 7.79 (d, J=1.7 Hz, 1H), 7.66 (dd, J=1.9, 0.9 Hz, 1H), 7.49 (dd, J=8.5, 1.8 Hz, 1H), 7.11 (d, J=1.8 Hz, 1H), 4.20 (t, J=6.5 Hz, 2H), 2.55 (t, J=7.1 Hz, 2H), 2.44 (s, 3H), 2.30 (s, 6H), 2.13-2.07 (m, 2H).

The coupling reaction of 63d with compound 28a as in Example 28 gave N-cyclopentyl-3-(5-((5-(3-(dimethyl-amino)propoxy)-7-methyl-9-oxo-9H-xanthen-3-yl)oxy)pyridin-2-yl)propanamide (63) in 70% yield: mp (CH$_2$Cl$_2$/hexanes) 180-182° C.; $^1$H NMR (CDCl$_3$) δ 8.40 (d, J=2.7 Hz, 1H), 8.31 (d, J=8.8 Hz, 1H), 7.68 (dd, J=1.8, 0.8 Hz, 1H), 7.40 (dd, J=8.4, 2.8 Hz, 1H), 7.30 (d, J=8.4 Hz, 1H), 7.09 (d, J=1.8 Hz, 1H), 7.02 (dd, J=8.8, 2.3 Hz, 1H), 6.99 (d, J=2.3 Hz, 1H), 6.00 (d, J=6.9 Hz, 1H), 4.23-4.15 (m, 3H), 3.17 (t, J=7.1 Hz, 2H), 2.66 (t, J=7.5 Hz, 2H) 2.50 (t, J=7.1 Hz, 2H), 2.44 (s, 3H), 2.26 (s, 6H), 2.10-2.03 (m, 2H), 1.98-1.90 (m, 2H), 1.64-1.55 (m, 4H), 1.36-1.29 (m, 2H); HPLC 97%; MS (APCI) m/z: 544.3 (M+H$^+$).

Example 64

N-Cyclopentyl-3-(5-((5-(3-((2R,6S)-2,6-dimethylpiperidin-1-yl)propoxy)-7-methyl-9-oxo-9H-xanthen-3-yl)oxy)pyridin-2-yl)propanamide

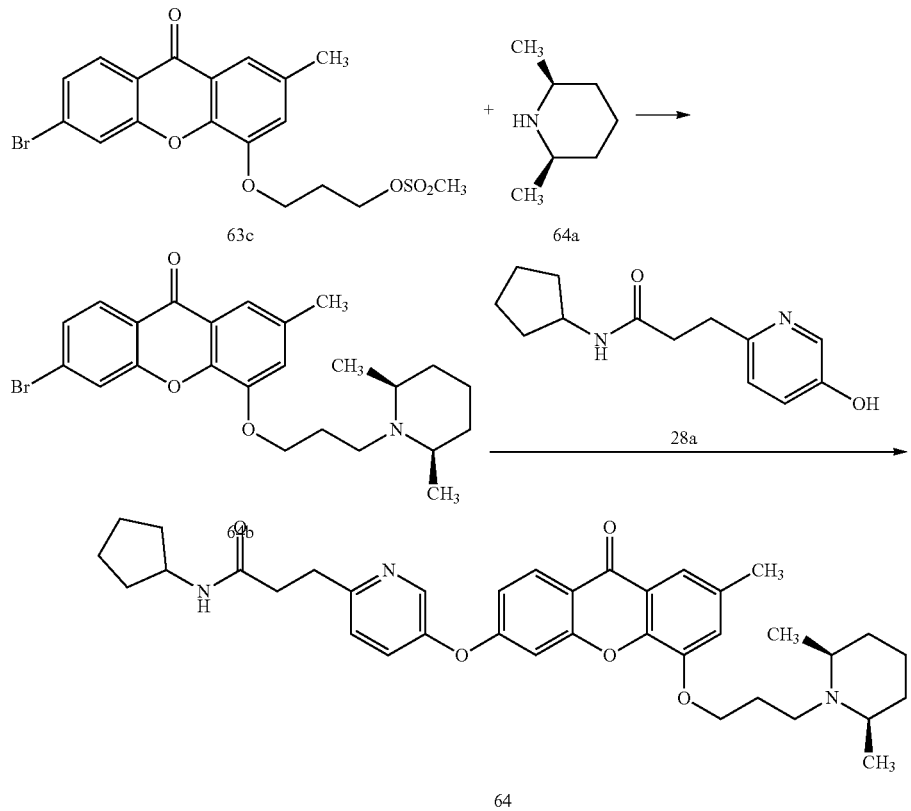

A mixture of crude 63c (224 mg, 51 mmol), (2R,6S)-2,6-dimethylpiperidine (64a) (0.14 mL, 1.2 mmol), K$_2$CO$_3$ (1.0 g, 7.2 mmol excess) and KI (1.0 g, 6 mmol) in DMSO (10 mL) was stirred at 20° C. for 20 h. The reaction mixture was diluted with water and the resulting precipitate was collected, washed with water, and dried. Chromatography on SiO$_2$ eluting with CH$_2$Cl$_2$/EtOAc 0-50% gave 6-bromo-4-(3-((2R,6S)-2,6-dimethylpiperidin-1-yl)propoxy)-2-methyl-9H-xanthen-9-one (64b): $^1$H NMR (CDCl$_3$) δ 8.19 (d, J=8.5 Hz, 1H), 7.70 (d, J=1.7 Hz, 1H), 7.66 (dd, J=1.8, 0.8 Hz, 1H), 7.49 (dd, J=8.5, 1.8 Hz, 1H), 7.05 (d, J=1.8 Hz, 1H), 4.10 (t, J=6.0 Hz, 1H), 3.10-3.06 (m, 2H), 2.56-2.45 (m, 2H), 2.44 (s, 3H), 2.07-2.00 (m, 2H), 1.72-1.60 (m, 3H), 1.40-1.28 (m, 3H), 1.23 (d, J=6.3 Hz, 3H).

The coupling reaction of 64b compound 28a as in Example 28 gave N-cyclopentyl-3-(5-((5-(3-((2R,6S)-2,6-dimethylpiperidin-1-yl)propoxy)-7-methyl-9H-xanthen-3-yl)oxy)pyridin-2-yl)propanamide (64) in 19% yield: mp (CH$_2$Cl$_2$/hexanes) 123-126° C.; $^1$H NMR (CDCl$_3$) δ 8.40 (d, J=2.7 Hz, 1H), 8.31 (d, J=8.9 Hz, 1H), 7.67 (bd, J=0.6 Hz, 1H), 7.40 (dd, J=8.4, 2.8 Hz, 1H), 7.30 (d, J=8.4 Hz, 1H), 7.04-7.01 (m, 2H), 6.84 (d, J=1.8 Hz, 1H), 6.07-5.97 (m, 1H)-4.23-4.12 (m, 1H) 4.08 (t, J=5.9 Hz, 2H), 3.17 (t, J=7.2 Hz, 2H), 3.06 (t, J=7.1 Hz, 2H), 2.66 (t, J=7.2 Hz, 2H), 2.58 (t, J=7.1 Hz, 1H), 2.44 (s, 3H), 2.01-1.85 (m, 5H), 1.66-1.53 (m 6H) 1.35-1.22 (m, 6H), 1.16 (d, J=6.0 Hz, 6H); MS (APCI) m/z: 612.4 (M+H$^+$).

Example 65

N-Cyclopentyl-3-(5-((5-(3-(4-ethylpiperazin-1-yl)propoxy)-7-methyl-9-oxo-9H-xanthen-3-yl)oxy)pyridin-2-yl)propanamide

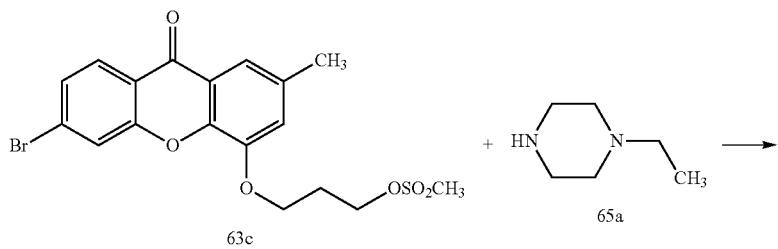

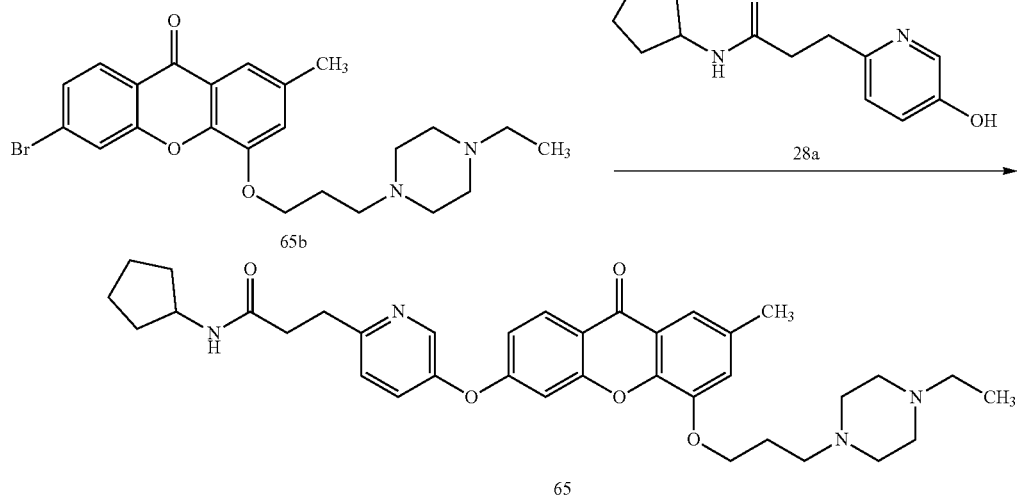

Similar reaction of crude 3-((6-bromo-2-methyl-9-oxo-9H-xanthen-4-yl)oxy)propyl methanesulfonate 63c and N-ethylpiperazine (65a) in DMSO gave 6-bromo-4-(3-(4-ethylpiperazin-1-yl)propoxy)-2-methyl-9H-xanthen-9-one 65b in 71% yield: $^1$H NMR (CDCl$_3$) δ 8.18 (d, J=8.5 Hz, 1H), 7.78 (d, J=1.7 Hz, 1H), 7.66 (brd, J=0.9 Hz, 1H), 7.49 (dd, J=8.5, 1.8 Hz, 1H), 7.10 (d, J=1.8 Hz, 1H), 4.20 (t, J=6.4 Hz, 2H), 2.60-2.41 (m, 14H), 2.15-2.08 (m, 2H), 1.10 (t, J=7.2 Hz, 3H); MS (APCI) m/z: 459.2 and 461.1 (M+H$^+$).

The coupling reaction of 6-bromo-4-(3-(4-ethylpiperazin-1-yl)propoxy)-2-methyl-9H-xanthen-9-one 65b and compound 28a as in Example 28 gave N-cyclopentyl-3-(5-((5-(3-(4-ethylpiperazin-1-yl)propoxy)-7-methyl-9-oxo-9H-xanthen-3-yl)oxy)pyridin-2-yl)propanamide (65) in 50% yield: mp (CH$_2$Cl$_2$/hexanes) 210-211° C.; $^1$H NMR (CDCl$_3$) δ 8.40 (d, J=2.6 Hz, 1H), 8.31 (d, J=8.8 Hz, 1H), 7.68 (bd, J=1.0 Hz, 1H), 7.40 (dd, J=8.4, 2.8 Hz, 1H), 7.30 (d, J=8.5 Hz, 1H), 7.08 (d, J=1.8 Hz, 1H), 7.03-7.00 (m, 2H), 6.01 (d, J=7.1 Hz, 1H), 4.23-4.15 (m, 3H), 3.18 (t, J=7.1 Hz, 2H), 2.66 (t, J=7.2 Hz, 2H), 2.60-2.39 (m, 14H), 2.12-2.05 (m, 2H), 1.98-1.90 (m, 2H), 1.65-1.56 (m, 4H), 1.37-1.29 (m, 2H), 1.09 (t, J=7.2 Hz, 3H). HPLC 95%; MS (APCI) m/z: 613.4 (M+H$^+$).

Example 66

N-Cyclopentyl-3-(5-((5-(3-(4-isopropylpiperazin-1-yl)propoxy)-7-methyl-9-oxo-9H-xanthen-3-yl)oxy)pyridin-2-yl)propanamide

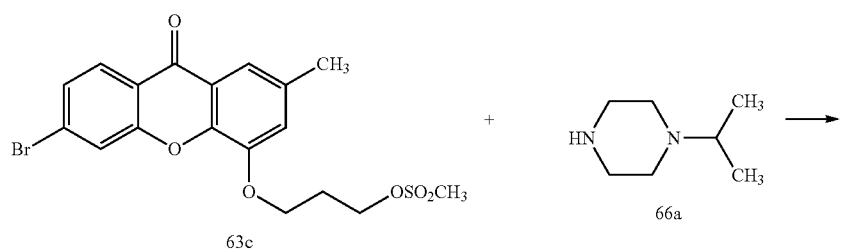

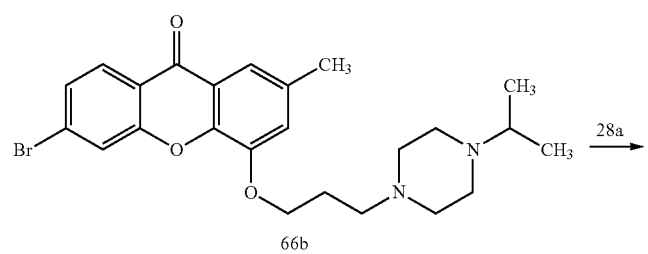

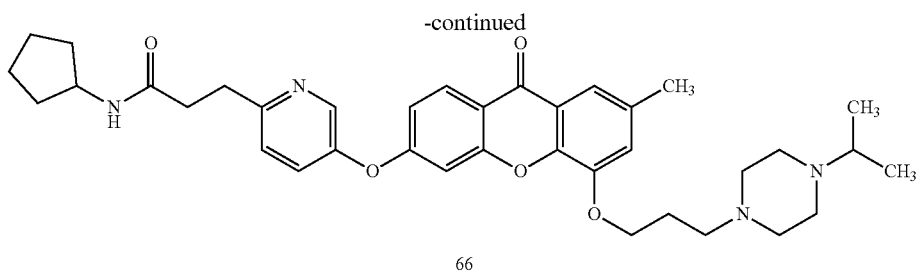

66

Reaction of crude 63c and N-isopropylpiperazine (66a) in DMSO gave 6-bromo-4-(3-(4-isopropylpiperazin-1-yl)propoxy)-2-methyl-9H-xanthen-9-one (66b) in 76% yield: mp (diisopropyl ether) 126-128° C.; $^1$H NMR (CDCl$_3$) δ 8.19 (d, J=8.5 Hz, 1H), 7.78 (d, J=1.7 Hz, H), 7.67 (dd, J=1.8, 0.8 Hz, 1H), 7.49 (dd, J=8.5, 1.8 Hz, 1H), 7.10 (s, J=1.8 Hz, 1H), 4.20 (t, J=6.1 Hz, 2H), 2.69-2.59 (m, 11H), 1.91 (m, 2H), 1.65-1.56 (m, 4H), 1.37-1.29 (m, 2H), 1.06 (d, J=6.5 Hz, 6H) HPLC 96%. MS (APCI) m/z: 627 (M+H$^+$).

Example 67

N-Cyclopentyl-3-(5-((5-(3-((3S,5R)-3,5-dimethylpiperazin-1-yl)propoxy)-7-methyl-9-oxo-9H-xanthen-3-yl)oxy)pyridin-2-yl)propanamide

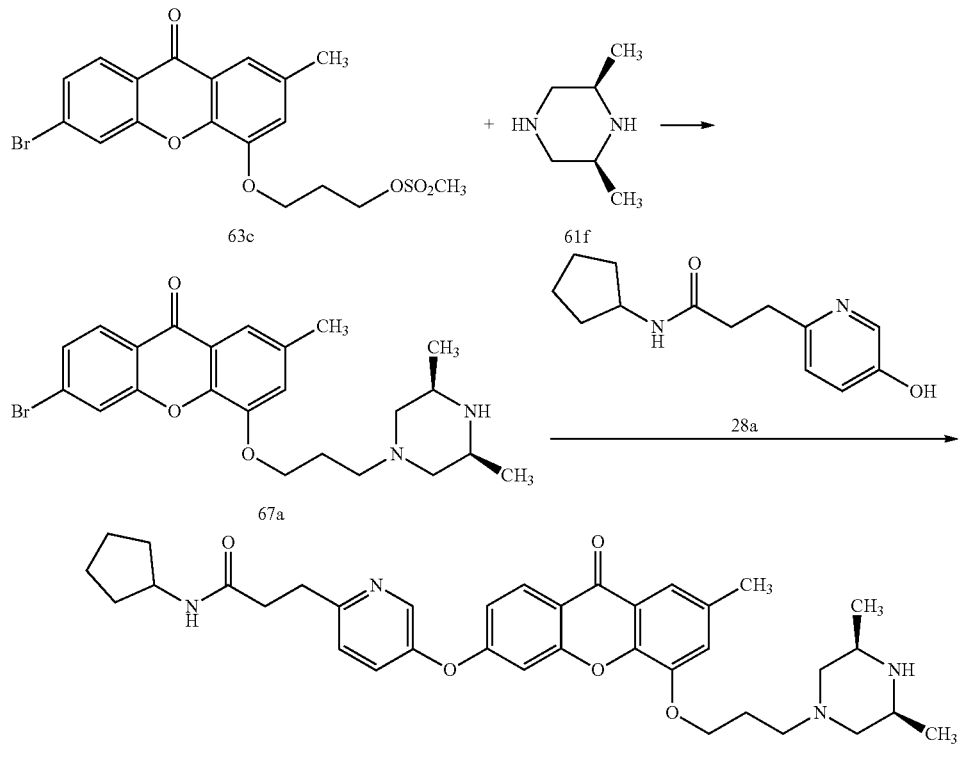

2.44 (s, 3H), 2.15-2.08 (m, 2H), 1.07 (d, J=6.5 Hz, 6H); MS (APCI) m/z: 473 and 475 (M+H$^+$).

The coupling reaction of 66b with compound 28a as in Example 28 gave N-cyclopentyl-3-(5-((5-(3-(4-isopropylpiperazin-1-yl)propoxy)-7-methyl-9-oxo-9H-xanthen-3-yl)oxy)pyridin-2-yl)propanamide ( ) in 67% yield: mp (CH$_2$Cl$_2$/MeOH) 205-208° C.; $^1$H NMR (CDCl$_3$) δ 8.40 (d, J=2.7 Hz, 1H), 8.31 (d, J=8.7 Hz, 1H), 7.68 (dd, J=1.8, 0.8 Hz, 1H), 7.40 (dd, J=8.4, 2.8 Hz, 1H), 7.30 (d, J=8.4 Hz, 1H), 7.08 (d, J=1.8 Hz, 1H), 7.03-7.00 (m, 2H), 6.00 (d, J=7.2 Hz, 1H), 4.23-4.15 (m, 3H), 3.18 (t, J=7.1 Hz, 2H), 2.68-2.55 (m, 12H), 2.44 (s, 3H), 2.12-2.05 (m, 2H), 1.98-

To a solution of crude compound 63c (0.6 mmol) in DMSO (6 mL) was added cis 2,6-dimethyl piperazine (61f) (137 mg, 1.2 mmol) and K$_2$CO$_3$ (500 mg, 3.6 mmol). The reaction mixture was stirred at 20° C. for 20 h, and then diluted with aq. NaCl solution to give a white precipitate. Chromatography on neutral Al$_2$O$_3$, eluting with CH$_2$Cl$_2$/EtOAc 0-50% gave a partially clean product, which was triturated with diisopropyl ether to give 6-bromo-4-(3-((3S,5R)-3,5-dimethylpiperazin-1-yl)propoxy)-2-methyl-9H-xanthen-9-one (67a) (156 mg, 54%): mp (diisopropyl ether) 130-132° C.; $^1$H NMR (CDCl$_3$) δ 8.21 (d, J=8.5 Hz, 1H), 7.82 (d, J=1.7 Hz, 1H), 7.69 (dd, J=1.9, 0.8 Hz, 1H), 7.51 (dd, J=8.5, 1.8 Hz, 1H), 7.12 (d, J=8.5 Hz, 1H), 4.22 (t, J=6.4 Hz, 2H), 3.01-2.93 (m, 2H), 2.89-2.86 (m, 2H), 2.61 (t, J=7.2 Hz, 1H), 2.47 (s, 3H), 217-2.11 (m, 2H), 1.67 (t, J=10.6, Hz, 1H), 1.10 (d, J=6.4 Hz, 6H); MS (APCI) m/z: 459 and 461 (M+H⁺).

The coupling reaction of 67a with compound 28a as in Example 28 gave N-cyclopentyl-3-(5-((5-(3-((3S,5R)-3,5-dimethylpiperazin-1-yl)propoxy)-7-methyl-9-oxo-9H-xanthen-3-yl)oxy)pyridin-2-yl)propanamide (67) in 52% yield: mp (diisopropyl ether) 188-192° C.; $^1$H NMR (CDCl$_3$) δ 8.40 (d, J=2.7 Hz, 1H), 8.32 (d, J=8.6 Hz, 1H), 7.68 (d, J=0.9 Hz, 1H), 7.40 (dd, J=8.4, 2.8 Hz, 1H), 7.30 (d, J=8.5 Hz, 1H), 7.08 (d, J=1.8 Hz, 1H), 7.03-7.00 (m, 2H), 5.98 (d, J=7.3 Hz, 1H), 4.23-4.15 (m, 3H), 3.18 (t, J=7.1 Hz, 2H), 2.96-2.88 (m, 2H), 2.83-2.81 (m, 2H), 2.66 (t, J=7.1 Hz, 2H), 2.54 (t, J=7.2 Hz, 2H), 2.44 (s, 3H), 2.12-2.05 (m, 2H), 1.98-1.90 (m, 2H), 1.63-1.58 (m, 6H), 1.37-1.58 (m, 2H), 1.05 (d, J=6.36 Hz, 6H). HPLC 98.5%.

Example 68

N-Cyclopentyl-3-(5-((7-methyl-9-oxo-5-(3-((3S,5R)-3,4,5-trimethylpiperazin-1-yl)propoxy)-9H-xanthen-3-yl)oxy)pyridin-2-yl)propanamide xanthen-9-one (68a) in 54% yield: $^1$H NMR (CDCl$_3$) δ 8.19 (d, J=8.5 Hz, 1H), 7.79 (d, J=1.7 Hz, 1H), 7.67 (dd, J=1.8, 0.8 Hz, 1H), 7.49 (dd, J=8.5, 1.8 Hz, 1H), 7.10 (d, J=1.8 Hz, 1H), 4.20 (t, J=6.4 Hz, 2H), 2.83-2.81 (m, 2H), 2.56 (t, J=7.3 Hz, 2H), 2.44 (s, 3H), 2.29 (s, 3H), 2.25-2.35 (m, 2H), 2.13-2.07 (m, 2H), 1.95 (t, J=10.8 Hz, 2H), 1.11 (d, J=6.2 Hz, 6H). MS m/z: 473.3 and 475.2 (M+H⁺).

The coupling reaction of 68a with compound 28a as in Example 28 gave N-cyclopentyl-3-(5-((7-methyl-9-oxo-5-(3-((3S,5R)-3,4,5-trimethylpiperazin-1-yl)propoxy)-9H-xanthen-3-yl)oxy)pyridin-2-yl)propanamide (68) in 70% yield: mp (CH$_2$Cl$_2$/hexanes) 193-196° C.; $^1$H NMR (CDCl$_3$) δ 8.40 (d, J=2.6 Hz, 1H), 8.31 (d, J=8.9 Hz, 1H), 7.68 (dd, J=1.8, 0.8 Hz, 1H), 7.39 (dd, J=8.4, 2.8 Hz, 1H), 7.30 (d, J=8.4 Hz, 1H), 7.08 (d, J=1.9 Hz, 1H), 7.03-7.00 (m, 1H), 5.97 (d, J=7.0 Hz, 1H), 4.23-4.15 (m, 3H), 3.17 (t, J=7.1 Hz, 2H), 2.79-2.76 (m, 2H), 2.66 (t, J=7.1 Hz, 1H), 2.50 (t, J=7.2 Hz, 1H), 2.44 (s, 3H), 2.26 (s, 3H), 2.26-2.27 (m, 2H), 2.10-2.04 (m, 2H), 1.98-1.86 (m, 4H), 1.65-1.54 (m), 1.36-

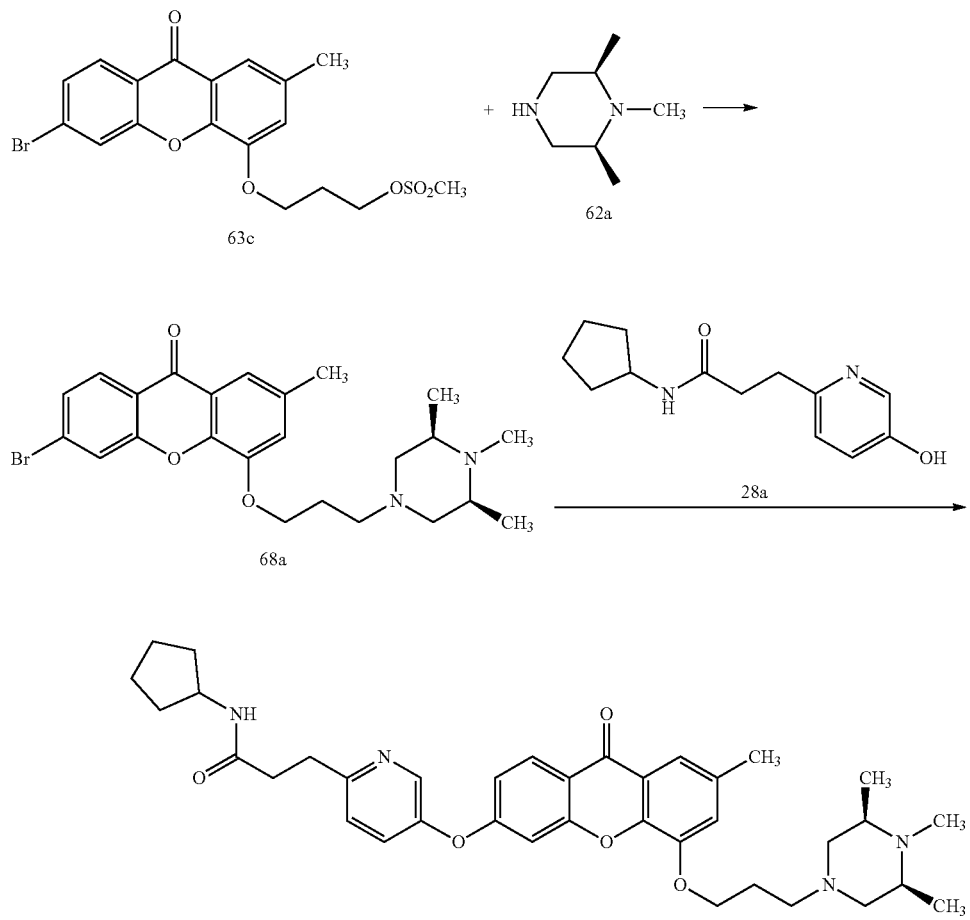

Reaction of crude 63c with (2S,6R)-1,2,6-trimethylpiperazine (62a) (WO 2012/082689) gave 6-bromo-2-methyl-4-(3-((3S,5R)-3,4,5-trimethylpiperazin-1-yl)propoxy)-9H- 1.29 m, 2H), 1.08 (d, J=6.2 Hz, 6H), HPLC 95.4%, HRMS Calcd. for C$_{37}$H$_{36}$N$_4$O$_5$: m/z 627.3556 (M+H⁺); found m/z 627.35560.

Example 69

N-Cyclopentyl-3-[5-({7-methyl-5-[3-(4-morpholinyl)propoxy]-9-oxo-9H-xanthen-3-yl}oxy)-2-pyridinyl]propanamide

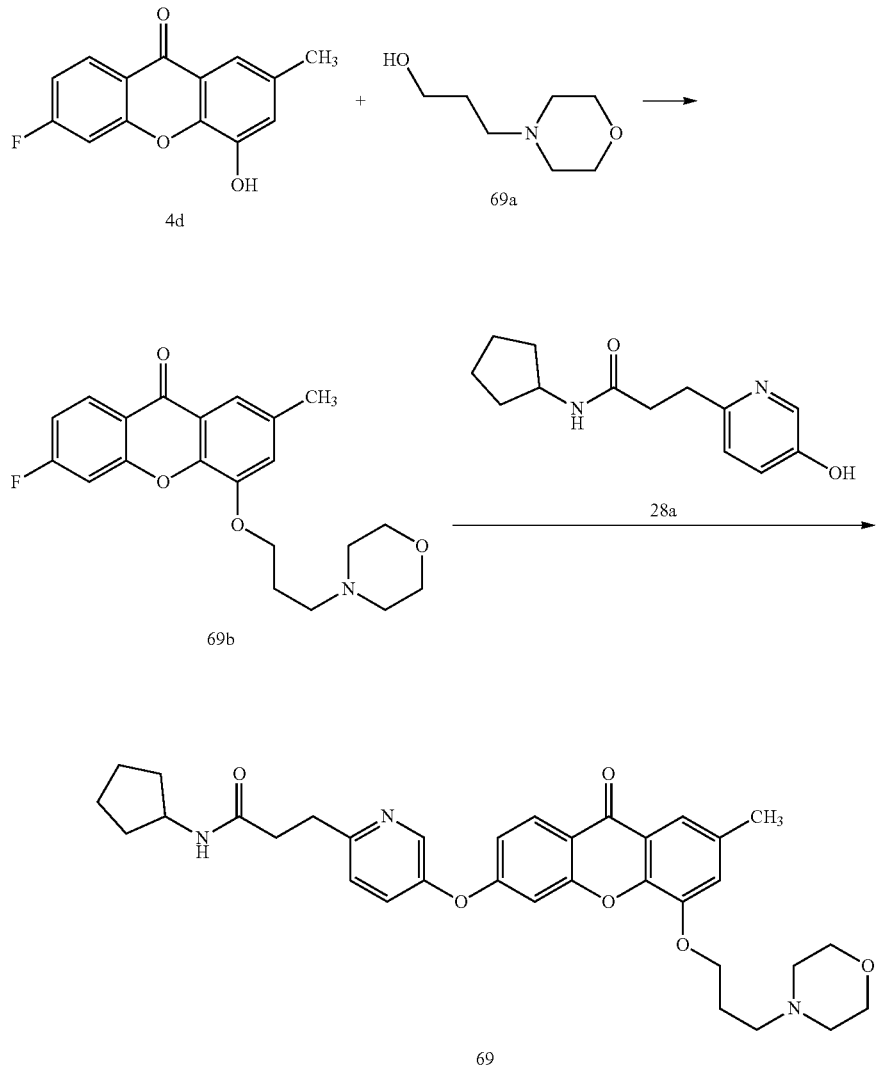

A mixture of compound 4d (200 mg, 0.82 mmol), 3-morpholino-1-propanol (69a) (178 mg, 1.23 mmol), diisopropyl azodicarboxylate (DIAD) (250 mg, 123 mmol), and PPh$_3$ (323 mg, 1.23 mmol) in THF (10 mL) was stirred for 20 h under N$_2$ at 20° C. The reaction mixture was absorbed into SiO$_2$ and chromatographed using SiO$_2$/EtOAc/MeOH(1-3%)/0.5% Et$_3$N to give 6-fluoro-2-methyl-4-[3-(4-morpholinyl)propoxy]-9H-xanthen-9-one (69b): $^1$H NMR (DMSO-d$_6$) δ 8.24 (dd, J=8.8, 6.6 Hz, 1H), 7.62 (td, J=9.8, 3.0 Hz, 1H), 7.51 (br s, 1H), 7.38 (br s, 1H), 7.35 (d, J=8.8, 2.3 Hz, 1H), 4.23 (t, J=6.4 Hz, 2H), 3.60-3.56 (m, 4H), 2.56 (m, 2H), 2.42 (s, 3H), 2.41-2.39 (m, 2H), 1.99 (t, J=6.8 Hz, 2H); 1.99 (pentet, J=6.7, 6.5 Hz, 2H).

The coupling reaction of 28a and 69b as in Example 11 gave N-cyclopentyl-3-[5-({7-methyl-5-[3-(4-morpholinyl)propoxy]-9-oxo-9H-xanthen-3-yl}oxy)-2-pyridinyl]propanamide (69) in 60% yield: mp (EtOAc) 209-212° C.; $^1$H NMR (DMSO-d$_6$) δ 8.44 (d, J=2.8 Hz, 1H), 8.19 (d, J=8.8 Hz, 1H), 7.79 (d, J=7.2 Hz, 1H), 7.64 (dd, J=2.9, 8.5 Hz, 1H), 7.50-7.51 (m, 1H), 7.38 (d, J=8.5 Hz, 1H), 7.36 (d, J=1.8 Hz, 1H), 7.12 (dd, J=2.4, 8.9 Hz, 1H), 6.99 (d, J=2.4 Hz, 1H), 4.20 (t, J=6.5 Hz, 2), 3.95-4.00 (m, 1H), 3.56 (t, J=4.6 Hz, 4H), 3.00 (t, J=7.2 Hz, 2H), 2.45 (t, J=7.1 Hz, 2H), 2.42 (s, 3H), 2.33 (br. s, 4H), 1.92-1.99 (m, 2H), 1.72-1.79 (m, 2H), 1.55-1.63 (m, 2H), 1.43-1.52 (m, 2H), 1.27-1.36 (m, 2H); $^{13}$C NMR (DMSO-d$_6$) δ 175.0, 170.6, 162.8, 157.8, 156.8, 149.3, 147.3, 144.3, 141.6, 133.9, 128.6, 128.5, 124.0, 121.6, 118.9, 116.6, 115.9, 114.6, 104.5, 67.5, 66.2, 54.7, 53.4, 50.1, 34.8, 32.8, 32.3, 25.7, 23.4, 20.9; MS (APCI) m/z: 586.3 (M+H$^+$); HPLC purity: 96.8%;

Example 70

N-Cyclopentyl-3-(5-((7-methyl-5-((1-methylpyrrolidin-3-yl)oxy)-9-oxo-9H-xanthen-3-yl)oxy)pyridin-2-yl)propanamide

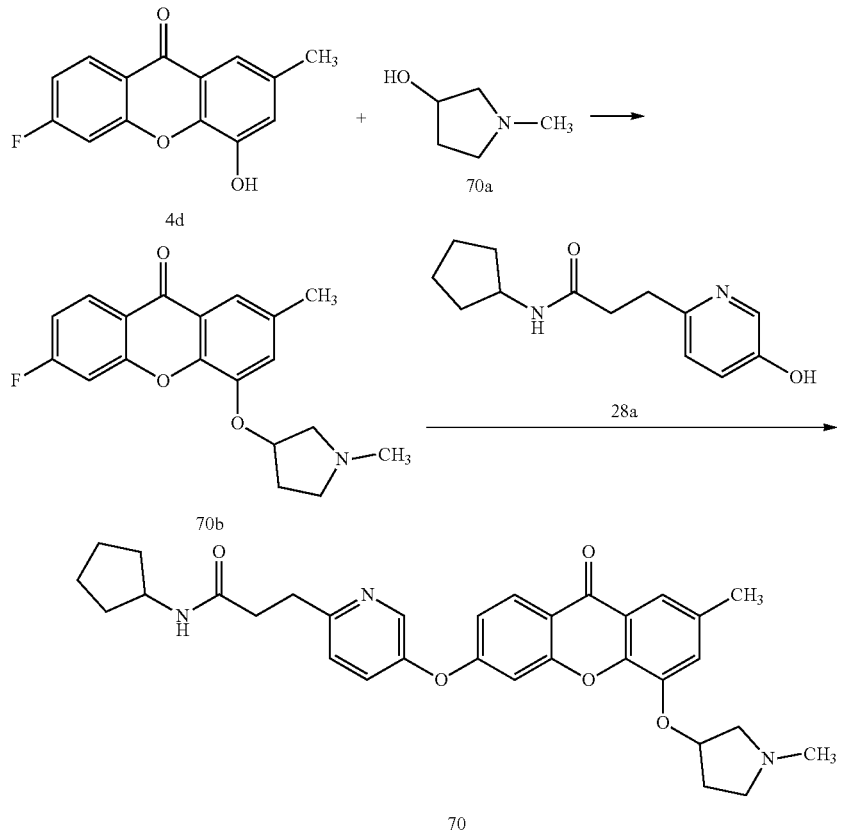

Mitsunobu reaction of 6-fluoro-4-hydroxy-2-methyl-9H-xanthen-9-one (4d) and 3-hydroxy-1-methylpyrrolidine (70a) as in Example 69 gave impure 6-fluoro-2-methyl-4-((1-methylpyrrolidin-3-yl)oxy)-9H-xanthen-9-one (70b) in 21% yield: $^1$H NMR (CDCl$_3$) δ 8.34 (dd, J=8.9, 6.4 Hz, 1H), 7.68 (br d, J=0.9 Hz, 1H), 7.25 (ddd, J=9.5, 2.2 Hz, 1H), 7.09 (dt, J=8.8, 8.8, 2.4 Hz, 1H), 6.97 (d, J=1.7 Hz, 1H), 4.98-4.93 (m, 1H), 3.00-2.89 (m 2H), 2.66-2.38 (m 2H), 2.46 (s, 3H), 2.44 (s, 3H), 2.34-2.13 (m, 2H).

The coupling reaction of compound 28a with crude 70b as in Example 11 gave N-cyclopentyl-3-(5-((7-methyl-5-((1-methylpyrrolidin-3-yl)oxy)-9-oxo-9H-xanthen-3-yl)oxy)pyridin-2-yl)propanamide (70) in 40% yield: mp (CH$_2$Cl$_2$/hexanes) 192-195° C.; $^1$H NMR (CDCl$_3$) δ 8.40 (d, J=2.7 Hz, 1H), 8.31 (d, J=8.8 Hz, 1H), 7.68 (brd, J=0.9 Hz, 1H), 7.40 (dd, J=8.4, 2.8 Hz, 1H), 7.30 (d, J=8.4 Hz, 1H), 7.03 (dd, J=8.8, 2.3 Hz, 1H), 6.97 (d, J=2.3 Hz, 1H), 6.94 (d, J=1.8 Hz, 1H), 6.01 (d, J=7.4 Hz, 1H), 4.95-4.91 (m, 1H), 4.24-4.15 (m, 1H), 3.18 (t, J=7.1 Hz, 2H), 2.98-2.82 (m, 3H), 2.67 (t, J=7.1 Hz, 2H), 2.50-2.36 (m, 2H), 2.44 (s, 3H), 2.42 (s, 3H), 2.15-2.08 (m 1H), 1.98-1.90 (m, 2H), 1.65-1.54 (m, 2H), 1.38-1.25 (m, 4H); HPLC 87%; MS (APCI) m/z: 542.3 (M+H$^+$).

Example 71

N-Cyclopentyl-3-[5-({7-methyl-5-[(1-methyl-4-piperidinyl)oxy]-9-oxo-9H-xanthen-3-yl}oxy)-2-pyridinyl]propanamide

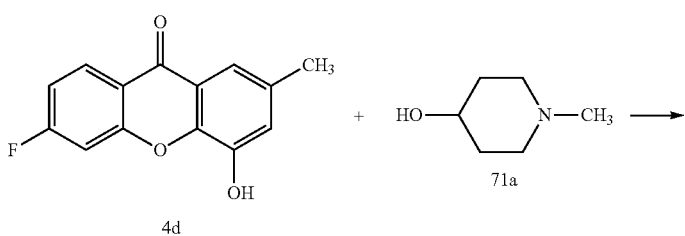

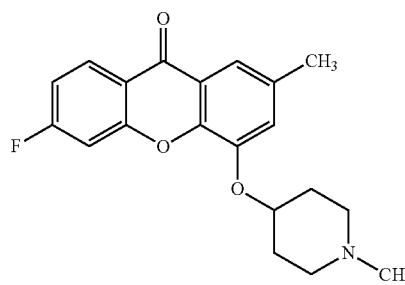

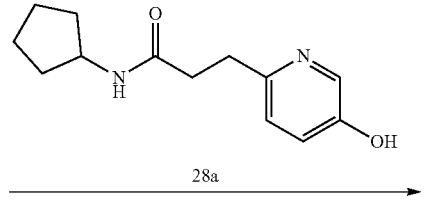

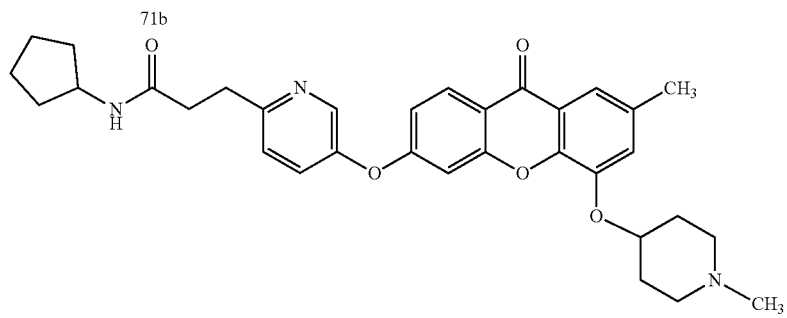

Mitsunobu coupling reaction of 4d with 4-hydroxy-1-methylpiperidine (71a) as in Example 69 gave impure 6-fluoro-2-methyl-4-[(1-methyl-4-piperidinyl)oxy]-9H-xanthen-9-one (71b) which was directly in the next step.

The coupling reaction of 28a with crude 71b as in Example 11 gave N-cyclopentyl-3-[5-({7-methyl-5-[(1-methyl-4-piperidinyl)oxy]-9-oxo-9H-xanthen-3-yl}oxy)-2-pyridinyl]propan-amide (71): mp (EtOAc) 175-178° C.; $^1$H NMR (CDCl$_3$) δ 8.40 (d, J=2.6 Hz, 1H), 8.31 (d, J=9.4 Hz, 1H), 7.73-7.72 (br, 1H), 7.39 (dd, J=8.4, 2.8 Hz, 1H), 7.30 (d, J=8.5 Hz, 1H), 7.12 (d, J=1.9 Hz, 1H), 7.02-6.98 (m, 2H), 5.97 (d, J=7.1 Hz, 1H), 4.42-4.34 (m, 1H), 4.19 (qd, J=13.50, 6.8 Hz, 1H), 3.18 (t, J=7.2 Hz, 2H), 2.81-2.73 (m, 2H), 2.66 (t, J=7.2 Hz, 2H), 2.44 (s, 3H), 2.31 (s, 1H), 2.30-2.24 (m, 2H), 2.10-2.02 (m, 2H), 1.99-1.89 (m, 4H), 1.66-21.55 (m, 2H), 1.37-1.27 (m, 2H); MS (APCI) m/z: 556.3 (M+H$^+$).

Example 72

(R)—N-Cyclopentyl-3-(5-((7-methyl-5-((1-methylpyrrolidin-2-yl)methoxy)-9-oxo-9H-xanthen-3-yl)oxy)pyridin-2-yl)propanamide

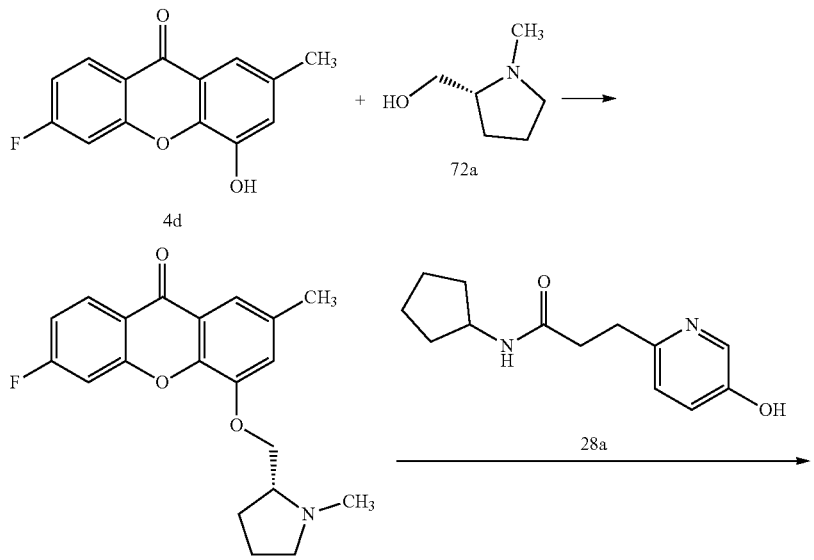

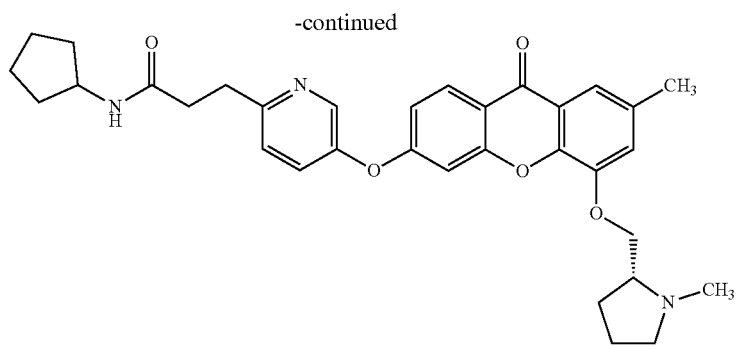

72

Mitsunobu coupling reaction of 4d with (R)-(1-methylpyrrolidin-2-yl)methanol (72a) as in Example 69 gave impure 6-fluoro-2-methyl-4-{[(2R)-1-methylpyrrolidinyl]methoxy}-9H-xanthen-9-one (72b) which was directly in the next step.

The reaction of 28a with crude 72b as in Example 11 gave (R)—N-cyclopentyl-3-(5-((7-methyl-5-((1-methylpyrrolidin-2-yl)methoxy)-9-oxo-9H-xanthen-3-yl)oxy)pyridin-2-yl)propanamide (72): mp 161-162° C.; $^1$H NMR (DMSO-$d_6$) δ 8.44 (d, J=2.9 Hz, 1H), 8.19 (d, J=8.9 Hz, 1H), 7.79 (d, J=7.2 Hz, 1H), 7.65 (ddd, J=8.4, 4.1, 2.9 Hz, 1H), 7.42-7.36 (m, 2H), 7.11 (ddd, J=13.7, 8.9, 2.4 Hz, 1H), 6.97 (d, J=2.3 Hz, 1H), 4.06 (ddd, J=15.6, 9.7, 5.3 Hz, 1H), 3.98 (dd, J=13.5, 6.6 Hz, 1H), 3.02-2.96 (m, 4H), 2.41 (s, 3H), 2.18 (s, 3H), 1.90-2.20 (m, 4H), 1.69-1.79 (m, 3H), 1.53-1.66 (m, 5H), 1.43-1.52 (m, 3H), 1.28-1.36 (m, 2H); MS (APCI) m/z: 556.3 (M+H$^+$); HPLC purity: 91%.

Example 73

(S)—N-Cyclopentyl-3-(5-((7-methyl-5-((1-methylpyrrolidin-2-yl)methoxy)-9-oxo-9H-xanthen-3-yl)oxy)pyridin-2-yl)propanamide

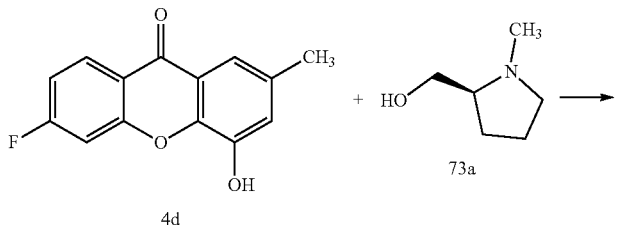

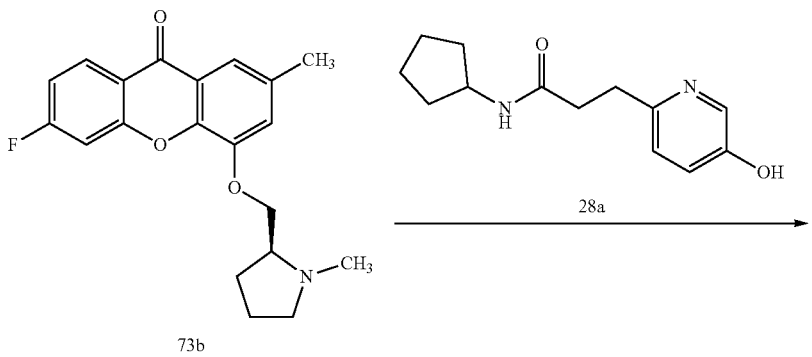

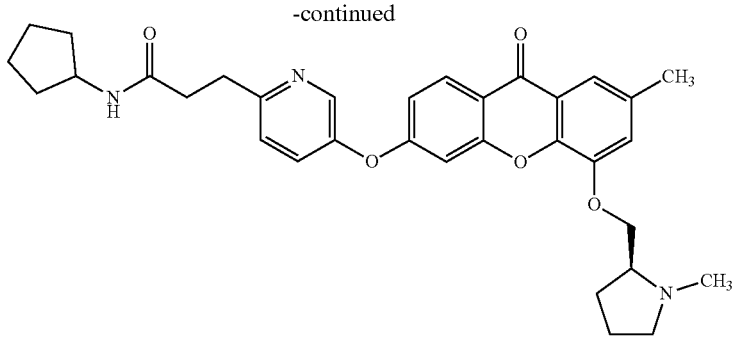

Mitsunobu coupling reaction of 4d with (S)-(1-methylpyrrolidin-2-yl)methanol (73a) as in Example 69 gave impure 6-fluoro-2-methyl-4-{[(2S)-1-methylpyrrolidinyl]methoxy}-9H-xanthen-9-one (73b) which was directly in the next step.

The reaction of 28a with crude 73b as in Example 11 gave (S)—N-cyclopentyl-3-(5-((7-methyl-5-((1-methylpyrrolidin-2-yl)methoxy)-9-oxo-9H-xanthen-3-yl)oxy)pyridin-2-yl)propanamide (73): mp 205-208° C.; $^1$H NMR (DMSO-$d_6$) δ 8.45 (d, J=2.8 Hz, 1H), 8.19 (d, J=8.9 Hz, 1H), 7.79 (d, J=7.2 Hz, 1H), 7.65 (dd, J=8.5, 2.9 Hz, 1H), 7.50 (br, 1H), 7.39 (d, J=8.5 Hz, 1H), 7.35 (d, J=1.8 Hz, 1H), 7.13 (dd, J=8.9, 2.4 Hz, 1H), 6.93 (d, J=2.3 Hz, 1H), 4.18 (t, J=6.8 Hz, 2H), 3.98 (dd, J=13.6, 6.7 Hz, 1H), 3.00 (t, J=7.7 Hz, 2H), 2.93 (dd, J=7.2, 2.5 Hz, 1H), 2.42 (s, 3H), 2.22 (s, 3H); MS (APCI) m z: 556.3 (M+H$^+$).

Example 74

N-Cyclopentyl-3-(5-((7-methyl-5-((1-methylpiperidin-2-yl)methoxy)-9-oxo-9H-xanthen-3-yl)oxy)pyridin-2-yl)propanamide

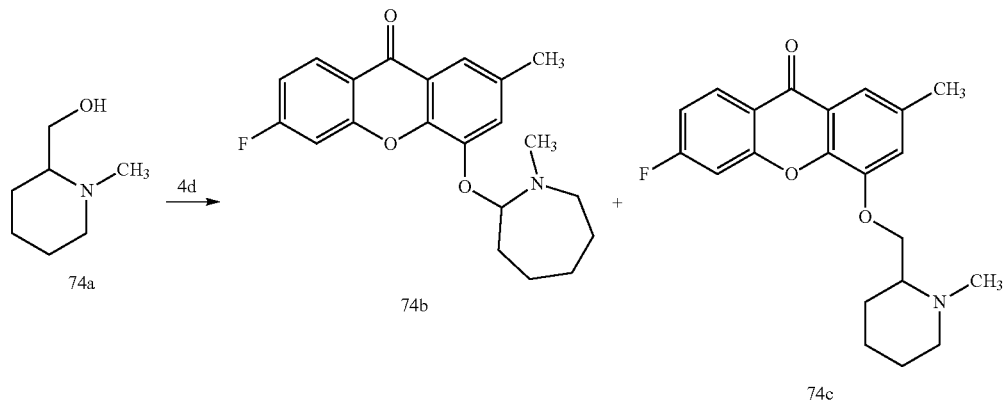

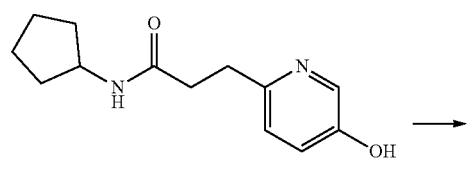

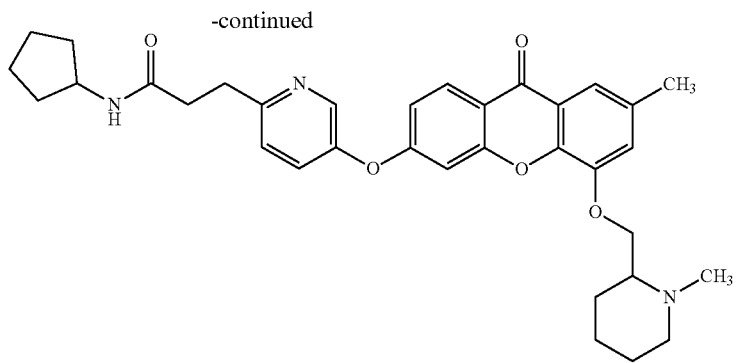

74

A mixture of (1-methylpiperidin-2-yl)methanol (74a) (78 mg, 0.61 mmol, 1.3 eq), compound 4d (114 mg, 0.47 mmol), and PPh₃ (162.2 mg, 0.61 mmol, 1.3 eq) in dry THF (10 mL) under N₂ at 0° C. was treated with DIAD (0.12 mL 0.61 mmol) and the reaction mixture was stirred for two days, allowing it to warm to 20° C. The solvent was removed under vacuum, and the residue was partitioned between CH₂Cl₂ and dil. aq. HCl (the product did not go into the aqueous layer). The organic layer was separated and washed with aq. KOH, and dried (Na₂SO₄). Chromatographyon SiO₂ eluting with 50% CH₂Cl₂/hexanes then 50% CH₂Cl₂/EtOAc gave 6-fluoro-2-methyl-4-((1-methylazepan-2-yl)oxy)-9H-xanthen-9-one (74b) (8.0 mg 4.8%): ¹H NMR (CDCl₃) δ 8.34 (dd, J=8.9, 6.5 Hz, 1H), 7.70 (dd, J=1.8, 0.8 Hz, 1H), 7.25 (dd, J=9.4, 2.4 Hz, 1H), 7.12-7.07 (m, 2H), 4.62-4.56 (m, 1H), 2.98 (dd, J=13.6, 4.2 Hz, 1H), 2.88 (dd, J=13.6, 7.2 Hz, 1H), 2.75-2.69 (m, 1H), 2.64-2.59 (m, 1H), 2.46 (s, 3H), 2.44 (s, 3H), 2.25-2.17 (m, 1H), 2.02-1.94 (m, 1H), 1.89-1.75 (m, 3H), 1.67-1.58 (m, 1H).

Further elution gave 6-fluoro-2-methyl-4-((1-methylpiperidin-2-yl)methoxy)-9H-xanthen-9-one (74c) (30 mg, 18%): ¹H NMR (CDCl₃) δ 8.35 (dd, J=8.9, 6.4 Hz, 1H), 7.70 (dd, J=1.8, 0.8 Hz, 1H), 7.27 (dd, J=9.5, 2.3 Hz, 1H), 7.13-7.08 (m, 2H), 4.22 (dd, J=9.7, 4.8H, 1H), 4.11 (dd, J=9.7, 4.6 Hz, 1H), 2.97-2.89 (m, 1H), 2.47 (s, 3H), 2.45 (s, 3H), 2.26-2.17 (m, 1H), 1.96-1.83 (m, 2H), 1.71-1.55 (m, 2H), 1.45-1.26 (m, 2H).

The coupling reaction of compound 28a and compound 74c as in Example 11 gave N-cyclopentyl-3-(5-((7-methyl-5-((1-methylpiperidin-2-yl)methoxy)-9-oxo-9H-xanthen-3-yl)oxy)pyridin-2-yl)propanamide (74) in 58% yield: mp (CH₂Cl₂/MeOH) 197-200° C.; ¹H NMR (CDCl₃) δ 8.40 (d, J=2.6 Hz, 1H), 8.31 (d, J=8.8 Hz, 1H), 7.70 (dd, J=1.9, 0.8 Hz, 1H), 7.39 (dd, J=8.4, 2.8 Hz, 1H), 7.29 (d, J=8.4 Hz, 1H), 7.06 d, J=2.0 Hz, 1H), 7.02 (d, J=2.2 Hz, 1H), 6.99 (dd, J=8.8, 2.3 Hz, 1H), 4.97 (brd, J=6.7 Hz, 1H), 4.23-4.15 (m, 2H), 4.08 (dd, J=9.8, 4.8 Hz, 1H), 3.17 (t, J=7.1 Hz), 2.94-2.86 (m, 1H), 2.45 (s, 3H), 2.43 (s, 3H), 2.22-2.16 (m, 1H), 1.98-1.88 (m, 3H), 1.83-1.78 (m, 1H), 1.66-1.50 (m, 5H), 1.43-1.28 (m, 1H); MS (APCI) m/z: 570.3 (M+H⁺).

Example 75

N-Cyclopentyl-3-(5-((7-methyl-5-(2-(1-methylpyrrolidin-2-yl)ethoxy)-9-oxo-9H-xanthen-3-yl)oxy)pyridin-2-yl)propanamide

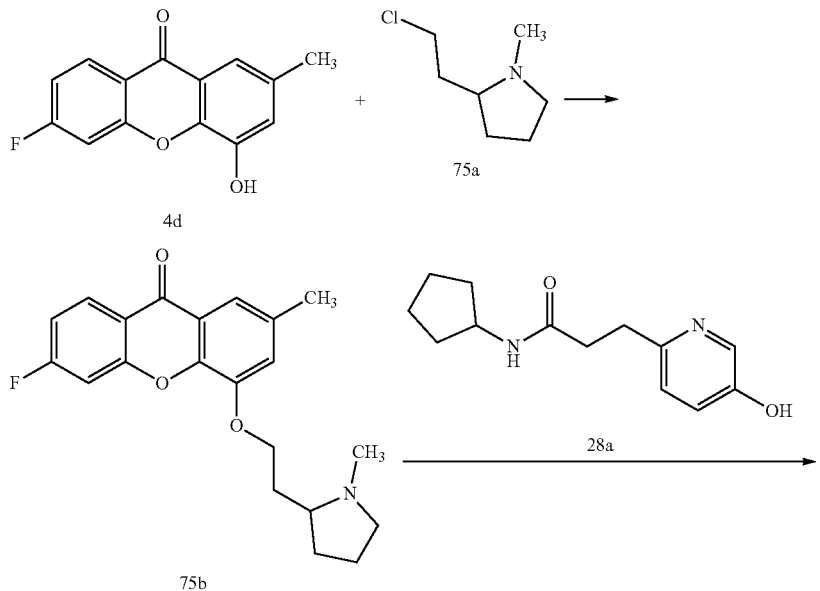

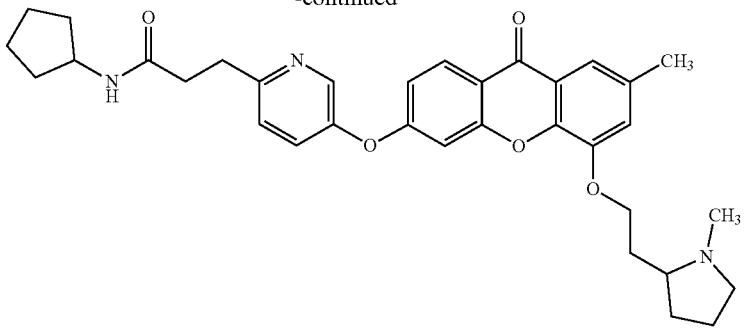

75

A mixture of 4d (200 mg, 0.82 mmol), 2-(2-chloroethyl)-1-methylpyrrolidine (75a) (151 mg, 0.82 mmol), Cs$_2$CO$_3$ (802 mg, 2.46 mmol) and NaI (123 mg, 0.82 mmol) in DMF (2 mL) was heated for 24 h at 80° C. The reaction mixture was partitioned between EtOAc and water, and the organic layer was dried (Na$_2$SO$_4$). Chromatography on SiO$_2$, eluting with EtOAc/MeOH (0-5%)/0.1% Et$_3$N gave 6-fluoro-2-methyl-4-(2-(1-methylpyrrolidin-2-yl)ethoxy)-9H-xanthen-9-one (75b) (140 mg, 48%): $^1$H NMR (DMSO-d$_6$) δ 8.24 (ddd, J=9.0, 6.6, 2.8 Hz, 1H), 7.57 (ddd, J=12.3, 9.9, 2.4 Hz, 1H), 7.51 (ddd, J=4.7, 1.9, 0.9 Hz, 1H), 7.38-7.31 (m, 2H), 4.79-4.72 (m, 1H), 4.21 (t, J=6.8 Hz, 1H), 2.96 (td, J=7.9, 2.7 Hz, 1H), 2.58-2.52 (m, 1H), 2.42 (s, 3H), 2.28 (s, 3H), 2.19-2.05 (m, 2H), 2.00-1.74 (m, 3H), 1.68-1.54 (m, 2H), The coupling reaction of 28a with 75b as in Example 11 gave N-cyclopentyl-3-(5-((7-methyl-5-(2-(1-methylpyrrolidin-2-yl)ethoxy)-9-oxo-9H-xanthen-3-yl)oxy)pyridin-2-yl)propanamide (75) in 21% yield: mp 161-162° C.; $^1$H NMR (DMSO-d$_6$) δ 8.45 (d, J=2.8 Hz, 1H), 8.19 (d, J=8.9 Hz, 1H), 7.79 (d, J=7.2 Hz, 1H), 7.65 (dd, J=8.5, 2.9 Hz, 1H), 7.50 (br, 1H), 7.39 (d, J=8.5 Hz, 1H), 7.35 (d, J=1.8 Hz, 1H), 7.13 (dd, J=8.9, 2.4 Hz, 1H), 6.93 (d, J=2.3 Hz, 1H), 4.18 (t, J=6.8 Hz, 2H), 3.98 (td, J=13.6, 6.7 Hz, 1H), 3.32-3.29 (m, 1H), 3.00 (t, J=7.7 Hz, 2H), 2.93 (td, J=7.0, 2.6 Hz, 1H), 2.42 (s, 3H), 2.22 (s, 3H), 2.22-2.18 (m, 1H), 2.16-1.90 (m, 4H), 1.80-1.69 (m, 3H), 1.66-1.42 (m, 8H), 1.32 (td, J=14.5, 7.6 Hz, 2H); MS (APCI) m/z: 570.3 (M+H$^+$).

Example 76

N-Cyclopentyl-3-(5-((7-methyl-5-((1-methylpiperidin-3-yl)methoxy)-9-oxo-9H-xanthen-3-yl)oxy)pyridin-2-yl)propanamide

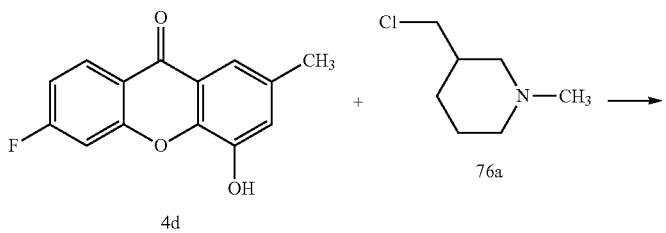

4d        76a

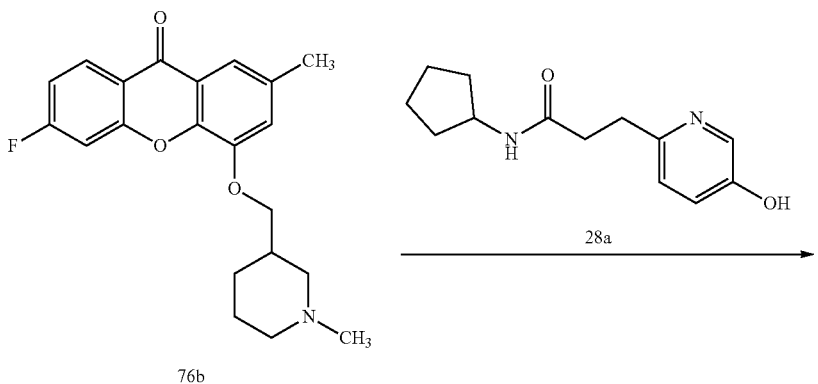

76b        28a

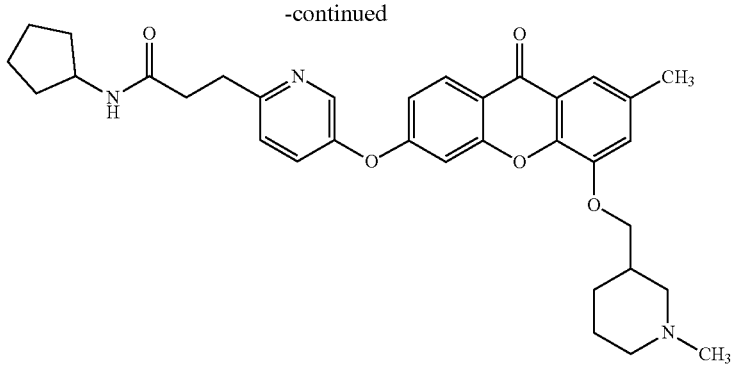

76

The alkylation reaction of 4d with 3-(chloromethyl)-1-methylpiperidine (76a) as in Example 75 gave 6-fluoro-2-methyl-4-((1-methylpiperidin-3-yl)methoxy)-9H-xanthen-9-one (76b) in 31% yield: $^1$H NMR (CDCl$_3$) δ 8.35 (dd, J=8.9, 6.4 Hz, 1H), 7.68 (br, 1H), 7.25 (dd, 9.4, 2.4 Hz), 7.10 (ddd, J=8.9, 8.3, 2.4 Hz, 1H), 7.07 (d, J=1.8 Hz, 1H), 4.01 (pentet, J=9.3 Hz, 2H), 3.05 (d, J=9.8 Hz, 1H), 2.78 (d, J=11.3 Hz, 1H), 2.32-2.26 (m, 1H), 2.44 (s, 1H), 2.32 (s, 1H), 2.07-1.84 (m 3H), 1.82-1.65 (m, 2H), 1.28-1.15 (m, 1H); MS (APCI) m/z: 356.2 (M+H$^+$).

The coupling reaction of 28a with 76b as in Example 11 gave N-cyclopentyl-3-(5-((7-methyl-5-((1-methylpiperidin-3-yl)methoxy)-9-oxo-9H-xanthen-3-yl)oxy)pyridin-2-yl)propanamide (76): mp 191-193° C.; $^1$H NMR (CDCl$_3$) δ 8.40 (d, J=2.7 Hz, 1H), 8.31 (d, J=8.8 Hz, 1H), 7.68 (dd, J=1.9, 0.9 Hz, 1H), 7.40 (dd, J=8.4, 2.8 Hz, 1H), 7.30 (d, J=8.5 Hz, 1H), 7.05 (d, J=1.9 Hz, 1H), 7.01 (dd, J=8.8, 2.4 Hz, 1H), 6.98 (d, J=2.3 Hz, 1H), 6.02 (d, J=7.1 Hz, 1H), 4.19 (qd, J=13.6, 7.0 Hz, 1H), 3.98 (pd, J=8.8, 3.0 Hz, 2H), 3.18 (t, J=7.2 Hz, 2H), 3.04 (d, J=10.9 Hz, 1H), 2.76 (d, J=10.8 Hz, 1H), 2.66 (t, J=7.2 Hz, 2H), 2.44 (s, 3H), 2.32-2.22 (m, 1H), 2.28 (s, 3H), 2.00-1.70 (m, 7H), 1.65-1.55 (m, 5H), 1.37-1.24 (m, 3H), 1.15 (ddd, J=14.8, 11.7, 3.8 Hz, 1H; MS (APCI) m/z: 570.3 (M+H$^+$).

Biological Activity

Receptor tyrosine kinase assays were carried out by ThermoFisher Scientific, using their SelectScreen® Biochemical Kinase Profiling Service: Assay 336 for CSF-1R (FMS) and Assay 540 for KDR (VEGFR2) (see, for example, www.thermofisher.com/nz/en/home/products-and-services/services/custom-services/screening-and-profiling-services/selectscreen-profiling-service/selectscreen-kinase-profiling-service.html). Inhibitors were supplied at 10 mM dissolved in DMSO and scientists at ThermoFisher Scientific diluted this to a top working concentration of 10 μM.

IC$_{50}$ values were determined using the Z'-LYTE® activity assay, with ATP concentration used at Km app for the specific assay (500 μM ATP for CSF-1R (FMS) and 75 μM ATP for KDR (VEGFR2)).

The Z'-LYTE® biochemical assay employs a fluorescence-based, coupled-enzyme format and is based on the differential sensitivity of phosphorylated and non-phosphorylated peptides to proteolytic cleavage. The peptide substrate is labelled with two fluorophores—one at each end—that make up a FRET (fluorescence resonance energy transfer) pair.

In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the following equation (1) below.

$$\text{Emission ratio} = \frac{\text{Coumarin Emission (445 nm)}}{\text{Fluorescein Emission (520 nm)}} \quad (1)$$

A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation.

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

1. Assay Conditions

Test Compounds

The Test Compounds are screened in 1% DMSO (final) in the well. For 10 point titrations, 3-fold serial dilutions are conducted from the starting concentration of the customer's choosing.

Peptide/Kinase Mixtures

All Peptide/Kinase Mixtures are diluted to a 2× working concentration in the appropriate Kinase Buffer (see section Kinase Specific Assay Conditions for a complete description).

ATP Solution

All ATP Solutions are diluted to a 4× working concentration in Kinase Buffer (50 mM HEPES pH 7.5, 0.01% BRIJ-35, 10 mM MgCl$_2$, 1 mM EGTA).

ATP Km apparent is previously determined using a Z'-LYTE® assay.

Development Reagent Solution

The Development Reagent is diluted in Development Buffer (see section Kinase-Specific Assay Conditions—Direct and Cascade for a complete description).

10× Novel PKC Lipid Mix:
2 mg/ml Phosphatidyl Serine, 0.2 mg/ml DAG in 20 mM HEPES, pH 7.4, 0.3% CHAPS For 5 mL 10X Novel PKC Lipid Mix:
1. Add 10 mgs Phosphatidyl Serine (Avanti Polar Lipids Part #8400032C or 840039C) and 1 mg DAG (Avanti Polar Lipids Part #800811C) to a glass tube.
2. Remove the chloroform from lipid mixture by evaporating to a clear, thin film under a stream of nitrogen. Continuous rotation of the tube, at an angle to ensure maximum surface area of the lipid solution, will promote the thinnest film.
3. Add 5 mLs resuspension buffer, 20 mM HEPES, 0.3% CHAPS, pH 7.4, to the dried lipid mix
4. Heat gently to 50-60° C. for 1-2 minutes and vortex in short intervals until the lipids are dissolved to a clear or slightly hazy solution. The lipids are typically in solution after 2-3 heat/vortex cycles.
5. Cool to room temperature, aliquot into single use volumes and store at −20° C.

Assay Protocol
Bar-coded Corning, low volume NBS, black 384-well plate (Corning Cat. #4514)
1. 2.5 µL—4× Test Compound or 100 nL 100× plus 2.4 µL kinase buffer
2. 5 µL—2× Peptide/Kinase Mixture
3. 2.5 µL—4× ATP Solution
4. 30-second plate shake
5. 60-minute Kinase Reaction incubation at room temperature
6. 5 µL—Development Reagent Solution
7. 30-second plate shake
8. 60-minute Development Reaction incubation at room temperature
9. Read on fluorescence plate reader and analyze the data 2. Assay Controls
The following controls are made for each individual kinase and are located on the same plate as the kinase:
0% Phosphorylation Control (100% Inhibition Control)
The maximum Emission Ratio is established by the 0% Phosphorylation Control (100% Inhibition Control), which contains no ATP and therefore exhibits no kinase activity. This control yields 100% cleaved peptide in the Development Reaction.
100% Phosphorylation Control
The 100% Phosphorylation Control, which consists of a synthetically phosphorylated peptide of the same sequence as the peptide substrate, is designed to allow for the calculation of percent phosphorylation. This control yields a very low percentage of cleaved peptide in the Development Reaction.
The 0% Phosphorylation and 100% Phosphorylation Controls allow one to calculate the percent Phosphorylation achieved in a specific reaction well. Control wells do not include any kinase inhibitors.
0% Inhibition Control
The minimum Emission Ratio in a screen is established by the 0% Inhibition Control, which contains active kinase. This control is designed to produce a 10-50%* phosphorylated peptide in the Kinase Reaction.
* Cascade assays may produce up to 70% phosphorylated peptide.
Known Inhibitor
A known inhibitor control standard curve, 10 point titration, is run for each individual kinase on the same plate as the kinase to ensure the kinase is inhibited within an expected $IC_{50}$ range previously determined.

The following controls are prepared for each concentration of Test Compound assayed:
Development Reaction Interference
The Development Reaction Interference is established by comparing the Test Compound Control wells that do not contain ATP versus the 0% Phosphorylation Control (which does not contain the Test Compound). The expected value for a non-interfering compound should be 100%. Any value outside of 90% to 110% is flagged.
Test Compound Fluorescence Interference
The Test Compound Fluorescence Interference is determined by comparing the Test Compound Control wells that do not contain the Kinase/Peptide Mixture (zero peptide control) versus the 0% Inhibition Control. The expected value for a non-fluorescence compound should be 0%. Any value >20% is flagged.
3. Data Analysis
The following equations are used for each set of data points:

$$\text{Emission ratio (using values corrected for background fluorescence)} = \frac{\text{Coumarin Emission (445 nm)}}{\text{Fluorescein Emission (520 nm)}} \quad (1)$$

$$\text{Correction for Background Fluorescence} = FI_{Sample} - FI_{TCFI\ Ctl} \quad (2)$$

$$\% \text{ Phosphorylation (\% Phos)} = \quad (3)$$
$$\left\{1 - \frac{(\text{Emission Ratio} \times F_{100\%}) - C_{100\%}}{(C_{0\%} - C_{100\%}) + [\text{Emission Ratio} \times (F_{100\%} - F_{0\%})]}\right\} * 100$$

$$\% \text{ Inhibition} = \left\{1 - \frac{\% \text{ Phos}_{Sample}}{\% \text{ Phos}_{0\%\ Inhibition\ Ctl}}\right\} * 100 \quad (4)$$

$$Z' \text{ (using Emission Ratio values)} = \quad (5)$$
$$1 - \frac{3 * Stdev_{0\%\ Phos\ Ctl} + 3 * Stdev_{0\%\ Inhibition}}{Mean_{0\%\ Phos\ Ctl} - Mean_{0\%\ Inhibition}}$$

$$\text{Difference Between Data Points (single point only)} = \quad (6)$$
$$|\% \text{ Inhibition}_{Point\ 1} - \% \text{ Inhibition}_{Point\ 2}|$$

$$\text{Development Reaction Interference } (DRI)(\text{no } ATP \text{ control}) = \frac{\text{Emission Ratio}_{DRI\ Ctl}}{\text{Emission Ratio}_{0\%\ Phos\ Ctl}} \quad (7)$$

$$\text{Test Compound Fluorescence Interference } (TCFI) = \frac{FI_{TCFI\ Ctl}}{FI_{0\%\ Inhibitor\ Ctl}} \quad (8)$$
(check both Coumarin and Fluorescein emissions)

$FI$ = Fluorescence Intensity
$C100\%$ = Average Coumarin emission signal of the 100% Phos. Control
$C0\%$ = Average Coumarin emission signal of the 0% Phos. Control
$F100\%$ = Average Fluorescein emission signal of the 100% Phos. Control
$F0\%$ = Average Fluorescein emission signal of the 0% Phos. Control
$DRI$ = Development Reation Interference
$TCFI$ = Test Compound Fluorescence Interference Graphing Software XLfit from IDBS was used as the graphing software. The dose response curve is curve fit to a sigmoidal dose-response model. If the bottom of the curve does not fit between −20% & 20% inhibition, it is set to 0% inhibition. If the top of the curve does not fit between 70% and 130% inhibition, it is set to 100% inhibition.

4. Kinase-Specific Assay Conditions

CSF-1R (FMS)

The 2×CSF-1R (FMS)/Tyr 01 mixture is prepared in 50 mM HEPES pH 7.5, 0.01% BRIJ-35, 10 mM MgCl2, 1 mM EGTA. The final 10 μL Kinase Reaction consists of 0.1-12.3 ng CSF-1R (FMS) and 2 μM Tyr 01 in 50 mM HEPES pH 7.5, 0.01% BRIJ-35, 10 mM $MgCl_2$, 1 mM EGTA. After the 1 hour Kinase Reaction incubation, 5 μL of a 1:256 dilution of Development Reagent B is added.

KDR (VEGFR2)

The 2×KDR (VEGFR2)/Tyr 01 mixture is prepared in 50 mM HEPES pH 7.5, 0.01% BRIJ-35, 10 mM MgCl2, 1 mM EGTA. The final 10 μL Kinase Reaction consists of 0.5-15 ng KDR (VEGFR2) and 2 pVM Tyr 01 in 50 mM HEPES pH 7.5, 0.01% BRIJ-35, 10 mM $MgCl_2$, 1 mM EGTA. After the 1 hour Kinase Reaction incubation, 5 μL of a 1:256 dilution of Development Reagent B is added.

5. Table of Kinase ATP Km Bins and Inhibitor Validation

Table 1 below provides specifications and data around each kinase. The representative $IC_{50}$ value with a known inhibitor for each kinase was determined at the ATP bin nearest to the ATP Km app.

TABLE 1

Kinase specifications and data

| Kinase | Z'-LYTE ® Substrate | ATP Km app (μM) | ATP Bin (μM) | Inhibitor | $IC_{50}$ (nM) |
|---|---|---|---|---|---|
| CSF-1R (FMS) | Tyr 01 | 450 | 500 | Tyrphostin AG1478 | 6480 |
| KDR (VEGFR2) | Tyr 01 | 78 | 75 | Staurosporine | 6.35 |

6. Assay Results

CSF-1R and VEGFR2 $IC_{50}$ values for compounds of the invention obtained by the above described assays are summarised in Table 2 below.

TABLE 2

CSF-1R and VEGFR2 $IC_{50}$ values for compounds of the invention

| Example | CSF-1R Enzyme $IC_{50}$* | VEGFR2 Enzyme $IC_{50}$* |
|---|---|---|
| 1 | C | D |
| 2 | A | C |
| 3 | B | D |
| 4 | B | nd |
| 5 | A | C |
| 6 | A | A |
| 7 | A | D |
| 8 | B | D |
| 9 | A | D |
| 10 | A | D |
| 11 | A | D |
| 12 | A | D |
| 13 | A | D |
| 14 | A | D |
| 15 | A | D |
| 16 | A | D |
| 17 | B | D |
| 18 | A | D |
| 19 | B | D |
| 20 | A | D |
| 21 | A | D |
| 22 | A | D |
| 23 | A | D |
| 24 | A | D |
| 25 | A | D |
| 26 | A | D |
| 27 | A | D |
| 28 | A | D |
| 29 | A | D |
| 30 | B | C |
| 31 | A | B |
| 32 | A | A |
| 33 | B | D |
| 34 | B | C |
| 35 | B | nd |
| 36 | B | C |
| 37 | A | D |
| 38 | A | D |
| 39 | C | nd |
| 40 | A | D |
| 41 | B | nd |
| 42 | A | D |
| 43 | A | C |
| 44 | A | D |
| 45 | A | C |
| 46 | A | D |
| 47 | A | nd |
| 48 | B | D |
| 49 | A | D |
| 50 | A | D |
| 51 | A | D |
| 52 | C | nd |
| 53 | B | D |
| 54 | A | D |
| 55 | A | D |
| 56 | A | D |
| 57 | A | D |
| 58 | A | D |
| 59 | A | D |
| 60 | A | D |
| 61 | A | D |
| 62 | A | D |
| 63 | A | D |
| 64 | A | D |
| 65 | A | D |
| 66 | A | C |
| 67 | A | D |
| 68 | A | D |
| 69 | A | D |
| 70 | A | D |
| 71 | A | C |
| 72 | A | D |
| 73 | A | D |
| 74 | A | D |
| 75 | A | D |
| 76 | A | D |

*A < 0.1 μM; B. 0.1-1.0 μM; C. 1.0-10 μM; D > 10 μM; nd. No data.

In Vivo Efficacy Study

1. Preparation of the Dimethanesulfonate Salt of Compound 22

To a solution of N-cyclopentyl -3-(5-((5-(2-(dimethylamino)ethoxy)-7-methyl-9-oxo-9H-xanthen-3-yl)-oxy)pyridin-2-yl)propanamide (compound 22, see Example 22) in a mixture of $CH_2Cl_2$ and MeOH, was added methanesulfonic acid (2.1 equivalents) at 20° C., and the resulting solution was stirred for 30 min. After removal of the solvents under vacuum, the resulting gluey material was redissolved in MeOH, and the solvent was evaporated again. This process was repeated four times before the residue was again dissolved in MeOH, and diluted with EtOAc. The MeOH was removed by evaporation to give a white powdery solid, which was quickly collected by filtration, as it was very hydroscopic. The solid was dried in a vacuum desiccator containing $P_2O_5$ to afford the dimethanesulfonate of compound 22, as a white solid: mp (MeOH/EtOAc) 138-140° C.; $^1$H NMR (DMSO-$d_6$) δ 9.61 (br, 1H), 8.47 (br m, 1H), 8.22 (d, J=9.5 Hz, 1H), 7.82 (d, J=7.3 Hz, 1H), 7.67 (dd, J=8.4, 2.5 Hz, 1H), 7.61 (dd, J=1.8, 0.8 Hz, 1H), 7.47 (d, J=1.7 Hz, 1H), 7.43 (d, J=8.4 Hz, 1H), 7.13-7.10 (m, 2H), 4.53-4.51 (m, 2H), 4.02-3.91 (m 1H), 3.64-3.60 (m, 2H), 3.02 (t, J=7.5 Hz, 2H), 2.95 (s, 3H), 2.93 (s, 3H), 2.53 (br m, 2H), 2.45 (s, 3H) 2.31 (s, 6H), 1.81-1.73 (m, 2H), 1.65-1.56 (m, 2H), 1.52-1.44 (m, 2H), 1.37-1.28 (m, 2H).

2. Mice

Specific pathogen-free NIH-III female mice were inoculated with 5×106 NZM12 human melanoma cells and then tumours allowed to grow to 100 mm$^3$ before drug dosing was started with the dimethanesulfonate salt of compound 22, PLX3397 (Pexidartinib, a known CSF-1R inhibitor), or a control of vehicle alone. The dimethanesulfonate salt of Compound 22 was formulated in 20% hydroxypropyl-β-cyclodextrin and administered daily to 4 mice for 14 days by i.p. injection and PLX3397 was formulated in 5% DMSO/95% methylcellulose and dosed daily to 4 mice for 14 days by oral gavage.

3. Preparation of Leukocytes

Blood was collected in tubes coated with 2.5 mM EDTA. Erythrocytes were lysed using ACK lysis solution. Remaining leukocytes were washed twice by centrifugation at 250×g in FACS buffer containing 5 mM EDTA and 0.5% BSA.

4. Antibodies

Anti-CD11b and anti-CD24 antibodies were purchased from Biolegend.

5. Flowcytometry

Leukocytes were stained with either anti-CD11b or anti-CD24 antibodies at the concentration of 1.25 ug/ml and subjected to flowcytometry analysis in a BD Accuri C6 system using FL-2A and FL-4 channels, respectively. Data were analysed using BD Accuri C6 Plus software and FCS Express Software.

6. Results

Figure 2:
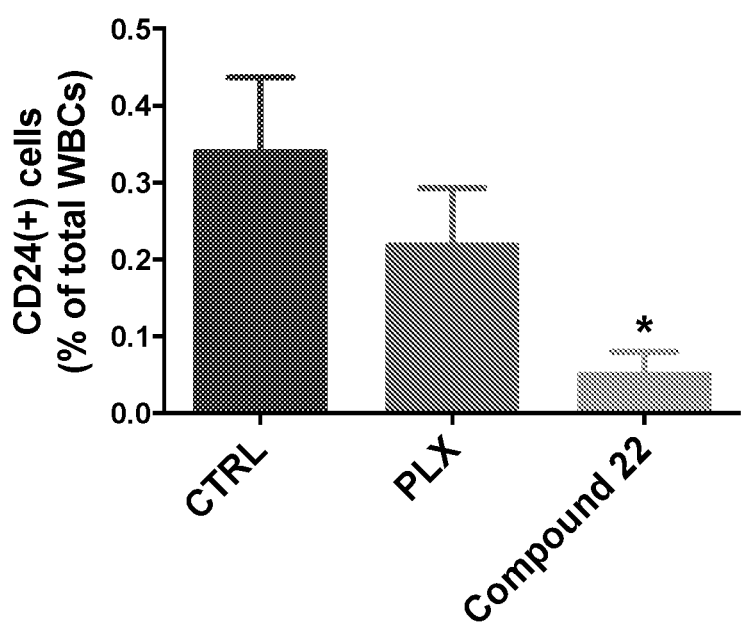
FIG. 2 is a graph showing the levels of CD24 positive cells (CD24(+)) following treatment of mice bearing melanoma xenografts with the dimethanesulfonate salt compound 22 of the invention ("Compound 22"), PLX3397 (Pexidartinib, "PLX"), and a control ("CTRL").

Treatment of mice bearing melanoma xenografts with the dimethanesulfonate salt of compound 22 reduced the levels of CD11b and CD24 positive cells to a similar or greater extent compared with treatment with PLX3397, as shown in FIGS. 1 and 2. In these figures * equals a level of significance of P<0.05 and ** equals a level of significance of P<0.01 versus controls using a paired t-test analysis. The findings confirms the two compounds both reduce the number of cells of myeloid lineage in the treated mice which is consistent with the compounds having in vivo activity against the CSF1 receptor.

INDUSTRIAL APPLICABILITY

The compounds of formula (I) described herein have useful kinase inhibitory activity, in particular inhibitory activity against CSF-1R. As such, these compounds are useful for treating various diseases and conditions, such as those mediated by CSF-1R activity as described herein. Such diseases and conditions include, for example, proliferative or neoplastic diseases and conditions such as cancers and bone, inflammatory, and autoimmune diseases and conditions.

Any documents referred to herein including, but not limited to, patents, patent applications, journal articles, books, and the like, are incorporated herein by reference in their entirety. Any section headings used herein are for organizational purposes only and are not to be construed as limiting the subject matter described.

Although the invention has been described by way of example and with reference to particular embodiments, it is to be understood that modifications and/or improvements may be made without departing from the scope of the invention.

The invention claimed is:

1. A compound of formula (I):

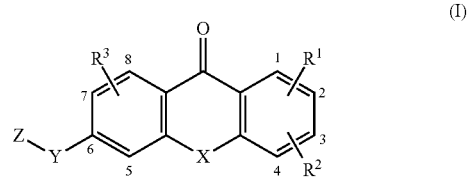

wherein:

X is NR$^4$, O, S, SO, SO$_2$, Se or Te and R$^2$ is G at any one of positions 2 to 4; or X is NG$^1$ and R$^2$ is H, D, NR$^6$R$^7$, OR$^6$, SR$^8$, halogen, CF$_3$, OCF$_3$, CN, NR$^6$COR$^8$, NR$^6$S$_2$R$^8$, or C$_{1-4}$alkyl optionally substituted with one or more independently selected R$^a$;

Y is CHR$^6$, CO, CHR$^6$NR$^5$, CHR$^6$O, CHR$^6$S, CHR$^6$SO$_2$, CONR$^5$, NR$^5$, NR$^5$CO, NR$^5$SO$_2$, O, OCHR$^6$, S, SO, SO$_2$, SCHR$^6$, SO$_2$CHR$^6$, or SO$_2$NR$^5$;

Z is W or —W$^1$—Y$^1$—W$^2$;

R$^1$ and R$^3$ are each independently H, D, NR$^6$R$^7$, OR$^6$, SR$^8$, halogen, CF$_3$, OCF$_3$, CN, NR$^6$COR$^8$, NR$^6$SO$_2$R$^8$, or C$_{1-4}$alkyl optionally substituted with one or more independently selected R$^a$;

R$^4$ is H or C$_{1-6}$alkyl optionally substituted with one or more independently selected R$^b$;

R$^5$ is H or C$_{1-4}$alkyl optionally substituted with one or more independently selected R$^c$;

R$^6$ and R$^7$ at each instance are each independently H or unsubstituted C$_{1-4}$alkyl;

R$^8$ at each instance is independently unsubstituted C$_{1-4}$alkyl;

G is -J$^1$-L$^1$-NR$^{9a}$R$^{10a}$, -J$^1$-L$^2$-NR$^{9b}$R$^{10b}$, -J$^1$-L$^3$CR$^{11}$R$^{12}$R$^{13}$, -L$^{10}$-NR$^{9a}$R$^{10a}$, -L$^{20}$-NR$^{9b}$R$^{10b}$, or -L$^{30}$-CR$^{11}$R$^{12}$R$^{13}$;

G$^1$ is -L$^1$-NR$^{9a}$R$^{10a}$, -L$^2$-NR$^{9b}$R$^{10b}$, or -L$^3$-cR$^{11}$R$^{12}$R$^{13}$;

J$^1$ is O, NR$^6$S, —(C$_{1-3}$alkylene)O—*, —(C$_{1-3}$alkylene)NR$^6$—*, or —(C$_{1-3}$alkylene)S—*, wherein each alkylene is unsubstituted and wherein * denotes the bond to L$^1$, L$^2$, or L$^3$;

L$^1$ and L$^2$ are each independently C$_{2-6}$alkylene, —C$_{2-3}$alkylene-J$^2$-C$_{2-3}$alkylene-*, —(C$_{1-3}$alkylene)$_a$-A-(C$_{1-3}$alkylene)$_b$-*, —C$_{2-3}$alkylene-J$^2$-(C$_{1-3}$alkylene)$_a$-A-(C$_{1-3}$alkylene)$_b$-*, or —(C$_{1-3}$alkylene)$_a$-A-(C$_{1-3}$alkylene)$_b$-J$^2$C$_{2-3}$alkylene-*, wherein each alkylene is unsubstituted and wherein * denotes the bond to NR$^{9a}$R$^{10a}$ or NR$^{9b}$R$^{10b}$;

L$^3$ is a bond, C$_{1-6}$alkylene, —C$_{2-6}$alkylene-J$^2$-*, —C$_{2-3}$alkylene-J$^2$-C$_{1-3}$alkylene-*, —(C$_{1-3}$alkylene)$_a$-

A-(C$_{1-3}$alkylene)$_b$-*, —C$_{2-3}$alkylene-J$^2$-(C$_{1-3}$alkylene)$_a$-A-(C$_{1-3}$alkylene)$_b$-*, or —(C$_{1-3}$alkylene)$_a$-A-(C$_{1-3}$alkylene)$_b$-J$^2$-(C$_{1-3}$alkylene)-*, wherein each alkylene is unsubstituted and wherein * denotes the bond to CR$^{11}$R$^{12}$R$^{13}$;

L$^{10}$ and L$^{20}$ are each independently C$_{1-6}$alkylene, —C$_{1-3}$alkylene-J$^2$-C$_{2-3}$alkylene-*, —(C$_{1-3}$alkylene)$_a$-A-(C$_{1-3}$alkylene)$_b$-*, —C$_{1-3}$alkylene-J$^2$-(C$_{1-3}$alkylene)$_a$-A-(C$_{1-3}$alkylene)$_b$-*, or —(C$_{1-3}$alkylene)$_a$-A-(C$_{1-3}$alkylene)$_b$-J$^2$-C$_{2-3}$alkylene-*, wherein each alkylene is unsubstituted and wherein * denotes the bond to NR$^{9a}$R$^{10a}$ or NR$^{9b}$R$^{10b}$;

L$^{30}$ is C$_{1-6}$alkylene, —C$_{1-6}$alkylene-J$^2$-*, —C$_{1-3}$alkylene-J$^2$-C$_{1-3}$alkylene-*, —(C$_{1-3}$alkylene)$_a$-A-(C$_{1-3}$alkylene)$_b$-*, —C$_{1-3}$alkylene-J$^2$-(C$_{1-3}$alkylene)$_a$-A-(C$_{1-3}$alkylene)$_b$-*, or —(C$_{1-3}$alkylene)$_a$-A-(C$_{1-3}$alkylene)$_b$-J$^2$-(C$_{1-3}$alkylene)$_c$-*, wherein each alkylene is unsubstituted and wherein * denotes the bond to CR$^{11}$R$^{12}$R$^{13}$;

A is 3 to 7-membered cycloalkylene optionally substituted with one or more independently selected R$^d$;

J$^2$ is O, NR$^6$, or S;

a, b, and c are each independently 0 or 1;

R$^{9a}$ and R$^{10a}$ are each independently H, unsubstituted C$_{1-6}$alkyl, or unsubstituted 3 to 10-membered cycloalkyl;

R$^{9b}$ and R$^{10b}$ together with the nitrogen atom to which they are attached form a 4 to 10-membered heterocyclyl or 5 to 10-membered heteroaryl, optionally substituted with one or more independently selected R$^g$;

R$^{11}$ and R$^{12}$ together with the carbon atom to which they are attached form a 4 to 10-membered heterocyclyl comprising at least one ring nitrogen atom, optionally substituted with one or more independently selected R$^g$; and R$^{13}$ is H, C$_{1-4}$alkyl optionally substituted with one or more independently selected R$^h$, or the second bond of a double bond between R$^{11}$ or R$^{12}$ and the carbon atom to which they are attached; or R$^{11}$ and R$^{12}$ together with the carbon atom to which they are attached form a 5 to 10-membered heteroaryl comprising at least one ring nitrogen atom, optionally substituted with one or more independently selected R$^g$; and R$^{13}$ is the second bond of a double bond between R$^{11}$ or R$^{12}$ and the carbon atom to which they are attached;

W is 6 to 10-membered aryl or 5 to 10-membered heteroaryl, optionally substituted with one or more independently selected R$^i$;

W$^1$ is phenylene or 5 or 6-membered hetereoarylene, optionally substituted with one or more independently selected R$^x$;

Y$^1$ is C$_{1-6}$alkylene-J$^4$-*, —(C$_{1-3}$alkylene)-J$^4$-*, —(C$_{1-3}$alkylene)-J$^5$-(C$^{1-3}$alkylene)-*, -J$^5$-(C$_{1-3}$alkylene)-*, or -J$^6$-C$_{1-3}$alkylene-J$^7$-*, wherein each alkylene is unsubstituted and wherein * denotes the bond to W$^2$;

J$^4$ is O, NR$^{14}$, S, NR$^{15}$CO, CONR$^{14}$, NR$^{15}$CONR$^{14}$, OCONR$^{14}$, or NR$^{15}$COO;

J$^5$ is O, NR$^{15}$, S, NR$^{15}$CO, CONR$^{15}$, NR$^{15}$CONR$^{15}$, OCONR$^{15}$, or NR$^{15}$COO;

J$^6$ is O, NR$^{15}$, or S;

J$^7$ is O, NR$^{14}$, S, NR$^{15}$CO, or CONR$^{14}$;

R$^{14}$ and R$^{15}$ at each instance are each independently H or C$_{1-3}$alkyl optionally substituted with one or more independently selected R$^j$;

W$^2$ is:
(a) 3 to 10-membered cycloalkyl or 4 to 10-membered heterocyclyl, optionally substituted with one or more independently selected R$^m$, or
(b) 6 to 10-membered aryl or 5 to 10-membered heteroaryl, optionally substituted with one or more independently selected R$^n$;

or R$^{14}$ and W$^2$ together with the nitrogen atom to which they are attached form:
(a) a 4 to 10-membered heterocyclyl, optionally substituted with one or more independently selected R$^m$, or
(b) a 5 to 10-membered heteroaryl, optionally substituted with one or more independently selected R$^n$;

R$^a$, R$^b$, R$^c$, and R$^h$ at each instance are each independently selected from F, OCF$_3$, and O(unsubstituted C$_{1-4}$alkyl);

R$^d$ and R$^g$ at each instance are each independently selected from D, NR$^6$R$^7$, OR$^6$, SR$^8$, halogen, CF$_3$, OCF$_3$, CN, SO$_2$R$^8$, NR$^6$COR$^8$, NR$^6$SO$_2$R$^8$, and C$_{1-4}$alkyl optionally substituted with one or more substituents independently selected from F, OCF$_3$, and O(unsubstituted C$_{1-4}$alkyl);

R$^i$, R$^x$, and R$^n$ at each instance are each independently selected from D, NR$^6$R$^7$, OR$^6$, SR$^8$, halogen, CF$_3$, OCF$_3$, CN, SO$_2$R$^8$, and C$_{1-4}$alkyl optionally substituted with one or more substituents independently selected from F, OCF$_3$, and O(unsubstituted C$_{1-4}$alkyl);

R$^j$ at each instance is independently selected from F and D;

R$^m$ at each instance is independently selected from D, NR$^6$R$^7$, OR$^6$, SR$^8$, F, CF$_3$, OCF$_3$, CN, SO$_2$R$^8$, and C$_{1-4}$alkyl optionally substituted with one or more substituents independently selected from F, OCF$_3$, and O(unsubstituted C$_{1-4}$alkyl);

or a pharmaceutically acceptable salt, solvate, or stereoisomer thereof.

2. The compound of claim 1, wherein the compound of formula (I) is a compound of formula (I-1), (I-2), or (I-3):

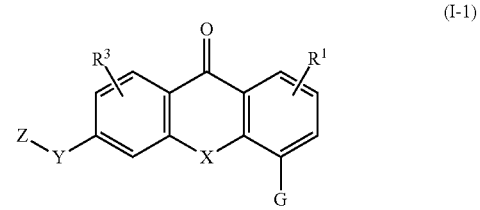

(I-1)

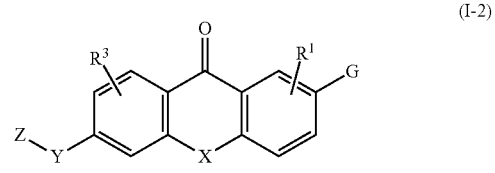

(I-2)

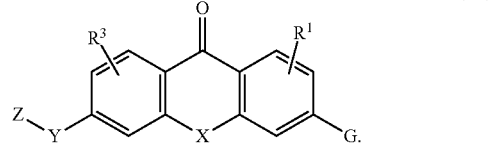

(I-3)

3. The compound of claim 1, wherein X is NR$^4$, O, S, SO, or SO$_2$.

4. The compound of claim 1, wherein X is O or S.

5. The compound of claim 1, wherein the compound of formula (I) is a compound of the formula (I-4):

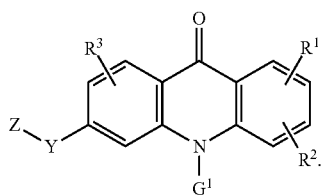

(I-4)

6. The compound of claim 1, wherein:
$L^1$ is $(CH_2)_{2-6}$ or $(CH_2)_{2-3}$-$J^2$-$(CH_2)_{2-3}$;
$L^2$ is $(CH_2)_{2-6}$ or $(CH_2)_{2-3}$-$J^2$-$(CH_2)_{2-3}$;
$L^3$ is a bond, $(CH_2)_{1-6}$, $(CH_2)_{2-6}J^2$, or $(CH_2)_{2-3}$-$J^2$-$(CH_2)_{1-3}$;
$L^{10}$ is $(CH_2)_{1-6}$ or $(CH_2)_{1-3}$-$J^2$-$(CH_2)_{2-3}$;
$L^{20}$ is $(CH_2)_{1-6}$ or $(CH_2)_{1-3}$-$J^2$-$(CH_2)_{2-3}$;
$L^{30}$ is $(CH_2)_{1-6}$, $(CH_2)_{1-6}$-$J^2$, or $(CH_2)_{1-3}$-$J^2$-$(CH_2)_{1-3}$.

7. The compound of claim 1, wherein G is -$J^1$-$L^1$-$NR^{9a}R^{10a}$, -$J^1$-$L^2$-$NR^{9b}R^{10b}$, or -$J^1$-$L^3$-$CR^{11}R^{12}R^{13}$.

8. The compound of claim 1, wherein $J^1$ is O.

9. The compound of claim 1, wherein:
(a) $R^{9a}$ and $R^{10a}$ are each independently H or unsubstituted $C_{1-6}$alkyl, or $R^{9b}$ and $R^{10b}$ together with the nitrogen atom to which they are attached form an optionally substituted 4 to 7-membered heterocyclyl or optionally substituted 5 or 6-membered heteroaryl; or
(b) $R^{11}$ and $R^{12}$ together with the carbon atom to which they are attached form an optionally substituted 4 to 7-membered heterocyclyl or an optionally substituted 5 or 6-membered heteroaryl.

10. The compound of claim 1, wherein Y is O, $NR^5$, $CH_2$, CO, S, SO, or $SO_2$.

11. The compound of claim 1, wherein:
(a) W is an optionally substituted phenyl or an optionally substituted 5 or 6-membered heteroaryl; or
(b) $W^1$ is an optionally substituted 5-membered heteroarylene attached to Y and $Y^1$ in a 1,3-relationship or an optionally substituted phenylene or optionally substituted 6-membered heteroarylene attached to Y and $Y^1$ in a 1,3- or 1,4-relationship; and
$W^2$ is an optionally substituted 4 to 7-membered cycloalkyl, optionally substituted 4 to 7-membered heterocyclyl, optionally substituted 5 or 6-membered heteroaryl, or optionally substituted phenyl;
or $R^{14}$ and $W^2$ together with the nitrogen atom to which they are attached form an optionally substituted 4 to 7-membered heterocyclyl, or optionally substituted 5 or 6-membered heteroaryl.

12. The compound of claim 1, wherein $Y^1$ is $(CH_2)_{1-6}$, -$J^4$-*, —$(CH_2)_{1-3}$-$J^4$-*, —$(CH_2)_{1-3}$-$J^5$-$(CH_2)_{1-3}$—*, -$J^5$-$(CH_2)_{1-3}$—*, or -$J^6$-$(CH_2)_{1-3}$-$J^7$-*; and/or wherein:
$J^4$ is O, $NR^{14}$, $NR^{15}CO$, $CONR^{14}$, or $NR^{15}coNR^{14}$;
$J^5$ is O, $NR^{15}$, $NR^{15}CO$, $CONR^{15}$, or $NR^{15}CONR^{15}$;
$J^6$ is O or $NR^{15}$;
$J^7$ is O, $NR^{14}$, $NR^{15}CO$, or $CONR^{14}$.

13. The compound of claim 1, wherein $Y^1$ is —$(CH_2)_{1-4}$—*, —$CONR^{14}$—*, —$NR^{15}CONR^{14}$—*, —$O(CH_2)_{1-3}$—*, —$NR^{15}(CH_2)_{1-3}$—*, —$(CH_2)_{1-3}CONR^{14}$—*, —$(CH_2)_{1-3}NR^{15}CO$—*, —$NR^{15}(CH_2)_{1-3}CONR^{14}$—*, or —$(CH_2)_{1-3}NR^{15}CONR^{14}$—*.

14. The compound of claim 1, wherein
(a) $Y^1$ is $C_{1-6}$alkylene-$J^4$-*, —$(C_{1-3}$alkylene)-$J^5$-$(C_{1-3}$alkylene)-*, or -$J^5$-$(C_{1-3}$alkylene)-*; and $W^2$ is an optionally substituted 6 to 10-membered aryl or an optionally substituted 5 to 10-membered heteroaryl; or (b) $Y^1$ is —$(C_{1-3}$alkylene)-$J^4$-* or -$J^6$-$C_{1-3}$alkylene-$J^7$-*; and $W^2$ is an optionally substituted 3 to 10-membered cycloalkyl, optionally substituted 4 to 10-membered heterocyclyl, optionally substituted 6 to 10-membered aryl, optionally substituted 5 to 10-membered heteroaryl; or $R^{14}$ and $W^2$ together with the nitrogen atom to which they are attached form an optionally substituted 4 to 10-membered heterocyclyl or an optionally substituted 5 to 10-membered heteroaryl.

15. The compound of claim 1, wherein $R^3$ is H.

16. The compound of claim 1, wherein the compound of formula (I) is (a) a compound of formula (IA-1), (IA-2), or (IA-3):

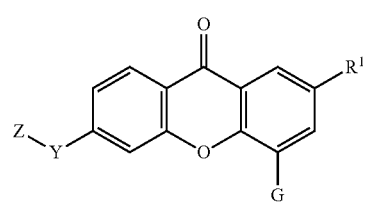
(IA-1)

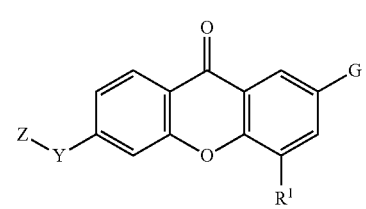
(IA-2)

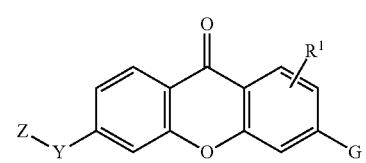
(IA-3)

wherein:
G is —O—$(CH_2)_{2-4}$—$NR^{9a}R^{10a}$, —O—$(CH_2)_{2-4}$—$NR^{9b}R^{10b}$, —O—$(CH_2)_{1-4}$—$CR^{11}R^{12}R^{13}$, or —O—$CR^{11}R^{12}R^{13}$;

(b) a compound of formula (IC-1):

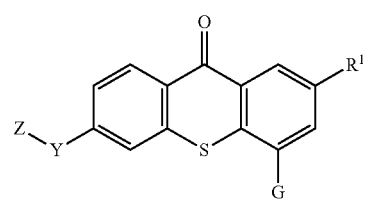
(IC-1)

wherein:
G is —O—$(CH_2)_{2-4}$—$NR^{9a}R^{10a}$, —O—$(CH_2)_{2-4}$—$NR^{9b}R^{10b}$, or —O—$(CH_2)_{1-4}$—$CR^{11}R^{12}R^{13}$; or (c) a compound of the formula (ID):

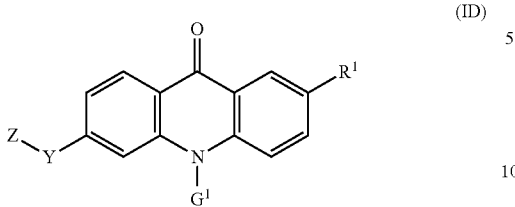

wherein:
G$^1$ is —(CH$_2$)$_{2-4}$—NR$^{9a}$R$^{10a}$, —(CH$_2$)$_{2-4}$—NR$^{9a}$R$^{10b}$, or —(CH$_2$)$_{1-4}$—CR$^{11}$R$^{12}$R$^{13}$.

17. The compound of claim 1, wherein the compound of formula (I) is:
5-[2-(Dimethylamino)ethoxy]-3-phenoxy-9H-xanthen-9-one;
3-({[2-(Dimethylamino)ethoxy]-9-oxo-9H-xanthen-3-yl}oxy)-N-phenylbenzamide;
5-[2-(Dimethylamino)ethoxy]-3-({6-[2-(4-methoxyphenyl)ethyl]-3-pyridinyl}oxy)-9H-xanthen-9-one;
4-[2-(Dimethylamino)ethoxy]-2-methyl-6-phenoxy-9H-xanthen-9-one;
3((5-(2-(Dimethylamino)ethoxy)-7-methyl-9-oxo-9H-xanthen-3-yl)oxy)-N-phenylbenz-amide;
1-(3((5-(2-(Dimethylamino)ethoxy)-7-methyl-9-oxo-9H-xanthen-3-yl)oxy)phenyl)-3-phenylurea;
4-(2-(Dimethylamino)ethoxy)-6-(3-methoxy-4-((4-methylbenzyl)oxy)phenoxy)-2-methyl-9H-xanthen-9-one;
4-(2-(Dimethylamino)ethoxy)-6-((6-methoxypyridin-3-yl)oxy)-2-methyl-9H-xanthen-9-one;
6-((5,6-Dimethoxypyridin-3-yl)oxy)-4-(2-(dimethylamino)ethoxy)-2-methyl-9H-xanthen-9-one;
4-(2-(Dimethylamino)ethoxy)-6-((6-((4-methoxybenzyl)oxy)pyridin-3-yl)oxy)-2-methyl-9H-xanthen-9-one;
4-(2-(Dimethylamino)ethoxy)-6-((6-((6-methoxypyridin-3-yl)methoxy)pyridin-3-yl)oxy)-2-methyl-9H-xanthen-9-one;
4-(2-(Dimethylamino)ethoxy)-6-((5-methoxy-6-((4-methoxybenzyl)oxy)pyridin-3-yl)-oxy)-2-methyl-9H-xanthen-9-one;
4-(2-(Dimethylamino)ethoxy)-2-methyl-6-((6-((6-(trifluoromethyl)pyridin-3-yl)meth-oxy)pyridin-3-yl)oxy)-9H-xanthen-9-one;
4-(2-(Dimethylamino)ethoxy)-6-((6-((4-methoxybenzyl)amino)pyridin-3-yl)oxy)-2-methyl-9H-xanthen-9-one;
4-(2-(Dimethylamino)ethoxy)-2-methyl-6-((6-((4-(trifluoromethoxy)benzyl)amino)-pyridin-3-yl)oxy)-9H-xanthen-9-one;
4-(2-(Dimethylamino)ethoxy)-6-((6-(((6-methoxypyridin-3-yl)methyl)amino)pyridin-3-yl)oxy)-2-methyl-9H-xanthen-9-one;
6-((6-Aminopyridin-3-yl)oxy)-4-(2-(dimethylamino)ethoxy)-2-methyl-9H-xanthen-9-one;
4-(2-(Dimethylamino)ethoxy)-6-((6-(4-methoxyphenethyl)pyridin-3-yl)oxy)-2-methyl-9H-xanthen-9-one;
4-(2-(Dimethylamino)ethoxy)-6-((6-methoxypyridin-3-yl)methyl)-2-methyl-9H-xanthen-9-one;
(2-(Dimethylamino)ethoxy)-6-(6-((4-methoxybenzyl)oxy)nicotinoyl)-2-methyl-9H-xanthen-9-one;
3-(5-((5-(2-(Dimethylamino)ethoxy)-7-methyl-9-oxo-9H-xanthen-3-yl)oxy)pyridin-2-yl)-N-(pyridin-3-yl)propanamide;
N-Cyclopentyl-3-(5-((5-(2-(dimethylamino)ethoxy)-7-methyl-9-oxo-9H-xanthen-3-yl)-oxy)pyridin-2-yl)propanamide;
4-(2-(Dimethylamino)ethoxy)-2-methyl-6-((6-(3-oxo-3-(pyrrolidin-1-yl)propyl)pyridin-3-yl)oxy)-9H-xanthen-9-one;
4-(2-(Dimethylamino)ethoxy)-2-methyl-6-((6-(3-morpholino-3-oxopropyl)pyridin-3-yl)oxy)-9H-xanthen-9-one;
N-Cyclopentyl-2-((5-(((5-(2-(dimethylamino)ethoxy)-7-methyl-9-oxo-9H-xanthen-3-yl)-oxy)pyridin-2-yl)amino)acetamide;
N-(2-(5-((5-(2-(Dimethylamino)ethoxy)-7-methyl-9-oxo-9H-xanthen-3-yl)oxy)pyridin-2-yl)ethyl)cyclopentanecarboxamide;
N-(2-(5-((5-(2-(Dimethylamino)ethoxy)-7-methyl-9-oxo-9H-xanthen-3-yl)oxy)pyridin-2-yl)ethyl)pyrrolidine-1-carboxamide;
3-(5-((5-(2-Aminoethoxy)-7-methyl-9-oxo-9H-xanthen-3-yl)oxy)pyridin-2-yl)-N-cyclo-pentylpropanamide;
N-Cyclopentyl-3-(5-((7-methyl-5-(2-(methylamino)ethoxy)-9-oxo-9H-xanthen-3-yl)oxy)-pyridin-2-yl)propanamide;
4-[3-(Dimethylamino)propoxy]-2-methyl-6-phenoxy-9H-xanthen-9-one;
3-((5-(3-(Dimethylamino)propoxy)-7-methyl-9-oxo-9H-xanthen-3-yl)oxy)-N-phenyl-benzamide;
1-(3-((5-(3-(Dimethylamino)propoxy)-7-methyl-9-oxo-9H-xanthen-3-yl)oxy)phenyl)-3-phenylurea;
2-Methyl-4-(3-morpholinopropoxy)-6-phenoxy-9H-xanthen-9-one;
4-(4-(Dimethylamino)butoxy)-2-methyl-6-phenoxy-9H-xanthen-9-one;
2-Methyl-4-(1-methylpiperidin-4-yl)methoxy)-6-phenoxy-9H-xanthen-9-one;
2-Methyl-4-(2-(1-methylpiperidin-4-yl)ethoxy)-6-phenoxy-9H-xanthen-9-one;
N-Cyclopentyl-3-(5-((7-methyl-9-oxo-5-(2-(pyrrolidin-1-yl)ethoxy)-9H-xanthen-3-yl)-oxy)pyridin-2-yl)propanamide;
N-Cyclopentyl-3-(5-((7-methyl-9-oxo-5-(2-(piperidin-1-yl)ethoxy)-9H-xanthen-3-yl)oxy)pyridin-2-yl)propanamide;
2-Chloro-4-[2-(dimethylamino)ethoxy]-6-phenoxy-9H-xanthen-9-one;
3-({7-Chloro-5-[2-(dimethylamino)ethoxy]-9-oxo-9H-xanthen-3-yl}oxy)-N-phenyl-benzamide;
2-Chloro-4-[2-(dimethylamino)ethoxy]-6-({6-[2-(4-methoxyphenyl)ethyl]-3-pyridinyl}-oxy)-9H-xanthen-9-one;
3-(5-((7-Bromo-5-(2-(dimethylamino)ethoxy)-9-oxo-9H-xanthen-3-yl)oxy)pyridin-2-yl)-N-cyclopentylpropanamide;
N-Cyclopentyl-3-(5-((5-(2-(dimethylamino)ethoxy)-7-methyl-9-oxo-9H-xanthen-3-yl)thio)pyridin-2-yl)propanamide;
N-Cyclopentyl-3-(5-((7-(2-(dimethylamino)ethoxy)-9-oxo-9H-xanthen-3-yl)oxy)pyridin-2-yl)propanamide;
N-Cyclopentyl-3-(5-((7-(2-(dimethylamino)ethoxy)-5-methyl-9-oxo-9H-xanthen-3-yl)oxy)pyridin-2-yl)propanamide;
N-Cyclopentyl-3-(5-((7-(2-(dimethylamino)ethoxy)-5-methoxy-9-oxo-9H-xanthen-3-yl)oxy)pyridin-2-yl)propanamide;
N-Cyclopentyl-3-(5-((6-(2-(dimethylamino)ethoxy)-9-oxo-9H-xanthen-3-yl)oxy)phenyl)propanamide;

4-(2-(Dimethylamino)ethoxy)-2-methyl-6-phenoxy-9H-thioxanthen-9-one;

3-((5-(2-(Dimethylamino)ethoxy)-7-methyl-9-oxo-9H-thioxanthen-3-yl)oxy)-N-phenylbenzamide;

4-(2-(Dimethylamino)ethoxy)-6-((6-(4-methoxyphenethyl)pyridin-3-yl)oxy)-2-methyl-9H-thioxanthen-9-one;

N-Cyclopentyl-3-(5-((5-(2-(dimethylamino)ethoxy)-7-methyl-9-oxo-9H-thioxanthen-3-yl)oxy)pyridin-2-yl)propanamide;

10-(3-(Dimethylamino)propyl)-2-methyl-6-(phenylthio)acridin-9(10H)-one;

4-(2-(Dimethylamino)ethoxy)-2-methyl-6-(pyridin-3-yloxy)-9H-xanthen-9-one;

4-(2-(Dimethylamino)ethoxy)-2-methyl-6-((6-(3-(4-methylpiperazin-1-yl)-3-oxopropyl)pyridin-3-yl)oxy)-9H-xanthen-9-one;

N-Cyclopentyl-3-(5-((5-(2-(diethylamino)ethoxy)-7-methyl-9-oxo-9H-xanthen-3-yl)oxy)pyridin-2-yl)propanamide;

N-Cyclopentyl-3-[5-({7-methyl-5-[2-(4-morpholinyl)ethoxy]-9-oxo-9H-xanthen-3-yl}oxy)-2-pyridinyl]propanamide;

N-Cyclopentyl-3-([5-({5-[2-(diisopropylamino)ethoxy]-7-methyl-9-oxo-9H-xanthen-3-yl}oxy)-2-pyridinyl]propanamide;

N-Cyclopentyl-3-(5-((7-methyl-5-(2-(4-methylpiperazin-1-yl)ethoxy)-9-oxo-9H-xanthen-3-yl)oxy)pyridin-2-yl)propanamide;

N-Cyclopentyl-3-(5-((7-methyl-9-oxo-5-(2-(4-(2,2,2-trifluoroethyl)piperazin-1-yl)ethoxy)-9H-xanthen-3-yl)oxy)pyridin-2-yl)propanamide;

N-Cyclopentyl-3-(5-((7-methyl-5-((1-methylpiperidin-3-yl)oxy)-9-oxo-9H-xanthen-3-yl)oxy)pyridin-2-yl)propanamide;

N-Cyclopentyl-3-(5-((5-(2-((3S,5R)-3,5-dimethylpiperazin-1-yl)ethoxy)-7-methyl-9-oxo-9H-xanthen-3-yl)oxy)pyridin-2-yl)propanamide;

N-Cyclopentyl-3-(5-((7-methyl-9-oxo-5-(2-((3S,5R)-3,4,5-trimethylpiperazin-1-yl)ethoxy)-9H-xanthen-3-yl)oxy)pyridin-2-yl)propanamide;

N-Cyclopentyl-3-(5-((5-(3-(dimethylamino)propoxy)-7-methyl-9-oxo-9H-xanthen-3-yl)oxy)pyridin-2-yl)propanamide;

N-Cyclopentyl-3-(5-((5-(3-((2R,6S)-2,6-dimethylpiperidin-1-yl)propoxy)-7-methyl-9-oxo-9H-xanthen-3-yl)oxy)pyridin-2-yl)propanamide;

N-Cyclopentyl-3-(5-((5-(3-(4-ethylpiperazin-1-yl)propoxy)-7-methyl-9-oxo-9H-xanthen-3-yl)oxy)pyridin-2-yl)propanamide;

N-Cyclopentyl-3-(5-((5-(3-(4-isopropylpiperazin-1-yl)propoxy)-7-methyl-9-oxo-9H-xanthen-3-yl)oxy)pyridin-2-yl)propanamide;

N-Cyclopentyl-3-(5-((5-(3-((3S,5R)-3,5-dimethylpiperazin-1-yl)propoxy)-7-methyl-9-oxo-9H-xanthen-3-yl)oxy)pyridin-2-yl)propanamide;

N-Cyclopentyl-3-(5-((7-methyl-9-oxo-5-(3-((3S,5R)-3,4,5-trimethylpiperazin-1-yl)propoxy)-9H-xanthen-3-yl)oxy)pyridin-2-yl)propanamide;

N-Cyclopentyl-3-[5-({7-methyl-5-[3-(4-morpholinyl)propoxy]-9-oxo-9H-xanthen-3-yl}oxy)-2-pyridinyl]propanamide;

N-Cyclopentyl-3-(5-((7-methyl-5-((1-methylpyrrolidin-3-yl)oxy)-9-oxo-9H-xanthen-3-yl)oxy)pyridin-2-yl)propanamide;

N-Cyclopentyl-3-[5-({7-methyl-5-[(1-methyl-4-piperidinyl)oxy]-9-oxo-9H-xanthen-3-yl}oxy)-2-pyridinyl]propanamide;

(R)—N-Cyclopentyl-3-(5-((7-methyl-5-((1-methylpyrrolidin-2-yl)methoxy)-9-oxo-9H-xanthen-3-yl)oxy)pyridin-2-yl)propanamide;

(S)—N-Cyclopentyl-3-(5-((7-methyl-5-((1-methylpyrrolidin-2-yl)methoxy)-9-oxo-9H-xanthen-3-yl)oxy)pyridin-2-yl)propanamide;

N-Cyclopentyl-3-(5-((7-methyl-5-((1-methylpiperidin-2-yl)methoxy)-9-oxo-9H-xanthen-3-yl)oxy)pyridin-2-yl)propanamide;

N-Cyclopentyl-3-(5-((7-methyl-5-(2-(1-methylpyrrolidin-2-yl)ethoxy)-9-oxo-9H-xanthen-3-yl)oxy)pyridin-2-yl)propanamide;

N-Cyclopentyl-3-(5-((7-methyl-5-((1-methylpiperidin-3-yl)methoxy)-9-oxo-9H-xanthen-3-yl)oxy)pyridin-2-yl)propanamide; or a pharmaceutically acceptable salt, solvate, or stereoisomer thereof.

18. A pharmaceutical composition comprising a compound of the formula (I) according to claim 1 or a pharmaceutically acceptable salt, solvate, or stereoisomer thereof; and a pharmaceutically acceptable carrier.

\* \* \* \* \*